US010272226B2

(12) United States Patent
Cragg et al.

(10) Patent No.: US 10,272,226 B2
(45) Date of Patent: Apr. 30, 2019

(54) AUTO-FEEDBACK VALVE FOR A SLEEP APNEA DEVICE

(71) Applicant: Fresca Medical, Inc., San Clemente, CA (US)

(72) Inventors: Andrew H. Cragg, Edina, MN (US); John Logan, Plymouth, MN (US); Haim Nissimov, Laguna Hills, CA (US); Richard Christian Ewers, Fullerton, CA (US); Mark Alan Adler, Carlsbad, CA (US); Eugene G. Chen, Carlsbad, CA (US); John Edwin Trusheim, Chaska, MN (US); John Eugene Nolting, Poway, CA (US); Stephen William Anderson, Minneapolis, MN (US); Kevin Nai Hong Chen, Palos Verdes Estates, CA (US)

(73) Assignee: FRESCA MEDICAL, INC., San Clemente, CA (US)

( * ) Notice: Subject to any disclaimer, the term of this patent is extended or adjusted under 35 U.S.C. 154(b) by 361 days.

(21) Appl. No.: 14/278,398

(22) Filed: May 15, 2014

(65) Prior Publication Data

US 2014/0246024 A1    Sep. 4, 2014

Related U.S. Application Data

(63) Continuation-in-part of application No. 13/860,926, filed on Apr. 11, 2013, now Pat. No. 9,333,318.
(Continued)

(51) Int. Cl.
*A61M 16/20*   (2006.01)
*A61M 16/08*   (2006.01)
(Continued)

(52) U.S. Cl.
CPC ............. *A61M 16/208* (2013.01); *A61B 5/11* (2013.01); *A61B 5/4809* (2013.01);
(Continued)

(58) Field of Classification Search
CPC ............ A61M 16/206; A61M 16/0866; A61M 16/201; A61M 16/0057; A61M 16/209;
(Continued)

(56) References Cited

U.S. PATENT DOCUMENTS 4,207,884 A *  6/1980  Isaacson ............. A61M 16/208
                                                  128/200.24
4,316,458 A *  2/1982  Hammerton-Fraser ......................
                                                  A61M 16/20
                                                  128/205.13

(Continued)

FOREIGN PATENT DOCUMENTS

GB          2021421 A      12/1979
WO     1997041812 A1      11/1997
(Continued)

OTHER PUBLICATIONS

International Search Report dated Nov. 18, 2014 in PCT/US2014/038215 (6 pages).

*Primary Examiner* — Gregory A Anderson
*Assistant Examiner* — Margaret M Luarca
(74) *Attorney, Agent, or Firm* — Manuel de la Cerra

(57) ABSTRACT

A device for treating a patient suffering from obstructive sleep apnea or snoring can include an expiratory valve connected to a manifold. The expiratory valve can include a body portion including a feedback port configured to be connected to an air flow generator. The expiratory valve can include a plunger at least partially disposed in the body portion. The expiratory valve can include a pressurizing chamber positioned between an end of the plunger and an
(Continued)

end of the expiratory valve. The pressurizing chamber can be configured to receive air from the air flow generator through the feedback port.

14 Claims, 83 Drawing Sheets

Related U.S. Application Data

(60) Provisional application No. 61/623,855, filed on Apr. 13, 2012, provisional application No. 61/775,430, filed on Mar. 8, 2013, provisional application No. 61/823,553, filed on May 15, 2013, provisional application No. 61/838,191, filed on Jun. 21, 2013, provisional application No. 61/962,501, filed on Nov. 8, 2013, provisional application No. 61/909,956, filed on Nov. 27, 2013, provisional application No. 61/927,355, filed on Jan. 14, 2014.

(51) Int. Cl.
*A61M 16/00* (2006.01)
*A61B 5/00* (2006.01)
*A61B 5/11* (2006.01)
*A61M 16/06* (2006.01)
*A61M 16/10* (2006.01)

(52) U.S. Cl.
CPC ....... *A61B 5/4836* (2013.01); *A61M 16/0057* (2013.01); *A61M 16/06* (2013.01); *A61M 16/0683* (2013.01); *A61M 16/0833* (2014.02); *A61M 16/0866* (2014.02); *A61M 16/0875* (2013.01); *A61M 16/201* (2014.02); *A61M 16/206* (2014.02); *A61M 16/0069* (2014.02); *A61M 16/0688* (2014.02); *A61M 16/107* (2014.02); *A61M 16/202* (2014.02); *A61M 16/209* (2014.02); *A61M 2016/0027* (2013.01); *A61M 2016/0039* (2013.01); *A61M 2016/0661* (2013.01); *A61M 2205/18* (2013.01); *A61M 2205/3375* (2013.01); *A61M 2205/3553* (2013.01); *A61M 2205/3561* (2013.01); *A61M 2205/3584* (2013.01); *A61M 2205/3592* (2013.01); *A61M 2205/42* (2013.01); *A61M 2205/505* (2013.01); *A61M 2205/52* (2013.01); *A61M 2205/8206* (2013.01); *A61M 2205/8237* (2013.01); *A61M 2205/8281* (2013.01); *A61M 2209/06* (2013.01); *A61M 2209/088* (2013.01); *A61M 2230/04* (2013.01); *A61M 2230/18* (2013.01); *A61M 2230/205* (2013.01); *A61M 2230/63* (2013.01); *Y10T 29/49826* (2015.01)

(58) Field of Classification Search
CPC ...... A61M 2205/42; A61M 2205/8281; A61M 2016/0039
See application file for complete search history.

(56) References Cited

U.S. PATENT DOCUMENTS

| | | |
|---|---|---|
| 4,823,828 A | 4/1989 | McGinnis |
| 5,301,689 A * | 4/1994 | Wennerholm ............ A61F 5/56 128/205.25 |
| 5,649,533 A | 7/1997 | Oren |
| 5,881,718 A | 3/1999 | Astra Aktiebolag |
| 6,581,601 B2 | 6/2003 | Ziaee |
| 6,595,212 B1 | 7/2003 | Arnott |
| 6,662,803 B2 | 12/2003 | Gradon et al. |
| 6,923,181 B2 | 8/2005 | Tuck |
| 7,063,086 B2 | 6/2006 | Shahbazpour et al. |
| 7,066,174 B1 | 6/2006 | Smith et al. |
| 7,735,491 B2 | 6/2010 | Doshi et al. |
| 7,856,979 B2 | 12/2010 | Doshi et al. |
| 7,992,564 B2 | 8/2011 | Doshi et al. |
| 8,210,182 B2 | 7/2012 | Duquette et al. |
| 8,215,308 B2 | 7/2012 | Doshi et al. |
| 8,235,046 B2 | 8/2012 | Doshi et al. |
| 8,240,309 B2 | 8/2012 | Doshi et al. |
| 8,291,909 B2 | 10/2012 | Doshi et al. |
| 8,297,285 B2 | 10/2012 | Henry et al. |
| 8,302,606 B2 | 11/2012 | Doshi et al. |
| 8,365,736 B2 | 2/2013 | Doshi et al. |
| 8,371,300 B2 | 2/2013 | Rapoport |
| 8,371,304 B2 | 2/2013 | Duquette et al. |
| 8,573,201 B2 | 11/2013 | Rummery et al. |
| 8,839,791 B2 | 9/2014 | Allum et al. |
| 8,844,529 B2 | 9/2014 | Selvarajan et al. |
| 8,844,531 B2 | 9/2014 | Witt et al. |
| 8,844,533 B2 | 9/2014 | Allum et al. |
| 9,027,553 B2 | 5/2015 | Witt et al. |
| 9,072,855 B2 | 7/2015 | McAuley et al. |
| 9,132,250 B2 | 9/2015 | Allum et al. |
| 9,138,555 B2 | 9/2015 | McAuley et al. |
| 9,144,658 B2 | 9/2015 | Li et al. |
| 2003/0127096 A1 | 7/2003 | McAuliffe |
| 2006/0276718 A1 * | 12/2006 | Madaus ................ A61B 5/087 600/538 |
| 2008/0228137 A1 * | 9/2008 | Aljuri ............ A61B 17/12104 604/99.04 |
| 2009/0194109 A1 | 8/2009 | Doshi |
| 2010/0252041 A1 | 10/2010 | Kapust et al. |
| 2010/0282253 A1 * | 11/2010 | Newman, Jr. ....... A61M 16/208 128/202.22 |
| 2011/0155133 A1 | 6/2011 | Barnes et al. |
| 2011/0253147 A1 | 10/2011 | Gusky et al. |
| 2011/0259331 A1 | 10/2011 | Witt et al. |
| 2011/0259340 A1 | 10/2011 | Witt et al. |
| 2012/0215124 A1 * | 8/2012 | Fisher ................... A61M 16/12 600/532 |
| 2012/0227742 A1 | 9/2012 | Witt et al. |
| 2012/0111331 A1 | 10/2012 | Witt et al. |
| 2012/0325205 A1 * | 12/2012 | Allum ............... A61M 16/0666 128/201.13 |
| 2012/0325211 A1 | 12/2012 | Allum |
| 2012/0325218 A1 | 12/2012 | Brambilla |
| 2012/0330183 A1 | 12/2012 | Allum |
| 2013/0133656 A1 | 5/2013 | Nightingale et al. |
| 2013/0184602 A1 | 7/2013 | Brambilla |
| 2013/0186394 A1 * | 7/2013 | Hallett .................. A61M 16/06 128/201.13 |
| 2013/0255684 A2 | 10/2013 | Allum et al. |
| 2014/0053846 A1 | 2/2014 | Wood |
| 2015/0034079 A1 | 2/2015 | Allum et al. |
| 2015/0040907 A1 | 2/2015 | Hakim |
| 2015/0128948 A1 | 5/2015 | Rapoport |

FOREIGN PATENT DOCUMENTS

| | | |
|---|---|---|
| WO | 2001032251 A1 | 5/2001 |
| WO | 2002015969 A2 | 2/2002 |
| WO | 2009089807 A1 | 7/2009 |
| WO | 2012048364 A1 | 4/2012 |

* cited by examiner

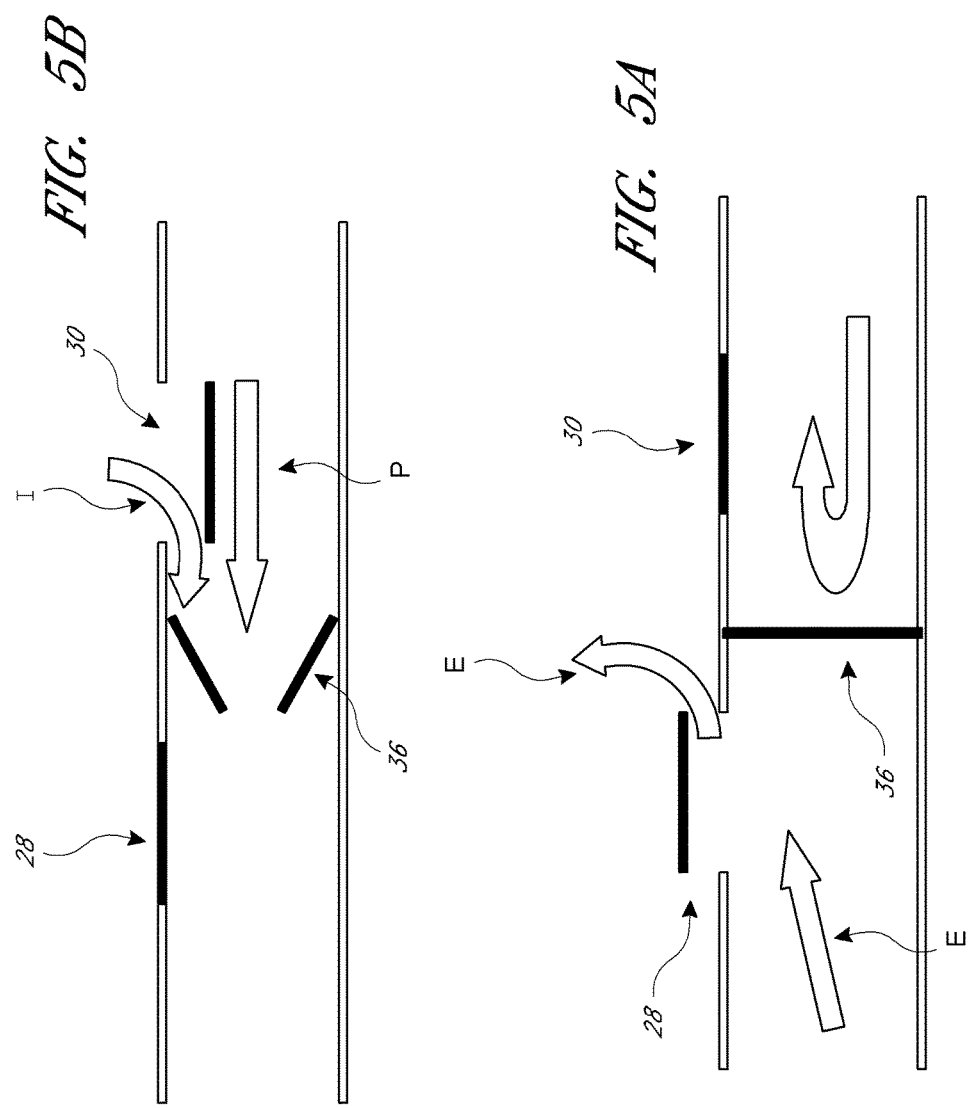

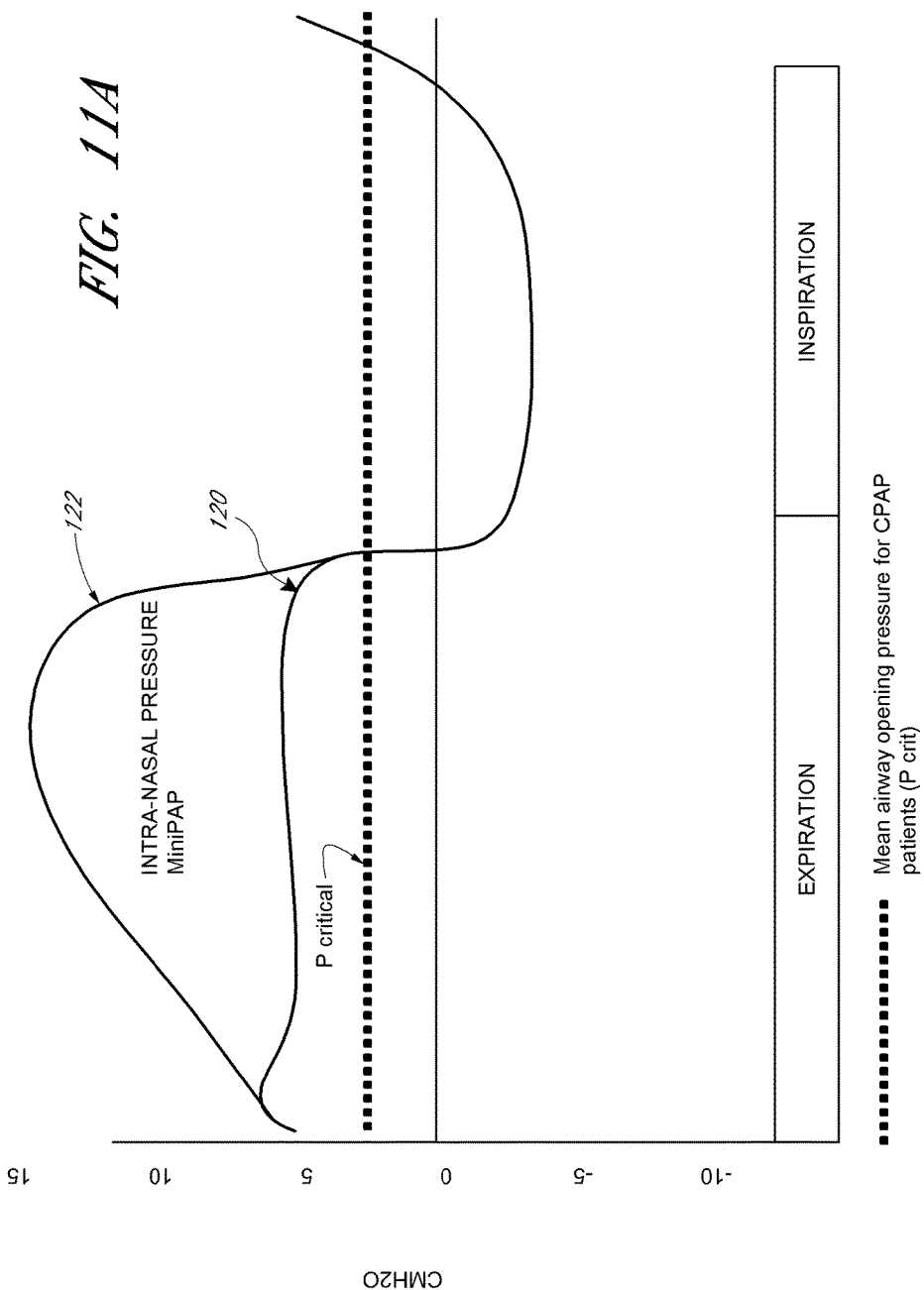

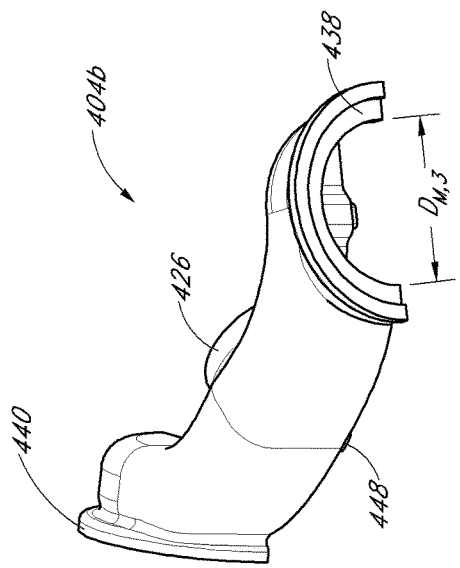
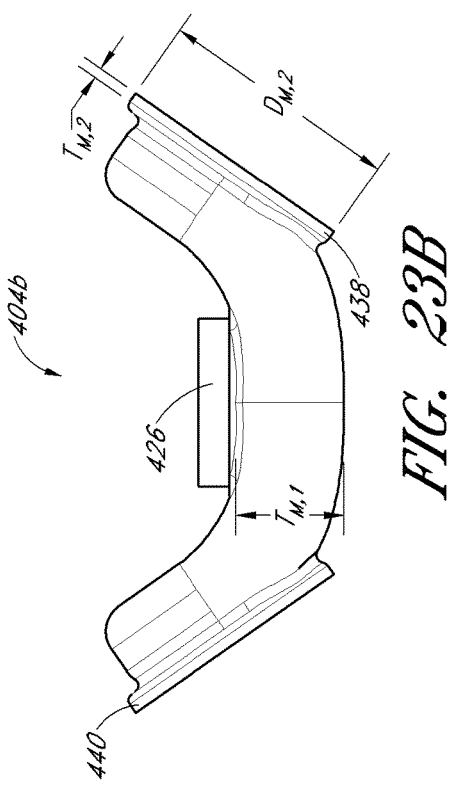
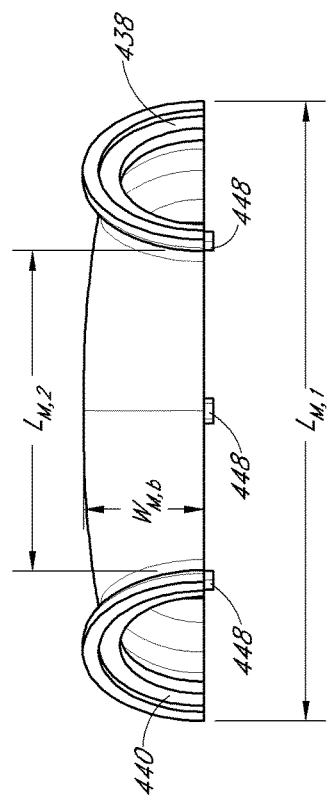
FIG. 23A
FIG. 23B
FIG. 23C

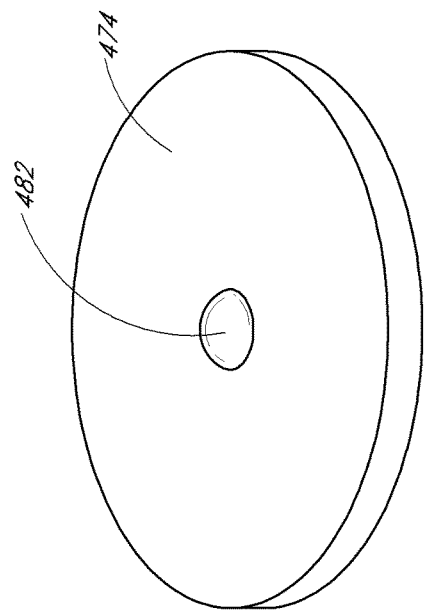
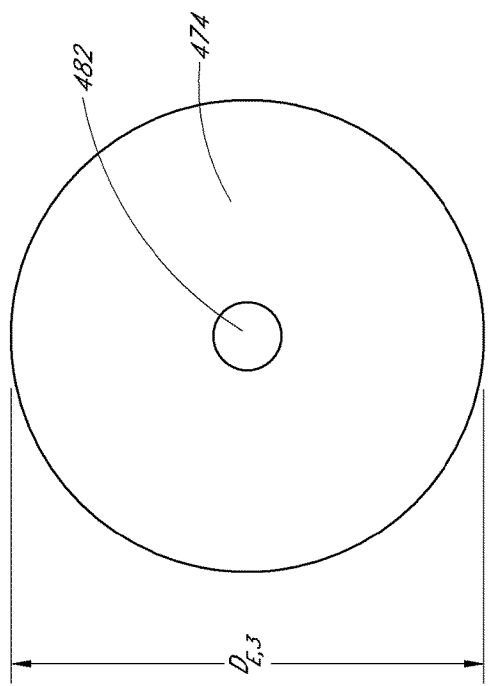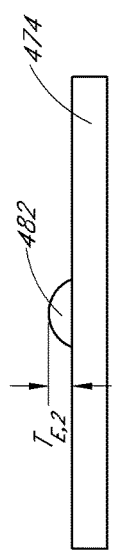

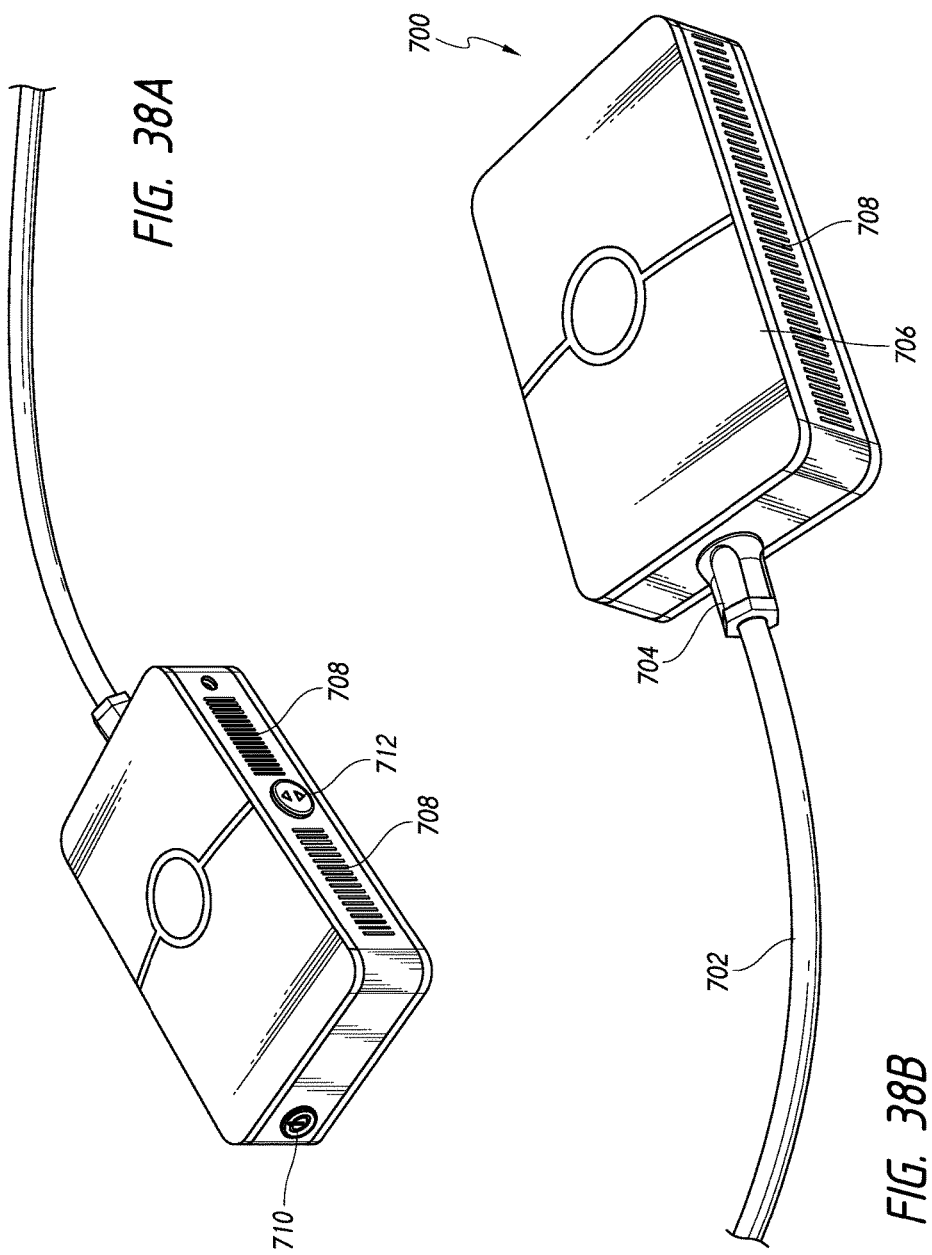

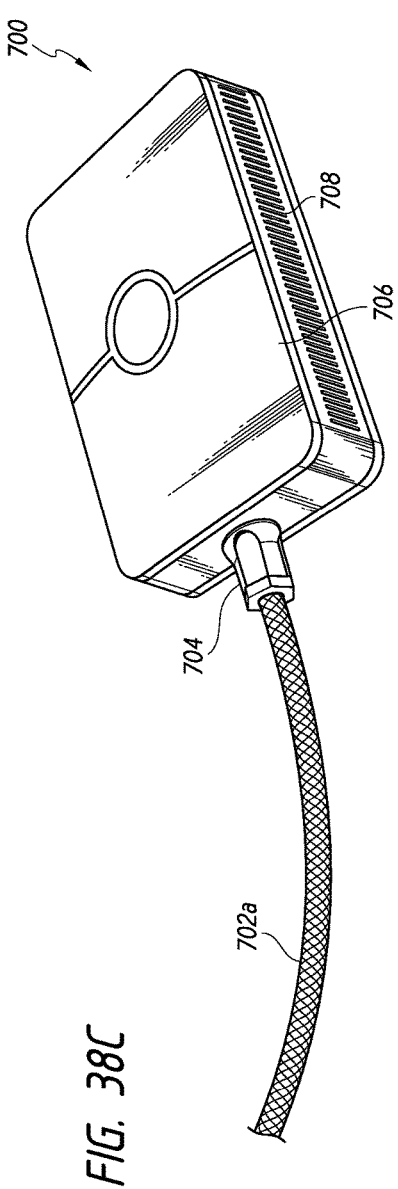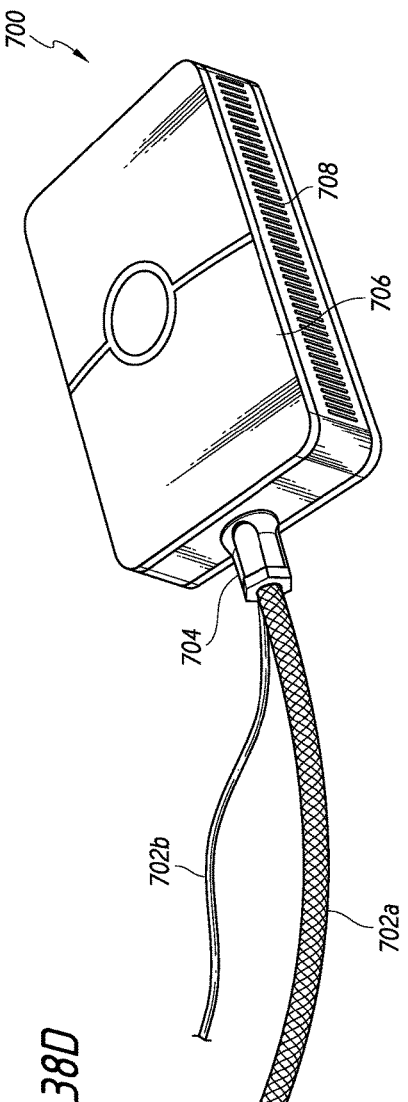
FIG. 38C
FIG. 38D

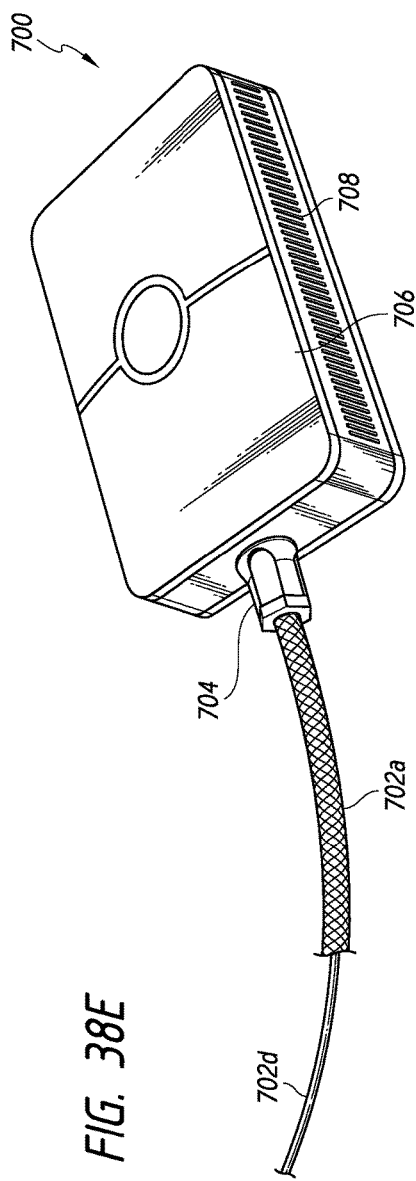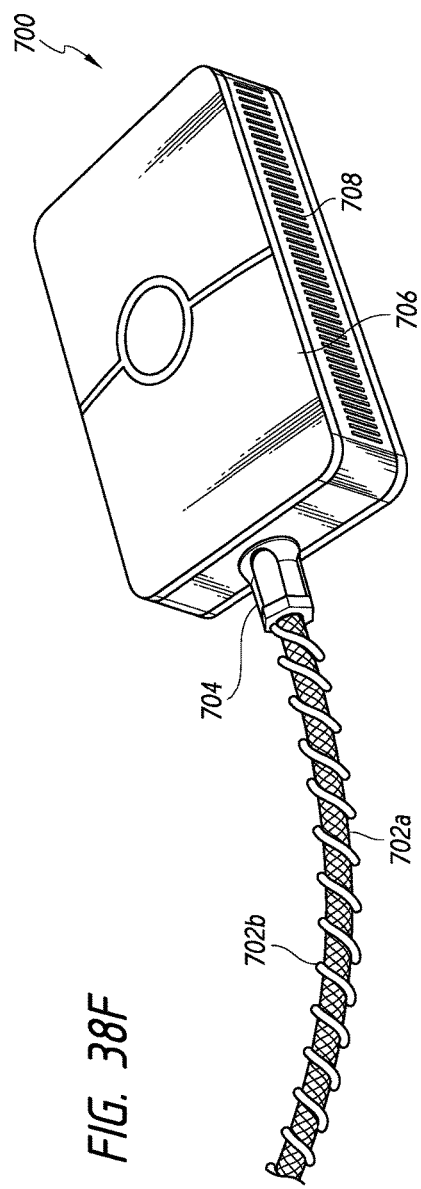

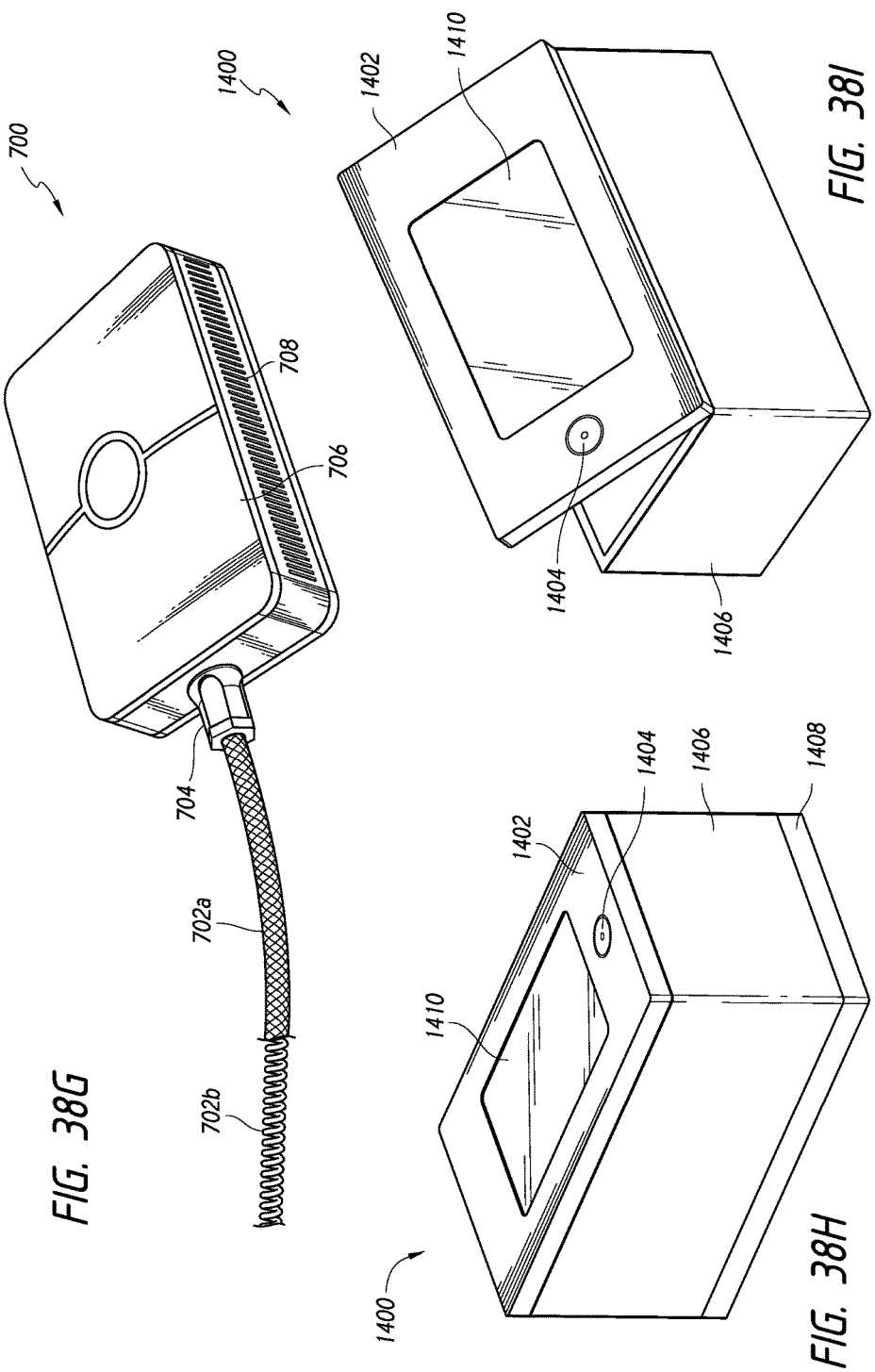

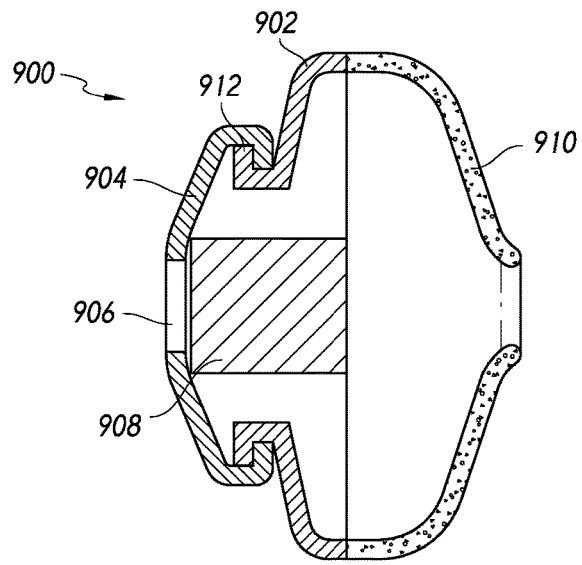
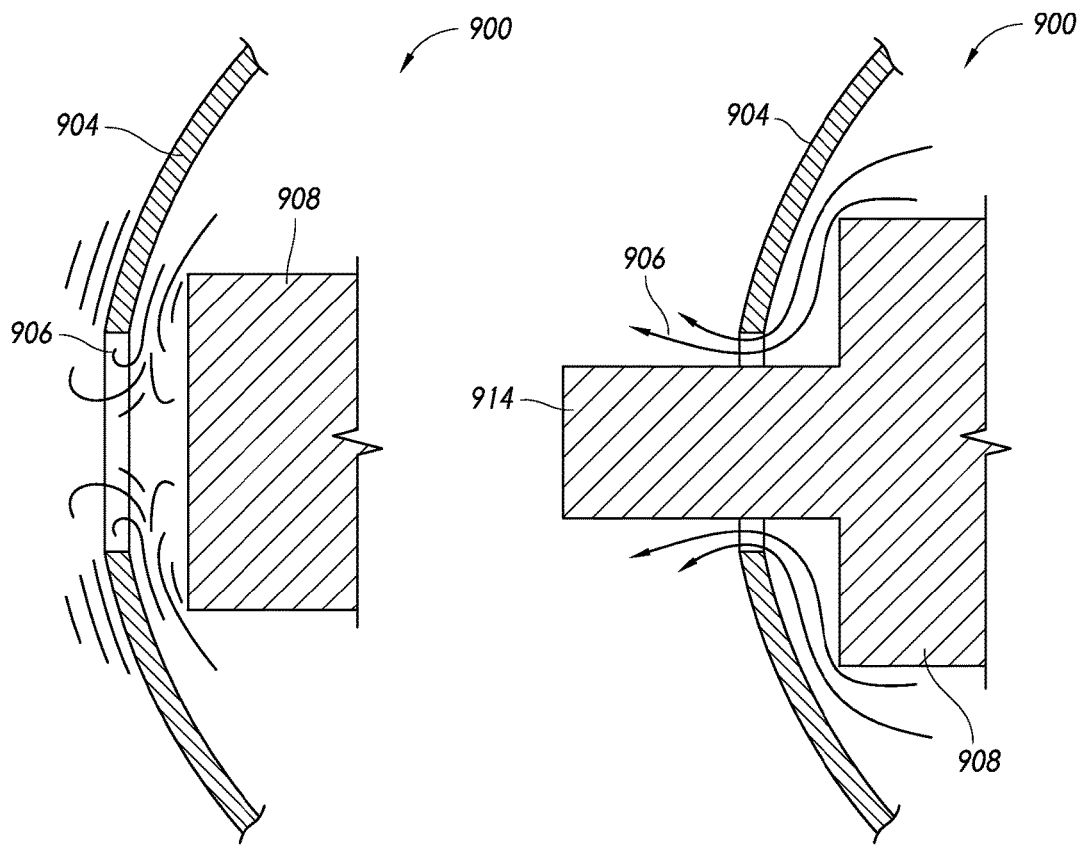
FIG. 42
FIG. 43
FIG. 44

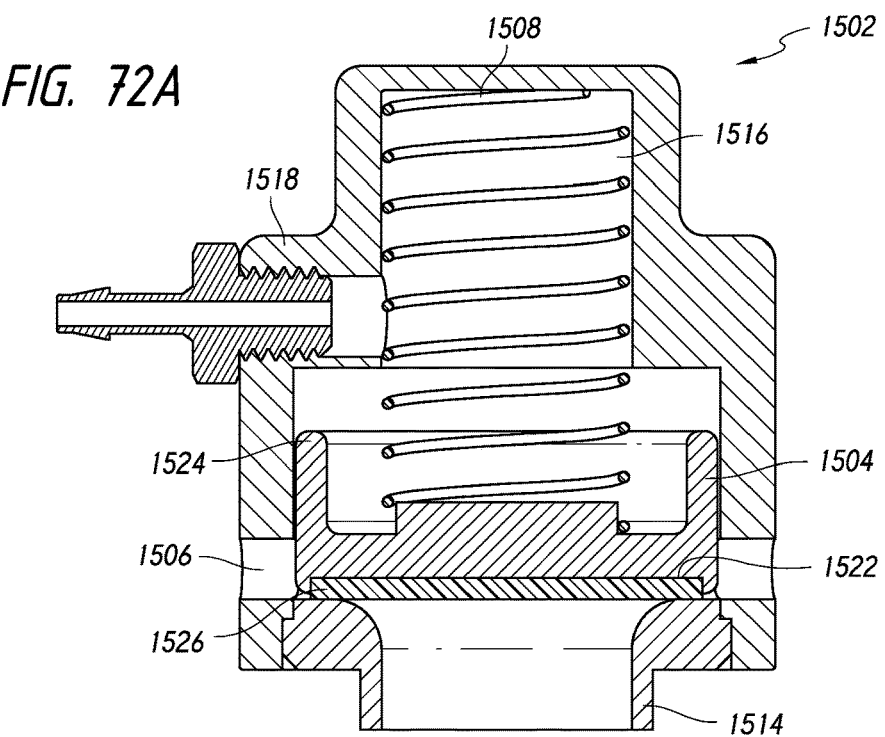
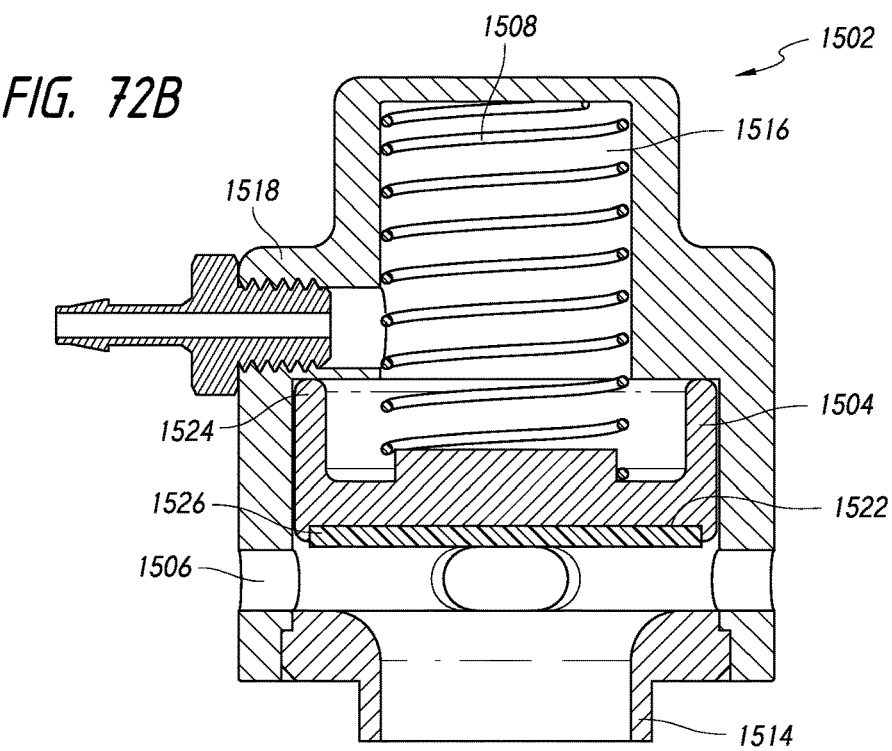

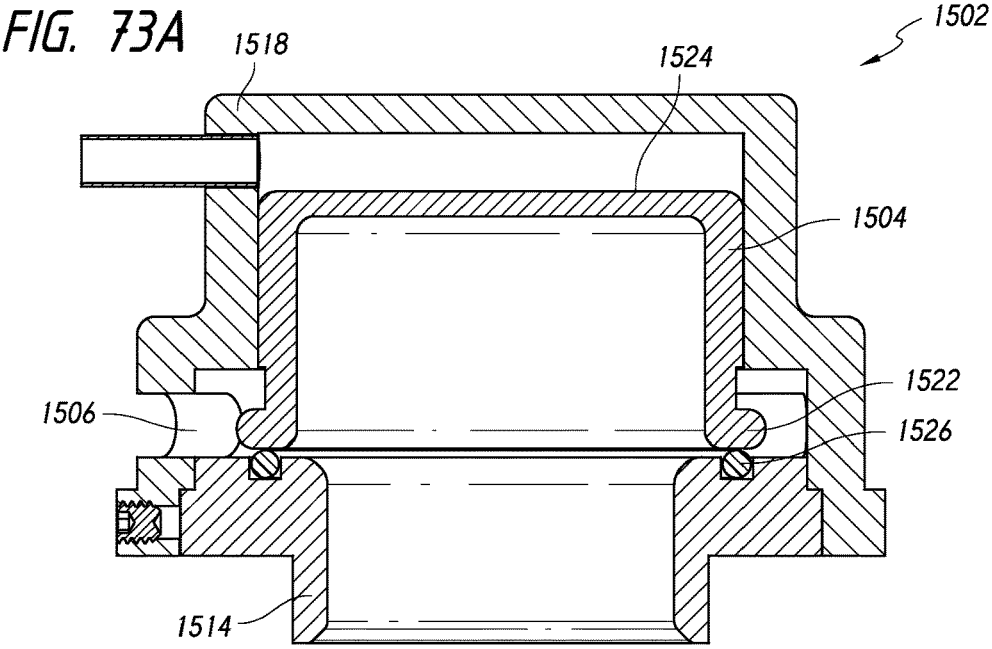
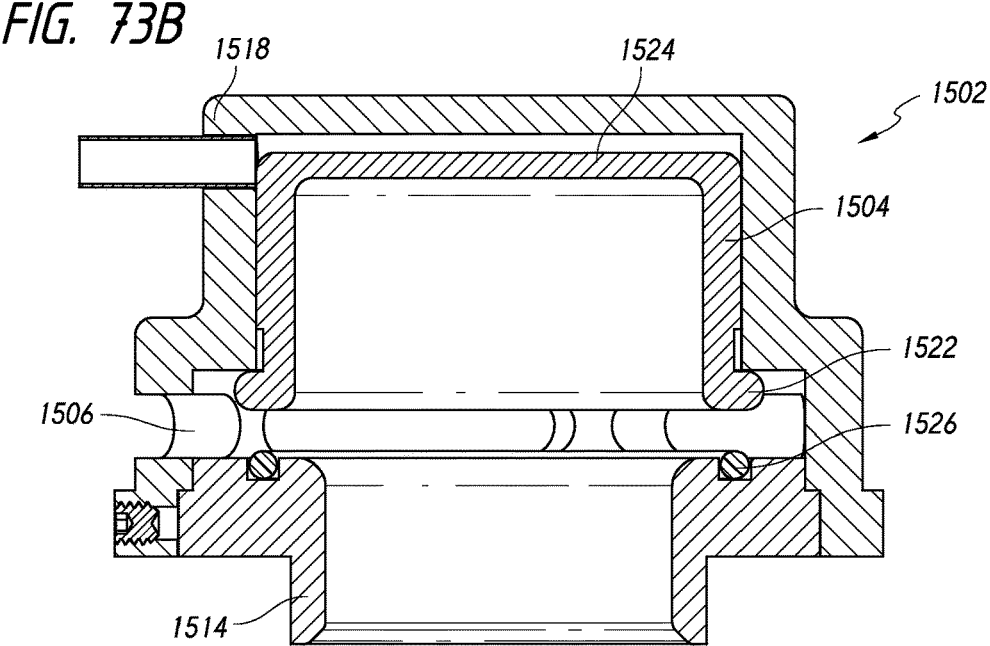

AUTO-FEEDBACK VALVE FOR A SLEEP APNEA DEVICE

INCORPORATION BY REFERENCE TO ANY PRIORITY APPLICATIONS

This application is a continuation-in-part of U.S. patent application Ser. No. 13/860,926, filed Apr. 11, 2013, titled "Sleep Apnea Device," which claims priority benefit under 35 U.S.C. § 119(e) of U.S. Provisional Application Ser. No. 61/623,855, filed Apr. 13, 2012, titled "Sleep Apnea Device" and U.S. Provisional Application Ser. No. 61/775,430, filed Mar. 8, 2013, titled "Sleep Apnea Device," all of which are hereby incorporated by reference in their entirety. This application also claims priority benefit under 35 U.S.C. § 119(e) of U.S. Provisional Application No. 61/823,553, filed May 15, 2013, titled "Sleep Apnea Device," U.S. Provisional Application No. 61/838,191, filed Jun. 21, 2013, titled "Sleep Apnea Device," U.S. Provisional Application No. 61/962,501, filed Nov. 8, 2013, titled "Sleep Apnea Device," U.S. Provisional Application No. 61/909,956, filed Nov. 27, 2013, titled "Sleep Apnea Device," and U.S. Provisional Application No. 61/927,355, filed Jan. 14, 2014, titled "Valve with Pressure Feedback," all of which are hereby incorporated by reference in their entirety.

BACKGROUND

Field

The present invention is related to medical systems, devices and methods. More specifically, the invention is related to systems, devices and methods for treating obstructive sleep apnea or snoring.

Description of the Related Art

Obstructive sleep apnea (OSA) is a common medical disorder that can be quite serious. Approximately 1 in 22 Americans (about 12,000,000 people) suffer from OSA, and many cases go undiagnosed. Chronic fatigue has long been recognized as the hallmark of OSA, but more recently, large clinical studies have shown a strong link between OSA, strokes and death.

Obstructive sleep apnea is a condition in which the flow of air pauses or decreases during breathing while one is asleep, because the airway has become narrowed, blocked, or floppy. (See FIG. 1A illustrating an airway A during normal breathing and FIG. 1B illustrating the airway A during OSA.) A pause in breathing is called an apnea episode, while a decrease in airflow during breathing is called a hypopnea episode. Almost everyone has brief apnea or hypopnea episodes while they sleep. In OSA, however, apnea episodes occur more frequently and/or last longer than in the general population. OSA has become an increasingly costly medical condition in recent years, as the disorder is more prevalent in obese people and obesity has become significantly more prevalent. Unfortunately, the currently available options for treating OSA are not ideal.

A person with OSA usually begins snoring heavily soon after falling asleep. Often the snoring gets louder. The snoring is then interrupted by a long silent period during which there is no breathing. This is followed by a loud snort and gasp, as the person attempts to breathe. This pattern repeats. Many people wake up unrefreshed in the morning and feel sleepy or drowsy throughout the day. This is called excessive daytime sleepiness (EDS). People with sleep apnea may act grumpy, impatient, or irritable, be forgetful, fall asleep while working, reading, or watching TV, feel sleepy or even fall asleep while driving, or have hard-to-treat headaches. OSA sufferers may also experience depression that becomes worse, hyperactive behavior (especially in children), or leg swelling (if severe).

The most widely used therapy for OSA is Continuous Positive Airway Pressure (CPAP). As shown in FIG. 2, a CPAP system typically 10 consists of a mask 12a-12c fitting in or over the nose or nose and mouth, an air pressurizing console 14 and a tube 16 connecting the two. CPAP works by pressurizing the upper airway throughout the breathing cycle, essentially inflating the airway to keep it open and thus creating what is sometimes referred to as a "pneumatic splint." Because the masks 12a-12c typically leak air, CPAP systems have to provide an airflow rate of up to 200 liters per minute (approximate figure based on unpublished data). This high flow rate makes breathing feel quite uncomfortable for many patients and requires a relatively large, noisy pressurizing console 14. Additionally, the high required flow rates of CPAP often cause discomfort during exhalation due to increased resistance, as well as nasal dryness, dry mouth, ear pain, rhinitis, abdominal bloating and/or headaches The overwhelming shortcoming of CPAP is poor patient compliance. Over half of all patients who try CPAP stop using it. Patients dislike the side effects mentioned above, as well as having to wear an uncomfortable, claustrophobic mask, being tethered to a pressurizing console, the noise of the console, traveling with a bulky device, and a loss of personal space in bed.

Many CPAP devices and alternatives to CPAP have been developed, but all have significant shortcomings. Less invasive attempts at OSA treatment, such as behavior modification, sleep positioning and removable splints to be worn in the mouth, rarely work. A number of different surgical approaches for treating OSA have also been tried, some of which are still in use. For example, Uvulopalatopharyngoplasty (UPPP) and Laser Assisted Uvula Palatoplasty (LAUP) are currently used. Surgical approaches, however, are often quite invasive and not always effective at treating OSA.

One alternative approach to OSA treatment is to provide a pneumatic splint during the expiratory portion of the respiratory cycle by producing a partial blockage in the nose or mouth, thus slowing the release of air during expiration and increasing positive pressure in the airway. The simplest way to form an expiratory pneumatic splint, pursing the lips, has been shown to open the upper airway and improve breathing in emphysema patients. This type of maneuver is generically labeled Expiratory Positive Airway Pressure (EPAP).

Ventus Medical, Inc. (http://www.proventtherapy.com/ventus_medical) has developed a removable nasal EPAP device to produce such a pneumatic splint during exhalation (the Provent® Sleep Apnea Therapy). (See, for example, Doshi et al., U.S. Patent Application Pub. No. 2006/0150978.) This device restricts exhalation by forcing expired air through several small orifices attached to the nose. This is labeled a Fixed Orifice Resistor (FOR). One shortcoming of this therapy is that 1) the fixed hole exhalation valve does not have a capped maximum pressure, 2) the pressure increases immediately upon exhalation and therefore makes it difficult to exhale, and 3) with no assistance of additional pressure from an external source, if the patient has an apneic event there is no 'rescue pressure'. A further disadvantage is that the Provent® device or any FOR restricts expiratory airflow using a fixed hole for resistance. This leads to an uncomfortable spike in nasal pressure at the beginning of expiration when airflow is highest and a less efficacious decrease in nasal pressure at the end of expiration when airflow is lowest. Another shortcoming of the Provent® device is that it produces the pneumatic splint only during exhalation—i.e., there is no increased pressure during inhalation.

In addition, the device is not effective in mouth breathers or patients who become mouth breathers when resistance is added to the nasal passages. Thus, the Provent® device is useful only in moderate cases of OSA that do not convert to mouth breathing.

Although snoring is not as severe a condition as OSA, it does affect lives adversely. Snoring can adversely affect sleep quality and can make sleeping with a spouse or other partner difficult. Although many snoring therapies have been tried, including Breathe Right® Nasal Strips and more invasive approaches in more severe cases, no ideal solution has been found.

Therefore, it would be advantageous to have improved systems, devices and methods for treating OSA and/or snoring. Ideally, such systems, devices and methods would be less cumbersome than currently available CPAP systems, to improve patient compliance. Also ideally, such systems, devices and methods would provide some of the advantages of an expiratory pneumatic splint. At least some of these objectives will be met by the embodiments described in this application.

BRIEF SUMMARY

The various embodiments described below are directed to the treatment of obstructive sleep apnea, snoring and/or possibly other conditions with a device and system that are smaller, lighter and less cumbersome than a traditional CPAP system, with fewer side effects and less discomfort. As mentioned above, currently available CPAP systems generally include three components—an airflow generator, a mask, and a tube connecting the two. Various embodiments described in this application provide improvements in one, two or all three of these components or provide a solution with fewer components, thus facilitating the treatment of sleep apnea and/or snoring. The systems described herein can include any combination of an air flow generator, a mask, and/or the air supply tube described below.

One improvement provided by the embodiments described herein is variable resistance to expiratory air flow using a resistive mechanism other than infused external air that increases over the course of expiration, thus providing an easier, more comfortable start to expiration while maintaining airway pressure toward the end of expiration (e.g., by decreasing resistance to expiratory flow when intranasal pressure reaches a threshold pressure and/or by gradually increasing resistance to expiratory air flow until intranasal pressure reaches the threshold pressure). Another improvement in various embodiments is that lower air flow rates are used (e.g., less than or equal to 20 L/min), while still supplying the desired therapeutic pressure (e.g., between about 4 cm H2O and 20 cm H2O), thus requiring less power and smaller device components than traditional CPAP and reducing side effects. Still another improvement is a less cumbersome, more form fitting mask that reduces air leaks and is more comfortable to wear than current CPAP masks and eliminates the need for high flow rates (to compensate for air leaks). The devices described herein can be used in connection with a small diameter hose (e.g., having a diameter of less than or equal to about 15 mm), thus decreasing the bulkiness of the system. These and other improvements, described in further detail below, may help improve patient compliance and overall treatment ofسleep apnea. In some embodiments, the devices and methods described may also be used to treat snoring.

Certain aspects of the present disclosure are directed toward a system for treating a patient suffering from obstructive sleep apnea or snoring may include: a mask having a contact surface for forming a seal between the mask and the patient's face such that the mask surrounds at least the patient's nostrils; a portable air flow generator configured to generate air flow at a relatively low flow rate; a tube connecting the air flow generator and the mask such that air flow from the generator passes through the air flow generator valve; a one-way, variable resistance expiratory valve coupled with the mask or the tube to allow exhaled air to exit the mask during exhalation; and an air flow generator valve coupled with the mask or the tube to allow air from the air flow generator to enter the mask during inspiration. The expiratory valve may provide less resistance to expired air during an early portion of expiration than during a later portion of expiration.

In some embodiments, the mask may surround the patient's nostrils and mouth. Optionally, the system may further include an inspiration valve in the mask or the tube that opens during inspiration to allow outside air to enter the mask. In various embodiments, the expiratory valve may have an opening pressure of between about 0 cm H2O and about 20 cm H2O, and more preferably between about 2 cm H2O and about 5 cm H2O. In some embodiments, the expiratory valve may open at an opening pressure of about 0-5 cm H2O and close at a pressure of at least about 5 cm H2O.

In some embodiments, the expiratory valve may generate an intra-airway pressure of about 0-5 cm H2O during the early portion of expiration and an intra-airway pressure of about 5-20 cm H2O during the later portion of expiration. More generally, the expiratory valve generates greater intra-airway pressure during the later portion of expiration than during the early portion. To accomplish this, the expiratory valve may open to a largest effective orifice size at an opening pressure and close continuously during expiration. In some embodiments, the expiratory valve may open to a largest effective orifice size at an opening pressure and close incrementally during expiration. In some embodiments, the expiratory valve may open to a largest effective orifice size at an opening pressure and immediately close when intranasal pressure falls below the opening pressure. Furthermore, in some embodiments, the effective orifice size of the expiratory valve may be larger during the early portion of expiration and smaller during the later portion of expiration. For example, the effective orifice size may be larger during the early portion of expiration and a smaller during the later portion of expiration.

To maintain the desired intra-airway pressure, the expiratory valve can pop-off when intra-airway pressure reaches a threshold pressure (e.g., between about 4 cm H2O and about 20 cm H2O, such as between about 5 cm H2O and 10 cm H2O, between about 10 cm H2O and about 15 cm H2O, or between about 15 cm H2O and about 20 cm H2O). The expiratory valve can close immediately when the intra-airway pressure falls below the threshold pressure. In certain aspects, the expiratory valve can have a noise level of less than or equal to about 15 dB, preferably less than or equal to about 10 dB. In certain aspects, the expiratory valve can have a low profile to decrease the size of the mask (e.g., having a height between about 0.25 inches and about 1.5 inches, preferably less than or equal to about 0.5 inches).

In some embodiments, the system may further include a controller for opening and closing the expiratory valve.

Optionally, a wireless device may be included for sending signals to the controller to open and close the valve. In some embodiments, the expiratory valve may open and close in response to expiratory pressure generated by exhalation of the patient. In some embodiments, the expiratory valve may open at an opening pressure and close completely at an end of expiration.

Any of a wide variety of one-way, variable resistance expiratory valves may be used. In one embodiment, for example, the expiratory valve may be a Nitinol disk valve including a Nitinol plate that flexes to allow expired air to pass through the valve. In some embodiments, the expiratory valve may be an elastic membrane with multiple small apertures, where the elastic membrane expands in response to increasing expiratory pressure to enlarge the diameter of the apertures, thus allowing expired air to pass through the membrane, and shrinks in response to decreasing expiratory pressure to shrink the diameter of the apertures, thus helping to maintain pressure in the patient's pharynx. In some embodiments, the expiratory valve may be an aperture that opens to an initial opening diameter and closes during expiration. In some embodiments, the expiratory valve may include a tube having multiple holes and a spring loaded hole blocker disposed within the tube and configured to block fewer holes at a start of expiration and an increasing number of holes during expiration, such that resistance increases during expiration. In some embodiments, the expiratory valve may be an air resistance wheel coupled with a spring that increases resistance of the wheel during expiration. In some embodiments, the expiratory valve may be an elastomeric tube with an internal diameter of 2-5 mm that is compressed on by a fulcrum. The fulcrum is further acted on by the pressure of expired air such that increasing expiratory airflow causes the fulcrum to release pressure on the expiratory tube allowing more air to pass through the tube.

In some embodiments, the mask may further include a port for connecting with the tube to direct air into the air flow generator valve. The contact surface of the mask, in some embodiments, may include an adhesive. In many embodiments, the mask does not require a strap to remain in contact with the patient's face. In some embodiments, the mask forms an open space between the mask and the patient's face of no more than 10 milliliters, and the mask has a surface contact area with the patient's face of at least 5 square centimeters.

In various embodiments, the air flow generator may include, but is not limited to, a turbine pump, double bellows, a dual counter turbine or an air compressor and return. In various embodiment, the relatively low flow rate provided by the air flow generator may be between about 1 liter per minute and about 20 liters per minute. The airflow generator would have a back pressure or 2-20 cm H2O at flow rates of 1-20 liters per minute. In some embodiments, the air flow generator may be battery powered. Optionally, such embodiments may further include a breath-powered energy generation mechanism coupled with the mask and configured to charge the battery using energy generated from exhaled breath of the patient. In other embodiments, the air flow generator may be self-powered.

In some embodiments, the air flow generator may include a housing, a motor disposed in the housing, a turbine disposed in the housing and coupled with the motor, and a power source disposed in the housing and coupled with the motor. The housing may include an outflow port for connecting with the tube, a relief valve, and an air intake aperture. The power source, for example, may include a battery. In some embodiments, the housing may have a diameter of no more than about 4 cm and a length of no more than about 17 cm. Generally, in one embodiment, the air flow generator may weigh no more than about 1.5 pounds. The tube, in various embodiments, may have an outer diameter of no more than about 1.5 cm.

In some embodiments, the system may further include a sensor for sensing the occurrence of the apnea episode. Such embodiments may optionally further include a processor for processing sensed data from the sensor and providing a signal to the air flow generator to generate a higher flow rate than the relatively low flow rate. The sensor, for example, may be a pulse oximeter and/or an airflow rate sensor.

Certain aspects of the present disclosure are directed toward a device for treating a patient suffering from obstructive sleep apnea or snoring may include: a mask having a contact surface for forming a seal between the mask and the patient's face such that the mask surrounds at least the patient's nostrils; an air flow generator attached to the mask and configured to generate air flow at a relatively low flow rate; a one-way, variable resistance expiratory valve in the mask to allow exhaled air to exit the mask during exhalation; and an air flow generator valve in the mask to allow air from the air flow generator to enter the mask during inspiration. Again, the expiratory valve may provide less resistance to expired air during an early portion of expiration than during a later portion of expiration. Optionally, the mask may the patient's nostrils and mouth.

Certain aspects of the present disclosure are directed toward a method for treating a patient suffering from obstructive sleep apnea or snoring may involve providing a first amount of resistance to expiration during an early portion of an expiratory phase of breathing and providing a second, greater amount of resistance to expiration during a later portion of the expiratory phase. In one embodiment, providing the first and second amounts of resistance may involve providing a first amount of positive airflow into an airway of the patient during the early portion and providing a second, greater amount of positive airflow into the airway during the later portion.

In some embodiments, providing the first and second amounts of resistance may involve providing a mask that surrounds both nostrils of the patient's nose and providing a one-way, variable resistance expiratory valve in the mask. In one embodiment, the mask may surround the patient's nostrils and the patient's mouth. The mask and valve may have any characteristics described above. In some embodiments, the method may further involve opening and closing the expiratory valve using a controller coupled with the valve. In some embodiments, the method may further involve sending signals wirelessly to the controller.

Certain aspects of the present disclosure are directed toward a method for treating a patient suffering from obstructive sleep apnea or snoring may involve: providing a mask configured to contact the patient's face to form a seal between the mask and the face such that the mask surrounds the patient's nostrils; providing air flow into the mask at a relatively constant flow rate of about 1-12 liters per minute and a pressure of about 2-20 cm H2O, using a portable air flow generator and a tube connecting the generator to the mask; providing resistance to expiration of air from the patient via a one-way expiratory valve coupled with the mask or the tube, the expiratory valve having an opening pressure of about 0 cm H2O to about 20 cm H2O; and allowing inhalation of atmospheric air into the mask through a one-way inhalation valve on the mask or the tube.

In some embodiments, the mask may be configured to form the seal via an adhesive strip on the mask configured to surround the patient's nostrils. In some embodiments, the mask may be further configured to surround the patient's mouth. In some embodiments, the mask may be configured to form the seal and maintain contact with the patient's face without requiring a strap.

Oftentimes, providing resistance to expiration may involve providing resistance throughout at least a majority of an expiratory phase of a breathing cycle. In some embodiments, providing resistance to expiration may involve providing a first amount of resistance during an early portion of the expiratory phase and providing a second, greater amount of resistance during a later portion of the expiratory phase. In some embodiments, providing the amounts of resistance may involve providing increasing amounts of resistance throughout the expiratory phase and closing the expiratory valve at an end of the expiratory phase. In some embodiments, providing resistance to expiration may involve providing an increased resistance at an end of the expiratory phase. In some embodiments, the opening pressure is about 2-5 cm H2O.

Optionally, the method may further include providing air flow at a higher flow rate, compared to the relatively low flow rate, during or after an apnea episode. Such an embodiment may also further include detecting the apnea episode and switching the portable air flow generator from the relatively low flow rate to the higher flow rate, in response to the detected apnea episode. In some embodiments, providing the air flow at the higher flow rate may involve providing a pressure within a pharynx of the patient of approximately an opening pressure of the expiratory valve.

Optionally, the method may further include powering the air flow generator via a battery. The method may further include collecting energy from exhaled breath of the patient, using an energy collection device coupled with the mask, and using the energy to charge the battery.

Certain aspects of the present disclosure are directed toward a method for treating a patient suffering from obstructive sleep apnea or snoring may involve providing a first resistance to expired air at the beginning of an expiratory phase of a breathing cycle of the patient via a one-way, variable resistance expiratory valve on a device coupled with the patient, and providing a second, greater resistance to expired air later in the expiratory phase via the expiratory valve.

In some embodiments, the expiratory valve may include an opening that automatically adjusts from a first diameter, in which the first resistance is provided, to a second, smaller diameter, in which the second resistance is provided. In some embodiments, providing the second resistance may involve closing the valve from a larger diameter to a smaller diameter. In some embodiments, the method may further involve providing positive air flow to the patient during inhalation. In some embodiments, the expiratory valve may include multiple openings, and each opening automatically decreases in size to provide the second resistance.

Optionally, the method may further include sensing an apnea episode and providing the air flow at an increased flow rate in response to the sensed apnea episode. The device may include, for example, a mask secured over at least the patient's nose. In some embodiments, the mask may surround the patient's nostrils and mouth. In some embodiments, the device may include a tube coupled with a mask secured over at least the patient's nose. In some embodiments, providing the first and second resistances may involve continuously closing the valve.

Certain aspects of the present disclosure are directed toward a method for treating a patient suffering from obstructive sleep apnea or snoring may involve providing increasing resistance to air exhaled by the patient over the course of an expiratory phase of a breathing cycle via a variable airflow resistance device coupled with the patient to cover at least part of the patient's nose. In one embodiment, providing the increasing resistance may involve providing an opening pressure upon commencement of the expiratory cycle of about 2-5 cm H2O. As discussed previously, in some embodiments, the variable airflow resistance device may include a one-way valve on a mask, and the mask may surrounds two nostrils and/or a mouth of the patient. In some embodiments, the variable airflow resistance device may be a one-way valve coupled with a tube, which is coupled with a mask that covers two nostrils of the patient's nose.

Some embodiments may optionally include providing positive air flow to the patient during inhalation and/or exhalation. In some embodiments, the airway resistance device may include a one-way valve having multiple openings, and wherein each opening automatically decreases in size during the expiratory phase to provide the second resistance. In some embodiments, the airway resistance device may include a one-way valve, and providing the increasing resistance may involve allowing the valve to automatically close in response to decreased flow of exhaled air from the patient. In some embodiments, the airway resistance device may include a one-way valve, and providing the increasing resistance may involve continuously closing the valve during the expiratory phase.

Certain aspects of the present disclosure are directed toward a device for treating a respiratory disorder such as sleep apnea or snoring may include a nasal covering body for covering at least one nostril of a nose of a human and an airflow resistor on the nasal covering body configured to inhibit exhalation through the nostril more than inhalation through the nostril. The airflow resistor may provide increasing resistance during an expiratory phase of a breathing cycle.

In some embodiments, the airflow resistor may include a one-way, variable resistance valve in the nasal covering body, where the valve is closed during inspiration, opens at a predetermined opening pressure during the initial portion of the expiratory phase, and closes during the expiratory phase to providing the increasing resistance. In some embodiments, the valve completely closes at an end of the expiratory phase, while in some embodiments, it may stay slightly open.

In some embodiments, the nasal covering body covers both nostrils of the nose. In some embodiments, the nasal covering body may include a mask configured to surround both nostrils and at least a portion of the nose. In some embodiments, the mask may further surround a mouth of the human. In some embodiments, the mask may further include an adhesive surface for adhering to the nose. In some embodiments, the mask may include a custom made mask configured to conform to a shape of the human's nose. In some embodiments, the mask is configured to adhere to the nose without requiring a strap attached to the human's head. In some embodiments, the airflow resistor may include one resistor for each nostril. In some embodiments, the airflow resistor may include more than two resistors. In some embodiments, the mask may be configured to attach to a conventional CPAP system. In some embodiments, the mask may be configured to attach to a small diameter, low flow, airflow tube.

Certain aspects of the present disclosure are directed toward a method for treating a patient suffering from obstructive sleep apnea or snoring may involve: providing a nasal mask to be worn by the patient over the patient's nose, where the nasal mask is configured to remain coupled over the patient's nose without requiring a strap around any portion of the patient's head, providing a first resistance to expired air at the beginning of an expiratory phase of a breathing cycle of the patient via a one-way, variable resistance, expiratory valve on the mask or a tube coupled with the mask; and providing a second, greater resistance to expired air later in the expiratory phase via the expiratory valve.

In some embodiments, the mask may be a custom made mask configured to conform to a shape of the patient's nose, and the method may further include forming the custom made mask in accordance with the shape. In some embodiments, the mask may include an adhesive surface for coupling with the patient's nose or face.

Certain aspects of the present disclosure are directed toward a method for making a nasal mask for treating a patient suffering from obstructive sleep apnea or snoring, may involve assessing a shape of the patient's nose and/or an area of the patient's face surrounding the nose and making the nasal mask to conform to the patient's nose, based on the assessment of the shape. In some embodiments, assessing the shape of the patient's nose may involve acquiring a computed tomography scan of at least a portion of the patient's head. In some embodiments, making the mask may involve providing computed tomography data from the computed tomography scan to a manufacturing machine and using the manufacturing machine to make the mask, based on the computed tomography data. In some embodiments, assessing the shape of the patient's nose may involve attaching a trial nasal mask over the patient's nose. Assessing the shape of the patient's nose may involve attaching the mask in a first configuration over the patient's nose, and wherein making the nasal mask comprises altering the nasal mask into a second configuration to conform to the patient's nose.

Certain aspects of the present disclosure are directed toward a method for treating a patient suffering from obstructive sleep apnea or snoring may involve increasing resistance to expiration during an expiratory phase of breathing, such that a pressure curve derived from the patient's breathing during expiration begins at a first, lower pressure and increases to at least a second, higher pressure. In some embodiments, providing the increasing resistance may involve providing continuously increasing resistance such that the pressure curve has a gradual upward slope. In some embodiments, providing the increasing resistance may involve providing incrementally increasing resistance such that the pressure curve has a stepped upward slope.

Certain aspects of this disclosure are directed toward an expiratory valve including a frame, a membrane, an occluding member, and a noise reducing member. Any of the valve features disclosed in this specification can be included in any embodiment of the expiratory valve. For example, the membrane can be secured to the frame, and the membrane can include an opening. In some instances, the opening can be positioned along a central portion of the membrane. In some instances, the expiratory valve can include a restraint surrounding the opening. The restraint can be, for example, a grommet. In some instances, the expiratory valve can include one or more dampening members positioned on the membrane.

The occluding member can be configured to move between a closed position and an open position. In the closed position, the occluding member can be configured to occlude the opening. In some instances, the occluding member moves from the closed position to the open position when a pressure exceeds a threshold pressure between about 5 cm H2O and about 20 cm H2O. In some instances, a diameter of the occluding member is greater than a diameter of the opening.

The noise reducing member can be configured to extend at least partially through the opening. The noise reducing member can be configured to reduce an amount of noise produced by the expiratory valve to less than or equal to about 15 dB or less than or equal to about 10 dB. In some instances, the noise reducing member can be integrally formed with the occluding member. In some instances, a diameter of the noise reducing member can be less than a diameter of the opening. In some instances, a diameter of the noise reducing member can be less than a diameter of the occluding member. In some instances, the noise reducing member can include one or more grooves extending along a length of the noise reducing member. In some instances, the noise reducing member can include a number of openings. For example, the noise reducing member can include a sponge-like material.

In addition to or in alternative to the noise reducing member, the membrane can be pre-loaded with strain or tension to reduce noise. This can occur naturally based on the material properties or by adding material stiffeners, external braces, or struts to the membrane to absorb or dampen vibrations which would generate sound.

Certain aspects of this disclosure are directed toward an expiratory valve including a frame, a membrane, and an occluding member. The membrane can be secured to the frame, and the membrane can include a plurality of openings. The occluding member can be configured to move between a closed position and an open position. In the closed position, the occluding member can be configured to occlude the plurality of openings. The expiratory valve can produce an amount of noise that is less than or equal to about 15 dB or less than or equal to about 10 dB.

Certain aspects of this disclosure are directed toward a sleep apnea device including a mask and an expiratory valve. Any of the sleep apnea features, including the expiratory valve features, described in this specification can be included in any embodiment of the sleep apnea device. For example, the mask can include a contact surface for forming a seal between the mask and the patient's face, and the expiratory valve can be connected to the mask. The expiratory valve can be configured to move from a closed configuration to an open configuration when the intranasal pressure exceeds a threshold pressure. In some instances, the threshold pressure can be between about 5 cm H2O and about 20 cm H2O. In some instances, the expiratory valve can be configured to provide less resistance to expired air during an early portion of expiration than during a later portion of expiration. The expiratory valve can produce an amount of noise that is less than or equal to about 15 dB or less than or equal to about 10 dB.

Certain aspects of this disclosure are directed toward a sleep apnea device including a mask, a portable air flow generator, a tube, and an expiratory valve. Any of the sleep apnea features, including the expiratory valve features, described in this specification can be included in any embodiment of the sleep apnea device. For example, the mask can include a contact surface for forming a seal between the mask and the patient's face. The portable air flow generator can be configured to generate air flow at a flow rate of less than or equal to about 50 L/min. The tube can connect the air flow generator and the mask. The expiratory valve can connect to the mask. The expiratory valve can produce an amount of noise that is less than or equal to about 15 dB or less than or equal to about 10 dB. In some instances, the expiratory valve can be configured to provide less resistance to expired air during an early portion of expiration than during a later portion of expiration. In some instances, the flow rate can be adjustable, while still supplying the same amount of pressure.

The devices described herein can include a number of components. Generally, the components can be assembled by securing the expiratory valve and the inspiratory valve to a plate and/or a mask. A cover can be secured to the plate such that the plate and valves are disposed between the cover and the mask. One or more straps can be secured to the cover or plate. Additionally, one or more openings can be formed in the plate and/or mask. These openings can be in fluid communication with an air flow generator. The device can include a tube connecting the air flow generator to the plate or mask. One or more valves can be connected to the tube or air flow generator to allow the user to control the air flow rate.

These and other aspects and embodiments of the present invention are described further below in relation to the attached drawings.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIGS. 5A and 5B are diagrams demonstrating operation of multiple valves in a mask of an OSA treatment system, according to one embodiment.

FIG. 11A is a graph with an intranasal pressure curve demonstrating breathing mechanics with a positive airway pressure system and unobstructed breathing, according to one embodiment.

FIGS. 22A-C and 23A-C illustrate portions of the manifold illustrated in FIG. 20.

FIGS. 28A-33C illustrate an exemplary embodiment of an expiratory valve and each of its components.

FIGS. 38A and 38B illustrate an exemplary embodiment of an air flow generator.

FIG. 38C illustrates the air flow generator shown in FIGS. 38A and 38B connected to a braided air supply tube.

FIG. 38D illustrates the air flow generator and the braided tube shown in FIG. 38C with a feedback tube.

FIG. 38E illustrates the air flow generator and the braided tube shown in FIG. 38C with the feedback tube positioned within the braided tube.

FIG. 38F illustrates the air flow generator and the braided tube shown in FIG. 38C with the feedback tube coiled around the braided tube.

FIG. 38G illustrates the air flow generator and the braided tube shown in FIG. 38C with the feedback tube coiled within the braided tube.

FIG. 38H illustrates another embodiment of an air flow generator.

FIG. 38I illustrates the air flow generator shown in FIG. 38H with the lid portion in an open configuration.

FIG. 42 illustrates a cross-section of an embodiment of the expiratory valve in a closed configuration.

FIG. 43 illustrates the expiratory valve shown in FIG. 42 in an open configuration.

FIG. 44 illustrates another embodiment of the expiratory valve having a noise reducing member.

FIG. 72A illustrates an embodiment of an auto-feedback valve in a closed configuration.

FIG. 72B illustrates the auto-feedback valve shown in FIG. 72A in an open configuration.

FIG. 73A illustrates another embodiment of an auto-feedback valve in a closed configuration.

FIG. 73B illustrates the auto-feedback valve shown in FIG. 73A in an open configuration.

DETAILED DESCRIPTION

As discussed above in the Brief Summary, various embodiments described herein are directed to improved devices, systems and methods for treating obstructive sleep apnea (OSA) and/or snoring. In general, these embodiments seek to improve upon currently available CPAP systems and/or currently available expiratory flow resistor devices, such as the Provent® Sleep Apnea Therapy. In some embodiments, an improved mask alone may be provided, while in some embodiments a system including a mask, air flow generator, and possibly a tube for connecting the two, may be provided. Ideally, the embodiments described herein will effectively ameliorate sleep apnea or snoring with fewer side effects and less discomfort than CPAP or EPAP. In some embodiments, devices, systems and methods described herein may be used to treat other respiratory and/or pulmonary conditions, such as COPD or asthma. Thus, even though this description focuses on the treatment of OSA and/or snoring, the embodiments herein may be used in other treatments as well.

One way in which the embodiments herein may achieve the goals of improved therapy and reduced side effects is by reducing air leaks and patient discomfort with a face-conforming mask that does not require straps, thus allowing for lower airflow rates and pressures. Another improvement is a variable, one-way expiratory valve that provides lower resistance to expiration at the start of expiration and increased resistance over the course of the expiratory phase of breathing. This valve reduces the discomfort felt in currently available expiration resistance devices that require a high opening pressure. It also helps maintain airway pressure during and at the end of expiration, in contrast to currently available valves that provide reduced resistance, and thus reduced pressure, as expiratory airflow decreases during the expiratory phase. These and other improvements are described in greater detail below.

Figure 1A:
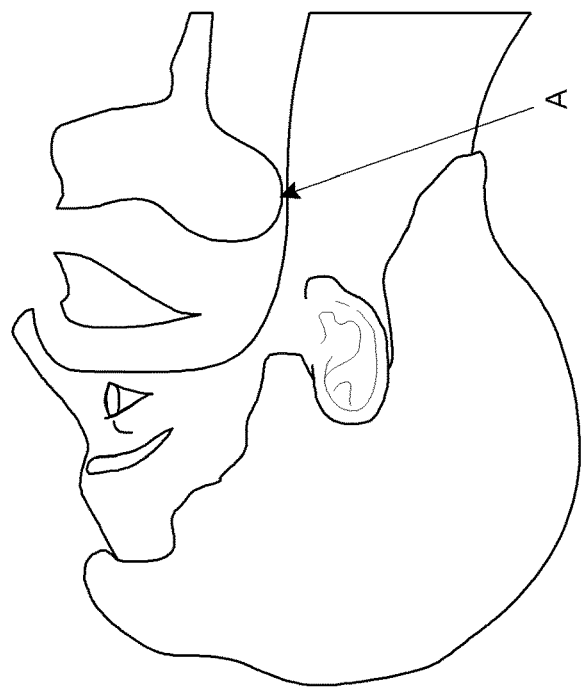
FIGS. 1A and 1B are side-view diagrams of a person's airway during normal breathing and during an episode of obstructive sleep apnea, respectively.
Figure 1B:
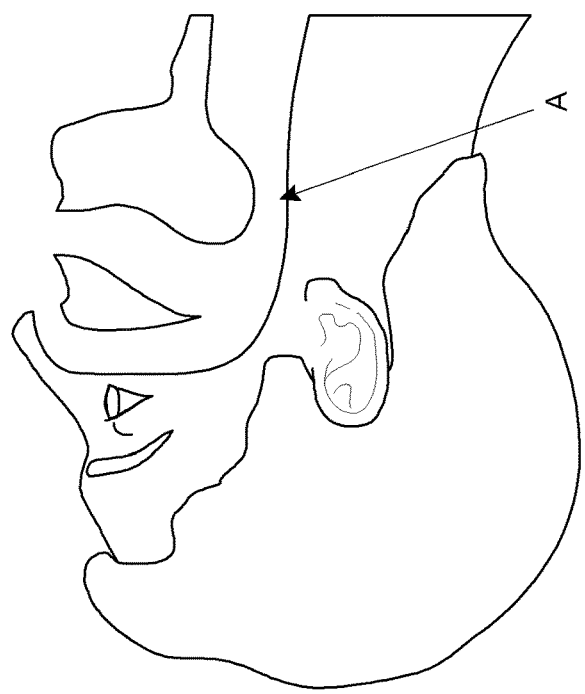
Figure 2:
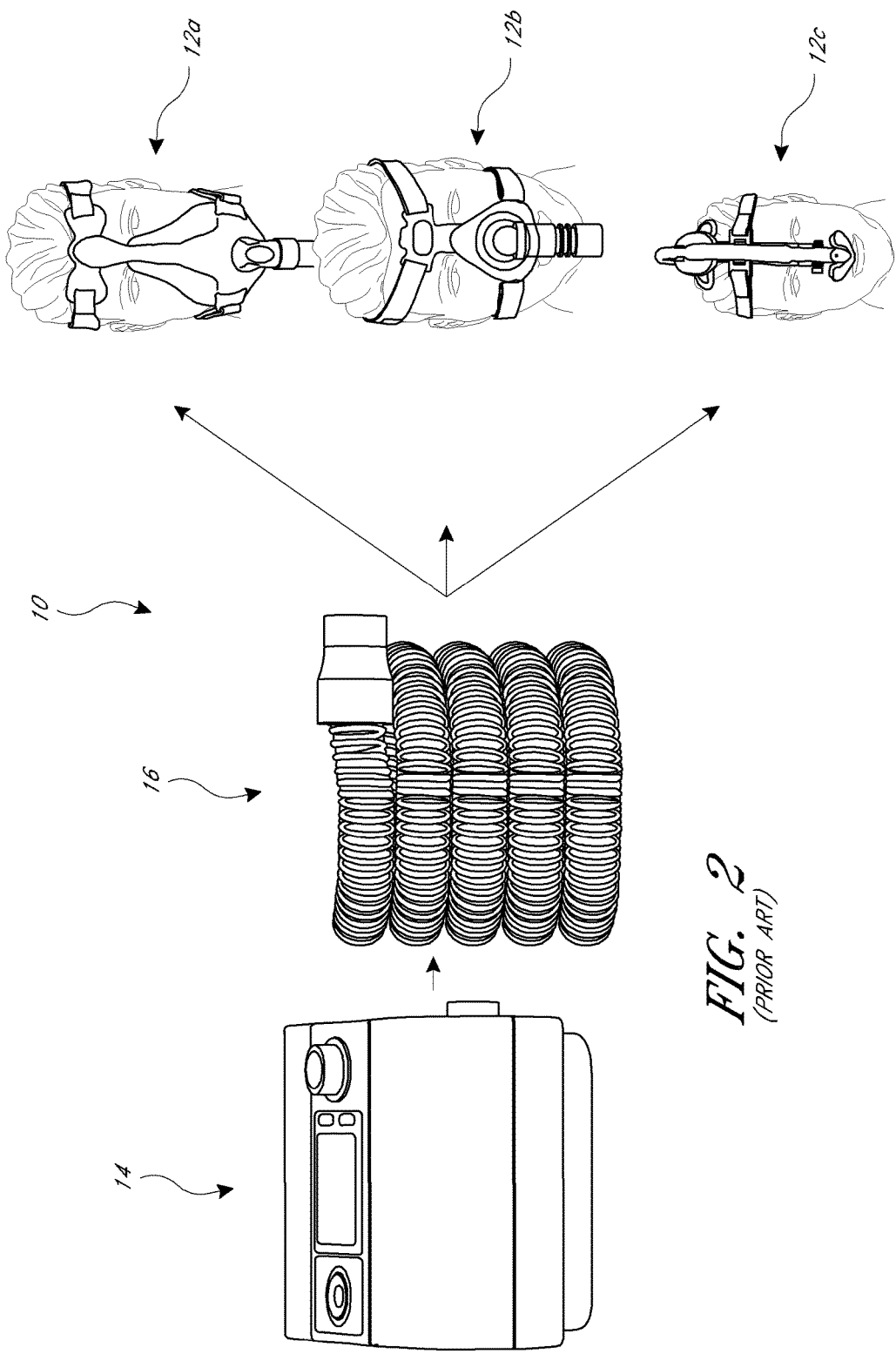
FIG. 2 is a perspective view of a conventional, prior art CPAP system.
Figure 3A:
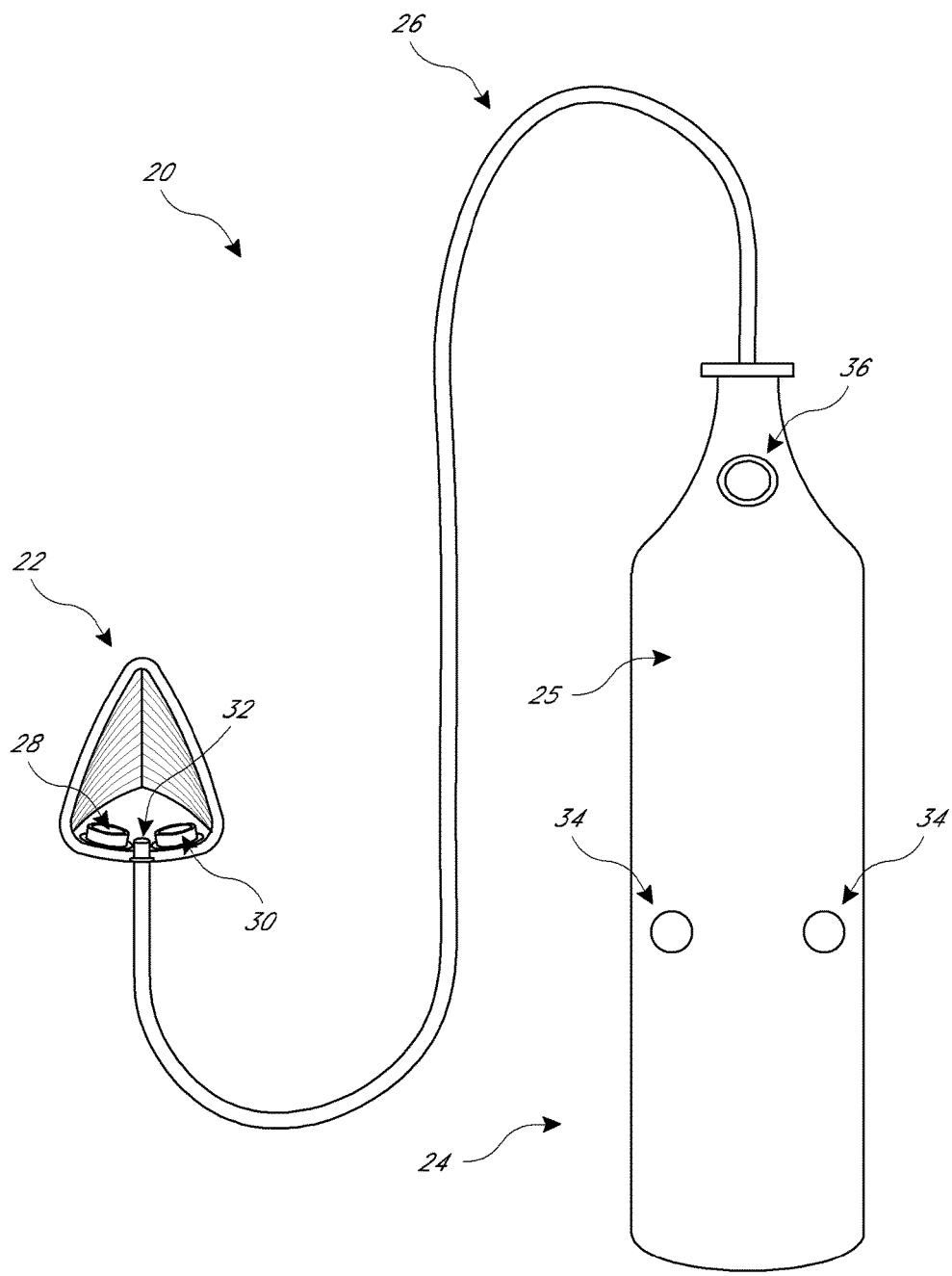
FIG. 3A is a perspective view of an OSA treatment system, according to one embodiment.

Referring now to FIG. 3A, in one embodiment, a system 20 for treating a patient suffering from OSA may include a mask 22, a portable air flow generator 24 and a tube 26 (or "tubing," "connector," or other analogous term) that connects the two. The view in FIG. 3A shows the inside of mask 22, which includes an expiratory valve 28 (which also may be called an "exhalation valve" or "expiratory valve"), an inspiration valve 30 (which also may be called an "inhalation valve" or "inspiratory valve"), and a port 32 for connecting tube 26 to mask 22.

In one embodiment, mask 22 is configured to fit snugly about the patient's nose and adheres to the patient's skin via an adhesive contact surface to form an airtight seal with the patient. Alternatively or additionally, mask 22 may be custom fitted to conform closely to the shape of a patient's nose. Mask 22 is generally configured to be lightweight, comfortable for the patient to wear, and airtight when adhered to the patient. The airtight seal prevents air leaks and thus obviates the need for the high flow rates generally associated with CPAP. In some embodiments, mask 22 may be configured to form an open space (or "dead space") between the mask and a wearer's face of less than or equal to about 10 milliliters and may have a contact surface that contacts the wearer's face of greater than or equal to about 5 square centimeters. Mask 22 may alternatively be made of a relatively soft material that moves in and out with breathing or a harder, less compliant material that resists movement with breathing. In various embodiments, mask 22 may cover the nose and mouth of the patient and/or may be attached via other means, such as by an elastic strap. Ideally, however, mask 22 will fit on the patient without the need for a strap, thus improving comfort and compliance. Various features and embodiments of mask 22 are described further below.

In some embodiments, a mask may cover the nose and mouth and may also include an energy converter for converting energy from the exhaled breath of a patient into energy that may be used to power or recharge a battery of air flow generator 24. Energy from the patient's breath may come in the form of airflow (wind) energy, heat of the breath, or both. This breath energy may pass through one or more turbines in the mask to convert the breath energy into electrical energy, and the electrical energy may in turn be passed through wiring to air flow generator 24. This is one example of a way in which air flow generator 24 may be self-powered.

In various embodiments, one or more components of system 20 may be moved or eliminated. For example, in one embodiment, one or both of valves 28 and 30 may be located somewhere within system 20 other than on mask 22. For example, one or both valves 28, 30 may be coupled with tube 26 in embodiment. In another embodiment, tube 26 may be eliminated, and a smaller air flow generator (not shown) may be attached directly to mask 22.

Air flow generator 24, according to one embodiment, may include a housing 25 having one or more air intake apertures 34 and one or more air release valves 36. Housing 25 typically holds an air flow generation device and a power source (not shown). Housing 25, and more generally air flow generator 24, are portable, in that they may be easily carried and manipulated by a patient. The term "portable" is not meant to designate any specific size or weight of the device, but instead is meant simply as a general descriptor of the device as being more lightweight and smaller than a typical CPAP air flow generator. In one embodiment, housing 25 may have a diameter of no more than about 4 cm, a length of no more than about 17 cm, and a weight of no more than about 1 pound. In one embodiment, air flow generator 24 as a whole, including housing 25 and its contents, may have a weight of no more than about 1.5 pounds. Generally, air flow generator 24 may be smaller and lighter weight than a typical CPAP air flow generator, largely due to the fact that system 20 requires lower air flow rates than a typical CPAP system. Air flow generator 24 and its various features are described in further detail below.

Tube 26 is configured to be a small, lightweight, flexible connector that generally does not interfere with patient sleeping or comfort. Again, due to the low air flow rate required by system 20, tube 26 may have a significantly smaller diameter than tubing used in typical CPAP systems. For example, in one embodiment, tube 26 may have an outer diameter of no more than about 2 cm and preferably no more than about 0.6 cm. Tube 26 may be made of any flexible, durable material, such as but not limited to polymers, such as PTFE, PEBAX or the like. Tube 26 may also have a length that adds to ease of use and patient comfort. In some embodiments, a patient may be provided with multiple tubes 26 of different lengths to accommodate different placements of housing 25 on the body. For example, in one embodiment, housing 25 may be strapped onto one of the patient's arms, using a strap similar to those used for iPods. In another embodiment, housing 25 may be clipped to the patient's clothing, such as a shirt or waste band. In yet other embodiments, housing 25 may be placed on a nightstand table while the patient is sleeping. Tube 26 may be provided with any suitable length to accommodate such uses of system 20.

Figure 3B:
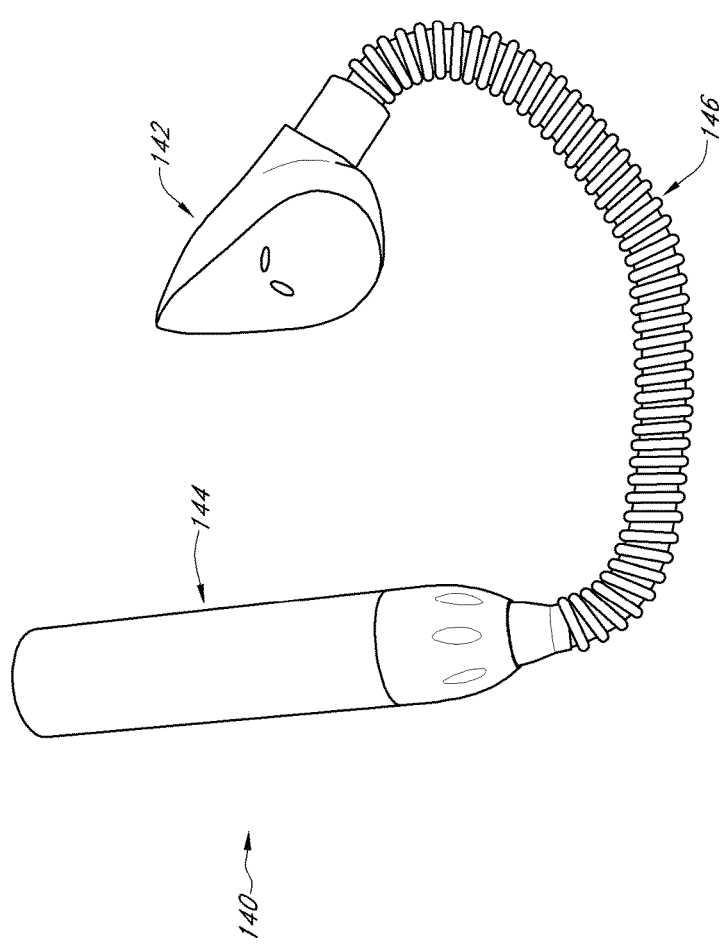
FIG. 3B is a perspective view of an OSA treatment system, according to another embodiment.

With reference now to FIG. 3B, another embodiment of a sleep apnea treatment system 140 is shown. Here, system 140 again includes a mask 142, air flow generator 144 and tube 146. Air flow generator 144 is the size and shape of an electric toothbrush handle, and mask 142 is custom formed to fit one patient's nose. This embodiment illustrates the small size that may be achieved in various embodiments.

Figure 3C:
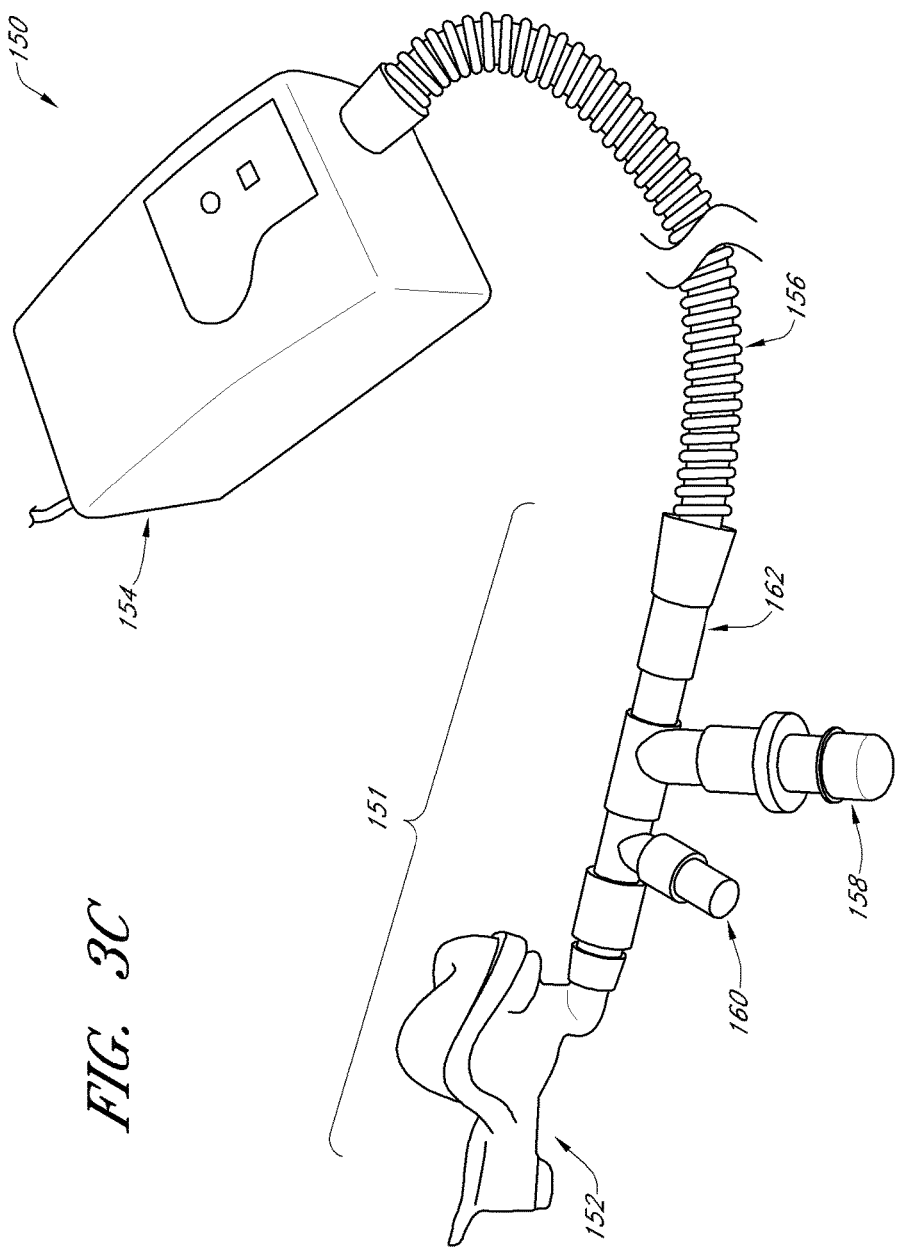
FIG. 3C is a perspective view of an OSA treatment system, according to another embodiment.

FIG. 3C illustrates another embodiment of a sleep apnea treatment system 150. This embodiment includes a CPAP air flow generator 154 and standard CPAP tubing 156, coupled with an adapter/mask combination device 151 for providing improved sleep apnea therapy. Combined device 151 includes a mask 152, a one-way inspiratory valve 160, a one-way peek end expiratory valve 158 (or "PEEP valve"), and a flow restrictor 162 in line with tubing 156. Flow restrictor 162 may function to restrict the flow of air from the CPAP air flow generator to a specified flow rate that is lower than typically provided by CPAP. For example, while an unrestricted CPAP air flow generator may provide free flow at rates of 160-200 liters/minute, flow restrictor 162 may restrict this rate to about 10-40 liters/minute or less in one embodiment. In such an embodiment, generator pressure may be set to a level of about 7 cm H2O, and the PEEP valve 158 may be set to a pressure of about 5 cm H2O. Of course, these are only exemplary levels and may be set to other levels in alternative embodiments. This embodiment illustrates the fact that an improved device 151 may be provided, which may be used to optimize currently available CPAP systems. In other embodiments, a system including an air generator and tube may be provided, as shown in FIGS. 3A and 3B. The embodiment shown in FIG. 3C also illustrates the fact that valves 158, 160 need not be positioned on mask 152.

Figure 4A:
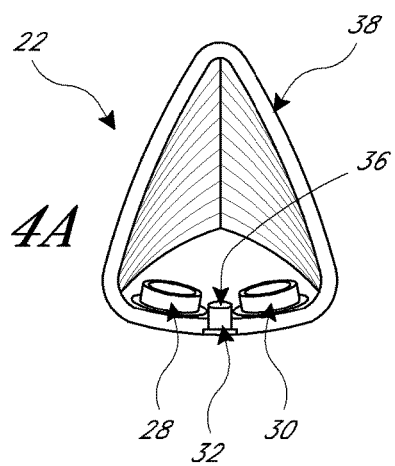
FIGS. 4A-4E are various views of a nasal mask for use with an OSA treatment system, according to one embodiment.
Figure 4E:
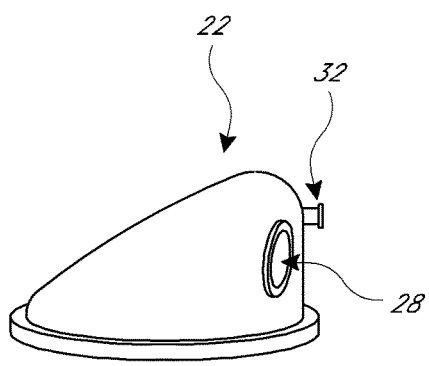
Figure 4C:
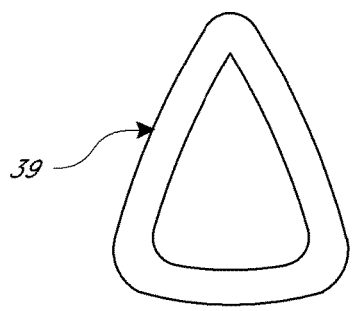
Figure 4D:
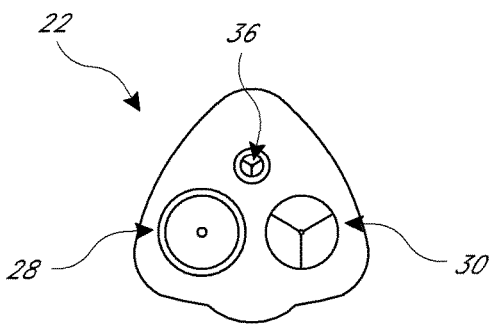
Figure 4B:
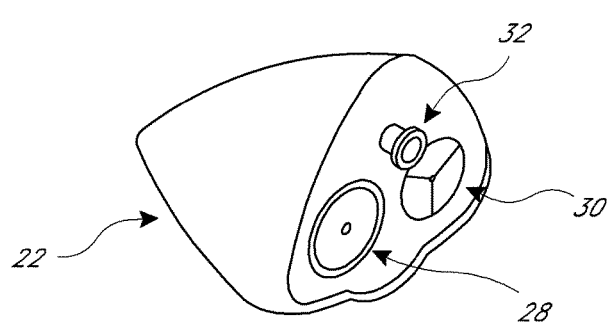

Referring now to FIGS. 4A-4E, mask 22 is described in further detail. According to one embodiment, mask 22 may include three one-way valves: expiratory valve 28, inspiration valve 30 and air flow generator valve 36, which is disposed within port 32. Mask 22 is shaped to fit over the patient's nose such that a contact surface 38 contacts and forms a seal with the patient's skin. In some embodiments, contact surface 38 may include an adhesive. For example, as pictured in FIG. 4C, in some embodiments, a double-sided adhesive strip 39 may be attached to contact surface 38 to form the seal between mask 22 and the patient's skin. Adhesive strip 39 may be covered with a protective material, which may be removed by a patient/user immediately before use to expose adhesive strip 39. FIG. 4A is an internal/posterior view, FIG. 4B is a perspective view, FIG. 4D is a bottom view, and FIG. 4E is a side view of mask 22.

In general, mask 22 is designed to cover (or "surround") both of a patient's nostrils and most, or all, of a patient's nose. In the embodiment shown, for example, mask 22 is configured to surround a patient's nose and adhere to the patient's face around the nose via contact surface 38 and adhesive strip 39. In embodiments like this one, mask 22 may come in a variety of sizes (small, medium and large, for example), and may be made of plastic of sufficient strength to maintain its shape during breathing without collapsing. Mask 22 is typically configured to adhere to the patient's face/nose without requiring a strap. In other embodiments, mask 22 may be made larger to cover the mouth as well. In still other alternative embodiments, mask 22 may be smaller. For example, in one embodiment, mask 22 may include an adhesive strip that is applied over the nostrils and is coupled with one, two or three valves 28, 30, 36. In another embodiment, it may be possible to cover only one nostril.

In some embodiments, which are not shown, a mask may cover a patient's nose and mouth or only the patient's mouth. Although these embodiments are not described in detail, the features of nasal mask 22 described herein may be equally applied to any such embodiments. In particular, a mask that covers a patient's nose and mouth may be beneficial for patients who might convert to mouth breathing if only their noses are covered. In some embodiments, therefore, an OSA or snoring treatment system may include both a nasal mask and a nose/mouth mask, so that a patient can choose one or the other depending on symptoms and success with the nasal mask. In other embodiments, a physician may select a mask based on an individual patient's needs. Whichever mask is provided in a given system, any and all mask features described herein may be included, regardless of whether the mask covers only the nose or the nose and mouth.

In yet other embodiments, mask 22 may be custom manufactured to conform to a particular patient's nose/face shape. In one embodiment, for example, mask 22 may come in a first configuration, which may be placed over a patient's nose, and then treated in some way to assume a second configuration that conforms to the patient's nose shape. For example, mask 22 may be molded to conform to the patient's face, may be treated with mild heat, may be placed under vacuum and/or the like to assume the second configuration. In another embodiment, a computed tomography (CT) scan of the patient's head (or portion of the head) may be taken, and the CT data from the scan may be used to design a custom fitting mask 22. In one embodiment, for example, CT scan data can be used to generate a negative image of the patient's face, from which a mold may be generated, and the mold may be used to form mask 22. In various embodiments, any suitable method of custom building devices or parts may be used to form mask 22.

FIGS. 5A and 5B provide a diagrammatic illustration of the working of valves 28, 30, 36 of system 20. According to various embodiments, valves may be any of a number of different types of valves, such as but not limited to flap valves, hinge-less valves, balloon valves, stepper valves, ball valves, shape memory flap valves, membrane valves, iris valves, flute valves, slit valves or the like. Several examples of such valves are described in greater detail below, and FIGS. 5A and 5B are thus provided to illustrate the general principles of the workings of valves 28, 30, 36 in system 20. Also, as mentioned above, valves 28, 30, 36 may all be positioned on mask 22, as in FIGS. 4A-4E, or one or more valves may be positioned along or at one end of tube 156, as shown in FIG. 3C.

As illustrated in FIG. 5A, upon exhalation, air flow generator valve 36 and inspiration valve 30 close. The closing of air flow generator valve 36 prevents rebreathing of exhaled air upon inspiration. Expiratory valve 28 is a one-way, variable resistance valve that will also remain closed until exhaled air generates a specified pressure within mask 22 (the "opening pressure"), at which point it will open to a first opening diameter (or opening configuration). For example, in various embodiments, the opening pressure for expiratory valve 28 may be between about 0 cm H2O and about 25 cm H2O, and more preferably between about 0 cm H2O and about 12 cm H2O, and even more preferably between about 2 cm H2O and about 5 cm H2O. Expiratory valve 28 is thus configured to open at an opening pressure that is less than the opening pressure of currently available expired air resistance devices, such as the Provent® device. This should provide improved patient comfort, because a device that requires a higher opening pressure is typically uncomfortable for a patient, as it is difficult to start exhaling. This difficulty in starting to exhale makes it feel difficult to breathe and produces a claustrophobic feeling. Expiratory valve 28 provides resistance to exhaled air and thus provides positive end-expiratory pressure ("PEEP") and/or expiratory positive airway pressure ("EPAP"). Both PEEP and EPAP help keep an airway open during the breathing cycle and thus help prevent OSA.

In some embodiments, once expiratory valve 28 opens at the opening pressure, it then begins to close as exhaled air flow decreases. In other words, during the expiratory phase of breathing with this type of expiratory valve 28, resistance increases as flow decreases. This increased resistance provides increasing intra-airway pressure (or at least stable intra-airway pressure) during the expiratory phase of breathing, thus helping to keep the airway open during the later portion of the expiratory phase and at the end of expiration as the body prepares to transition to inhalation. This increased resistance to exhalation during the expiratory phase is exactly the opposite of what occurs with currently available PEEP or EPAP valves, where resistance and pressure decrease during expiration, thus providing less of a pneumatic splint at end-expiration. Therefore, expiratory valve 28 may be advantageous relative to currently available valves that have only an open configuration and a closed configuration, because the increased resistance in response to decreased flow helps maintain the pneumatic splint throughout the expiratory phase. This advantage is described in further detail below in relation to several exemplary expiratory phase pressure curves.

In various embodiments, expiratory valve 28 may open at a predetermined opening pressure and may then either gradually/continuously close during the expiratory phase or may incrementally close during the expiratory phase. In other words, the valve may transition gradually from open to closed or may move in one or more increments. As will be described in greater detail below, in some embodiments, valve 28 may open and close in response to the breath, while in other embodiments, valve 28 may be driven open and closed by a timed mechanism. This mechanism may be timed according to the patient's breath or other physiological signals or may be pre-programmed at a desired timing, based on a desired or estimated breath pattern. In some embodiments, once valve 28 opens at the initial opening pressure, it may be able to open further, if expiratory flow initially increases during expiration. Valve 28 would then begin to close after achieving whatever is its most open configuration.

In some embodiments, the opening pressure for expiratory valve 28 may be set at a desired pressure and not changed. In some embodiments the opening pressure may be adjustable. For example, the opening pressure may be adjusted by a physician and/or by a patient/user. This may enhance compliance, for example, since some patients may find a certain opening pressure uncomfortable and want less opening resistance, while others may want a higher resistance to increase the force of their pneumatic splint. In some embodiments, additionally or alternatively, the opening pressure may be controlled electrically or magnetically to deliver intermittent or variable opening pressure. The combination of the opening pressure required to open expiratory valve 28 and the closure of air flow generator valve 36 and inspiration valve 30 upon exhalation provide an expiratory back pressure that creates the pneumatic splint to help keep the patient's airway open and prevent apnea episodes. Because expiratory valve 28 opens to a variable degree depending on the amount of air flow during exhalation, expiratory valve 28 thus provides variable resistance during exhalation, which produces improved pneumatic splinting and ease of breathing as compared to a valve that simply opens all the way at one pressure and closes at another pressure.

Referring now to FIG. 5B, at the end of expiration, expiratory valve 28 closes, and air flow generator valve 36 and inspiration valve 30 open to allow pressurized air (from air flow generator 24) and room air to flow into mask 22. This pressurized air feature does not exist with devices that simply provide resistance to expiration. In some embodiments, inspiration valve 30 may be eliminated, and all inspired air may be provided through air flow generator valve 36. It may be advantageous, however, to allow a user to inhale room air as well as pressurized air provided by air flow generator 24. In some embodiments, inspiration valve 30 and expiratory valve 28 may be combined into one valve that provides resistance to expired air and less or no resistance to inspired air.

Pressurized air provided through air flow generator valve 36 is typically provided at a relatively low flow rate, compared to conventional CPAP systems. In one embodiment, this low flow rate air is provided consistently throughout the breathing cycle, without any changes based on the patient's condition. In some embodiments, if the patient becomes apneic (experiences an apnea episode) at end expiration, system 20 may switch from the relatively low flow rate to a higher flow rate, to pressurize the nasopharynx in a manner similar to CPAP. In such an embodiment, one or more sensors are incorporated into or used with system 20, such as but not limited to a conventional apnea monitor or a pulse oximeter. This sensing/switching feature is optional, however.

Finally, at the end of inspiration, air flow generator valve 36 and inspiration valve 30 close, and the expiratory phase of the breathing cycle starts again. Valves 28, 30, 36 thus move again into the configuration shown in FIG. 5A.

Figure 6B:
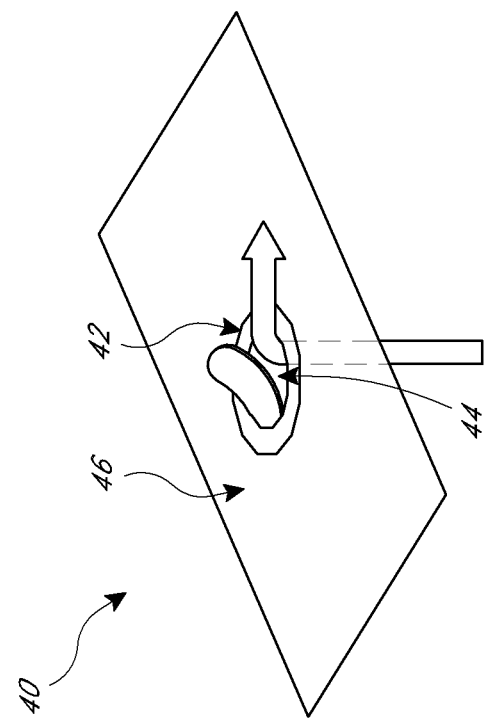
FIGS. 6A and 6B are perspective views of a Nitinol disc valve for use in a mask of an OSA treatment system, according to one embodiment.
Figure 6A:
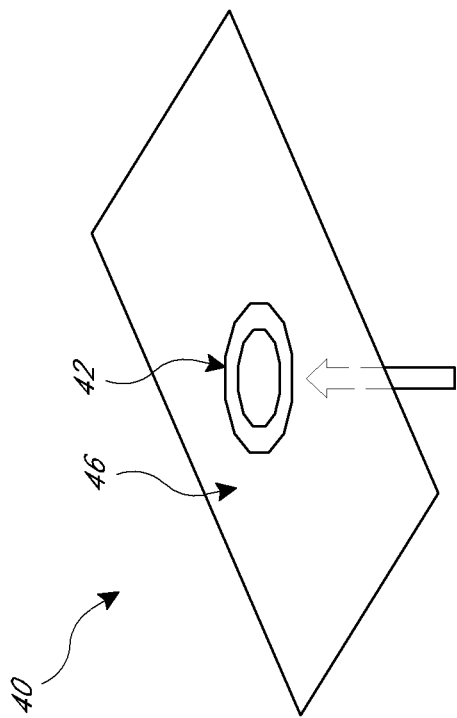

With reference now to FIGS. 6A and 6B, one embodiment of an expiratory valve 40 may be a disc valve made of a flexible material such as Nitinol. Valve 40 generally includes a substrate 46 with an aperture 44 and a plate 42 of flexible material, such as Nitinol in this embodiment, attached to substrate 46 in such a way that it covers aperture 44 and flexes to allow exhaled air (large arrow) to pass through aperture 44. FIG. 6A shows valve 40 closed, and FIG. 6B shows valve open. Nitinol, being a shape memory nickel-titanium alloy, flexes under the pressure of exhaled air to open valve 40 at a set opening pressure. Nitinol plate 42 then continues to flex further in response to increasing expired air flow to allow aperture 44 to grow in size, thus reducing resistance and maintaining airway pressure within a desired range. As air flow then decreases, Nitinol plate 42 resumes its earlier configuration to cover aperture 44 and close valve 40. In various embodiments, the opening pressure may be between about 3 cm H2O and about 12 cm H2O, and in one embodiment about 5 cm H2O. In some embodiments, the opening pressure may be outside this range. Also in some embodiments, shape memory materials other than Nitinol may be used for plate 42. The material and/or configuration of plate 42 may be selected to provide a desired opening pressure. For example, some properties that may affect opening pressure include thickness, alloy/material type, temperature of metal, strain properties of metal, lamination of the material, and the like.

Figure 6D:
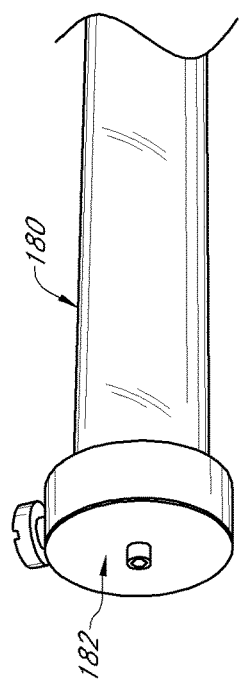
FIGS. 6C and 6D are perspective views of a Nitinol disc valve for use in a mask of an OSA treatment system, according to another embodiment.
Figure 6C:
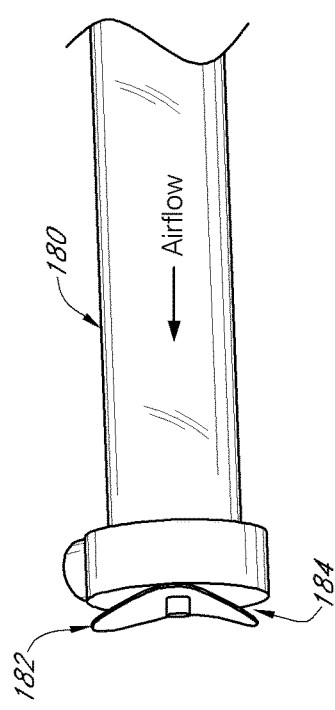

FIGS. 6C and 6D illustrate another example of a Nitinol flap valve 182, disposed at the end of a tube 180. When exhaled air moves through tube 180 with sufficient pressure, valve 182 flaps open to create an opening 184, as in FIG. 6C. As exhaled air flow decreases, opening 184 becomes smaller and finally closes, as in FIG. 6D.

Figure 7B:
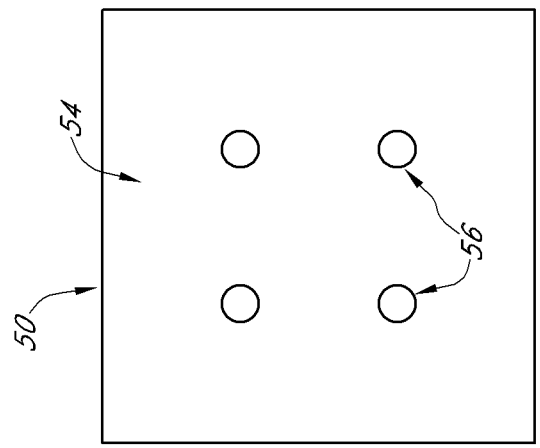
FIGS. 7A and 7B are diagrammatic frontal views of a flexible membrane valve for use in a mask of an OSA treatment system, according to one embodiment.
Figure 7A:
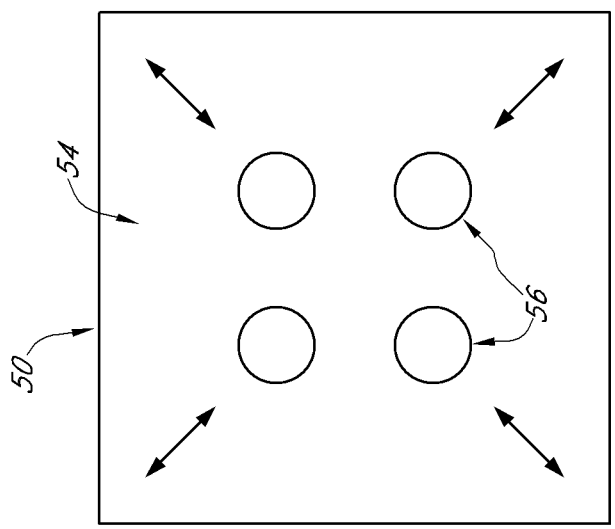

Referring now to FIGS. 7A and 7B, in another embodiment, an expiratory valve 50 may include a flexible, expanding membrane 54. Expanding membrane 54 includes multiple small apertures 56, which remain closed until a specified opening exhalation pressure is reached. When opening pressure is reached, apertures 56 open to a first diameter, as illustrated by FIG. 7A. If expiratory pressure were to increase after opening pressure, apertures 56 would open further. Otherwise, apertures 56 generally decrease in size over the course of the expiratory phase as exhalation air flow decreases (FIG. 7B), thus increasing resistance and maintaining pressure within the pharynx/airway (the pneumatic splint).

As mentioned above, in some embodiments, an expiratory valve may provide resistance to expired air that increases over the course of the expiratory phase. Such valves may be configured, for example, to open a predetermined amount when the opening pressure is reached and then close slowly over the course of expiration. This increasing resistance may help augment the pneumatic splint and thus help keep the airway open during expiration. It may be achieved, for example, by a valve that "pops" open at a given expiratory opening pressure and then elastically closes back down over the course of expiration. In some embodiments, such a valve may be programmed to open at an opening pressure and then close down during a certain amount of time. Additional embodiments of valves are described further below.

Figure 8:
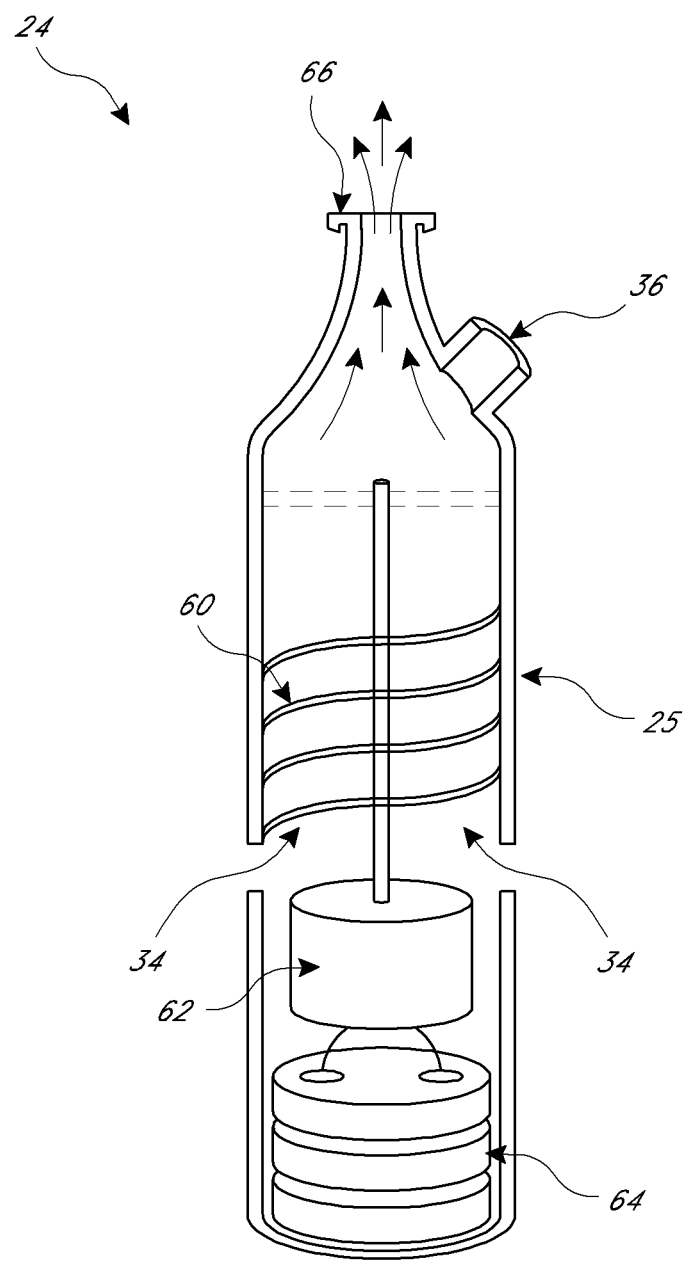
FIG. 8 is a cross-sectional view of a turbine air flow generator for use in an OSA treatment system, according to one embodiment.

Referring now to FIG. 8, because system 20 is configured to function at a lower air pressure and flow than traditional CPAP systems, there are a number of potential embodiments for an air flow generator to work with system 20. For example, in various embodiments, system 20 may include an air generator such as but not limited to a lithium powered turbine pump, a self-powered double bellows, a self-powered dual counter turbine or a self-powered air compressor and return. Any of these generators may be made significantly smaller than the typical CPAP air flow generator, due to the lower flow rates used in system 20.

In the embodiment illustrated in FIG. 8, air flow generator 24 includes housing 25, air intake apertures 34 and relief valve 36, as previously mentioned. Housing 25 also includes an air outflow aperture 66. A turbine 60 resides inside housing 25, coupled with a motor 62, which is coupled with a lithium battery 64 (or other power source in some embodiments). In use, battery 64 powers motor 62, which drives turbine 60, which pulls air in through air intake apertures 34 and pumps air out through air outflow aperture 66. This form of turbine air flow generator 24 is efficient enough, and air flow rates required by system 20 are low enough, that housing 25 can be made quite small. For example, in one embodiment, housing 25 may have a largest diameter of no more than about 6 cm and preferably no more than about 4 cm, and a length of no more than about 20 cm and preferably no more than about 17 cm. Additionally, the overall weight of air flow generator 24 may be about 1.5 pounds or less. Thus, size of air flow generator 24 may be comparable to that of a cell phone or electric toothbrush. This is significantly smaller than the typical CPAP air flow generator, which weighs approximately five pounds and measures approximately 10" by 8" by 6".

According to one embodiment, air flow generator 24 may provide an approximately constant air flow in a range of between about 1 liter per minute and about 20 liters per minute. This is significantly lower that the flow rates used in CPAP, which operate at flow rates as high as 200 liters of air per minute. Thus, a "low flow rate" for system 20 generally refers to a rate about 1-20 liters per minute, and a "high flow rate" for system 20 generally refers to a rate closer to the high end of the range of about 1-20 liters per minute. Thus, a "high flow rate" for system 20 is still typically lower than the flow rates used in CPAP. In some embodiments, air flow generator 24 may also sometimes operate at a flow rate below 1 liter per minute or may even provide no flow if a patient is breathing normally. Also in some embodiments, air flow generator 24 may provide air flow rates higher than 15 liters per minute, though generally flow rates will be lower than those used in CPAP.

The air pressure generated in air flow generator 24 is also typically less than the pressure required by a conventional CPAP machine. While conventional CPAP typically operates at about 4-20 cm of water, system 20 generally operates at the low end of a range of about 4-14 cm of water.

Relief valve 36 may be configured to open at a certain opening pressure to allow air to escape from housing 25, so that the air pressure delivered to mask 22 is not higher than desired. For example, in various embodiments, relief valve 36 may be set to open at a pressure of between about 10 cm H2O and about 20 cm H2O. In some embodiments, the opening pressure of relief valve 36 may be outside this range.

In some embodiments, air flow generator 24 may be configured to provide variable flow rates. In some embodiments, flow rates may be adjusted based on sensed data from a patient. For example, if a patient experiences an apnea episode, an apnea monitor attached to the patient may detect the episode and send a signal to air flow generator 24 to switch from its usual low air flow rate to a higher air flow rate. Such an embodiment may also optionally be capable of shutting off completely if the patient is breathing normally without requiring positive pressure/flow during inhalation. In such an embodiment, system 20 may include an apnea monitor or other sensor and a processor for receiving and processing signals to instruct air flow generator 24. The advantage of such a system 20 is that it provides for variable flow rates. An air flow generator 24 designed to provide a constant, low flow rate, however, allows for a simpler system 20, without sensors/monitors or processors. Such a system 20 may be smaller, less cumbersome and require less power. In addition, because the air flow rates of system 20 are so much smaller than those of conventional CPAP, positively directed, continuous airflow should not be uncomfortable for a patient.

In some embodiments, any of a number of different air flow generators may be used. These may include, but are not limited to, a self-powered double bellows, a self-powered dual counter turbine and/or a self-powered air compressor and return.

FIGS. 9-14 graphically illustrate breathing curves for different therapeutic devices and physiologic states. The normal resting breathing cycle is characterized by a rhythmic pattern of inspiration and expiration often with a pause at the end of expiration. Inspiration and expiration are often of relatively equal length (2-4 sec.) with a pause of shorter duration (1-2 sec.). As air moves through the nose and airway it encounters resistance due to natural narrowing of the passages. As such, pressure in the airway rises and falls during normal breathing.

Airway pressure is determined by a simple equation: $P = F \times R$, where F is airflow and R is resistance. Airflow (F) can be generated by the patient (inspiration and expiration) or by a machine such as a CPAP generator. Increasing airflow generally increases pressure (P) in a direct linear fashion. There is a natural resistance (R) in the nasal passages that causes moderate change in the airway pressure during normal respiration. Resistance can be increased naturally (e.g. stuffed nose) or by an external resistor. Increasing resistance generally increases pressure in a direct linear fashion.

Figure 9:
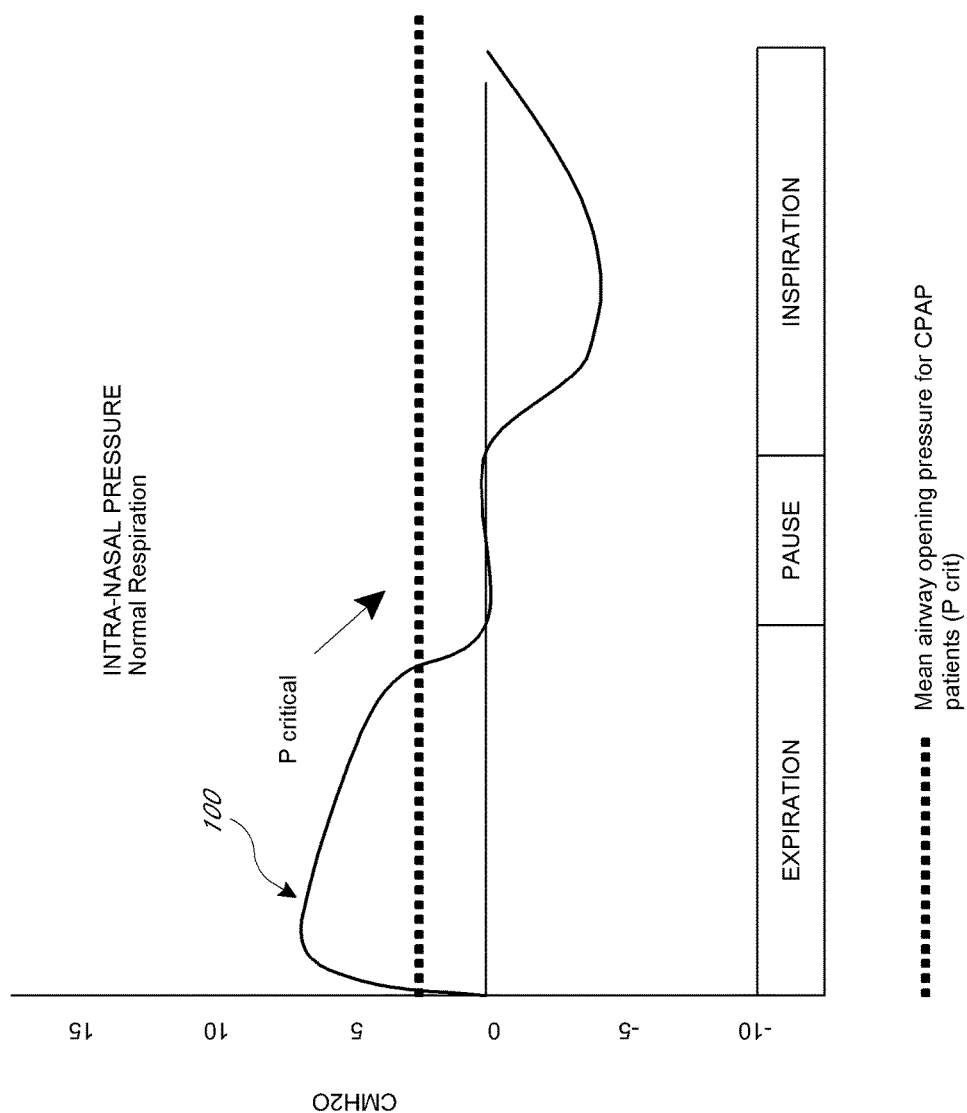
FIG. 9 is a graph with an intranasal pressure curve demonstrating normal respiratory mechanics.

Referring now to FIG. 9, an intranasal pressure curve 100 is shown for a complete, normal breathing cycle (expiration, end expiration pause, inspiration) in a person who does not have obstructive sleep apnea. The vertical axis shows intranasal pressure in cm H2O, and the horizontal axis represents one breath cycle, starting with the expiratory phase of breathing and ending at the end of the inspiratory phase. P critical is an approximated average pressure required to keep the airway open in OSA patients. The value for P critical varies from patient to patient, and thus is provided in these figures for exemplary purposes only.

In normal breathing without OSA, airway pressure is determined by expiratory flow and nasal resistance. Expiratory flow is variable and dependent on respiration, while nasal resistance is constant and independent of expiratory flow. The posterior pharynx stays open even at ambient air pressure (0 cm H2O) due to pharyngeal and glossal tone. In OSA patients, by contrast, the posterior pharynx becomes obstructed at end expiration as pharyngeal pressure drops below the critical pressure (P critical). In other words, such patients have insufficient PEEP (positive end expiratory pressure) and/or pharyngeal tone to keep their airways open. In experiments with OSA patients, the mean pressure required to partially open the airway is approximately 1 cm H2O. A mean nasal pressure of about 11 cm H2O is required to fully eliminate obstructive resistance in the pharynx, but flow increases are linear above P critical.

Figure 10A:
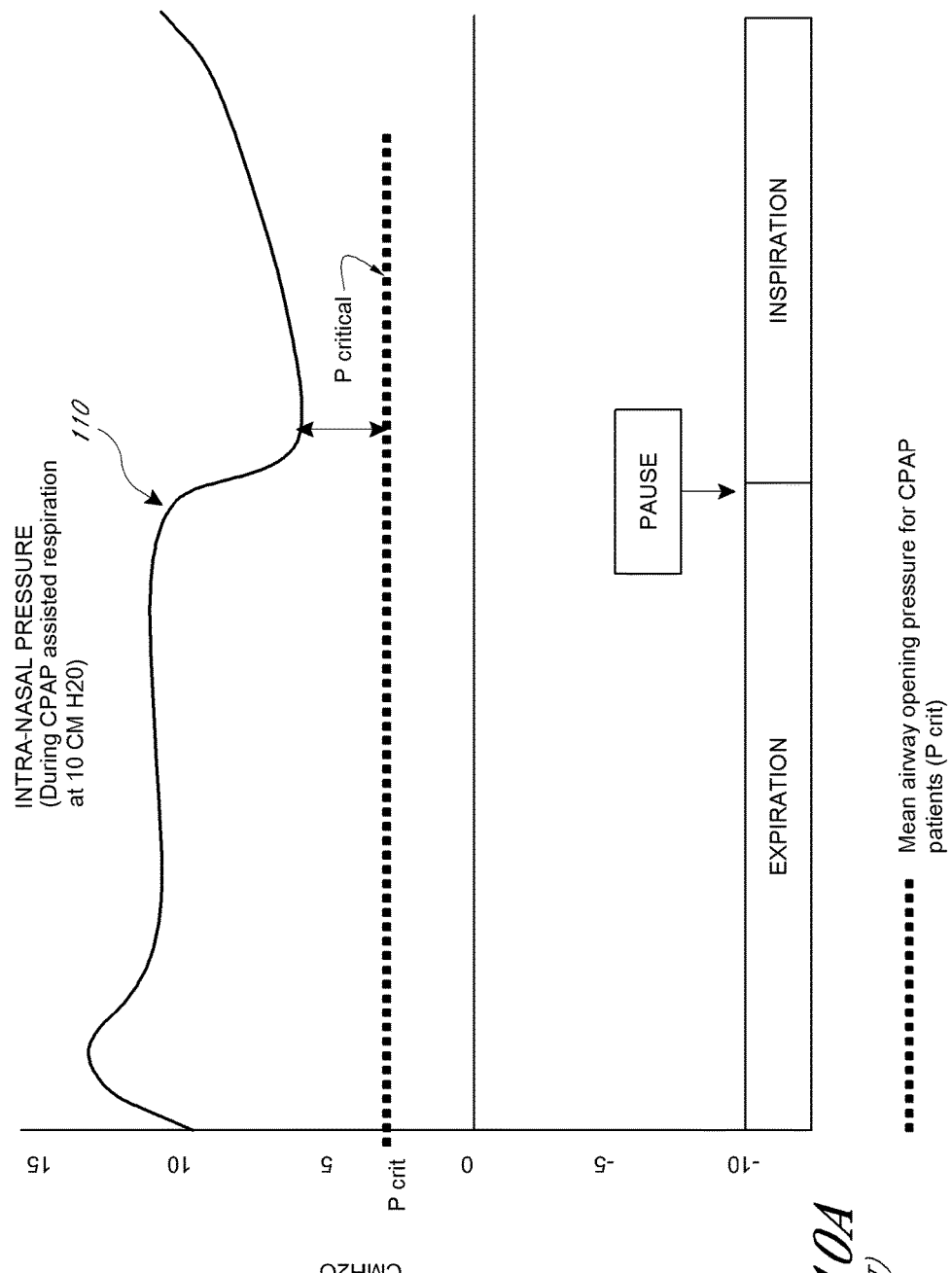
FIG. 10A is a graph with an intranasal pressure curve demonstrating breathing mechanics with OSA and conventional CPAP.

With reference to FIG. 10A, another intranasal pressure curve 110 is shown for a complete breathing cycle of a person using a CPAP system. CPAP works by keeping pharyngeal and nasal pressure above the critical pressure (P critical), as shown by curve 110, and thus preventing pharyngeal collapse. CPAP also slows expiration due to increased resistance caused by the restrictive nature of the mask and the high-rate inflow of air from the CPAP machine. This shortens the pause phase between expiration and inspiration.

With CPAP, resistance is determined by tubing and exit holes on the mask and remains relatively constant throughout the breathing cycle. Flow also remains constant because the CPAP system supplies a constant airflow to keep the pharynx open. Pressure is primarily related to the flow rate. As shown in FIG. 10A, a constant, high airflow rate increases pressure throughout the entire breathing cycle. Excess air flow is vented through holes on the CPAP mask which can lead to a frequent complaint of air blowing on the face. Excess air also circulates through the pharynx in a turbulent fashion which can lead to another frequent complaint of mucosal drying.

Shortcomings of CPAP include, however, discomfort due to the elevated expiratory resistance, air leaks from the CPAP mask that require high air flow rates to compensate, nasal dryness, ear pain, rhinitis, abdominal bloating and headaches that result from sinus pressure due to the required high flow rate. The high flow rate itself, which can be as high as 200 liters per minute in some cases, can be extremely uncomfortable, as a patient must exhale into what feels like a gale force wind being blown into his/her airway.

Figure 10B:
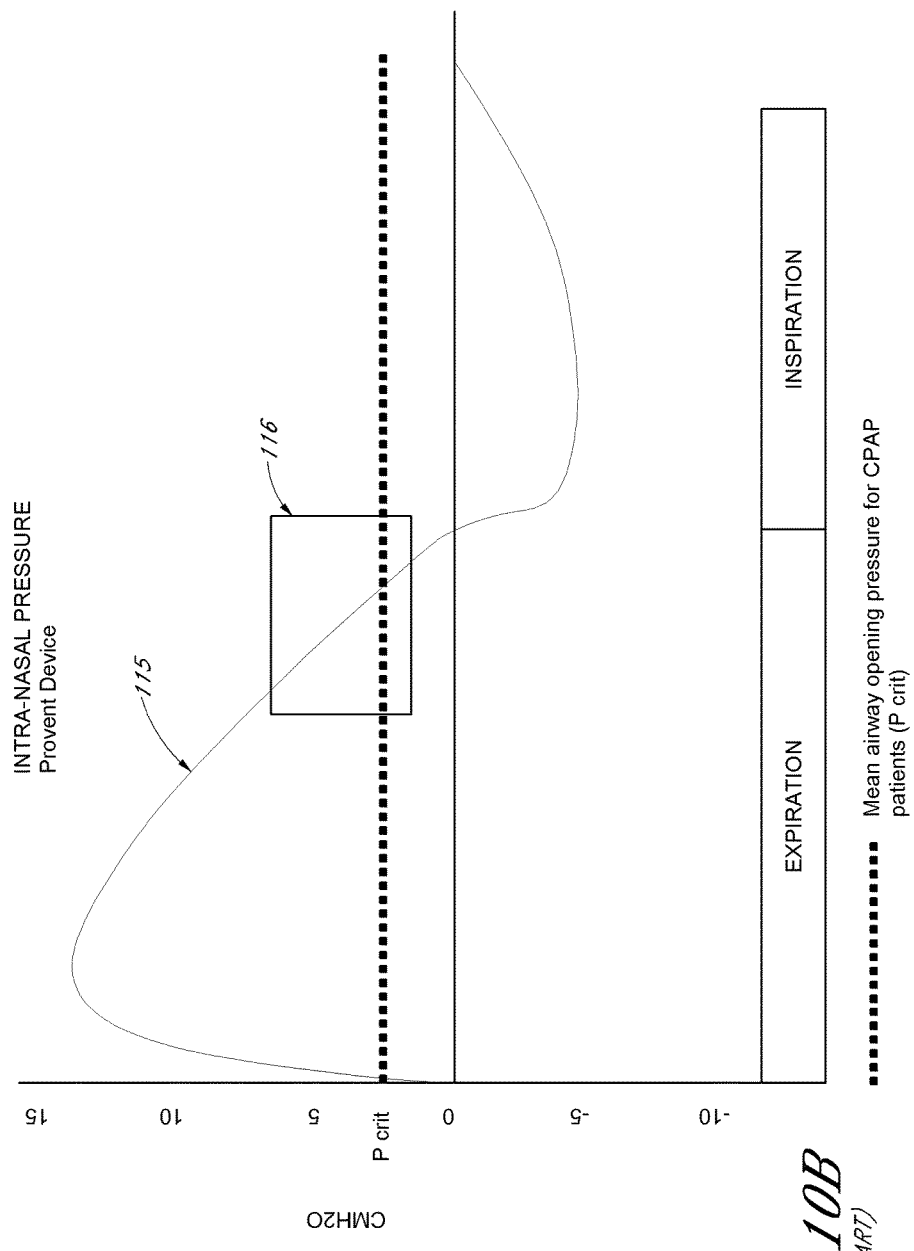
FIG. 10B is a graph with an intranasal pressure curve demonstrating breathing mechanics with OSA and a Provent® device.

Referring to FIG. 10B, another intranasal pressure curve 115 is shown, this time illustrating breathing mechanics of an OSA patient wearing a fixed orifice resistor EPAP device (e.g., Provent® Sleep Apnea Device (Ventus Inc.). The device uses one-way valves placed over each nostril to maintain constant resistance. Inspiration is minimally affected because the valves open when inhaling, but expiration is resisted because air must exit through small holes in the valve. This resistance to expiration raises intra-nasal pressure during expiration. In addition to maintaining a higher expiratory pressure, it is thought to work by slowing expiration to shorten the pause phase and thus lower the chance for airway collapse as well as to increase capillary pressure (auto-PEEP) leading to improved ventilation.

However, such a device has several drawbacks. First, intranasal pressure drops during expiration, because the valves of the device offer only fixed resistance. As flow decreases toward end expiration, pharyngeal pressure drops rapidly. This makes it difficult to maintain a therapeutic gap between P critical and end expiratory pressure. This is illustrated in FIG. 10B by the highlighted box 116. Within box 116, pharyngeal pressure can drop below P critical for long enough that collapse becomes more likely. In addition, if there is any pause between expiration and inspiration, intranasal pressure will drop to 0 cm H2O, since there is no active PAP (positive airway pressure). This would lead to complete airway collapse in many OSA patients. Finally, with such a device, the patient must first generate relatively high pressure to start exhaling through the device. This high pressure can be very uncomfortable, as it may make patients feel like they cannot exhale. Thus, many physicians believe the Provent® device is useful only for patients with very mild OSA or in those cases only for patients who can tolerate the high opening pressure.

Figure 11B:
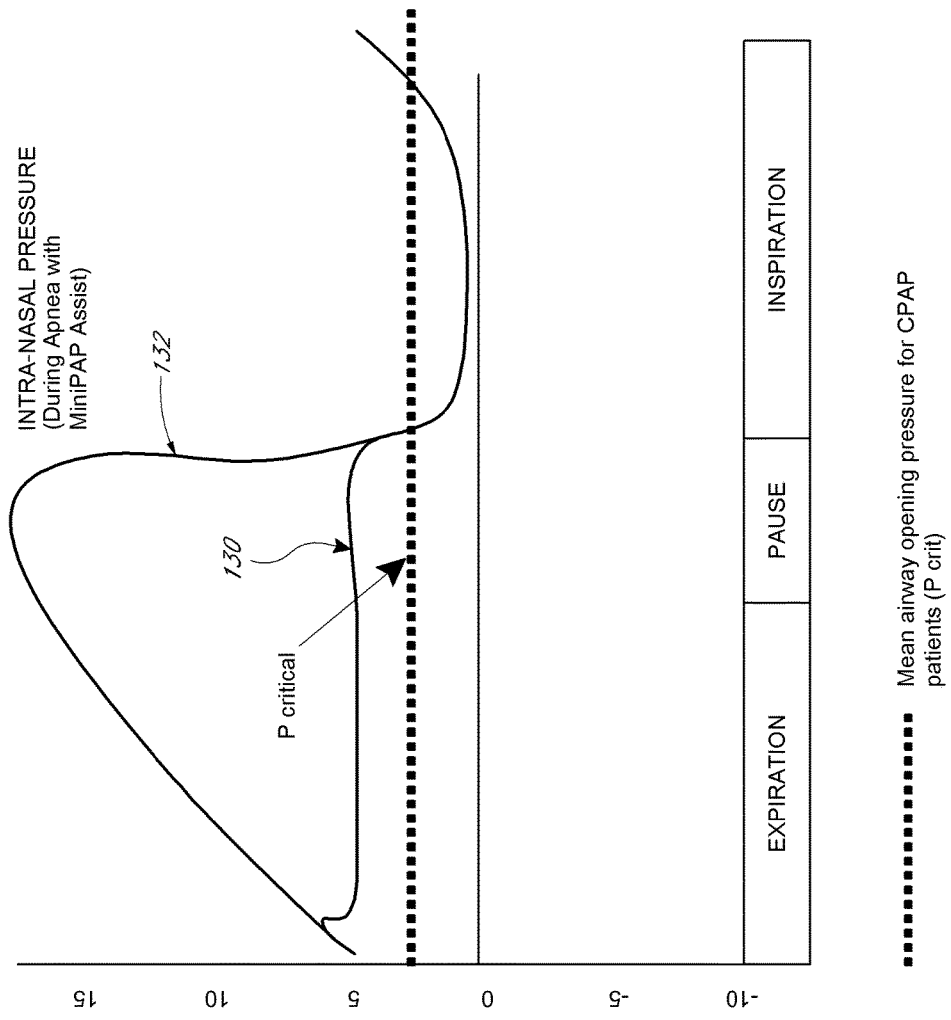
FIG. 11B is a graph with an intranasal pressure curve demonstrating breathing mechanics with a positive airway pressure system and apneic breathing, according to one embodiment.

Referring now to FIGS. 11A and 11B, various intranasal pressure curves 120, 122, 130, 132 are shown for breath cycles using the sleep apnea treatment system according to various embodiments described herein. Referring first to FIG. 11A, two alternative embodiments of curves 120, 122 for pressure vs. breath cycle are shown, each illustrating breathing assisted by a variable resistance, one-way expiratory valve but without any positive airway pressure (PAP) coming from an air flow generator. Either curve 120, 122 may be used, in various embodiments, as well as any of a number of curves in between or approximately the same as those shown in FIG. 11A. Looking first at curve 120, in one embodiment, the initial opening pressure is less (about 5 cm H2O) than the opening pressure shown in FIG. 10B (about 15 cm H2O). In addition, intra-nasal pressure remains significantly above P critical throughout the expiratory phase and does not dip down until the very end of expiration/beginning of inspiration. This maintenance of airway pressure through the expiratory phase should help ameliorate OSA. In the embodiment illustrated by curve 120, intra-nasal pressure remains relatively constant throughout expiration. The expiratory valve thus increases resistance sufficient to maintain approximately the same pressure despite decrease expiratory air flow.

In another embodiment, illustrated by curve 122, the expiratory valve may increase resistance in such a way that intra-nasal pressure increases through the expiratory phase. This increasing pressure may work even more effectively to keep the airway open toward the end of the expiratory phase. Furthermore, an even lower opening pressure than shown by either curve 120 or curve 122, such as an opening pressure of between about 0 cm H2O and about 5 cm H2O, may provide enhanced patient comfort, since the patient will not have to struggle to start expiration. During the expiratory phase, intra-nasal pressure may be increased to any suitable level, such as about 15 cm H2O, between about 5 cm and about 15 cm H2O, or in some cases even above 15 cm H2O. Thus, the systems and devices described herein may generate a pressure vs. breath cycle curve that looks like either of curves 120, 122 or, alternatively, any of a number of suitable curves in between or approximately the same as those shown.

In FIG. 11B, pressure curves 130 and 132 illustrate a breathing cycles of two patients using two embodiments of the sleep apnea treatment system as described herein, during apneic breathing and with the air flow generator turned on. During an apnea episode (the "Pause" segment labeled at the bottom of the chart), the air flow generator maintains airway pressure. The air flow generator also augments airway pressure during inspiration. Pressure curve 132 illustrates an intra-nasal pressure that increases during expiration, as discussed above. The lower flow rates of the embodiments described herein, combined with the variable expiratory resistance provided by the expiratory valve, helps provide many or all of the benefits of CPAP while reducing at least some of the side effects.

Figure 12B:
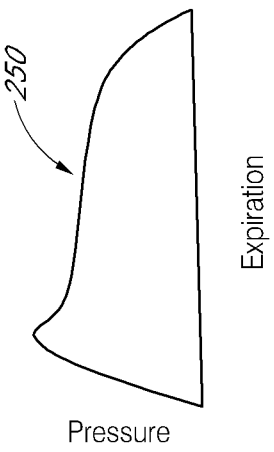
FIGS. 12A-12C are intra-nasal pressure vs. expiration curves for, respectively, a Provent® nasal insert, a conventional EPAP device, and a variable resistance expiratory resistance device according to one embodiment of the present disclosure.
Figure 12C:
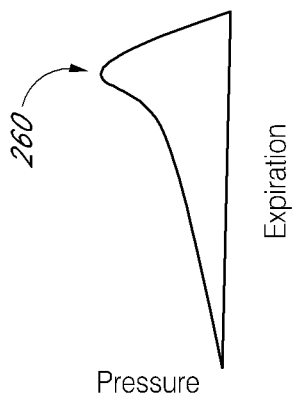

In one embodiment not yet described, a conventional newly invented PAP system may be programmed to provide a curve similar to the pressure vs. expiration curve 260, in FIG. 12C. In this embodiment, the PAP system could be programmed, such as with software, to provide an initial flow rate of positive air flow to the patient at the beginning and early portion of expiration and to increase the air flow rate during the later portion of expiration. Thus, a curve such as curve 260 may be provided, thus obviating at least some of the drawbacks of conventional CPAP. An air flow pattern of this type may be provided by timing the air flow rate changes according to an average breath cycle, or they may be customized for different patients.

Figure 12A:
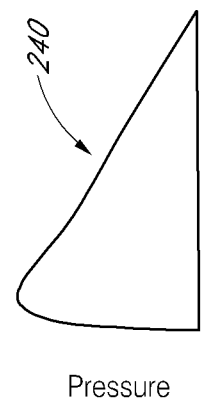

Referring now to FIGS. 12A-12C, pressure vs. expiratory phase curves for various expiration resistance devices are compared. FIG. 12A illustrates an estimated Provent® pressure curve 240 of the intra-nasal pressure during exhalation while wearing the Provent® device. As already described, the Provent® pressure curve 240 spikes immediately, as the patient tries to overcome the high resistance of the fixed orifice valve. The curve then dips quickly during expiration, thus providing insufficient intra-nasal pressure at end expiration. FIG. 12B illustrates a conventional EPAP valve pressure curve 250. EPAP curve 250 also has a high opening pressure but one advantage of a mechanical EPAP valve is that expiratory pressure is more constant during the expiratory phase compared with a fixed orifice valve.

In contrast to the two prior art pressure curves 240 and 250, as shown by the variable resistance pressure curve 260 in FIG. 12C, the variable resistance, one-way valves described herein open at a much lower opening pressure and provide increasing resistance (and thus intra-nasal pressure) during the expiratory phase. This helps keep a patient's pharynx and airway open without the discomfort of a high opening pressure.

Figure 13:
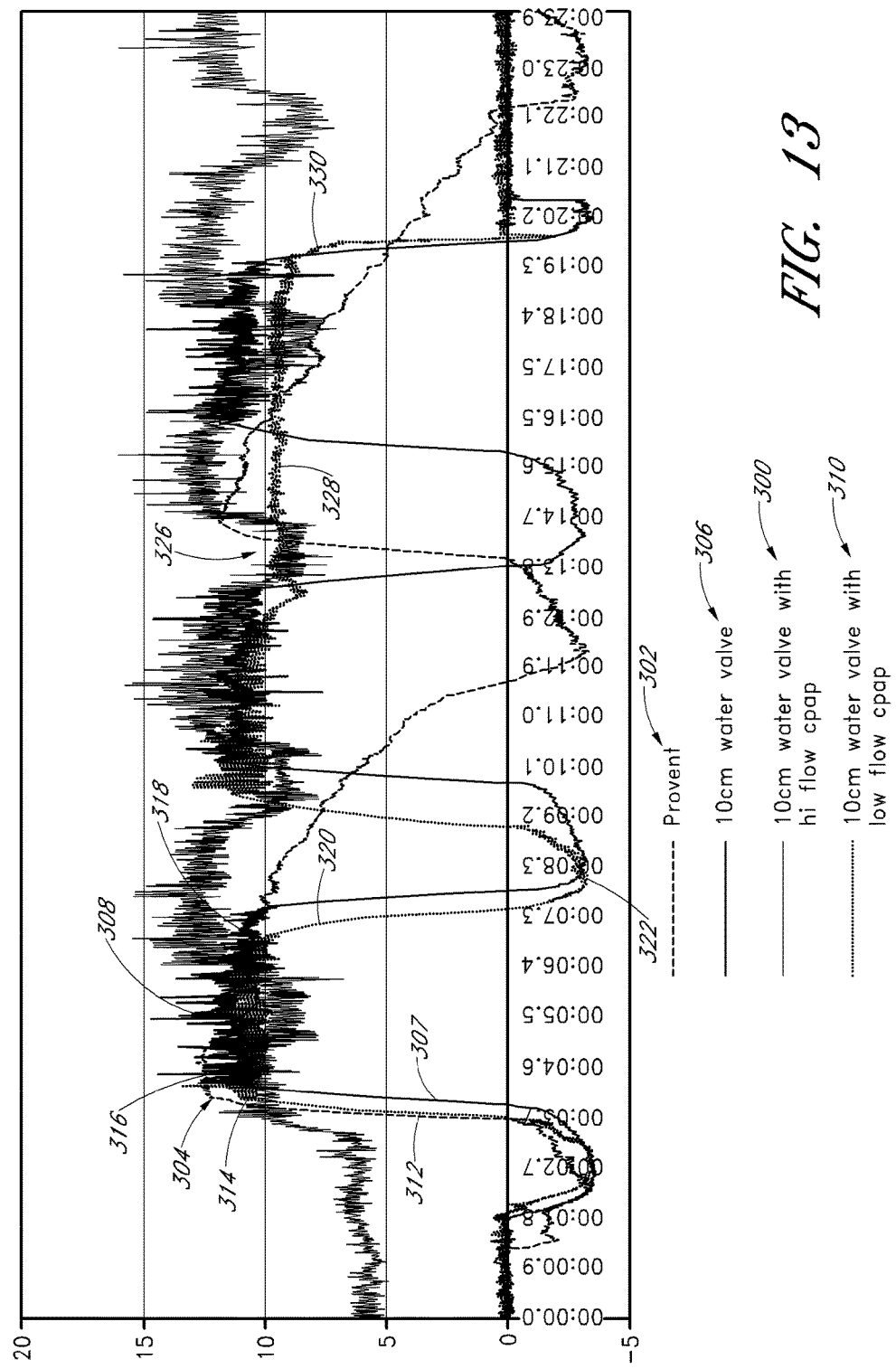
FIG. 13 is a graph comparing intranasal pressure curves for different devices including one embodiment of the present disclosure.
Figure 13A:
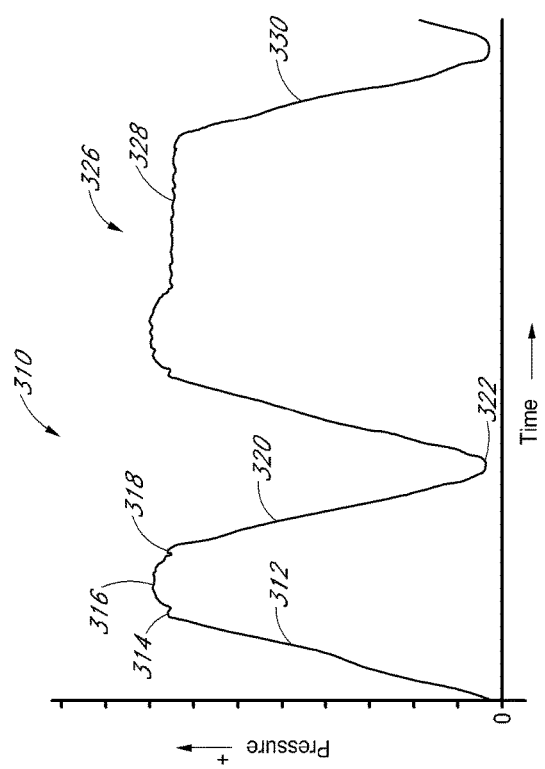
FIG. 13A illustrates the intranasal pressure curve demonstrating breathing mechanics according to the one embodiment shown in FIG. 13.

FIG. 13 compares respiratory curves for different sleep apnea devices. Specifically, FIG. 13 compares standard CPAP 300 and Provent® 302 with respiratory curves for some embodiments described herein 306, 310. FIG. 13A specifically illustrates the curve 310.

Figure 13B:
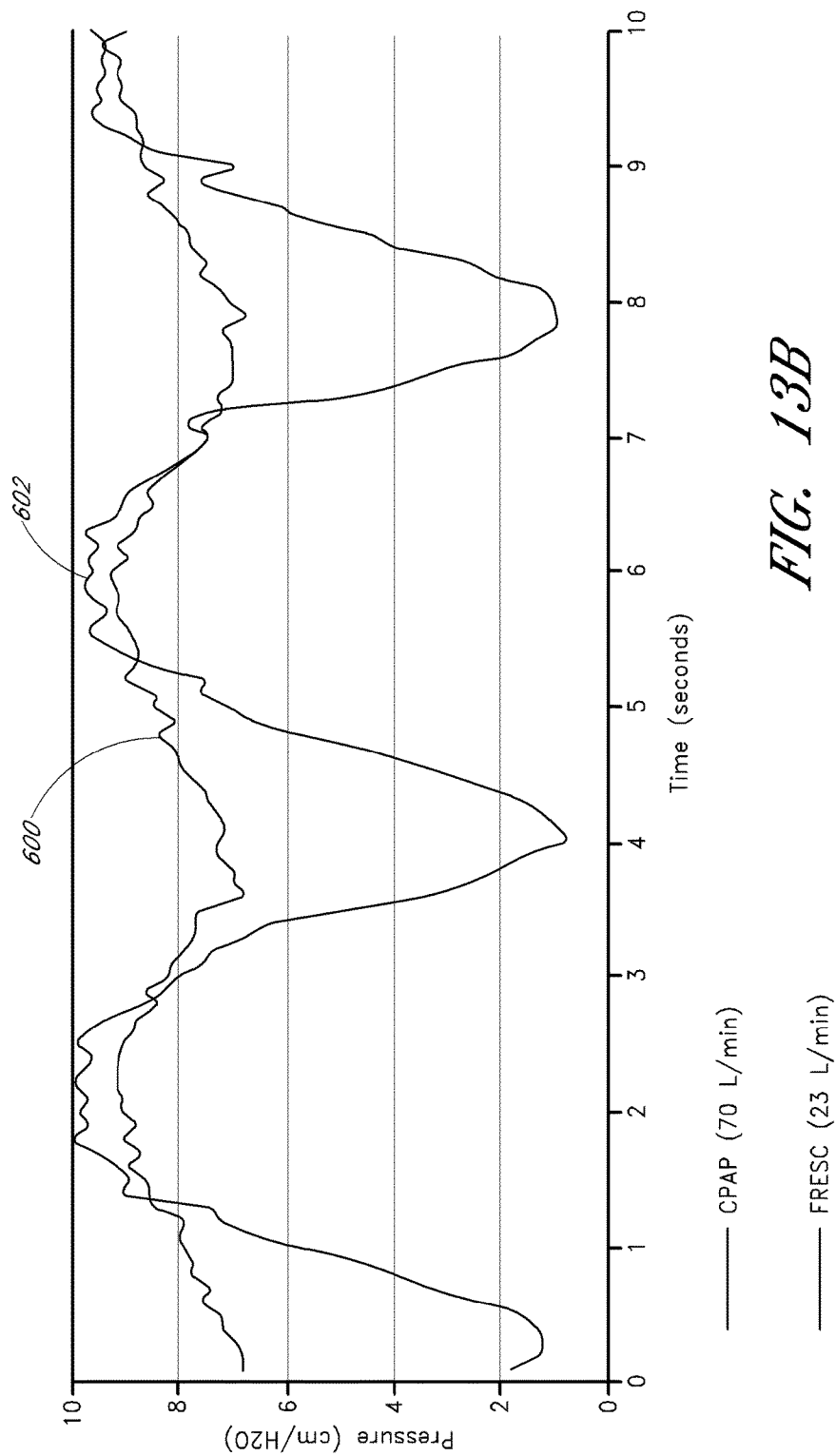
FIG. 13B is a graph comparing intranasal pressure curves for CPAP and the one embodiment shown in FIG. 13.

FIG. 13B is another graph comparing CPAP 600, and a curve 602 of an embodiment of a device 400 described herein with external airflow. The CPAP curve 600 can include features similar to the CPAP curve 300, while the curve 602 can include features similar to the curve 310. As described above, the CPAP curve 300 stays elevated during the breathing cycle because the airflow generator delivers air at high flow rates. The constant elevated pressure can make breathing generally difficult.

With Provent®, the respiratory curve 302 includes a sharp pressure transition 304 during the initial portion of exhalation because the Provent® device utilizes a fixed diameter hole to produce resistance. Accordingly, pressure is based primarily on the rate of exhalation. During initial expiration, the pressure starts at about 12 cm H2O and decreases gradually so that it is approximately 5 cm H2O near the end of expiration.

Curve 306 illustrates a respiratory curve for a device with an expiratory valve, as described herein, and no airflow generator. The expiratory valve can be configured to create pressure without external airflow. The expiratory valve used in curve 306 is configured to vary resistance and release pressure if the pressure exceeds a threshold pressure. As airflow increases, the expiratory valve can decrease resistance to keep pressure constant.

At the beginning of exhalation, the slope of the ramp 307 can be dependent on the force of exhalation. As expiratory force increases, the slope of the ramp 307 increases. However, above the threshold pressure, the valve can open and pressure can be controlled independent of flow. After the valve opens, the curve 306 can exhibit a plateau region 308. In the plateau region 308, the expiratory valve can maintain a generally constant pressure even as the rate of exhalation changes. The threshold pressure can be varied. In certain aspects, the pressure can remain generally constant and can be at least about 5 cm H2O and/or less than or equal to about 20 cm H2O. In certain aspects, the pressure can remain generally constant, e.g., variation within a range of no more than about 4 cm H2O, preferably no more than about 2 cm H2O; in one implementation, between about 8 cm H2O and 12 cm H2O or within about 9 cm H2O and about 11 cm H2O; and, in one embodiment, at about 10 cm H2O.

In some embodiments, there is no external airflow. Without the external airflow, the breathing curve 306 can reach a minimum pressure that is lower than CPAP's minimum pressure. Accordingly, even without external airflow, the breathing curve 306 can better resemble a normal breathing curve. In certain aspects, the minimum pressure can be less than or equal to 5 cm H2O, less than or equal to atmospheric pressure, or otherwise.

The curve 310 illustrates a respiratory curve for a device with an expiratory valve and an airflow generator supplying constant airflow. The expiratory valve can be configured to create pressure without external airflow. In certain aspect, the expiratory valve can be configured to open and release pressure if the pressure exceeds a threshold pressure. In certain aspects, the expiratory valve can vary resistance. In certain aspects, the resistance can be inversely dependent on flow. As airflow increases, resistance can decrease to keep pressure constant. In certain aspects, the expiratory valve can be a spring valve.

At the beginning of exhalation, the slope of the ramp 312 can be dependent on the rate of exhalation. The addition of air from the airflow generator can decrease the slope of the ramp 312 and create parabolic curve transitions 314, 318. In certain aspects, the change in pressure can be less than or equal to about 40 cm H2O/sec, less than or equal to about 15 cm H2O/sec, less than or equal to about 10 cm H2O/sec, or otherwise. In effect, the airflow generator can make exhalation more comfortable.

In certain aspects, above a threshold pressure, the valve can open and pressure can be maintained independent of flow. After the valve opens, the curve 310 can exhibit a plateau region 316. In the plateau region 316, the pressure can remain generally constant even as the rate of exhalation changes. In certain aspects, the pressure can remain generally constant and can be at least about 5 cm H2O and/or less than or equal to about 20 cm H2O. In certain aspects, the pressure can remain generally constant at about 10 cm H2O. If the pressure were to exceed the threshold pressure, expiration could become difficult.

The combination of the expiratory valve and the airflow generator can influence the transition 320 from exhalation to inhalation. If pressure is kept elevated until the point when inhalation begins, it is less likely that the throat will collapse enough to obstruct inhalation. In certain aspects, the device can include a column of air that can help maintain airway pressure at a desired level at the critical time when the patient changes from expiration to inspiration. In certain aspects, as pressure decreases, the expiratory valve can gradually close to help maintain pressure. At the end of expiration, the expiratory valve can close completely.

In certain aspects, the pressure at the end of expiration is at least about 5 cm H2O and/or less than or equal to about 20 cm H2O. In certain aspects, the pressure at the end of expiration is between about 9 cm H2O and about 11 cm H2O, and in one embodiment, about 10 cm H2O.

In certain aspects, the change in pressure can change from the pre-determined pressure to atmospheric pressure in less than about 1 second, less than about 0.5 seconds, or otherwise. In certain aspects, the pre-determined pressure can be at least about 5 cm H2O and/or less than or equal to about 20 cm H2O. In certain aspects, the pre-determined pressure can be about 10 cm H2O.

During inhalation, an inspiratory valve can open to allow ambient air to enter the device. The addition of airflow from the airflow generator can help round the bottom edge 322, which, in effect, eases the transition from exhalation to inhalation.

Although the curve 310 includes the application of an air flow generator, the air flow generator and related air supply sub-assembly supply air at a rate of less than or equal to about 60 L/min, less than or equal to about 40 L/min, less than or equal to about 20 L/min, or otherwise. In certain aspects, the airflow generator can be set at a pressure that is more than, less than or equal to about the threshold pressure of the expiratory valve. In certain aspects, the airflow generator can be set at a pressure that is at least about 5 cm H2O and/or less than or equal to about 20 cm H2O. In certain aspects, the airflow generator can be set at a pressure that is less than or equal to about 10 cm H2O.

With lower flow rates, the airflow generator maintains pressure during apneic events and improves comfort without high airflow. In addition, the breathing curve 310 can reach a minimum pressure that is lower than CPAP's minimum pressure. Accordingly, the breathing curve 306 can better resemble a normal breathing curve. In certain aspects, the minimum pressure can be less than or equal to about 5 cm H2O, less than or equal to atmospheric pressure, or otherwise.

The curve 310 simulates an apnea at the second curve 326. Even during an apneic event, the pressure can stay elevated 328 due to the inflow of air from the airflow generator. For example, if the user stops breathing during exhalation, the pressure generated from the airflow generator helps increase pressure until the pharynx reaches a pressure equal to that which opens the expiratory valve. If the user stops breathing during inhalation, the inspiratory valve closes and the pressure from the air flow generator helps raise the pressure again until the user inhales normally. When breathing resumes, the pressure decreases normally 330 for inspiration.

The combination of ambient air and the additional airflow can help rapidly pressurize the system 328 to quickly eliminate any apneas. In certain aspects, the system can re-pressurize the system from atmospheric pressure to a threshold pressure in less than about 5 second, less than about 3 second, or less than or equal to about one second. In certain aspects, the threshold pressure can be at least about 5 cm H2O and/or less than or equal to about 20 cm H2O. In certain aspects, the threshold pressure can be about 8 cm H2O, about 10 cm H2O, about 15 cm H2O, or otherwise.

In certain aspects, the device can re-pressurize with an airflow generator and air supply tubing administering airflow at less than or equal to about 60 L/min, less than or equal to about 40 L/min, less than or equal to about 20 L/min or otherwise.

In certain aspects, the system can re-pressurize the airway at a rate of at least about 10 cm H2O/second at an external air flow of less than or equal to about 60 L/min. In certain aspects, the system can re-pressurize the system at a rate of at least about 20 cm H2O/second at an external air flow of less than or equal to about 40 L/min. This rapid increase in pressure is also possible in part because of a lack of holes or leak paths in the device assembly and a low interior volume within the device assembly.

FIGS. 19-37 and the associated text describe an exemplary device assembly that can be used to achieve curve 306 or curve 310.

Figure 14:
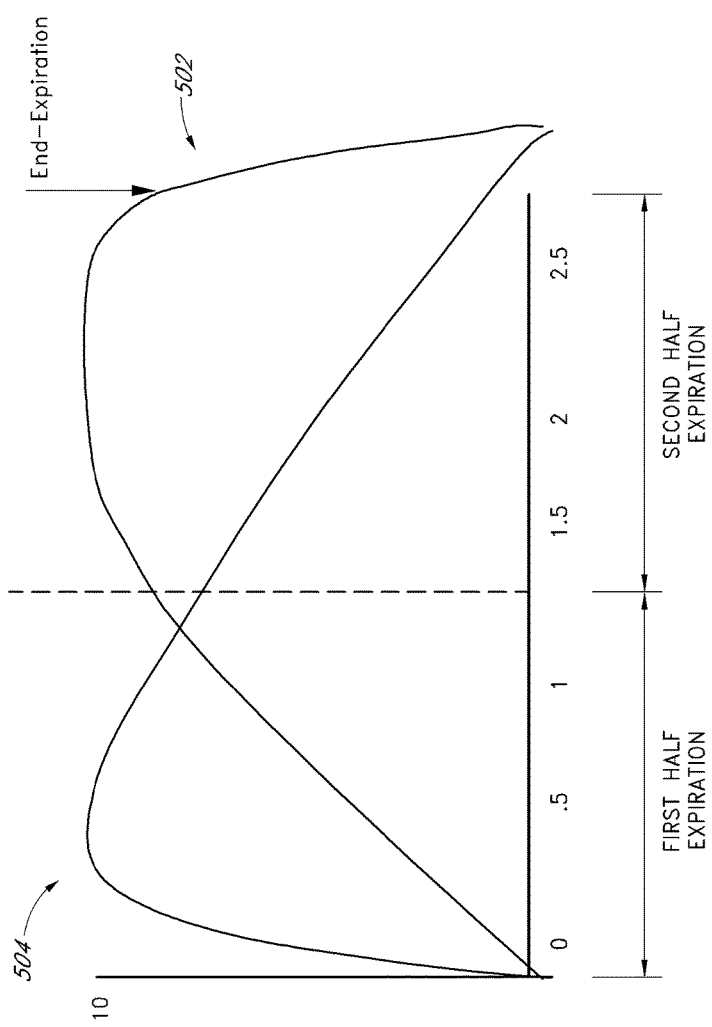
FIG. 14 is a graph comparing intranasal pressure curves for different devices including a device having a variable resistance valve capable of varying resistance independent of flow.

In certain variants, the expiratory valve can be a smart valve configured to apply an amount of resistance that is independent of flow. With the "smart valve," the device assembly can achieve high pressure even at low flow rates to maximize comfort. For example, if the flow rate is too high, the valve can open, so the pressure rises more slowly. If the flow rate is too low, the valve can close to help maintain pressure. FIG. 14 illustrates a smart valve curve 502 against a Provent® curve 504. The Provent® curve 504 exhibits features similar to the Provent® curve 302.

In certain aspects, the smart valve can help make expiration more comfortable by controlling one or more aspects of the breathing curve. As shown in curve 502, the smart valve can influence the slope of the ramp such that the rise in pressure is more gradual. In certain aspects, the rise in pressure is at a rate of no more than about 20 cm H2O/second, no more than about 12 cm H2O/second, and generally no more than about 10 cm H20/sec, or otherwise. Thus, the climb in pressure during exhalation to a reference pressure of 8 cm H2O requires greater than about 0.25 second, preferably greater than about 0.5 seconds, and, in some implementations, greater than about 1 second. In certain aspects, the expiratory valve can influence the slope of the ramp such that the mean pressure in the first half of expiration is less than the mean pressure in the second half of expiration.

In certain aspects, the expiratory valve can maintain a maximum pressure until the end of exhalation. In certain aspects, the maximum pressure is at least about 5 cm H20 and/or less than or equal to about 20 cm H2O. In certain aspects, the maximum pressure is between about 9 cm H2O and 11 cm H2O, and, in one embodiment, is about 10 cm H2O.

In certain aspects, the resistance at about 0.5 seconds before the end of expiration can be higher than the resistance at about 0.5 seconds after the beginning of expiration. In certain aspects, the pressure can drop from the maximum threshold pressure to atmospheric pressure in less than one second, less than 0.5 seconds, or otherwise. Maintaining an elevated pressure until the end of exhalation ensures that the airway pressure is maintained at a desired level at the critical time when the patient changes from expiration to inspiration.

In certain aspects, the expiratory valve can help create an average expiratory time of less than or equal to three seconds to mimic normal breathing.

Figure 15A:
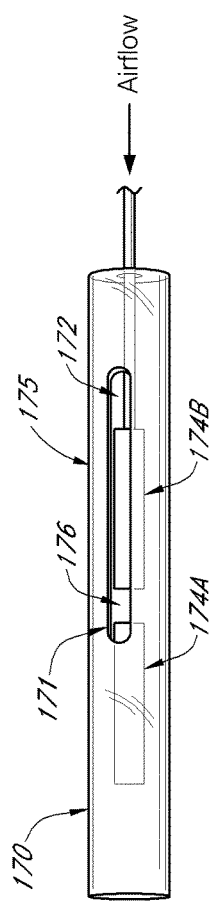
FIGS. 15A and 15B are perspective views of a slit-tube valve for providing variable resistance during expiration, according to one embodiment.
Figure 15B:
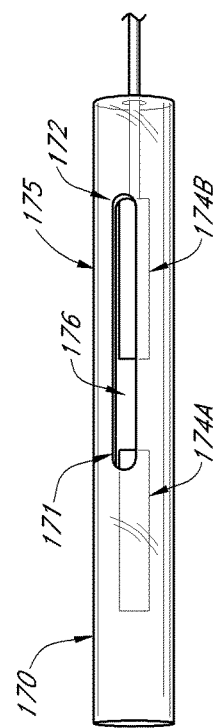

With reference now to FIGS. 15A and 15B, another variable resistance, one-way valve device 170, which may be used as part of an OSA device or system, is illustrated. In this embodiment, device 170 includes a tube 175 with a slit 171 and two opposing magnets, such as magnetic rods 174A and 174B, disposed in tube 175. As illustrated in FIG. 15A, rod 174B is displaced by airflow in the direction of rod 174A during an initial portion of the expiratory phase to shorten the gap 176 between them and create an opening 172 in slit 171, through which exhaled air may pass. As illustrated in FIG. 15B, as the expiratory airflow declines rod 174B will move farther away from rod 174A, thus closing opening 172. In various embodiments, one of rods 174 may be coupled with a stationary support member, and the other rod 174 may be free to move. In addition, rods 174 may have facing ends that either oppose or attract one another, according to various embodiments, and may be forced to move in one way or another, based on whether they tend to oppose or attract.

Figure 16A:
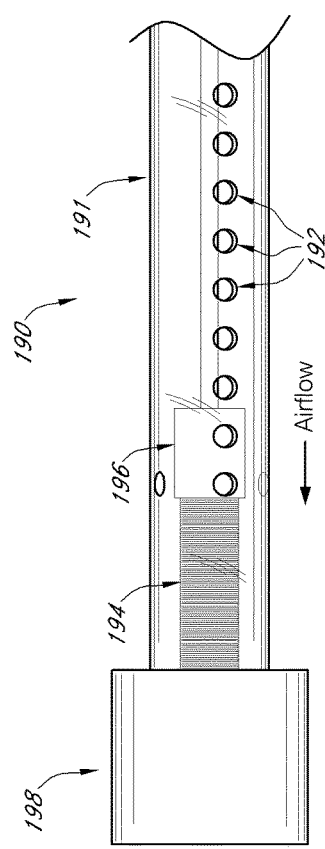
FIGS. 16A and 16B are perspective views of a fluted-tube valve for providing variable resistance during expiration, according to one embodiment.
Figure 16B:
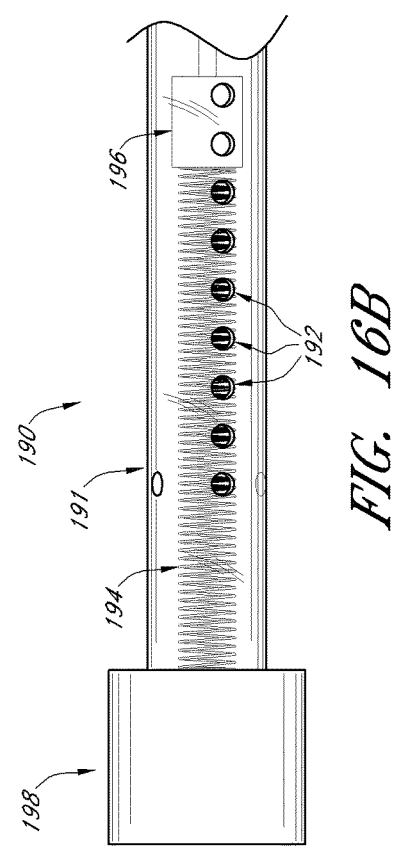

Referring now to FIGS. 16A and 16B, in another embodiment, a variable resistance valve device 190, which may be a one-way valve, may include a tube with multiple apertures 192 disposed along part of its length, and a movable airflow blocker 196, such as a piston or other movable wall carried within the tube. A spring 194 is attached at one end to airflow blocker 194, and at the other end to an attachment point such as the sidewall of the tube or a stationary support member 198. As illustrated in FIG. 16A, when a patient exhales ("<<Airflow"), the force of the exhaled air pushes against air flow blocker 196, which compresses spring 194 and exposes a number of apertures 192 in proportion to the exhaled air flow, through which exhaled air can escape from tube 191. As the flow of exhaled air decreases, as in FIG. 14B, spring 194 elongates, pushing airflow blocker through tube 191, such that fewer apertures 192 are exposed for the release of exhaled air. At the end of exhalation, no apertures 192 are available—i.e., valve 190 is closed. The apertures can be replaced by one or two or more axially extending slits, and the spring can be mounted for either compression or tension under exhaled airflow.

Figure 17A:
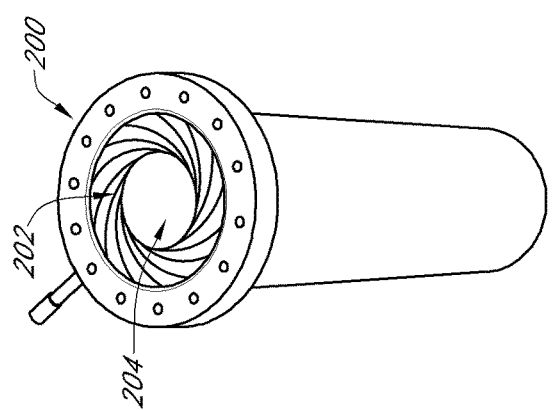
FIGS. 17A-17C are perspective views of an iris valve for providing variable resistance during expiration, according to one embodiment.
Figure 17B:
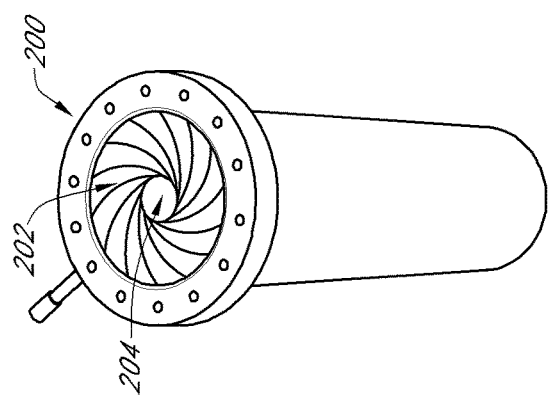
Figure 17C:
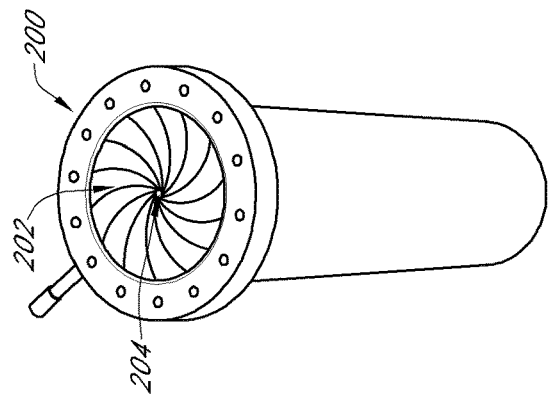

With reference now to FIGS. 17A-17C, in yet another embodiment, a variable resistance valve device 200, which may be a one-way valve, may include an iris valve 202 that opens and closes to allow exhaled air to escape while providing resistance to expired air. As shown in FIG. 17A, at the beginning of expiration, iris 202 may open to provide an opening 204 having a first diameter. As airflow decreases during the course of the expiratory phase, as in FIG. 17B, iris may close partially, so that opening 204 assumes a second, smaller diameter to maintain pressure above a predetermined minimum. Finally, toward the end of expiration, as in FIG. 17C, opening 204 may shrink to a third, smallest diameter and may close all the way at end expiration. As with the previously described embodiments, closure of valve 200 may occur in increments or continuously during expiration, according to various embodiments.

As mentioned above, the various embodiments of variable resistance, one-way, expiratory valves described in this application may generally be driven (or actuated) in one of two different ways. In some embodiments, expiratory valves may be automatically driven in response to the patient's breath. For example, a flap valve, comprising a flexible diaphragm of a resilient material, such as Nitinol, may open when the opening pressure of exhalation is achieved and then may close gradually as the flow of exhaled air decreases. A Nitinol valve may also change its shape in response to the heat from a patient's breath. In other embodiments, expiratory valves may be driven by mechanical or electromechanical means. For example, an iris valve as described in FIGS. 17A-17C may be electromechanically programmed to open and close with specified timing, or a blocker such as the one described in FIGS. 16A and 16B may be moved back and forth with a solenoid or other mechanical means. This timing may be according to general timing of breath cycles or may be customized for a patient. In some embodiments, an OSA treatment system may measure patient breathing patterns and use that information to time the opening and closing of a valve. The opening and closing of a valve may be actuated by a controller coupled with the valve, and the controller may receive instructions via wired or wireless electronic connections or by built-in electronics.

In various embodiments, an expiratory valve may be configured to open and close or may be electromechanically forced to open and close at any of a number of suitable pressures and combinations of pressures. In some embodiments, a valve may open and then close continuously/gradually during expiration, while in some embodiments, the valve may close in increments. In various embodiments, a valve may have an opening pressure of between about 0 cm H2O and about 15 cm H2O, or more preferably between about 2 cm H2O and about 5 cm H2O. In some embodiments, the expiratory valve may open at an opening pressure of about 0-5 cm H2O and close at a pressure of at least about 5 cm H2O. Alternatively or additionally, the valve may be configured to generate an intra-airway pressure of about 0-5 cm H2O during an early portion of expiration and an intra-airway pressure of about 5-20 cm H2O during a later portion of expiration. In some embodiments, the expiratory valve is configured to generate greater intra-airway pressure during the later portion of expiration than during the early portion. In some embodiments, an opening of the expiratory valve may have a larger surface area and/or diameter during the early portion of expiration and a smaller surface area and/or diameter during the later portion of expiration.

In one embodiment, a device for treating OSA and/or snoring may include simply a mask (or nostril insert or covering) for covering the nose (or at least the nostrils) of a patient, along with one or two variable resistance, one-way, expiratory valves. Such a device may be configured as a nasal pillow, a nose-only mask, a mouth-only mask, or a nose-and-mouth mask. Such a device may be used by itself, without any positive airflow device (airflow generator, tube, etc.), to help treat OSA and/or snoring by generating expiratory resistance during the expiratory phase of breathing. In some embodiments, such a device may also be compatible with a positive airflow generator—either a CPAP machine or a smaller, low-flow machine as described herein. In other embodiments, such a device may be a stand-alone therapy.

Figure 18B:
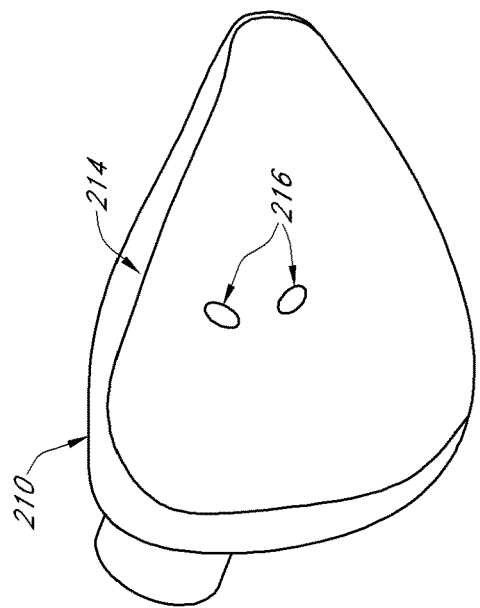
FIGS. 18A and 18B are perspective views of a custom made nasal mask, according to one embodiment.
Figure 18A:
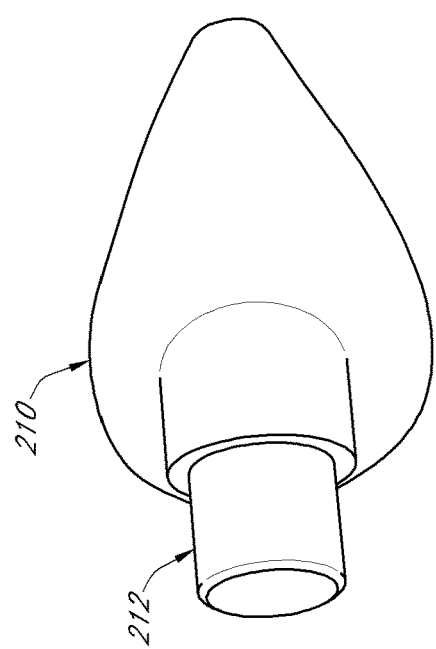

With reference now to FIGS. 18A and 18B, a prototype of one embodiment of a custom manufactured nasal mask 210 is illustrated. Nasal mask 210 generally includes a port 212 for attaching to an airflow generator tube, a sealing surface 214 for creating a seal (or at least for conforming with) the patient's face around the nose, and openings 216 for allowing breathing through the nostrils. Custom made mask 210 may be manufactured in any suitable fashion. In one embodiment, mask 210 may be made by placing a mask making material or standard-shaped mask over a patient's face, assessing the shape of the patient's face using the material, and then customizing the mask based on the assessment. In another embodiment, mask 210 may be made by assessing the patient's face in advance, such as by taking a digital photographic image or CT scan of the patient's head, and then using that data to form mask 210. For example, CT scan data may be used to make a negative image of the patient's face, and the negative image may be used to make a mold from which mask 210 may be formed.

As mentioned previously, in some embodiments, a mask may take any of a number of other forms and sizes. In some embodiments, for example, a mask may be configured similar to a nasal pillow. In other embodiments, a mask may be a nasal-only mask, resting over the patient's nose and surrounding the nostrils. In yet another embodiment, a mask may cover only the mouth of the patient, and in yet another embodiment, the mask may cover the patient's mouth and nose. In some embodiments, a mask may include an energy conversion device for converting breath energy into electrical energy. In some embodiments, a mask may alternatively or additionally include an air flow generator attached directly to the mask. In these and other embodiments, one or more straps may be attached to the mask to help attach it to a patient's head.

In many embodiments, however, such as the embodiment shown in FIGS. 18A and 18B, mask 210 is configured to conform to a patient's nose and/or includes a contact surface with adhesive, such that it may be comfortably worn over the nose without the use of any straps and without falling off. By conforming to the patient's face, forming a seal with the patient's face, or both, masks 210 described in this application will reduce or eliminate the air leaks that occur with currently available CPAP mask, thus eliminating the need for high-pressure, high-flow-rate air and thus eliminating many of the side effects of CPAP.

In some embodiments, the system that has been described herein may be used not only for providing air flow and resistance when needed to help treat OSA or snoring, but may also be used to deliver one or more airborne therapeutic substances to a patient. For example, an OSA system as described herein may be used to deliver oxygen, supplements, steroids, or any other medication or treatment that may be delivered in gaseous form or aerosolized. Some potential conditions that may be treated using the system as a therapeutic substance delivery device include but are not limited to COPD, rhinitis, pneumonia, acute respiratory distress syndrome, and/or acute lung injury.

Additionally, the OSA treatment system described herein may also be used to treat conditions other than OSA. For example, the system may be used to treat some patients with chronic obstructive pulmonary disease (COPD) or emphysema. In these cases, the system may be adjusted to provide a different amount of positive air flow than that used in treating OSA. In COPD or emphysema, for example, little or no positive air flow may be used, and the system may predominantly work by providing resistance to exhalation. The system may be similarly used in/adjusted for treatment of other disease states.

In various alternative embodiments, a device for treating OSA may include one or more nasal coverings to cover one or both nostrils and one or more expiration airflow resistors coupled with the nasal coverings in such a way as to provide resistance to expired/exhaled air. In one embodiment, for example, the nasal covering may be a mask similar to that shown in FIGS. 4A-4E. However, rather than attached to a tube and air flow generator, this alternative embodiment of a mask would not include an air flow generator valve and would be a stand-alone device. It may include one or multiple expiratory valves. It may also include an inspiration valve, or expiration and inspiration valve(s) may be combined, with resistance to expiration being greater than resistance to inspiration. The mask may form an airtight seal, as previously described. Such a device would thus help provide expiratory pressure (PEEP and/or EPAP), but would not provide enhanced inspiratory pressure. In some embodiments, the exhalation valve may increase resistance to exhaled air over the course of the expiratory phase, as described in detail above.

In one example of such an alternative embodiment, a nasal device such as those described in U.S. Pat. Nos. 8,061,357 and 7,798,148 (hereby incorporated by reference) may be improved by providing such a device with a variable resistance valve, as described above. Again, such a valve may be configured to open at an opening pressure and then gradually, continuously, and/or progressively close over the course of an expiratory phase to provide increasing amounts of resistance. In some embodiments, such a valve may open at an opening pressure and then open further during exhalation to provide decreased resistance and maintain pressure within a desired range. Such a device, with any of a number of "variable resistance" valves, may help provide PEEP and/or EPAP in a way not achieved by the valves described in the above-referenced patents. In various alternative embodiments, the variable resistance valve may be used on a single-nostril device, a two-nostril (whole-nose) device, a mask that covers the nose (both nostrils) or a mask that covers the nose and mouth. A single nostril device typically includes one valve, while two-nostril devices may include one valve or multiple valves, such as one valve per nostril. In some patients, a mask that covers the nose and mouth may be advantageous, since some patients switch to mouth breathing when experiencing resistance to exhaling through the nose.

Any of the valves described above may be used with these nasal covering/airway resistor embodiments. For example, valves may include but are not limited to the flap valve and the membrane valve described above. In alternative embodiments, valves that open initially at a predetermined opening pressure and later close down partially during exhalation to increase resistance may be used in some embodiments.

FIGS. 19-37 illustrate an exemplary embodiment of a device 400 configured to exhibit one or more respiratory properties discussed herein. The features of the device 400 described below are generally designed to create a unique breathing profile as discussed above, increase patient comfort, and create an aesthetically pleasing device. Increasing patient comfort will help increase patient compliance.

In certain aspects, the dimensions of the device 400 can be configured to decrease the total size and weight of the device 400 as compared to traditional CPAP devices. The embodiments described herein can unchain the customer from the bedside table where traditional CPAP air flow generators usually sit. In addition, the embodiments described herein can be travel size, so that they do not need to be checked at the airport. Further details regarding the dimensions of the device assembly are described below.

Figure 19:
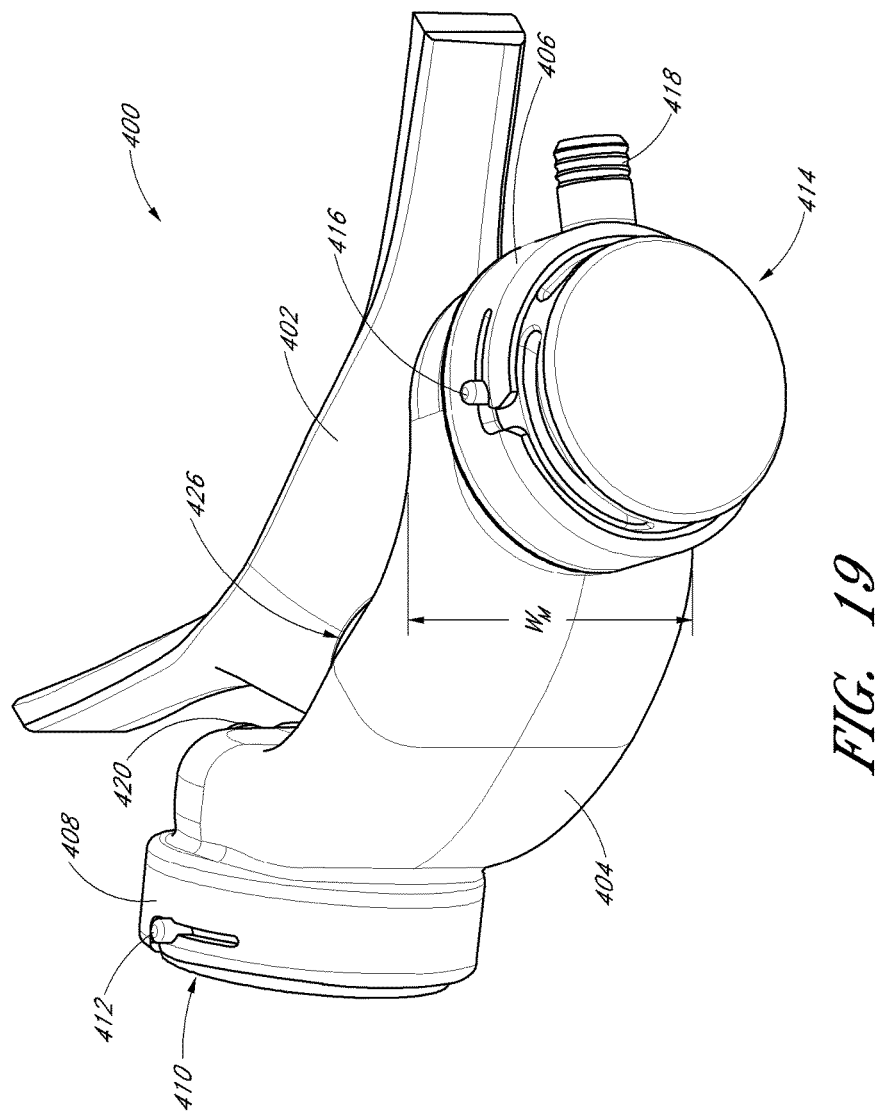
FIG. 19 illustrates an exemplary embodiment of a device assembly.

As shown in FIG. 19, the device 400 can be configured to be worn by a user. The mask portion 402 and/or manifold 404 can be secured to a user's face using any securing feature, including, but not limited to, a frame, an adhesive, straps, Velcro, and/or buckles. In certain aspects, the device 400 can be strapped to the user's face using one or more straps. In certain aspects, the straps are provided with a releasable connection to the device 400, such that they are replaceable or exchangeable. For example, the user can use one set of straps for travel or otherwise while awake and a different set of straps for bed. In certain aspects, the device assembly can include frame portions extending from the manifold 404 or mask 402. The frame portions can extend across at least a part of the user's face, for example, to a position near the user's ears or over the user's ears. At least a part of the frame portions can include a resilient material, such as a rubber material, to increase patient comfort.

In certain aspects, the mask portion 402 can include any of a variety of resilient materials capable of conforming to the user's face. For example, the mask portion 402 can include a gel to help conform the mask portion 402 to the user's face, or an interface comprising silicone or other elastomers or polymers known in the art.

In certain aspects, the mask portion 402 can include one or more openings configured to permit the inflow and outflow of air. Each of the one or more openings can be configured to be in air flow communication with, and potentially at least partially align with a nasal cavity. In certain aspects, the mask portion 402 can include two openings, each opening configured to align with a nasal cavity.

Figure 20:
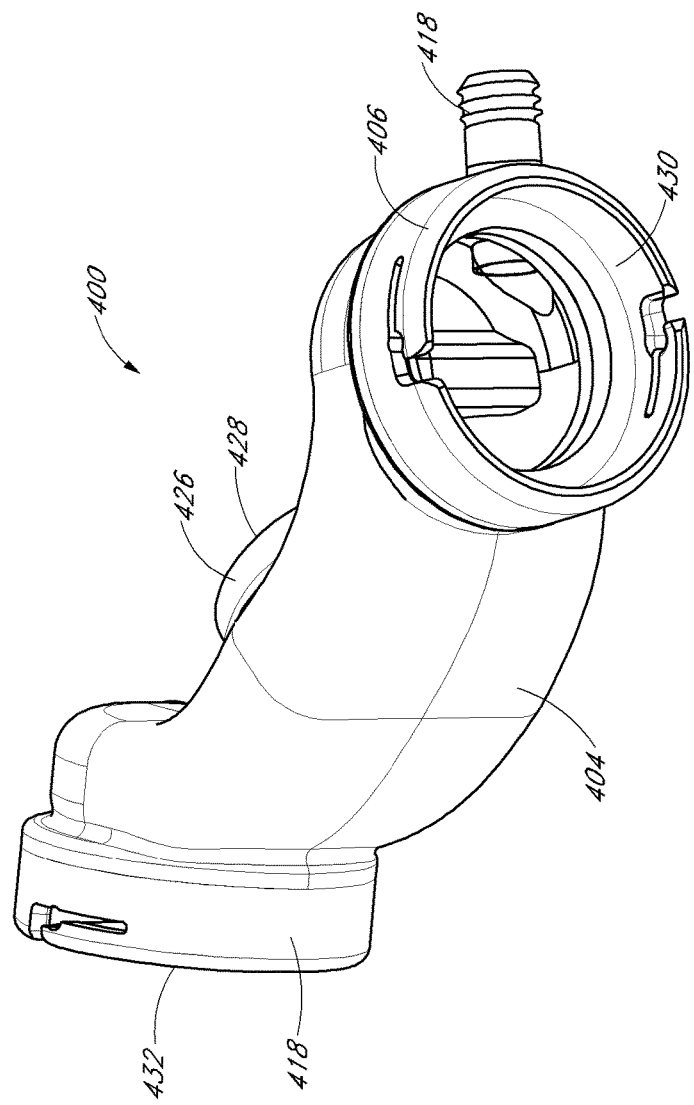
FIG. 20 illustrates an exemplary embodiment of a manifold of the device assembly illustrated in FIG. 19.
Figure 21A:
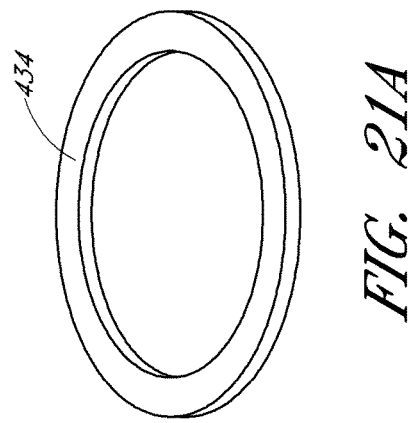
FIGS. 21A-C illustrate an exemplary embodiment of a valve seat seal of the device assembly illustrated in FIG. 19.
Figure 21C:
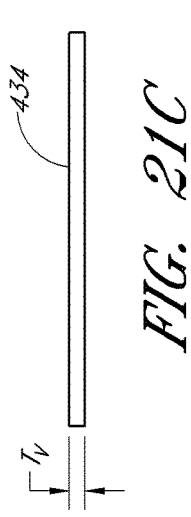
Figure 21B:
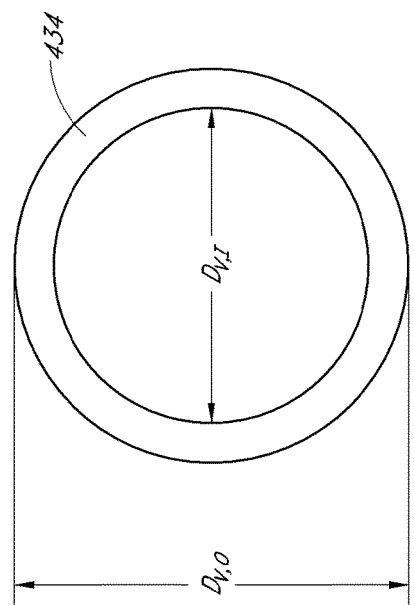

As shown in FIGS. 19-20, the device 400 can include a manifold 404. In certain aspects, the manifold 404 can be configured to generally fit the contours of the user's face. For example, the manifold 404 can have a generally curved configuration.

The mask portion 402 can be coupled directly or indirectly to the manifold 404. In certain aspects, the manifold 404 can directly engage the mask portion 402 using any connection mechanism, including, but not limited to, a detent, an adhesive, a curing technique, a molding technique, a screw-fit, a snap fit, and/or an interference fit. As shown in FIG. 20, the manifold 404 can include a fitting 426 designed to removably or permanently engage the mask portion 402.

In certain aspects, the manifold 404 can include one or more openings configured to permit the inflow and/or outflow of air through a valve, air supply tubing, and/or the mask. Unlike traditional CPAP devices, neither the manifold 404 nor the mask 402 typically includes intentional leak paths.

In certain aspects, the manifold 404 can include a mask opening 428 disposed on the same side of the manifold as the mask portion 402 and in communication with the user's nasal cavity. In certain aspects, the manifold 404 can include an inspiratory opening 432 in communication with an inspiratory valve 410 and/or an expiratory opening 430 in communication with an expiratory valve 414.

The manifold 404 can be directly or indirectly connected to one or more valves. In certain aspects, the manifold 404 can engage the mask portion 402 on a first side of the manifold 404 and engage the one or more valves on a second side of the manifold 404. In certain aspects, the mask portion 402 and valves can be positioned on the same side of the manifold 404. In some examples, the manifold 404 can be coupled to a first side of a valve, and the mask portion 402 can be coupled to a second side of the valve.

In certain aspects, the device 400 can include a separate inspiratory valve 410 and an exhalation valve 414 to help create tailored breathing profiles as described above. In certain aspects, the inhalation 410 and exhalation 414 valves are sized and positioned so that they do not blow on the patient in an uncomfortable way. In addition, the inhalation 410 and exhalation 414 valves can be sized and positioned for better aesthetics and ergonomics. In certain aspects, the valves can be configured to minimize noisy outflow. For example, the valves can be designed with smaller outlets. Further details regarding valve dimensions are described below.

In the exemplary embodiment shown in FIGS. 19-20, the manifold 404 can engage one or more valve inserts, such as an expiratory valve insert 406 and/or an inspiratory valve insert 408. Each valve insert 406, 408 can be coupled together with the manifold 404 using any connection mechanism, including, but not limited to, an adhesive, a cure technique, a molding technique, a detent, a screw-fit, a snap fit, and/or an interference fit.

Each valve insert 406, 408 can engage a valve 410, 414. The valve inserts 406, 408 can be configured to facilitate the exchange of valves 410, 414 depending on the desired resistance profiles. The ability to exchange valves can improve the capability of doctors to perform patient evaluations and customize or adjust the performance of the device 400.

In certain aspects, the inspiratory valve insert 408 can be coupled to the inspiratory valve 410. Although FIG. 19 illustrates a detent 412 connecting the inspiratory valve insert 408 and the inspiratory valve 410, the inspiratory valve insert 408 and the inspiratory valve 410 can be coupled together using any connection mechanism in alternative to or in addition to the detent 412, including, but not limited to, an adhesive, a cure technique, a molding technique, a screw-fit, snap fit, and/or an interference fit.

In certain aspects, the expiratory valve insert 406 can be coupled to the expiratory valve 414. Although FIG. 19 illustrates a detent 416 connecting the expiratory valve insert 406 and the expiratory valve 414, the expiratory valve insert 406 and the expiratory valve 414 can be coupled together using any connection mechanism in alternative to or in addition to the detent 416, including, but not limited to, an adhesive, a cure technique, a molding technique, a screw-fit, a snap fit, and/or an interference fit.

In certain aspects, one or both of the valves 410, 414 can be directly connected to the manifold 404 and/or mask 402 using any suitable connection mechanism, including, but not limited to, an adhesive, a cure technique, a molding technique, a detent, a screw-fit, a snap fit, and/or an interference fit.

In certain aspects, the device 400 can include one or more air supply connectors 418, 420 configured to engage one or more air supply tubes. Each connector 418, 420 can be coupled to the device 400 using any connection mechanism, including, but not limited to, an adhesive, a curing technique, a molding technique, a detent, a screw-fit, snap fit, and/or an interference fit. The connectors 418, 420 can permit the inflow of air from an air flow generator. Although FIGS. 19-20 illustrate the device 400 having a first air supply connector 420 positioned near the inspiratory valve 410 and a second air supply connector 418 positioned near the expiratory valve 414, the one or more air supply connectors 418, 420 can be positioned anywhere along the device 400 to provide air flow communication with the interior of the manifold, including, but not limited to, a front surface of the manifold 404, a side surface of the manifold 404, a rear surface of the manifold 404, and/or to the mask portion 402.

Figure 19A:
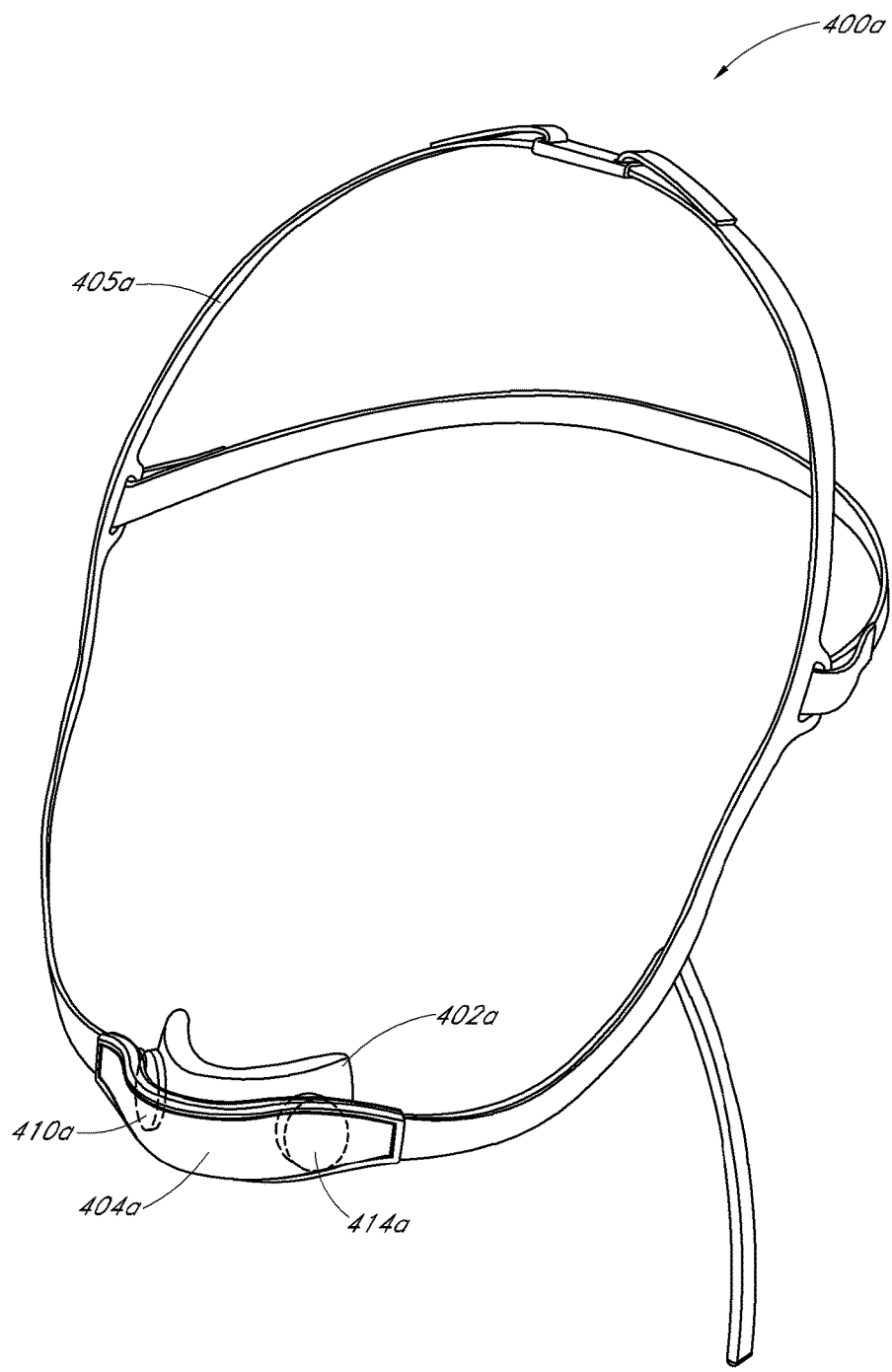
FIGS. 19A-B illustrate another exemplary embodiment of the device assembly.
Figure 19B:
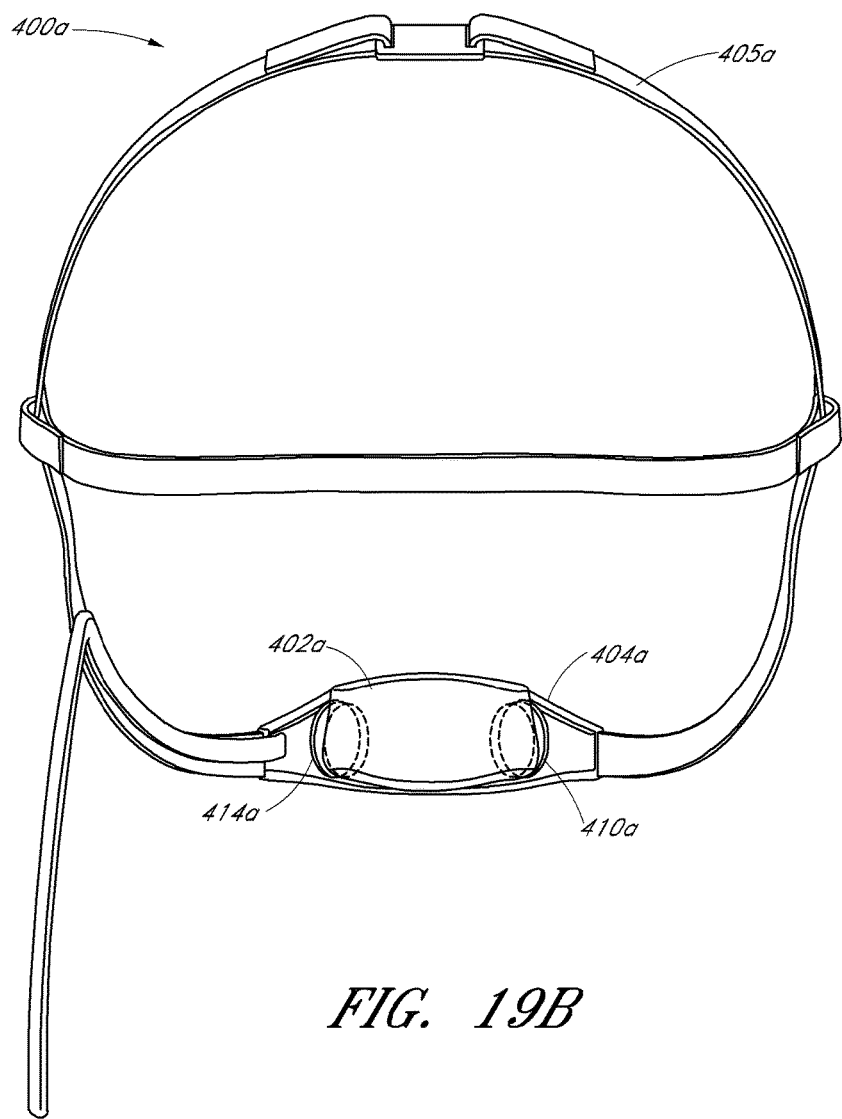

FIGS. 19A and 19B illustrate another embodiment of the device 400a including a mask 402a, a manifold 404a, and straps 405a. The device 400a can include any of the features (e.g., valves, connectors, etc.) described in connection with the device 400 shown in FIG. 19. In addition, the device 400a can include any of the dimensions described in connection with the device 400.

Although the components described with respect to FIGS. 19-20 and sub-components described below are described as separate components, one or more of the components and/or sub-components can be constructed together as a single integral component such as by molding. Each component of the device 400 is described in further detail down below.

The device 400 can include a valve seat seal 434 in contact with each valve insert 406, 408 or manifold 404. In certain aspects, the valve seat seal 434 can be an O-ring. The valve seat seal 434 can provide a sealing mechanism for ensuring that no air leaks or flow disruptions occur even during pressurization changes of less than or equal to about 0.001 psig. The valve seat seal 434 can be constructed using any number of suitable techniques, including, but not limited to machining, stamping, molding, SLA processing, or casting. In certain aspects, the valve seat seal 434 can be constructed from any medical grade polymers or metals, including, but not limited to, silicone, rubber, polyethylene, polyethylene terephthalate, Teflon®, copper, gold, palladium, and/or silver. In certain aspects, the valve seat seal 434 can include a material having a durometer of at least about 10 A and/or less than or equal to about 50 D.

In certain aspects, each valve insert 406, 409 and/or manifold 404 can include a support structure to support the valve seat seal 434, such as a ridge or a recess.

In certain aspects, the valve seat seal 434 can have a thickness $T_v$ of less than or equal to about 0.1 inches, less than or equal to about 0.04 inches, or otherwise. In certain aspects, the outer diameter $D_{V,O}$ of the seal 434 can be less than or equal to about an inner diameter of a valve insert 406, 408, greater than or equal to about an outer diameter of a valve 410, 414, greater than or equal to about a diameter of a manifold opening 430, 432, or otherwise. In certain aspects, the outer diameter $D_{V,O}$ of the seal 434 can be less than or equal to about 1.5 inches, less than or equal to about 1.0 inches, or otherwise. In certain aspects, the valve seat seal 434 can have an inner diameter $D_{V,I}$ of less than or equal to about 1.0 inches, less than or equal to about 0.8 inches, or otherwise.

Figure 22A:
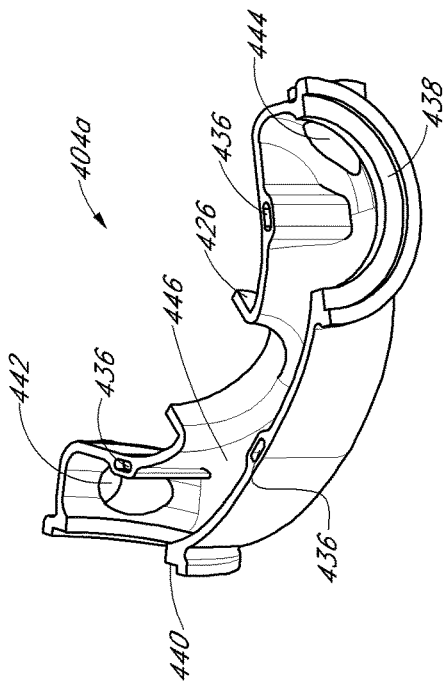
Figure 22B:
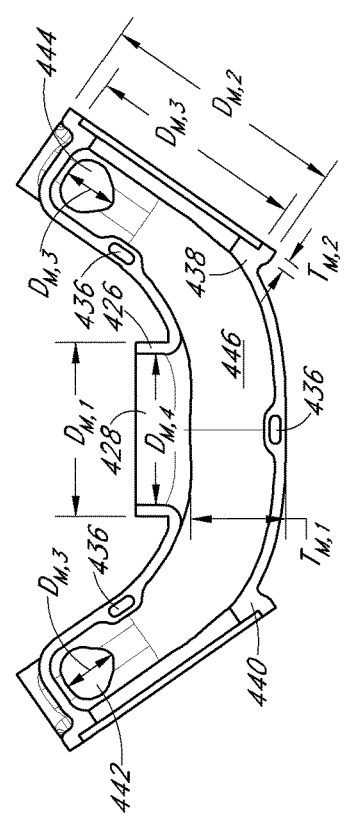
Figure 22C:
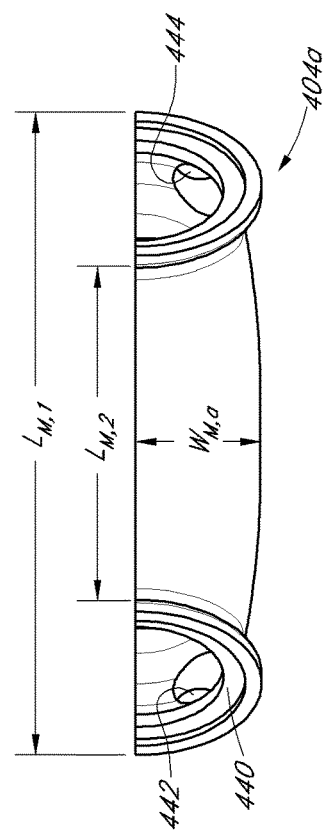

FIGS. 22-23 illustrate a bottom half portion 404a (FIGS. 22A-C) and a top half portion 404b (FIGS. 23A-C) of the manifold 404. The manifold 404 helps maintain the pressure and flow from the inspiratory valve 410 and flow to the expiratory valve 414. The manifold 404 also assists in communicating air supply to the user's air passageway.

Although FIGS. 22 and 33 illustrate the manifold 404 as two separate portions, the manifold can be constructed using any number of components, including a single component. With multiple components, the multiple components can be coupled using any suitable technique, including, but not limited to, bonding, molding, casting, insert molding, SLA processing, stamping, riveting/screwing together, or otherwise. As shown in FIGS. 22-23, the bottom half portion 404a can include one or more connection features 436, such as grooves, configured to mate with one or more corresponding features 448 on the top half portion 404b, such as protrusions.

The manifold 404 can include any medical grade polymers or metals, including, but not limited to, ABS, polycarbonate, nylon, Pebax®, acrylic, ceramic, carbon fiber, palladium, stainless steel, amorphous metal, and/or copper. In addition, the manifold 404 can be plated, coated with corrosion resistant materials, and/or painted.

Figure 35A:
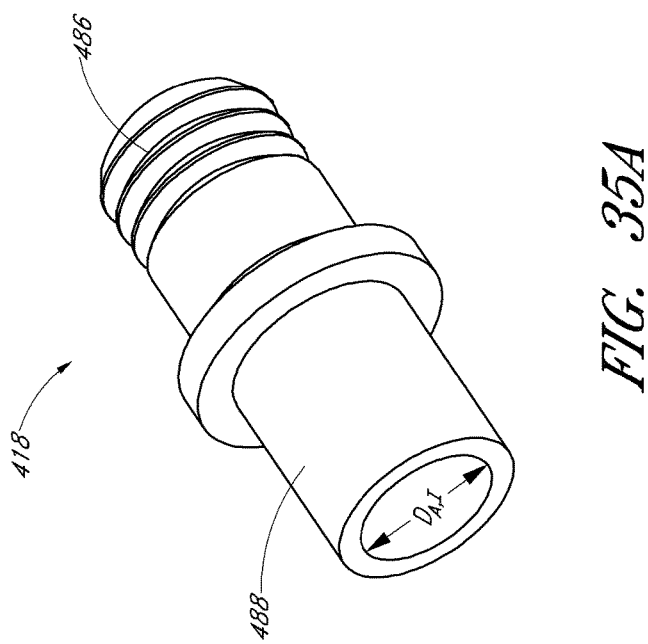
FIGS. 35A-35C illustrate an exemplary embodiment of an air supply connector.
Figure 35B:
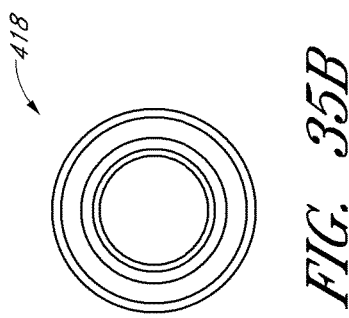
Figure 35C:
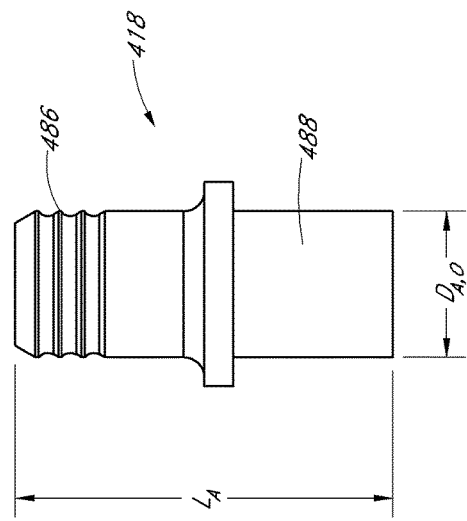

The manifold 404 can include one or more openings 442, 444 in communication with an airflow generator. As shown in FIGS. 22A-22C, the openings 442, 444 can be positioned on along a bottom surface of the manifold 404. However, as described above, the openings 442, 444 can be positioned elsewhere along the manifold 404 and/or mask 402. In certain aspects, the manifold 404 can connect to the air supply tubing (FIG. 36) using air supply connectors 418, 420 (FIGS. 35A-35C). In certain aspects, the manifold 404 can connect directly to the air supply tubing using any connection mechanism, including, but not limited to, adhesive bonding (e.g., using cyanoacrylate), curing (e.g., ultraviolet or otherwise), and/or insert molding.

In certain aspects, the manifold 404 can include one or more valve seats 438, 440 configured to mate with a corresponding feature of each valve insert 406, 408 or valve 410, 414. As shown in FIGS. 22C and 23C, the valve seat 438, 440 can be a recessed portion; however, the valve seat 438, 440 can additionally or alternatively include a groove, flange, protrusion, or otherwise.

The outer diameter $D_{M,2}$ of each of the valve seats 438, 440 can be the same or different. In certain aspects, the outer diameter $D_{M,2}$ the valve seats 438, 440 can be less than or equal to about 1.5 inches, less than or equal to about 1.0 inches, or otherwise. In certain aspects, the inner diameter $D_{M,3}$ the valve seats 438, 440 can be less than or equal to about 1.5 inches, less than or equal to about 1.0 inches, or otherwise.

In certain aspects, each of the valve seats 438, 440 can include a flange portion surrounding the valve seat 438, 440. In certain aspects, the thickness $T_{M,2}$ of each of the flange portions can be less than or equal to about 0.1 inches. In certain aspects, the thickness $T_{M,2}$ can be less than or equal to about 0.05 inches.

In certain aspects, the length $L_{M,2}$ between the valve seat 438 and the valve seat 440 can be less than or equal to about 2 inches, less than or equal to about 1.75 inches, or otherwise. In certain aspects, the $L_{M,2}$ between the valve seat 438 and the valve seat 440 can be less than or equal to two times the outer diameter of the valve seat $D_{M,2}$, less than or equal to about 1.75 times the outer diameter of the valve seat $D_{M,2}$, less than or equal to about 1.5 times the outer diameter of the valve seat $D_{M,2}$, or otherwise.

In certain aspects, the manifold 404 can have the mask opening 428 in communication with the user's naval cavity. In certain aspects, the mask opening 428 can have an outer diameter $D_{M,1}$ that can be less than or equal to an outer diameter $D_{M,2}$ of the valve seats 438, 440. In certain aspects, the mask opening 428 can have an inner diameter $D_{M,4}$ that can be less than or equal to an inner diameter $D_{M,3}$ of the valve seats 438, 440. In certain aspects, the mask opening 428 can have an outer diameter $D_{M,1}$ that can be less than or equal to about 1.0 inch, less than or equal to about 0.8 inches, or otherwise. In certain aspects, the mask opening 428 can have an inner diameter $D_{M,4}$ that can be less than or equal to about 0.8 inches, less than or equal to about 0.7 inches, or otherwise.

In certain aspects, the thickness of the manifold 404 can be generally uniform along a length of the manifold 404. In certain aspects, the thickness of the manifold 404 can taper toward the end portions of the manifold 404. In certain aspects, the thickness $T_{M,1}$ of the manifold 404 at the region of greatest thickness can be less than or equal to about 1.0 inches, less than or equal to about 0.5 inches, or otherwise. In at least a portion of the manifold 404, the thickness can be less than or equal to about 0.3 inches, less than or equal to about 0.25 inches, or otherwise.

In certain aspects, the diameter $D_{M,3}$ of each air supply opening can be less than or equal to about one-half the diameter $D_{M,2}$ of each valve seat, less than or equal to about one-third the internal diameter $D_{M,3}$ of a valve seat 438, 440, less than or equal to about one-fourth the internal diameter $D_{M,3}$ of a valve seat 438, 440, or otherwise. In certain aspects, the diameter $D_{M,3}$ of each air supply opening 442, 444 can be less than or equal to about 0.5 inches, less than or equal to about 0.25 inches, or otherwise.

In certain aspects, the width $W_M$ ($W_{M,a}+W_{M,b}$) of the manifold can be less than or equal to about three times the outer diameter $D_{M,2}$, less than or equal to about two times the outer diameter $D_{M,2}$, less than or equal to about 1.5 times the outer diameter $D_{M,2}$, or otherwise. In certain aspects, the width $W_M$ of the manifold 404 can be less than or equal to about 2 inches, less than or equal to about 1.5 inches, less than or equal to about 1.25 inches, or otherwise.

In certain aspects, the length $L_{M,1}$ of the manifold 404 can be less than or equal to about five times the size of the outer diameter $D_{M,2}$, less than or equal to about three times the size of the outer diameter $D_{M,2}$, less than or equal to about two times the size of the outer diameter $D_{M,2}$, or otherwise. In certain aspects, the length $L_{M,1}$ of the manifold 404 can be less or equal to about 3 inches, less than or equal to about 2.5 inches, or otherwise. In certain aspect, the length $L_{M,1}$ of the manifold 404 can be about 2.75 inches. In certain aspects, the length $L_{M,1}$ can be less than or equal to about 3 times the width $W_M$, less than or equal to about 2.5 times the width $W_M$, less than or equal to about 2 times the width $W_M$, or otherwise. In certain aspects, the length $L_{M,1}$ can be less than or equal to about 10 times the thickness $T_{M,1}$, less than or equal to about 6 times the thickness $T_{M,1}$, less than or equal to about 5 times the thickness $T_{M,1}$, or otherwise.

In certain aspects, the manifold 404 can carry air in an interior volume 446 of the manifold. Due to the reduced interior volume 446 of the manifold as compared to traditional CPAP device, as well as the inspiratory and expiratory valves, no intentional leak paths are necessary. In certain embodiments, the interior volume 446 of the manifold 404 and/or mask 402 can be less than about 150 mL, less than about 100 mL, less than 50 mL, or otherwise. In certain embodiments, an interior volume of the air supply tubes can be less than about 50 mL, less than about 20 mL, or less than about 15 mL. Accordingly, the ratio between the interior volume 446 of the manifold 404 and/or mask 402 to an interior volume of the air supply tubes can be about 5:1, 5:2, or otherwise.

FIGS. 24-27 illustrate an exemplary embodiment of the inspiratory valve 410 and each of its components. The inspiratory valve 410 can be a one-way valve, including, but not limited to, a flap valve. The inspiratory valve 410 can be configured to open during inhalation and close during exhalation. In certain aspects, the inspiratory valve 410 can be configured to open when the pressure gradient between the mask and ambient is less than or equal to about 0.01 psig.

The inspiratory valve 410 can be positioned anywhere along the flow path between the mask 402 and the air flow generator. For example, the inspiratory valve 410 can be positioned on the manifold 404 or along an air supply tube. In certain aspects, the inspiratory valve 410 can be positioned along an anterior surface of the manifold 404. In certain aspects, the inspiratory valve 410 can be positioned along a posterior surface of the manifold.

Figure 24A:
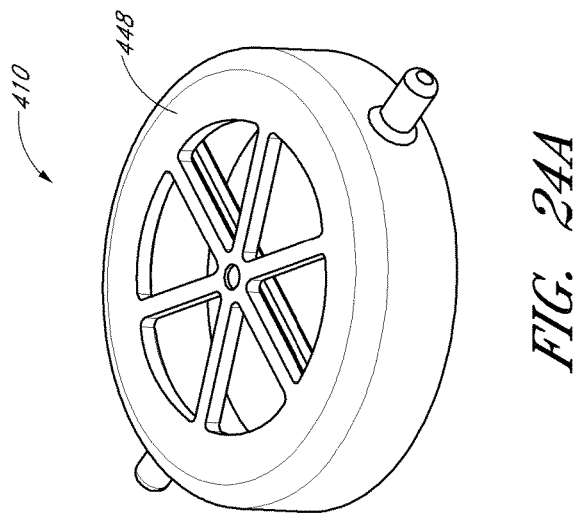
FIGS. 24A-27C illustrate an exemplary embodiment of an inspiratory valve and each of its components.
Figure 24B:
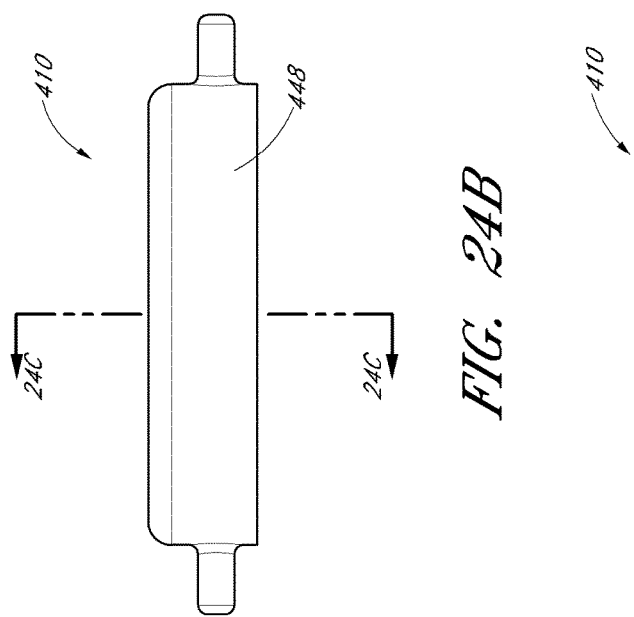
Figure 24C:
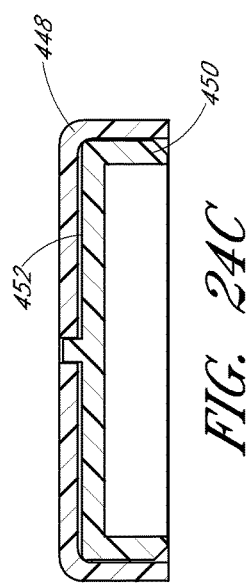

As shown in FIG. 24, the inspiratory valve 410 can include a cap 448, a body 450, and a membrane 452. Each of the inspiratory valve components can be coaxially aligned and substantially circular or cylindrical. An outer diameter of the body 450 can be less than an inner diameter of the cap 448, such that the body 450 can fit within the cap 448. The membrane 452 can be disposed between an inner surface of the cap 448 and an outer surface of the body 450.

Figure 25A:
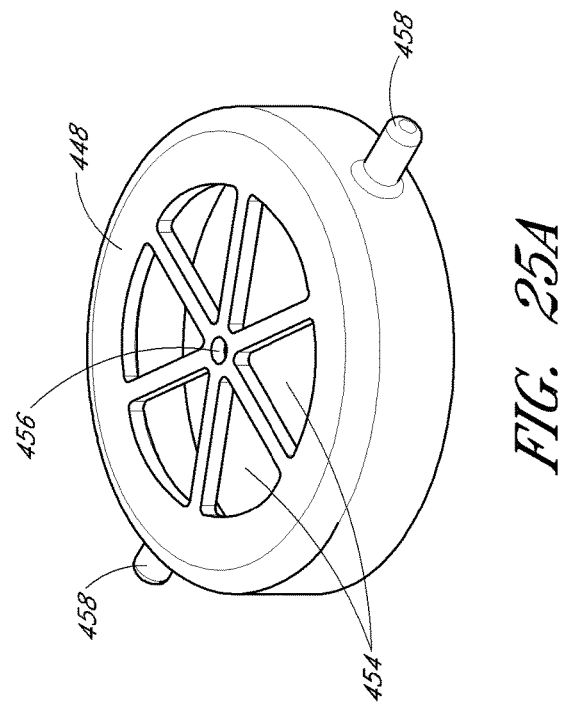
Figure 25B:
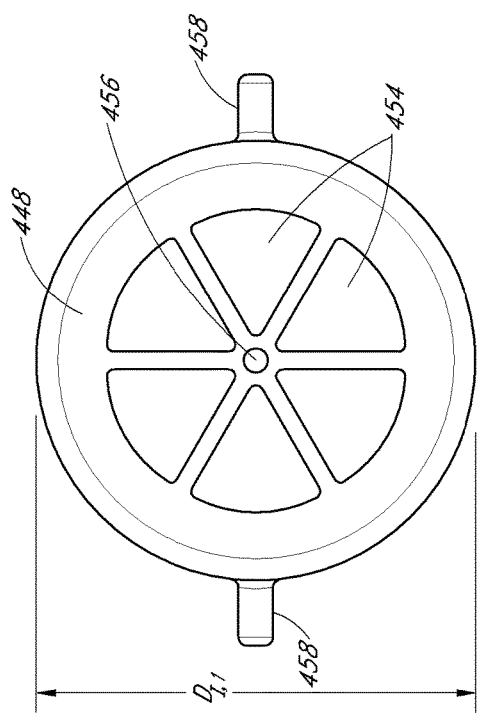
Figure 25C:

In certain aspects, the cap 448 and the body 450 can include metallic materials, including, but not limited to, aluminum, stainless steel, titanium, cobalt chrome, and/or nitinol. In certain aspects, the cap 448 and the body 450 can include plastic materials, including, but not limited to, Pebax®, Grilamid®, nylon, Delrin®, Teflon®, ABS, polycarbonate, and/or PVC. In certain aspects, the cap 448 and the body 450 can include any material having a durometer of at least about 30 A and/or less than or equal to about 95 D As shown in FIGS. 25A-25C, the cap 448 can include one or more openings 454 through which air can flow into the manifold 404. The cap 448 can include six openings 454 or otherwise. In certain aspects, the cap 448 can include an opening 456 for receiving a portion of the body 450. Although the opening 456 shown in FIG. 25A is centrally located, the opening 456 can also be off-center.

In certain aspects, the cap 448 can include one or more detent portions 458 for engaging the inspiratory valve insert 408. In certain aspects, the width $W_{I,1}$ of each detent portion 458 can be less than or equal to about 0.1 inches. Although, as described above, the inspiratory valve 410 can couple with the inspiratory valve insert 408 using any connection mechanism described herein.

In certain aspects, the outer diameter $D_{I,1}$ of the cap 448 can be less than or equal to about the outer diameter $D_{M,2}$ of at least one of the valve seats 438, 440. In certain aspects, the outer diameter $D_{I,1}$ of the cap 448 can be less than or equal to about 1.0 inch. In certain aspects the width $W_M$ ($W_{M,a}+W_{M,b}$) of the manifold 404 can be less than three times the outer diameter $D_{I,1}$, less than two times the outer diameter $D_{I,1}$, less than 1.5 times the outer diameter $D_{I,1}$, or otherwise. In certain aspects, the length $L_M$ of the manifold 404 can be less than about five times the outer diameter $D_{I,1}$, less than about three times the outer diameter $D_{I,1}$, or otherwise.

Figure 26A:
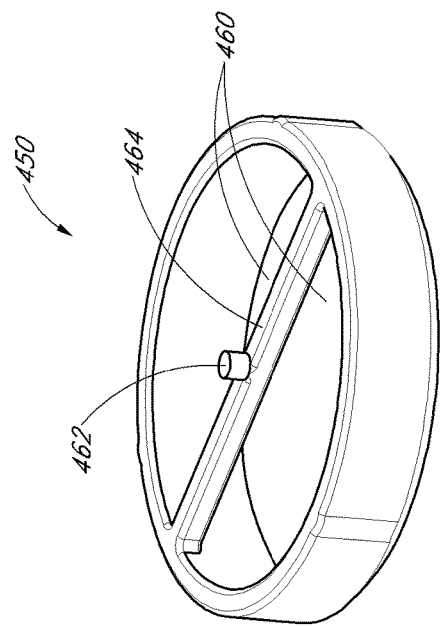
Figure 26B:
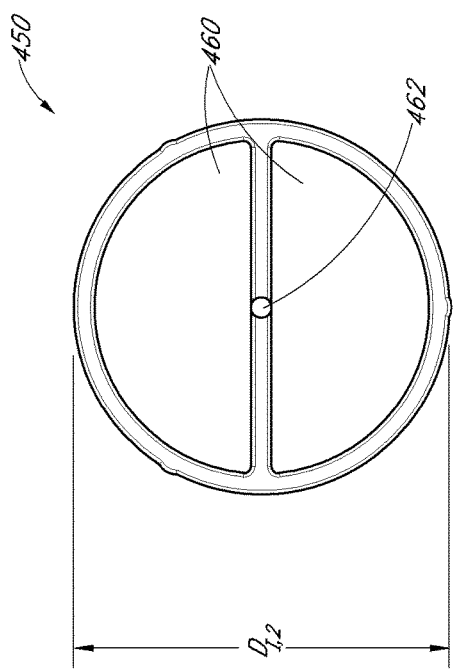
Figure 26C:
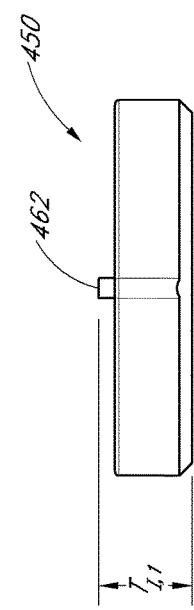

As shown in FIGS. 26A-26C, the body 450 can include one or more openings 460 to permit the inflow of air and movement of the membrane 452. For example, the body 450 can include a cross-bar 464 to create two openings 460. In certain aspects, the body 450 can include a protrusion 462 configured to be received by the opening 456 of the cap 448.

In certain aspects, the outer diameter of $D_{I,2}$ the body 450 can be less than or equal to about 1.0 inches, less than or equal to about 0.9 inches, or otherwise. In certain aspects, the thickness $T_{I,1}$ of the body 450 can be less than or equal to about one-third the outer diameter of $D_{I,2}$ the body 450, less than or equal to about one-fourth the outer diameter of $D_{I,2}$ the body 450, or otherwise. In certain aspects, the thickness $T_{I,1}$ of the body 450 can be less than or equal to about 0.25 inches.

Figure 27A:
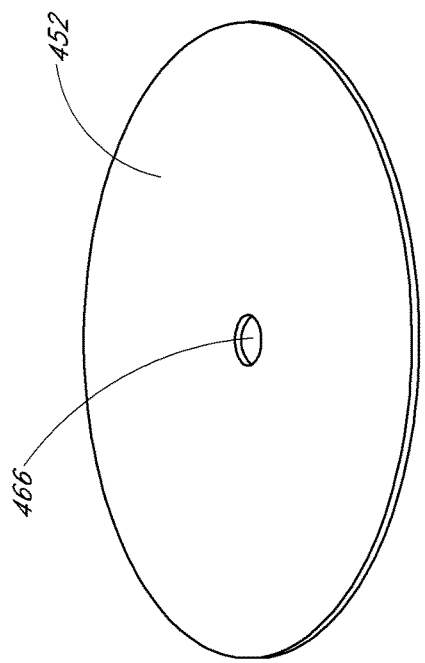
Figure 27B:
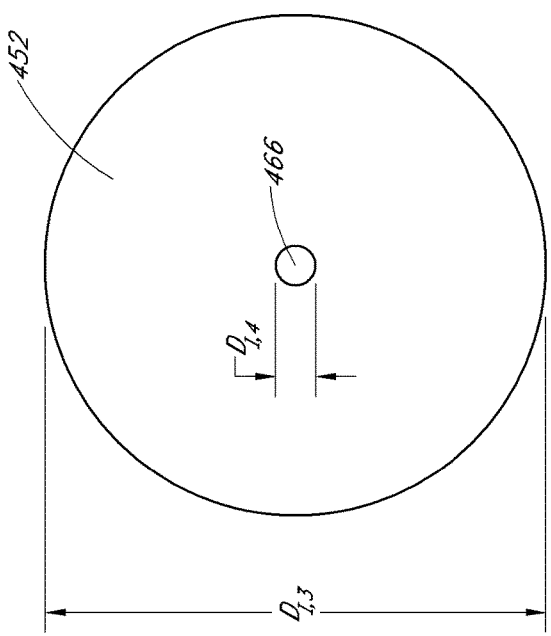
Figure 27C:
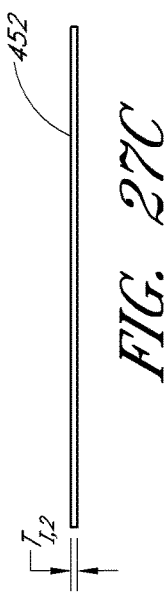
Figure 28A:
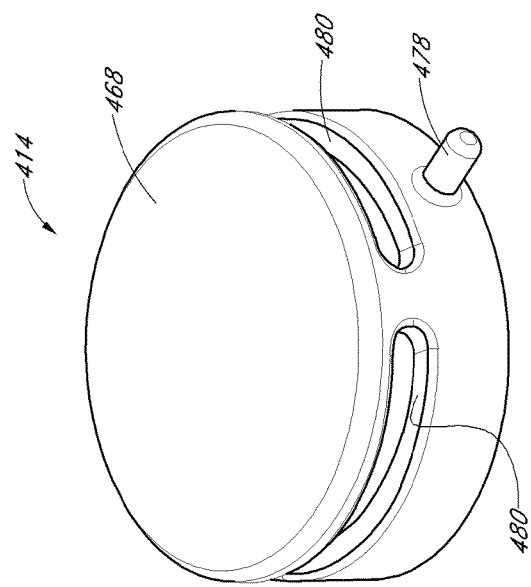
Figure 28B:
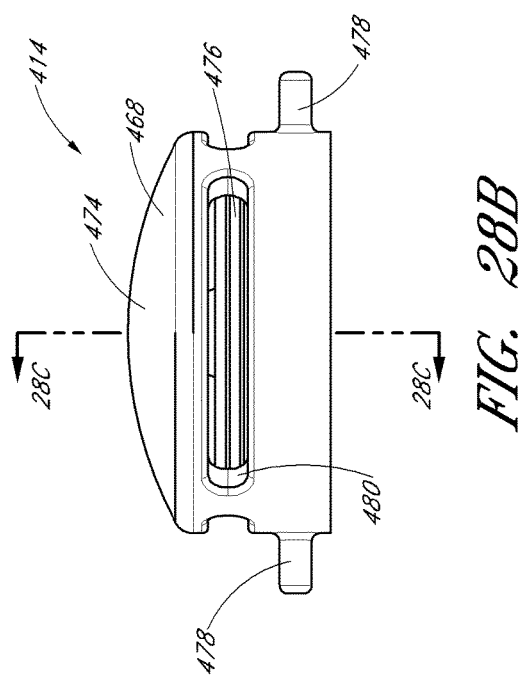
Figure 28C:
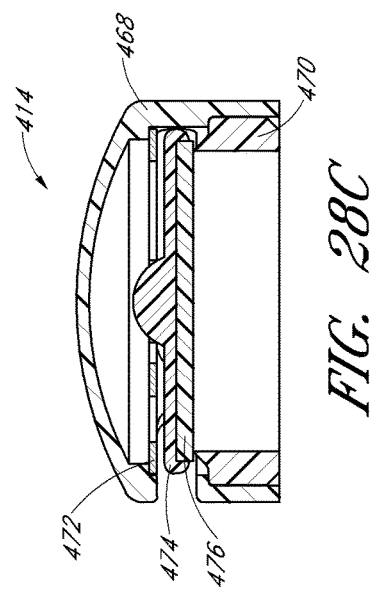

FIGS. 27A-27C illustrate different views of the membrane 452. In certain aspects, the membrane 452 can include a soft durometer material of less than or equal to about 50 D. In certain aspects, the membrane 452 can include a material including, but not limited to, rubber, silicone, nylon, and/or polyethylene. The membrane 452 can be manufactured using any suitable technique, including, but not limited to, extruding, casting, or molding. In certain aspects, the membrane 452 can include an opening 466, centrally located, or otherwise, configured to receive the protrusion 462 of the body 450. In certain aspects, a diameter $D_{I,3}$ of the membrane 452 can be less than or equal to about 1.0 inch, less than or equal to about 0.75 inches, or otherwise. In certain aspects, the diameter $D_{I,4}$ of the opening 466 can be less than or equal to about 0.1 inches, less than or equal to about 0.6 inches, or otherwise. In certain aspects, the thickness $T_{I,2}$ of the membrane can be less than or equal to about 0.01 inches.

FIGS. 28-33 illustrate an exemplary embodiment of an expiratory valve 414 and each of its components. In certain aspects, the expiratory valve can be a spring-loaded valve, a relief valve, smart valve, or otherwise.

The expiratory valve 414 can be positioned anywhere along the flow path between the mask 402 and the air flow generator. For example, the expiratory valve 414 can be positioned on the manifold 404 or along an air supply tube. In certain aspects, the expiratory valve 414 can be positioned along an anterior surface of the manifold 404. In certain aspects, the expiratory valve 414 can be positioned along a posterior surface of the manifold 404.

The expiratory valve 414 can be a one-way valve configured to create pressure without external air flow. In certain aspects, the expiratory valve 414 can be configured to open during period of exhalation when the pressure exceeds a threshold value. In certain aspects, the expiratory valve 414 can be configured to relieve pressure at a threshold pressure of at least about 5 cm H2O and/or less than or equal to about 20 cm H2O. In certain aspects, the threshold pressure can be within the range of about 8 cm H20 and about 12 cm H2O, and, in one embodiment, is about 10 cm H2O. In certain aspects, the expiratory valve 414 can close again when the pressure falls below the threshold pressure.

In certain scenarios, it may be desirable for the expiratory valve to vary resistance based on the flow rate. For example, the expiratory valve can be a spring-loaded valve configured to vary resistance. The change in resistance can be inversely dependent on flow. As air flow increases, the expiratory valve can decrease resistance to keep pressure substantially constant. As air flow decreases, the expiratory valve can increase resistance, which can facilitate the application of positive airway pressure.

In certain aspects, the expiratory valve 414 can include a cap 468, a body 470, a spring 472, a follower 474, and/or a seal 476. Each of the expiratory valve components can be coaxially aligned and substantially circular or cylindrical.

In certain aspects, the spring 472, the follower 474, and the seal 476 can be configured to create the necessary spring force to create the desired level of resistance. In certain aspects, the spring force can be at least about 0.001 lbs./inch in a low profile (less than or equal to about 25 mm height and less than or equal to about 25 mm diameter) minimal orifice opening area at least about 0.1 sq. mm for break pressure and a maximum of about 90 sq. mm for full head pressure opening. The desired level of resistance and/or threshold pressure can be adjustable and used for titration.

The cap 468 and the body 460 can be manufactured using any suitable technique, including, but not limited to, machining, molding, extruding, casting, or SLA processing. In certain aspects, the cap 468 and the body 460 can include a ceramic material or any metallic material, including, but not limited to aluminum (with or without a finish), stainless steel (e.g., 300 series), titanium, cobalt chrome, nitinol, and/or polymer. In certain aspects, the cap 468 and the body 460 can include a medical grade material having a durometer of at least about 50 A and/or less than or equal to about 50 D.

Figure 29A:
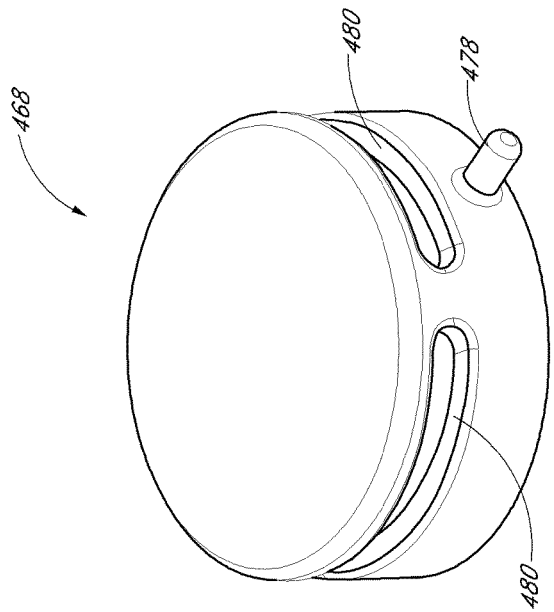
Figure 29B:
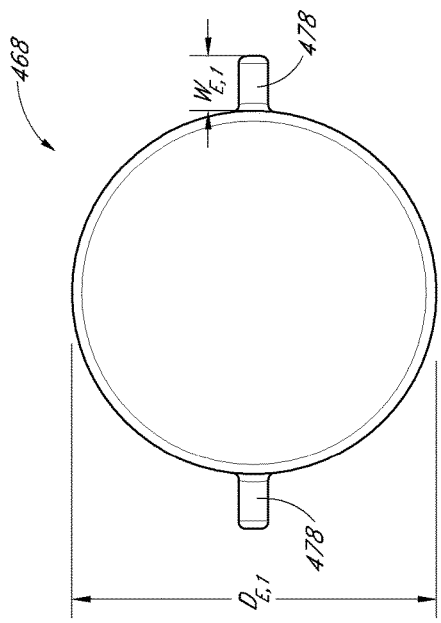
Figure 29C:
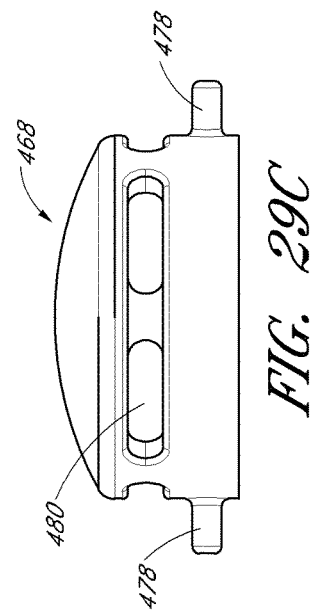

As shown in FIGS. 29A-29C, the cap 468 can include one or more openings 480 along a sidewall of the cap 468. In certain aspects, the cap 468 can include three openings 480 along the sidewall of the cap 468. These 480 openings permit the outflow of air through the valve 414.

In certain aspects, the expiratory valve 414 can include one or more detent portions 478 configured to couple the expiratory valve 414 to the expiratory valve insert 406. In certain aspects, the width $W_{E,1}$ of each detent portion 478 can be less than or equal to about 0.1 inches, less than or equal to about 0.08 inches, or otherwise. Although, as described above, any other connection mechanism discussed herein can be used to couple the expiratory valve 414 and the expiratory valve insert 406.

In certain aspects, the outer diameter $D_{E,1}$ of the cap 468 can be less than or equal to about the outer diameter $D_{M,2}$ of at least one of the valve seats 438, 440. In certain aspects, the outer diameter $D_{E,1}$ of the cap 468 can be less than or equal to about 1.0 inches. In certain aspects, the greatest width $W_M$ ($W_{M,a}+W_{M,b}$) of the manifold 404 can be less than three times the outer diameter $D_{E,1}$, less than two times the outer diameter $D_{E,1}$, less than 1.5 times the outer diameter $D_{E,1}$, or otherwise. In certain aspects, the length $L_M$ of the manifold 404 can be less than about five times the size of the outer diameter $D_{E,1}$, less than about three times the size of the outer diameter $D_{E,1}$, or otherwise.

Figure 30A:
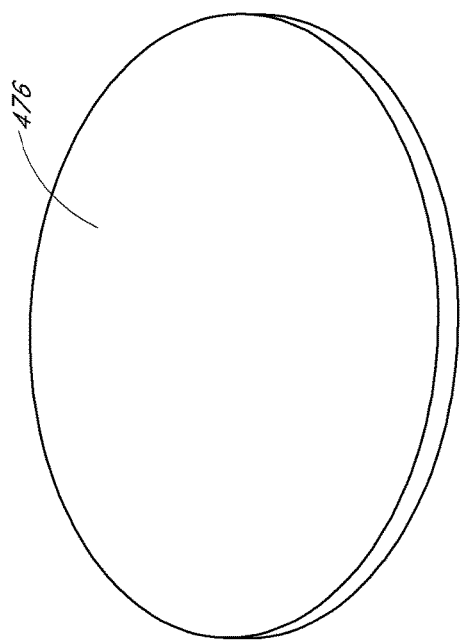
Figure 30B:
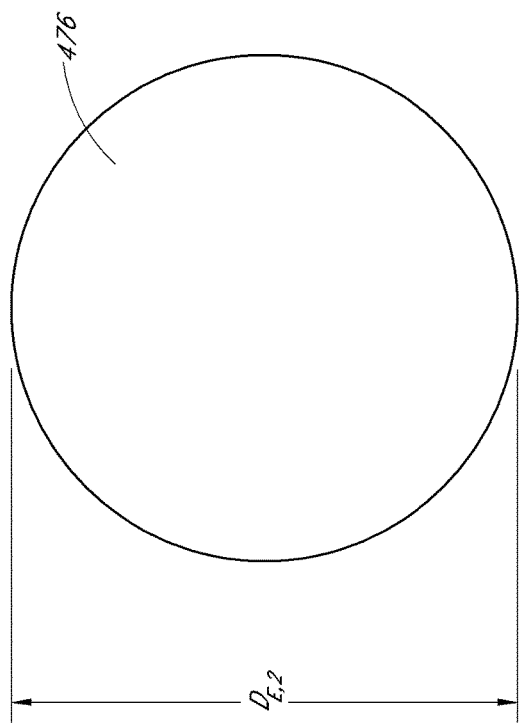
Figure 30C:
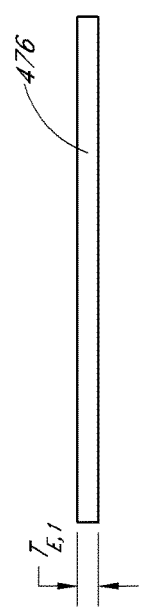

FIGS. 30A-30C illustrate different views of the seal 476, and FIGS. 31A-31C illustrate different views of the follower 474. In certain aspects, the follower 474 and the seal 476 can include any medical grade metallic or plastic material, including, but not limited to, aluminum, stainless steel (e.g., 300 series), cobalt chrome, palladium, nitinol, titanium, polyethylene, ABS, nylon, Pebax®, silicone, rubber, Teflon®, urethane, and/or Delrin®. In certain aspects, the follower 474 and the seal 476 can include any material having a durometer of at least about 20 A and/or less than or equal to about 50 D. In certain aspects, the follower 474 and the seal 476 can be constructed using any suitable manufacturing technique, including, but not limited to machining, extruding, casting, molding, or stamping.

In certain aspects, the diameter $D_{E,2}$ of the seal 476 can be less than the diameter $D_{E,1}$ of the cap 468. In certain aspects, the diameter $D_{E,1}$ of the seal 476 can be less than or equal to about 0.8 inches. In certain aspects, the thickness $T_{E,1}$ of the seal 476 can be less than or equal to about 0.1 inches, less than or equal to about 0.05 inches, about 0.04 inches, or otherwise.

As shown in FIGS. 31A-31C, the follower can include a protruding portion 482 about which the spring 472 can be positioned. In certain aspects, the diameter $D_{E,3}$ of the follower 474 can be less than the diameter $D_{E,1}$ of the cap 468 and/or greater than the diameter $D_{E,2}$ of the seal 476. In certain aspects, the diameter $D_{E,3}$ of the follower 474 can be less than or equal to about 1.0 inches, less than or equal to about 0.9 inches, or otherwise. In certain aspects, the thickness $T_{E,2}$ of the protrusion can vary depending on the desired spring force of the valve. For example, the thickness $T_{E,2}$ can be at least about 0.05 inches and/or less than or equal to about 0.1 inches.

Figure 32A:
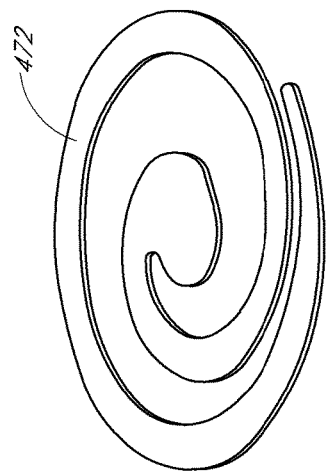
Figure 32B:
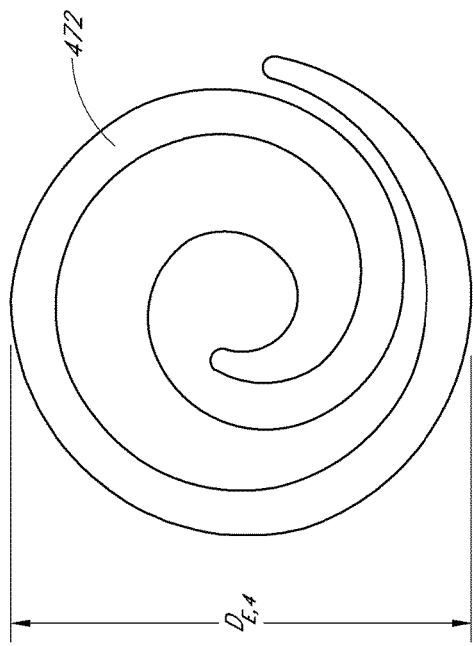
Figure 32C:
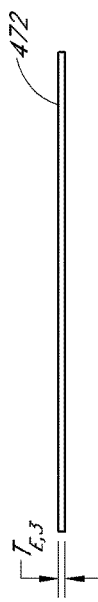

FIGS. 32A-32C illustrate different views of the spring 472. In certain aspects, the spring 472, the spring can be generally circular. In certain aspects, the spring 472 can include one or more protrusions extending from the spring 472 and coplanar with a top surface and/or bottom surface of the spring 472. In certain aspects, the spring 472 can include medical grade metallic or plastic materials, including, but not limited to, stainless steel (e.g., 300 series), nitinol, spring steel, palladium, copper, titanium, ABS, Pebax®, nylon, polyethylene, polyethylene terephthalate, and/or rubber. In certain aspects, the spring 472 can include a material having a durometer of at least about 10 A and/or less than or equal to about 50 D. The spring 472 can be manufactured using any suitable technique, including, but not limited to, laser cutting, water jetting, stamping, broaching, coining, machining, chemical etching, or electrical discharge machining.

In certain aspects, the diameter $D_{E,4}$ of the spring 472 can be less than the diameter $D_{E,1}$ of the cap 468, greater than the diameter $D_{E,2}$ of the seal 476, and/or substantially the same as the diameter $D_{E,3}$ of the follower 474. In certain aspects, the diameter $D_{E,4}$ of the spring 472 can be less than or equal to about 1.0 inches, less than or equal to about 0.9 inches, or otherwise. In certain aspects, the thickness $T_{E,3}$ of the spring 472 can vary depending on the desired spring force of the valve. For example, the thickness $T_{E,3}$ can be at least about 0.005 inches and/or less than or equal to about 0.015 inches.

In certain aspects, as the desired relief pressure increases, the thickness $T_{E,3}$ of the spring increases. In certain aspects, the thickness $T_{E,3}$ of the spring can increase linearly with the desired relief pressure. In certain aspects, for a threshold relief pressure of about 5 cm H2O, the thickness $T_{E,3}$ can be about 0.005 inches. In certain aspects, for a threshold relief pressure of about 7 cm H2O, the thickness $T_{E,3}$ can be about 0.007 inches. In certain aspects, for a threshold relief pressure of about 9 cm H2O, the thickness $T_{E,3}$ can be about 0.009 inches. In certain aspects, for a threshold relief pressure of about 11 cm H2O, the thickness $T_{E,3}$ can be about 0.011 inches. In certain aspects, for a threshold relief pressure of about 13 cm H2O, the thickness $T_{E,3}$ can be about 0.013 inches. In certain aspects, for a threshold relief pressure of about 15 cm H2O, the thickness $T_{E,3}$ can be about 0.015 inches.

Figure 33A:
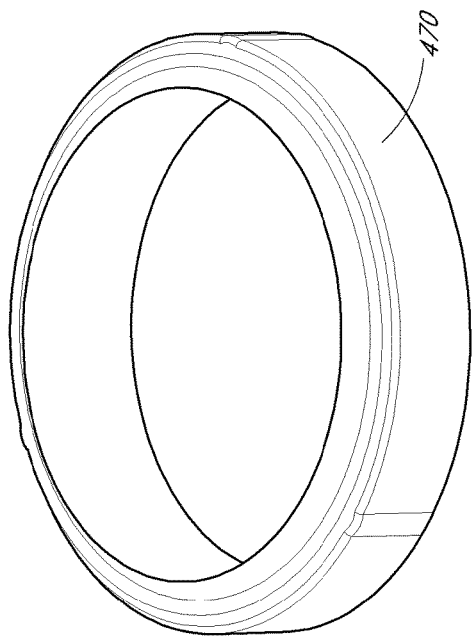
Figure 33B:
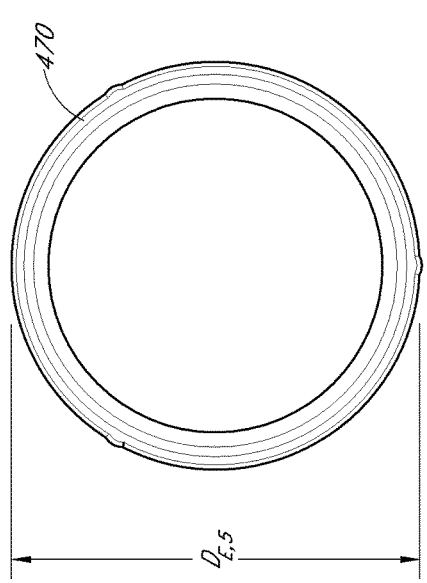
Figure 33C:
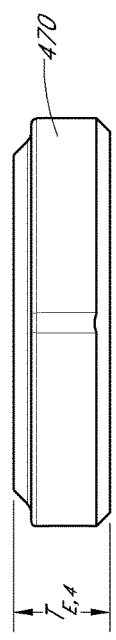

FIGS. 33A-33C illustrate different views of the body 470. In certain aspects, the diameter $D_{E,5}$ of the body 470 can be less than the diameter $D_{E,1}$ of the cap 468, and/or greater than the diameter of the seal 476, the follower 474, and/or the spring 472. In certain aspects, the diameter $D_{E,5}$ of the body 470 can be less than or equal to about 1.0 inches. In certain aspects, the thickness $T_{E,4}$ of the body 470 can be less than or equal to about one-third the diameter $D_{E,5}$ of the body 470, less than or equal to about one-fourth the diameter $D_{E,5}$ of the body 470, or otherwise. In certain aspects, the thickness $T_{E,4}$ of the body can be less than or equal to about 0.25 inches.

In certain variants, it may be desirable for the expiratory valve to vary resistance independent of flow rate. In doing so, the device assembly can increase pressure even during period of low flow to help maximize comfort. The smart expiratory valve can include any of the features of the expiratory valve 414 described herein.

In certain variants, it may be desirable to adjust the expiratory valve pressure setting. For example, it may be desirable to increase or decrease the threshold pressure during the titration process to help determine the ideal pressure setting for the user. In certain embodiments, the entire expiratory valve can be replaced with an expiratory valve having a different pressure setting. In certain embodiments, the expiratory valve can include a processor configured to adjust the pressure setting. For example, the technician can send the expiratory valve a signal to change the pressure setting. In certain aspects, the expiratory valve can include a wireless receiver configured to receive the signal sent from the technician. In certain aspects, when the air flow generator setting changes, the expiratory valve can receive a signal to adjust the pressure setting. In certain embodiments, the pressure settings can be automatically adjusted. For example, the expiratory valve can be smart valve configured to automatically adjust the pressure setting if the valve detects inadequate pressure or flow rates.

Figure 34A:
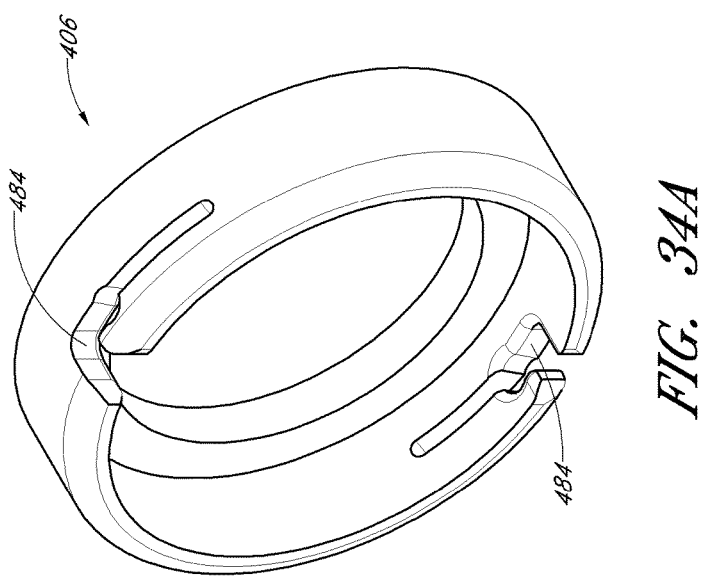
FIGS. 34A-34C illustrate an exemplary embodiment of a valve insert.
Figure 34B:
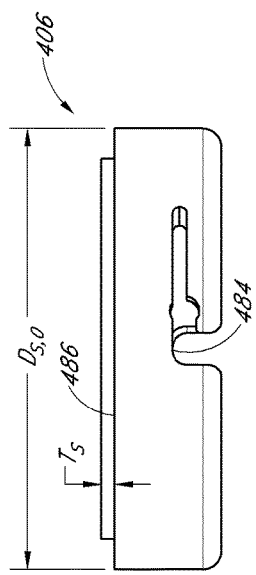
Figure 34C:
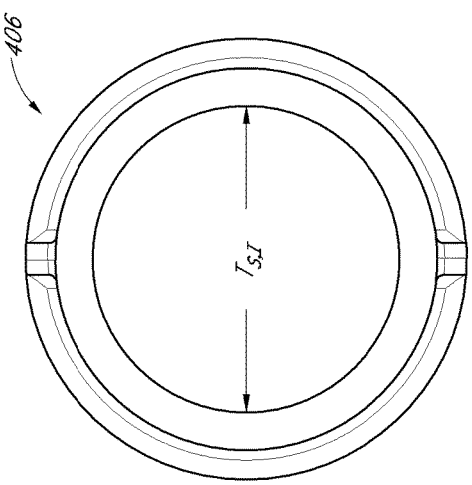

FIGS. 34A-34C illustrate an exemplary embodiment of the expiratory valve insert 406. The expiratory valve insert 406 can be configured to facilitate the exchange of valves depending on the desired relief pressure and improve the capability of doctors to perform patient evaluations. In certain aspects, the inspiratory valve insert 408 can be the same or substantially the same as the expiratory valve insert 406.

The valve insert 406 can be manufactured using any suitable technique, including, but not limited to, machining, molding, extruding, casting, or SLA processing. In certain aspects, the valve insert 406 can include a ceramic material or any metallic material, including, but not limited to aluminum (with or without a finish), stainless steel (e.g., 300 series), titanium, cobalt chrome, nitinol, and/or polymer. In certain aspects, the valve insert 406 can include a medical grade material having a durometer of at least about 50 A and/or less than or equal to about 50 D.

As shown in FIG. 34A, the insert 406 can include one or more detent receiving portions 484 for engaging the expiratory valve 414. In certain aspects, the insert 406 can include a flange portion 486 or other feature to mate with the valve seat 438. In certain aspects, the thickness $T_s$ of the flange portion 486 can be less than or equal to about 0.1 inches, less than or equal to about 0.5 inches, or otherwise. In certain aspects, the thickness $T_s$ of the flange portion can be about 0.035 inches.

In certain aspects, the outer diameter $D_{S,O}$ of the insert 406 can be less than or equal to about 1.5 inches, less than or equal to about 1.25 inches, less than or equal to about 1.0 inches, or otherwise. In certain aspects, the outer diameter $D_{S,I}$ of the insert 406 can be less than or equal to about 1.25 inches, less than or equal to about 1.0 inches, or otherwise.

As described earlier, the device 400 can include one or more air supply connectors 418, 420 to connect the device 400 to any standard air supply tubing. FIGS. 35A-35C illustrates an exemplary embodiment of an air supply connector 418. The connector 418 can be manufactured using any suitable technique, including, but not limited to, machining, molding, or SLA processing. In certain aspects, the connector 418 can include any material having a durometer of at least about 10 A and/or less than or equal to about 50 D. In certain aspects, the connector 418 includes any medical grade polymer material, including, but not limited to, ABS, PVC, nylon, Pebax®, polycarbonate, Delrin®, rubber, Teflon®, and/or urethane.

In certain aspects, the length $L_A$ of the connector 418 can be less than or equal to about 0.75 inches, less than or equal to about 0.65 inches, or otherwise.

In certain aspects, the connector 418 can include a first connector portion 488 configured to connect to the manifold 404. In certain aspects, the first connector portion 488 can be coupled to the manifold 404 using any connection mechanism, including, but not limited to, an adhesive, a curing technique, a molding technique, a detent, a screw-fit, snap fit, and/or an interference fit. In certain aspects, the outer diameter $D_{A,O}$ of the first connector portion 488 can be less than or equal to about 0.5 inches, less than or equal to about 0.25 inches, or otherwise. In certain aspects, the inner diameter $D_{A,I}$ of the first connector portion 488 can be less than or equal to about 0.25 inches, less than or equal to about 0.2 inches, or otherwise.

In certain aspects, the connector 418 can include a second connector portion 486 configured to connect to any standard air supply tubing. In certain aspects, the second connector portion 486 can be coupled to the air supply tubing using any connection mechanism, including, but not limited to, an adhesive, a curing technique, a molding technique, a detent, a screw-fit, snap fit, and/or an interference fit. In certain aspects, as shown in FIG. 35A, the second connector portion 486 can include a threaded region.

In certain aspects, the manifold 404 and/or mask 402 can be connected to one or more air supply tubes 494. In certain aspects, at least a portion of the air supply tubes 494 can be secured to a strap securing the device 400 to the user's face.

Noise-Mitigating Valves

FIGS. 42-50 illustrate further examples of an expiratory valve that can be used in connection with a sleep apnea device, for example, the device 400 or 400a. The expiratory valve can be positioned anywhere along the sleep apnea device, including, along a manifold or mask in airflow communication with the patient. For example, as shown in FIG. 19A, the device 400a can include a mask 402a configured to form a seal with the user's face. The mask 402a can at least partially surround the user's nostril and provide a passage to the user's nasal passage. The mask 402a can include a pliable material to facilitate the formation of the seal and to increase comfort. The mask 402a can be secured to a plate (not shown). The plate can be configured to receive an expiratory valve, an inspiratory valve, and/or one or more ports in fluid communication with an air flow generator. In some instances, the expiratory valve and/or inspiratory valve can be secured to the mask 402a in addition to or in alternative to the plate. In some instances, the device 400a can include a cover positioned on a side of the plate that is opposite the mask 402a.

The expiratory valve 900 can be configured to move between an open configuration and a closed configuration. The expiratory valve 900 can move from the closed configuration to the open configuration when the intranasal pressure exceeds a threshold pressure at which the user's airway remains open. The threshold pressure can be at least about 5 cm H2O and/or typically less than or equal to about 20 cm H2O. In some instances, the threshold pressure can be within about 2 cm H20 of each of about 5 cm H20, about 10 cm H2O, about 15 cm H2O, or about 20 cm H2O.

In some instances, the expiratory valve 900 can move from the open configuration to the closed configuration when the intranasal pressure falls below a closing pressure to maintain the intranasal pressure at a substantially constant level. The expiratory valve 900 can move to the closed configuration when the pressure falls below the threshold pressure or a pressure that is different from the threshold pressure. In some instances, the closing pressure differs from the threshold pressure by less than 2 cm H2O.

Figure 51:
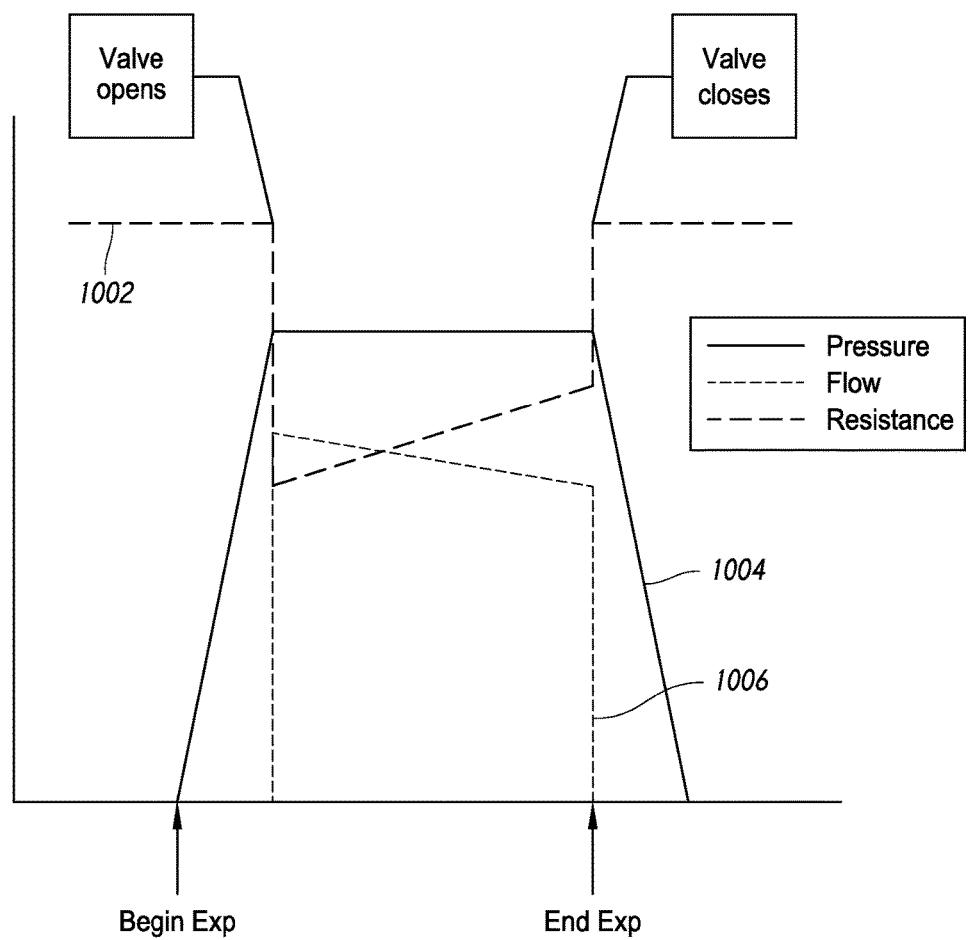
FIG. 51 is a graph illustrating the relationship between resistance, pressure, and flow, during a breathing cycle in which the user is using a device described herein.

In some instances, as shown in FIG. 51, the expiratory valve 900 can be configured to move between the open and closed configurations, such that the expiratory valve 900 opens at an early portion of exhalation. Line 1002 illustrates an exemplary pattern of resistance during one breathing cycle. As shown by line 1002, the expiratory valve 900 can provide less resistance to expired air during an early portion of exhalation than during a later portion of exhalation.

Line 1004 illustrates an exemplary pattern of intranasal pressure. The resistance levels can be controlled such that the intranasal pressure remains substantially constant during exhalation. The intranasal pressure can remain at a level that is between about 5 cm H2O and about 20 cm H2O. For example, the intranasal pressure can be within about 1 cm H2O of each of about 5 cm H2O, about 10 cm H2O, about 15 cm H2O, and about 20 cm H2O.

As described throughout this specification, a pre-selected pressure value can be maintained while supplying air from an air flow generator and an air supply tube assembly at any one of a variety of relative low rates, for example, less than or equal to about 60 L/min, less than or equal to about 50 L/min, less than or equal to about 40 L/min, less than or equal to about 30 L/min, less than or equal to about 20 L/min, or less than or equal to about 15 L/min. Additionally, as described below, the air flow generator can be configured to supply a constant amount of pressure, while allowing the user to adjust the flow rate for their comfort levels. For example, the device can include an adjustable valve, such as an iris valve, in the air flow generator or along the air supply tube that the user can easily adjust.

In addition, the expiratory valve 900 can be configured such that the exhalation flow rate at the early portion of an expiration cycle is greater than during the later portion of the same exhalation cycle. Line 1006 illustrates an exemplary pattern of exhalation flow rate during one breathing cycle. In some instances, the expiratory valve 900 can be configured to maintain exhalation flow rate at a rate that is within a range that varies by no more than about 3 L/second, and preferably no more than 1.5 L/second, such as between about 3 L/second and about 4 L/second. For example the exhalation flow rate can be about 3 L/second, about 3.25 L/second, about 3.5 L/second, about 3.75 L/second, or about 4 L/second.

The expiratory valve 900 can be a membrane valve. As shown in FIG. 42, the valve 900 can generally include a valve frame 902, a membrane 904, and an occluder 908. The valve 900 can be configured to move between a closed configuration (FIG. 42) and an open configuration (FIG. 43). In the closed configuration, the occluder 908 can prevent air from flowing through the opening 906 when intranasal pressure is below the opening threshold for the valve. As the intranasal pressure increases, the membrane 904 can elastically deform and move away from the occluder 908, thereby permitting air to flow around the occluder 908 and out of the opening 906.

The frame 902 can be generally planar or include a curved shape depending on the shape of the plate. As shown in the figures, the valve frame 902 can define a generally annular shape, such as a circular shape. The diameter of the largest portion of the valve frame can be less than or equal to about 1.0 inches, less than or equal to about 0.9 inches, or less than or equal to about 0.8 inches. Although, depending on the plate, the valve frame 902 can have a generally elliptical shape, a generally rectangular shape, a generally triangular shape, or otherwise.

An outer portion of the membrane 904 can be secured to the valve frame 902. For example, the valve frame 902 can include a lip portion 912 around which the membrane 904 can be secured.

The membrane 904 can have sufficient elastic properties to move between the closed configuration and a partially open configuration at the threshold pressure. The elastic properties can vary depending on a variety of variables, including the size of the membrane. A smaller diameter membrane can require greater elasticity than a larger diameter membrane to move between the closed configuration and the open configuration at the same threshold pressure. In some instances, when the membrane 904 is secured to the frame 902, sufficient tension can be applied to the membrane 904 such that the membrane 904 moves between the open and closed configurations at a pre-determined threshold pressure.

Figure 50:
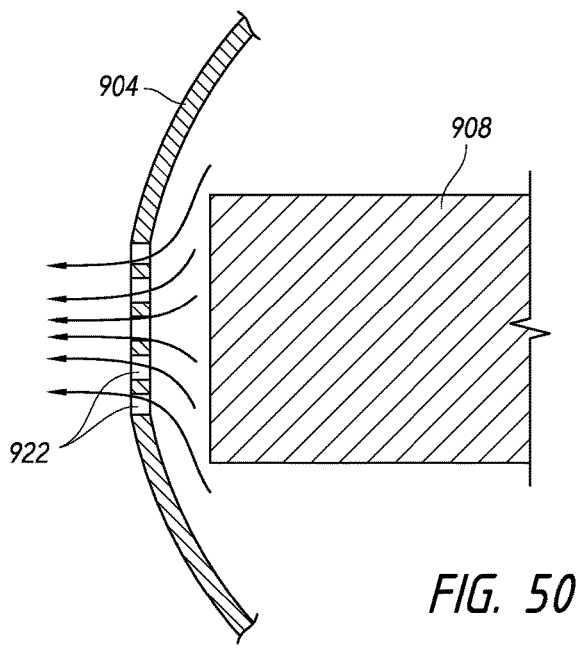
FIG. 50 illustrates yet another embodiment of the expiratory valve having a membrane with a plurality of openings.

Additionally, the membrane 904 can include one or more openings. For example, as shown in FIG. 42, the membrane 904 can include a single opening 906. In some instances, the single opening 906 can be disposed along a central portion of the membrane 904. The opening can include a diameter large enough to provide a sufficient exhalation flow rate, as explained above. As another example, as shown in FIG. 50, the membrane 904 can include at least two, at least four, at least six or more openings 922 each having a diameter smaller than the single opening 906. The combined area of the plurality of openings can selected to be large enough to provide sufficient exhalation flow rates. In some instances, the plurality of smaller openings 922 can be desirable because the plurality of openings 922 can limit membrane vibrations, thereby reducing noise levels.

As shown in FIG. 42, the valve 900 can include an occluder 908. The membrane 904 can be configured to rest on the occluder 908 when the valve 900 is in the closed configuration. In some instances, the occluder 908 can be generally aligned with the opening 906. The surface of the occluder 908 that is in contact with the membrane 908 can include an area that is greater than an area of the opening 906, such that when the valve 900 is in the closed configuration, air cannot escape through the opening 906 at pressures below the opening pressure. In some instances, the occluder 908 can include a generally circular cross-section. In other examples, the cross-section of the occluder 908 can be generally elliptical, generally rectangular, generally triangular, or otherwise. In some instances, the occluder 908 can be adjustable along the direction of the axis of airflow. For example, the occluder 908 can be configured to contact the membrane 904 without distending the membrane 904. In other examples, the occluder 908 can be configured to distend the membrane 904 in the effluent direction when the valve 900 is in the closed configuration. Distention can be by at least about 0.1 inches or more, depending upon the desired performance.

Generally, expiratory valves can produce large amounts of noise when the components of the valve vibrate and/or when turbulent air passes through the opening. For example, traditional CPAP devices can produce noise levels between about 20 dB and about 30 dB. Given these high noise levels, it can be desirable to design a sleep apnea device with reduced noise levels and controlled pitch. The expiratory valve 900 described in connection with FIGS. 42 and 43 can be configured to produce noise levels of less than or equal to about 20 dB. However, it can be desirable to further reduce noise levels. For example, the expiratory valve can include one or more noise mitigating features to dampen vibrations and/or reduce the turbulence of air flow through the opening. Examples of these noise mitigating features are described in connection with FIGS. 44-50. These noise mitigating features can reduce noise levels to no more than about 15 dB, or no more than about 12 dB, and, in some implementations, no more than about 10 dB, at an intranasal pressure of at least about 20 cm H2O.

The device can reduce the noise level without sacrificing therapeutic benefits. For example, the device can reduce the noise level as described above while still maintaining intranasal pressure at a substantially constant level between about 5 cm H2O and about 20 cm H2O or more, such as about 5 cm H2O, about 10 cm H2O, about 15 cm H2O, or about 20 cm H2O. Additionally, the device can reduce these noise levels while the user receives air from an air flow generator. The user can receive the air flow at a rate of at least about 10 L/min and/or less than or equal to about 60 L/min. For example, at a rate that is less than or equal to about 50 L/min, less than or equal to about 40 L/min, less than or equal to about 30 L/min, less than or equal to about 20 L/min and maintain the noise levels described above.

Figure 49:
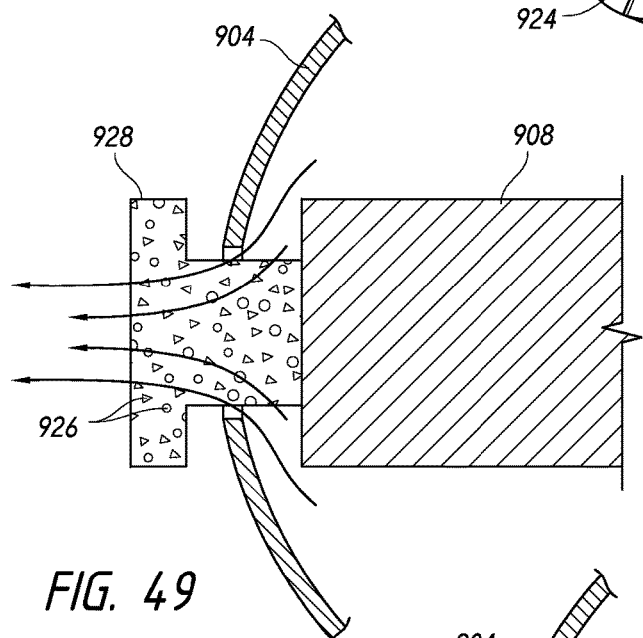
FIG. 49 illustrates yet another embodiment of the expiratory valve with a noise reducing member having a plurality of holes.

As shown in FIG. 44, the valve 900 can include a noise reducing member 914 configured to direct air flow through the opening 906 and reduce the amount of turbulence. In turn, the reduction in turbulent air flow can decrease membrane vibrations. The noise reducing member 914 can include a semi-rigid or rigid material, such as a metal or plastic material, and can be integrally or separately formed from the occluder 908. The noise reducing member 914 can be configured to at least partially extend through the opening, as shown in FIG. 44. For example, the noise reducing member 914 can include a diameter that is less than the diameter of the opening 906 when the valve is closed. Additionally, the noise reducing member 914 can include a diameter that is less than the diameter of the occluder 908. For example, the diameter of the noise reducing member 914 can be at least about 50% of the diameter of the opening 906, at least about 60% of the diameter of the opening 906, at least about 70% of the diameter of the opening 906, at least about 80% of the diameter of the opening 906, at least about 90% of the diameter of the opening 906, or at least about 95% of the diameter of the opening 906 in the closed configuration. In some instances, as shown in FIG. 49, the noise reducing member 914 can include a distal end portion 926 having a cross-sectional area including a diameter that is greater than the diameter of the opening 906 in the unstressed membrane.

Figure 45:
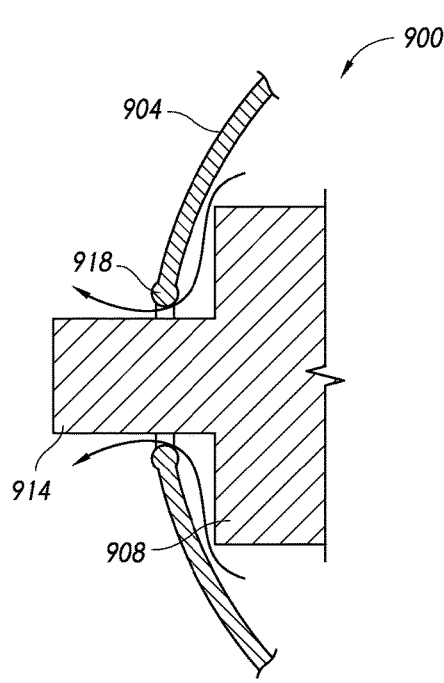
FIG. 45 illustrates yet another embodiment of the expiratory valve having a restraint.
Figure 46:
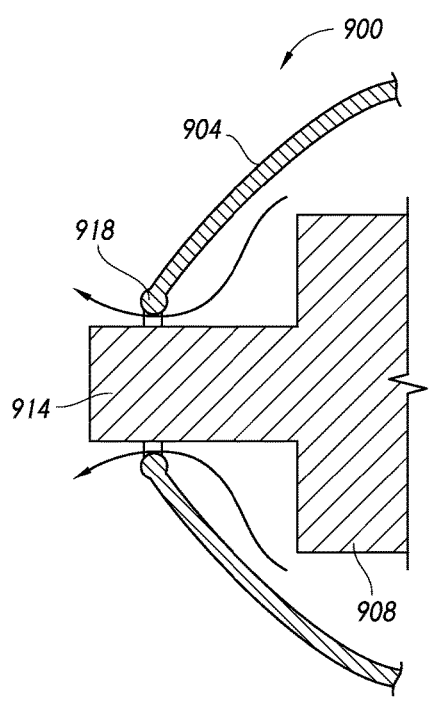
FIG. 46 illustrates the expiratory valve shown in FIG. 45 in an open configuration.

The amount of air passing through the opening 906 and the nature of the air flow (e.g., turbulent or laminar) can influence noise levels, so it can be desirable to limit the amount of open area through which air can escape the valve 900 and reduce the turbulence of the air flow. On the other hand, it can be desirable to include a larger opening 906 so that a large increase in expiratory flow does not cause intranasal pressure to significantly increase, which can make exhalation uncomfortable. Therefore, it can be desirable to maximize the diameter of the opening 906 to prevent substantial pressure increases, but maintain the size of the opening 906 to prevent increases in noise level. For example, it can be desirable to restrain expansion of the opening in response to increases in pressure. This can be accomplished in any of a variety of ways, such as by modifying the elasticity of the membrane adjacent the edge of the opening, providing a band or thickening around the opening, or adding a support, such as by surrounding the opening 906 with an annular restraint 918. As shown in FIGS. 45 and 46, with the restraint 918, the diameter of the opening 906 remains substantially the same when the valve 900 is in the closed configuration (FIG. 45) and when the valve 900 is in the open configuration (FIG. 46).

The restraint 918 can generally include a shape corresponding to the shape of the opening 906. The restraint 918 can include a semi-rigid or a rigid material. In some instances, the restraint 918 can be an annular membrane, a grommet, or a fiber with sufficient rigidity. As another example, rather than a separate restraint 918, the membrane 904 can include sections having varying durometers. A section of the membrane 904 surrounding the opening 906 can include a durometer that is greater than a remaining section of the membrane 904.

Figure 47:
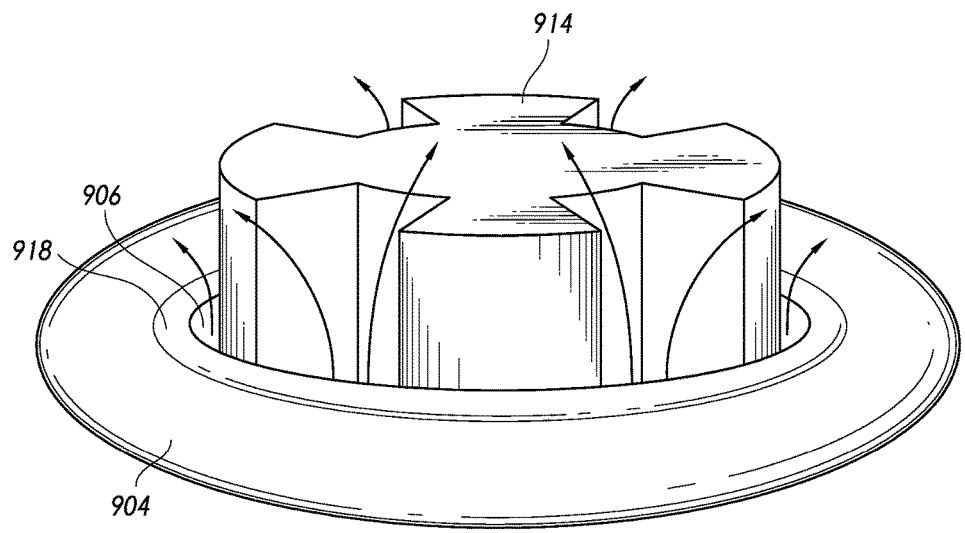
FIG. 47 illustrates yet another embodiment of the expiratory valve with a noise reducing member having grooves.

To maximize the amount of open area through which air can exit the expiratory valve 900 and encourage laminar flow, the noise reducing member 914 can include one or more axially extending grooves, channels, indentations, cuts, chamfers, or likewise. As shown in FIG. 47, the grooves 916 can extend along a length of the noise reducing member. In some instances, the noise reducing member 914 can include two grooves 916, three grooves 916, four grooves 916, or more. The grooves 916 can help maintain the intranasal pressure at a substantially constant level during exhalation.

In some instances, as shown in FIG. 49, a diameter of the noise reducing member 914 can be sufficiently large to fill the opening 906 and reduce the escape of air between the noise reducing member 914 and the opening 906, thereby reducing the amount of membrane vibration. For example, the diameter of the noise reducing member 914 can be substantially the same as the diameter of the opening 904. Additionally, the noise reducing member 914 can include an end portion 926 having a diameter that is greater than a diameter of the remaining portion of the noise reducing member 914 to further prevent air from escaping between the noise reducing member 914 and the opening 906. The diameter of the end portion 928 can be larger than the diameter of the opening 906.

In some instances, as shown in FIG. 49, the noise reducing member 914 can include a number of openings 926 through which air can exit the expiratory valve 900. The number and positioning of the openings 926 can be configured to reduce the amount of turbulent air flow and prevent vibrations. The total cross-sectional area of each of the openings 926 can be the same as the single opening 906 or the plurality of openings 922. The size of the openings 926 can be sufficiently large and numerous to prevent a significant increase in pressure and facilitate comfortable exhalation. In some examples, the noise reducing member 914 can include a sponge-like material.

In addition to or in alternative to the noise reducing member 914, the membrane 904 can be pre-loaded with strain or tension to reduce noise. This can occur naturally based on the material properties or by adding material stiffeners, external braces, or struts to the membrane to absorb or dampen vibrations which would generate sound. In some instances, a section of the membrane 904 can include a higher durometer or greater thickness than a remaining section of the membrane 904. In some instances, the entire membrane 904 can include a material having a durometer and or dimensions designed to reduce vibrations.

Figure 48:
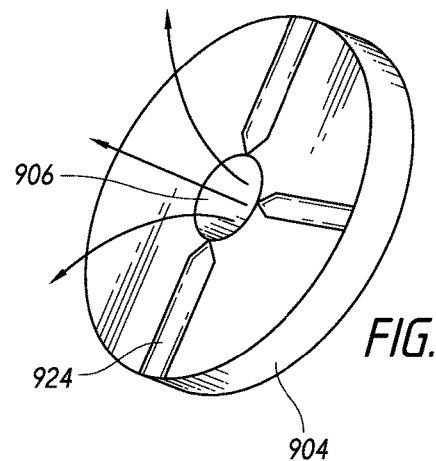
FIG. 48 illustrates an embodiment of a membrane having a number of dampening members.

The expiratory valve 900 can include a number of dampening members 924 secured any portion of the expiratory valve 900, for example, the membrane 904 or noise reducing member 914 (see, e.g., FIG. 48). For example, the dampening members 924 can apply strain or deflection to the membrane 904 to absorb or dampen vibrations. In some instances, the dampening members 924 can be secured to the membrane 904 and one or both of the noise reducing member 914 and the occluding member 908. In some instances, the dampening members 924 can be secured to the membrane 904 alone. The dampening members 924 can be applied in a non-tension or pre-tension configuration.

The dampening members 924 can include a semi-rigid or rigid material having a durometer that is greater than a durometer of the membrane 904. For example, the material can be a metal, a plastic, or a fibrous material bonded to or molded with the membrane 904.

As shown in FIG. 48, a number of dampening member 924 can extend radially across the membrane surface. The dampening members 924 can be circumferentially disposed around the membrane surface. However, other configurations and shapes are possible. For example, the dampening members 924 can be ring shaped, circular, or otherwise. Additionally, the dampening members 924 can be axially aligned or scattered around the membrane 906.

In use, the user can secure the device 400, 400a to the user's face to create a seal around the nasal passageway. During inspiration, the user inhales air from the air flow generator and/or from the inspiratory valve. For example, the device can be configured such that the inspiratory valve only opens when the inflow of air from the air flow generator is insufficient to keep the user's airway open. During exhalation, pressure within the mask can increase, causing the membrane 904 to move away from the occluder 908 when the intranasal pressure exceeds a threshold pressure. The threshold pressure can be at least about 5 cm H2O and/or less than or equal to about 20 cm H2O. In some instances, the threshold pressure can be about 5 cm H2O, about 10 cm H2O, about 15 cm H2O, or about 20 cm H2O. Once the expiratory valve 900 is in the open configuration, air is allowed to escape, thereby limiting the further increase in pressure. As the exhalation flow rate decreases and pressure decreases, the membrane 904 can move back to the closed configuration. For example, the membrane 904 can move back to the closed configuration, when the pressure within the mask falls below the threshold pressure. Moreover, the expiratory valve 900 can include any of the noise mitigating features described herein to reduce noise levels produced by the expiratory valve 900 to less than about 15 dB, or less than about 10 dB.

As described above, FIG. 51 illustrates the relationship between resistance 1002, pressure 1004, and exhalation flow rate 1006 during a breathing cycle. The combination of the expiratory valve 900, the seal formed by the mask 402a, and the air flow generator can ensure that the pressure does not fall below this threshold pressure.

Air Supply Sub-Assembly

Figure 36:
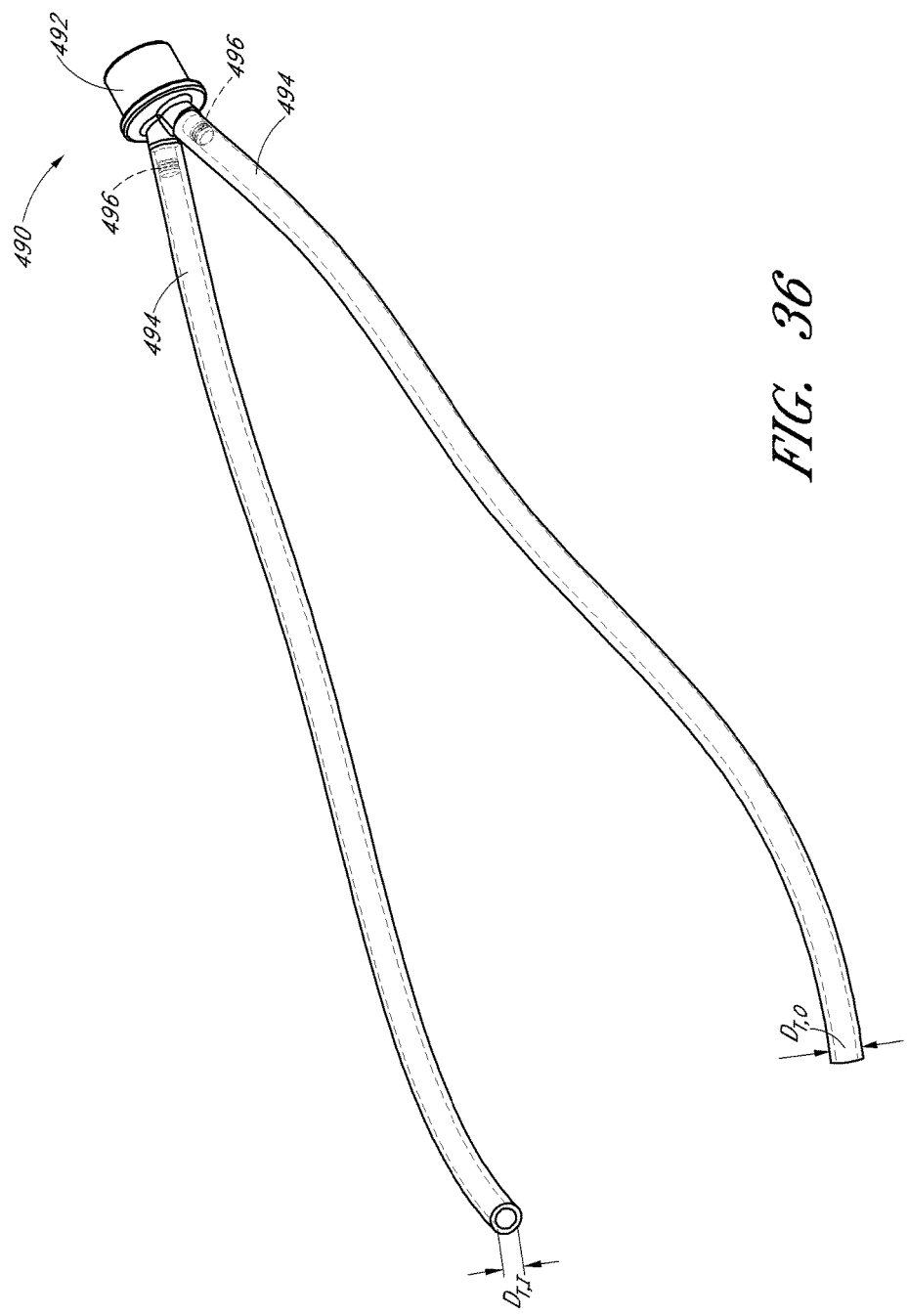
FIG. 36 illustrates an exemplary embodiment of an air supply sub-assembly.

FIG. 36 illustrates an exemplary embodiment of the air supply sub-assembly 490. The sub-assembly 490 can be configured to simultaneously maintain uniform pressure from the air flow generator to the interior volume of the manifold 404 and facilitate re-pressurization during the breathing cycle. The sub-assembly 490 can connect to the manifold 404 and/or air flow generator using a magnetic attachment, a screw fit, a friction fit, an adhesive, or otherwise. Although FIG. 36 illustrates the sub-assembly 490 having two tubes 494, the sub-assembly 490 may only include only one tube.

In certain aspects, the sub-assembly 490 can include two air supply tubes 494 and an airflow generator connector 492. In certain aspects, the sub-assembly 490 can be configured to reduce the industry standard flow rate from the airflow generator of greater than 150 L/min to no more than about 80 L/min, typically less than or equal to about 60 L/min. In certain aspects, the flow rate can be less than or equal to about 40 L/min or less than or equal to about 20 L/min. In certain aspects, the flow rate can be between about 10 L/min and about 30 L/min or between about 20 L/min and about 40 L/min. In certain aspects, the connector 492 can provide an initial constriction and/or the air supply tube(s) 494 can restrict air flow. For example, an outer diameter of the hose can be between about 3.0 mm and about 15.0 mm. In some embodiments, an inner diameter of those hose can be less than or equal to about 10.0 mm, e.g., between about 5.0 mm and about 10.0 mm. In some embodiments, a wall thickness of those hose can be less than or equal to about 1.0 mm, e.g., between about 0.5 mm and about 0.75 mm. The smaller hose is less bulky than traditional hoses for CPAP devices. In certain aspects, the connector 492 can include one or more valves to control air flow from the airflow generator.

The connector 492 can be manufactured using any suitable technique, including, but not limited to, machining, molding, or SLA processing. In certain aspects, the connector 492 can include any material having a durometer of at least about 10 A and/or less than or equal to about 50 D. In certain aspects, the connector 492 includes any medical grade polymer material, including, but not limited to, ABS, PVC, nylon, Pebax®, polycarbonate, Delrin®, rubber, Teflon®, and/or urethane.

In certain aspects, the connector 492 can include an inlet portion 498 having a single inlet connected to the air flow generator (not shown). In certain aspects, the outer diameter $D_{F,1}$ of the inlet portion 498 can be at least about three times the outer diameter $D_{A,O}$ of the first connector portion 488 and/or less than or equal to about four times the outer diameter $D_{A,O}$ of the first connector portion 488. In certain aspects, the outer diameter $D_{F,1}$ of the inlet portion 498 can be less than or equal to about 1.0 inch, less than or equal to about 0.9 inches, or otherwise.

Figure 37A:
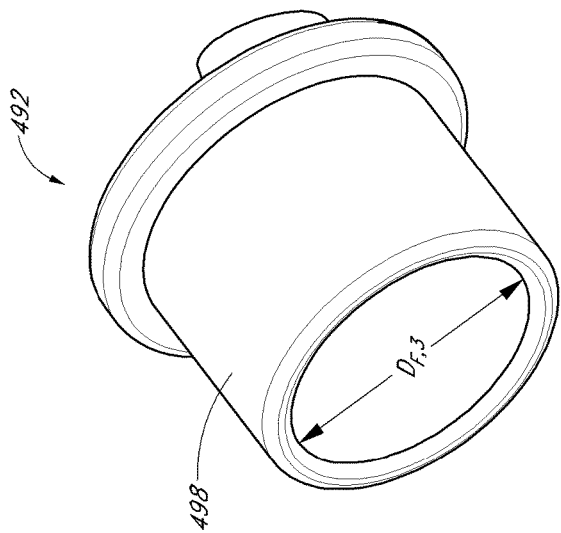
FIGS. 37A-C illustrate an exemplary embodiment of an air supply connector.
Figure 37B:
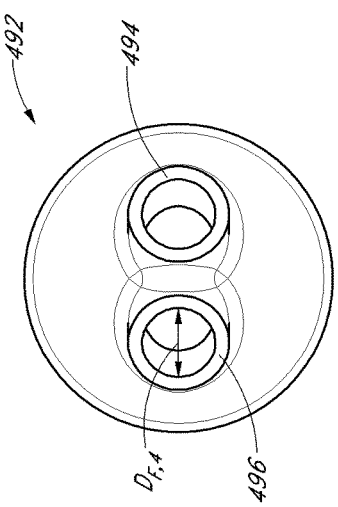
Figure 37C:
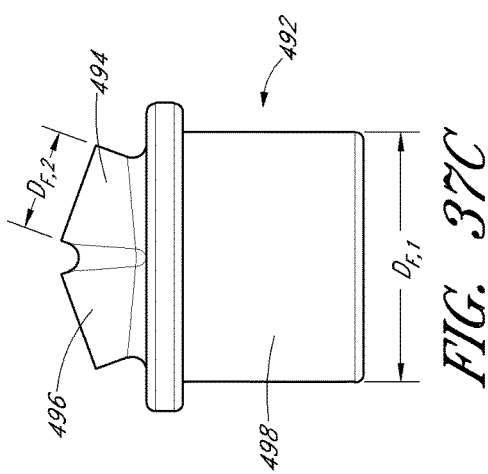

As shown in FIG. 37B, the connector 492 can include two outlet openings 494, 496, each configured to connect to an air supply tube 494. In certain aspects, the outer diameter $D_{F,2}$ of each outlet 494, 496 can be less than or equal to about one-third the outer diameter $D_{F,1}$ of the inlet portion 498, less than or equal to about one-fourth the outer diameter $D_{F,1}$ of the inlet portion 498, or otherwise. In certain aspects, the outer diameter $D_{F,2}$ of the outlet openings 494, 496 can be greater than or equal to the outer diameter $D_{A,O}$ of the first connector portion 488. In certain aspects, the outer diameter $D_{F,2}$ of each outlet 494, 496 can be less than or equal to about 0.3 inches, less than or equal to about 0.25 inches, or otherwise.

In certain aspects, the internal diameter $D_{F,4}$ of each outlet 494, 496 can be less than or equal to about one-third $D_{F,4}$ the internal diameter of the inlet portion 498, less than or equal to about one-fourth the inner diameter $D_{F,4}$ of the inlet portion 498, or otherwise. In certain aspects, the inner diameter $D_{F,4}$ of the outlet openings 494, 496 can be greater than or equal to the internal diameter $D_{A,I}$ of the first connector portion 488, less than or equal to about 1.5 times the internal diameter $D_{A,I}$ of the first connector portion 488, and/or less than or equal to about 1.25 times the internal diameter $D_{A,I}$ of the first connector portion 488.

The air supply tubing 494 can be manufactured using any suitable technique, including, but not limited to, extruding, casting, or necking to create the desired diameter. In certain aspects, the tubing 494 can include any medical grade polymer, including, but not limited to, Tygon®, urethane, Pellethane®, Tecoflex®, silicone, Pebax®, nylon, polyethylene terephthalate, polyethylene, and/or PVC. In certain aspects, the tubing 494 can include a support structure including a metallic material, including, but not limited to, stainless steel (e.g., 300 series), nitinol, steel, carbon fiber, tantalum, palladium, titanium, copper, and/or cobalt chrome.

In certain aspects, the tubing 494 can be configured with a smaller, outer diameter (e.g., between about 3.0 mm and about 15.0 mm) or smaller length as compared to traditional CPAP devices. With smaller tubing 494, the tubing 494 will not kink (e.g., capable of bending around a rod of 0.5 inches without appreciable kinking) and will be more user friendly. In certain aspects, the dimensions of the tubing 494 can be controlled to control the amount of air that flows to the mask. In certain aspects, the dimensions of the tubing can vary along the air supply tubing sub-assembly to vary flow. In certain aspects, the tubing 494 can be exchanged depending on the amount of air flow the user desires.

In certain aspects, the cross-section of the air supply tubing 494 can be generally circular or generally elliptical. In certain aspects, the tubing 494 can include an outer diameter $D_{T,O}$ of less than or equal to about the outer diameter $D_{F,1}$ of the first connector portion 498, less than or equal to about one-third of the outer diameter $D_{F,1}$ of the first connector portion 498, less than or equal to about one-fourth of the outer diameter $D_{F,1}$ of the first connector portion 498, or otherwise.

In certain aspects, the tubing 494 can include an internal diameter $D_{T,I}$ of less than or equal to about the internal diameter $D_{F,3}$ of the first connector portion 498, less than or equal to about 80% of the internal diameter $D_{F,3}$ of the first connector portion 498, less than or equal to about 50% of the internal diameter $D_{F,3}$ of the first connector portion 498, less than or equal to about 25% of the internal diameter $D_{F,3}$ of the first connector portion 498, less than or equal to about 20% of the internal diameter $D_{F,3}$ of the first connector portion 498, or otherwise. In certain aspects, the tubing 494 can include an internal diameter $D_{T,I}$ of less than or equal to about the internal diameter $D_{F,4}$ of the outlet opening 496, less than or equal to about three-fourths the internal diameter $D_{F,4}$ of the outlet opening 496, or otherwise. In certain aspects, the tubing 494 can include an internal diameter $D_{T,I}$ of less than or equal to about 0.75 inches, less than or equal to about 0.5 inches, less than or equal to about 0.25 inches, less than or equal to about 0.2 inches, or otherwise. In certain aspects, the tubing 494 can include an internal diameter $D_{T,I}$ of at least about 0.15 inches and/or less than or equal to about 0.25 inches.

FIGS. 38A and 38B illustrates another example of an air supply tubing 702. The air supply tubing 702 can be a single lumen tubing for air delivery only and can include any of the features described above in connection with air supply tubing 494. In certain variants, the air supply tubing 702 can include additional lumens to monitor one or more parameters of the system, including, but not limited to, pressure, flow temperature, and humidity.

In certain aspects, the air supply tubing 702 can be configured with a smaller, outer diameter (e.g., between about 3.0 mm and about 15.0 mm) and/or a smaller length than traditional CPAP devices. In certain aspects, an inner diameter of the air supply tubing can be less than or equal to about 10 mm, e.g., between about 5.0 mm and about 10.0 mm. Unlike traditional CPAP hoses, which usually weigh over 100 grams, the air supply tubing 702 can weigh less than or equal to about 20 grams.

In some embodiments, the air supply tubing 702 can include a generally circular or elliptical cross-section having a cross-sectional area of less than or equal to about 1.5 sq. inches, less than or equal to about 1.4 sq. inches, less than or equal to about 1.3 sq. inches. In certain aspects, the air supply tubing 702 can include a length of less than or equal to about two feet. In contrast to traditional CPAP devices, the smaller tubing is less likely to kink (e.g., capable of bending around a rod of 0.5 inches without appreciable kinking) and will be more user friendly. Further, the air supply tubing 702 can be crush resistance (e.g., requires at least about 0.25 lbs., such as at least about 0.5 inches, preferably at least about 1 lb. or at least about 3 lbs. of clamping force to crush shut).

The air supply tubing 702 can connect to the air flow generator 700 via an air hose connector 704. The air hose connector 704 can include a mechanical, electrical, magnetic, adhesive, welded/fused, or other attachment described herein. In certain aspects, the air supply tubing 702 can removably connect to the air flow generator 700. For example, an actuation member (e.g., button or switch) can be used to engage or disengage the air supply tubing 702. The actuation member can be actuatable with less than 300 gram-force.

In certain aspects, the air supply tubing 702 can be configured to maintain a constant therapeutic pressure (e.g., between about 4 cm H2O and about 20 cm H2O) even when the air flow supplied from the air flow generator 700 varies or the diameter of the air supply tubing 702 varies. Although high air flow rates can cause discomfort, the addition of at least some external air flow can create comfort. In certain aspects, the air supply tubing 702 can include one or more valves to allow the user to adjust air flow to their comfort level and still maintain pressure.

In certain aspects, the air flow generator 700 can be set to a pressure similar to traditional CPAP devices (e.g., at least about 100 L/min), but the airflow can be restricted (e.g., to less than or equal to about 20 L/min) and/or controlled by a restrictor that can adjust the air flow while maintaining constant therapeutic pressure (e.g., between about 4 cm H2O and about 20 cm H2O). The restrictor can be the air supply tubing 702 itself or a separate component disposed within the air supply tubing 702. The ability to adjust the flow rate enables the device 400 to maintain pressure without the discomfort from a high flow rate of air from the air generator 700.

The air supply tubing 702 can include a plastic or woven material having a hardness of less than or equal to about 35 D. The air supply tubing 702 material can include, but is not limited to, PET, polyethylene, polypropylene, polyimide, polyamide, nylon, Teflon®, cotton, polyester, urethane, Grilamid®, or Grilamid® with blending agents.

As shown in FIG. 38C, the air supply tubing 702a can be a braided sleeve constructed from a plurality of polymer strands (e.g., between about 8 strands and about 128 strands, preferably less than or equal to about 32 strands). The use of a polymer strands can decrease the weight of the tubing 702a (e.g., to less than or equal to about 20 grams for a 6-foot tubing 702a) to reduce the bulkiness of the system and reduce the size of the head straps necessary to support the system. In certain aspects, each strand can have a circular or oval cross-section. The diameter of each monofilament can be between 0.001 in and 0.010 in, which can decrease the thickness of the tubing 702a.

The strands can run as single discrete single braid elements or be braided in multiple strands (e.g., two, three, four, five, six, or more) lying next to each other (i.e., multi-filar). Each strand can cross over a counter wound path and cross under a counterwound path (i.e., one-over-one-under) or can be in variations (e.g., two over-two under). After braiding, the tubing 702a can be fit over a mandrel (e.g., about 0.3 in or about 0.5 in) and be heat set (e.g., at about 250° F.) in an oven for a period of time (e.g., about one hour). After heat treatment, the braid can be cooled and then can be coated in a translucent RTV silicone dispersion, urethane, latex, or another suitable material.

The tubing 702a can be constructed such the tubing 702a can be stretched from an unstretched length to a stretched length that is double the unstretched length. A diameter of the stretched tubing 702a can have an internal diameter that is at least about 50% of an internal diameter of the unstretched tubing 702a. When the stretched tubing 702a is released, the tubing 702a can return to the unstretched length. Since the tubing 702a is resilient, unintentional tugs on the tubing 702a do not cause an immediate corresponding tug on the hose.

Advantageously, the braided construction permits the tubing 702a to expand, contract, and elongate when bent to prevent kinking, e.g., allowing the tubing 702a to bend around a rod having a diameter of about 0.5 in without appreciable kinking). When the tubing 702a is bent, the outside surface of the tubing 702a can stretch, while the inside surface of the tubing 702a can contract.

In some embodiments, the air supply sub-assembly can include two air supply tubes having different diameters, e.g., a first tubing 702a can deliver air to the manifold and a second feedback tubing 702b can deliver air to the expiratory valve, so the expiratory valve provides the desired resistance (see, e.g., FIGS. 38D to 38G). The tubings 702a, 702b can connect to the air flow generator 700 using the same connector (as shown), separate connectors, or the tubing 702b can split off from the tubing 702a. The first tubing 702a can have a diameter between about 3.0 mm and about 15.0 mm, while the second tubing 702b can have a diameter of less than or equal to about 3.0 mm (e.g., less than or equal to about 2.0 mm, such as between about 1.25 mm and about 1.75 mm or between about 1.0 mm and about 1.5 mm).

The tubings 702a, 702b can run in parallel, free of any connection (see FIG. 38D) or be maintained next to each other by bands, tape, glue, an oversleeve, co-extruded jacket, heat shrink, dip molding a bonding skin, or otherwise.

In some embodiments, as shown in FIG. 38E, it may be desirable to position tubing 702b within tubing 702a to provide a less cumbersome or tangled configuration.

In some embodiments, as shown in FIG. 38F, the tubing 702b can wrap around the outside of the tubing 702a. This configuration can further reduce the likelihood of kinking. Since the feedback portion of the system forms a closed system, air flow through the feedback tubing 702b is minimal and nearly static. Any pressure drop through a tortuous tubing 702b is minimal, thus making the coiled tubing 702b feasible.

In some embodiments, as shown in FIG. 38G, the tubing 702b can be both coiled and positioned within the tubing 702a. This configuration provides a simple, relatively smooth system to the user, but still takes advantage of the coiled tubing 702b to help maintain a kink resistant structure air supply tube assembly.

Figure 52:
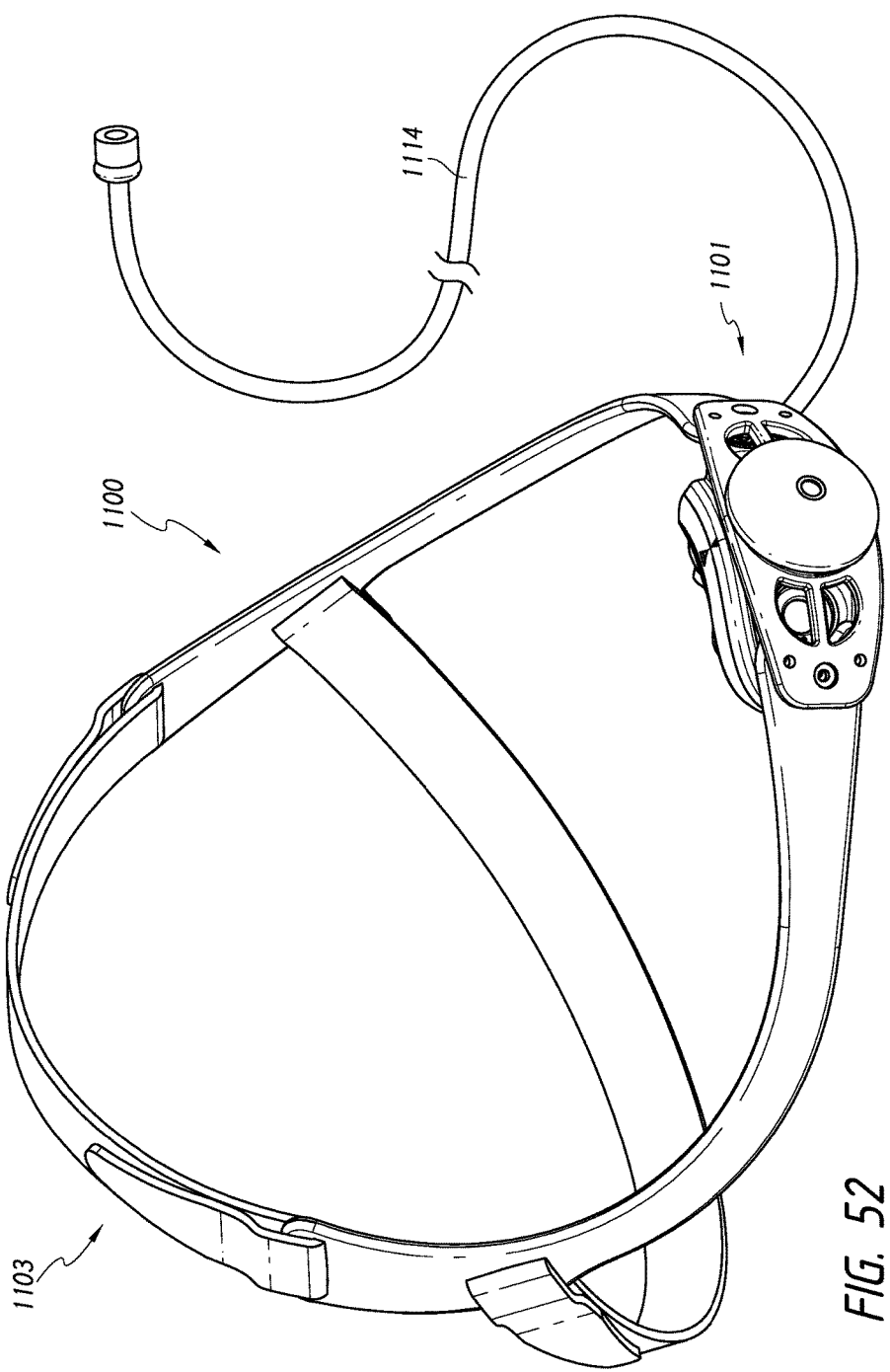
FIG. 52 illustrates another embodiment of a sleep apnea device.

FIG. 52 illustrates an air supply tubing 1114 secured to a sleep apnea device 1100. The air supply tubing 1114 can be secured to one of the ports 1116. In some embodiments, the air supply tubing 1114 can include a cross-sectional area of less than or equal to about 1.5 sq. inches and a length of at least about 5 feet and/or less than or equal to about 7 feet, for example, about 6 feet. In some embodiments, the air supply tubing 1114 can include an internal diameter of less than or equal to about 10 mm, preferably between about 4 mm and about 8 mm, such as about 6 mm. The small diameter air supply tubing 1114 can be more aesthetically desirable and can be positioned to avoid obstructing the user. For example, the air supply tubing 1114 can be secured along at least a portion of the headgear portion 1103.

Although not shown, an end of the air supply tubing 1114 can connect to an airflow generator, such as the airflow generator 700. The airflow generator can be a fan, a positive displacement pump, or any other airflow generating device described herein. The airflow generator 700 can provide a pressure between about 0 cm H2O and 30 cm H2O, preferably between about 0 cm H2O and about 20 cm H2O, such as between about 0 cm H2O and about 15 cm H2Oor between about 5 cm H2O and about 20 cm H2O. Further, the air flow generator 700 can provide a flow rate between about 0 L/min and about 50 L/min, preferably less than or equal to about 30 L/min, for example, between about 15 L/min and about 30 L/min, such as about 20 L/min or 25 L/min. In some embodiments, the airflow generator 700 provides a pressure of about 10 cm H2O at a flow rate of about 20 L/min.

An active expiratory valve, such as the valves 1106, 1106a, and 1106b, alone or in combination with the small diameter air supply tubing 1114 can provide sufficient therapeutic pressure and provide substantially constant therapeutic pressure independent of the exhalation flow rate. In contrast, the therapeutic pressure provided by traditional CPAP, which includes a passive valve (e.g., a perforated plate) and a large bore tube, is dependent on flow rate. As such, if a user robustly exhales, the pressure will spike making it more difficult for the user to breathe. If the flow rate is too low, the system cannot generate sufficient therapeutic back pressure. Further, unlike the devices described herein, traditional CPAP devices cannot function with a small bore air supply tubing because the traditional CPAP device would be unable to generate sufficient therapeutic pressure. In addition, the large bore tubing acts as a damper. Without the large bore tube, the user would experience a greater number of and/or more severe pressure spikes.

As described above in connection with the air supply tubing 702, it can be desirable to produce an elongate, kink resistant, crush resistant, flexible tube for air delivery. The tubing can include an elongate coil with a coil spacing of between 0.025 in. and 0.150 in. The coil can be at least about 5 feet and/or less than or equal to about 7 feet long. Further, the coils can be constructed from a flat wire to reduce the profile on the tubing ID. These coils can be constructed from stainless steel ribbon that is 5×10 thousandth of an inch to 20×60 thousandth of an inch.

Separately an extrusion can be made of a soft plastic or elastomer, preferably silicone. The extrusion can be made with an internal diameter to form an interference fit with the coil. By way of example, a coil with an outer diameter of about 0.3 in. is paired with an extrusion having an internal diameter of about 0.270 in. The extrusion preferably has a wall thickness between about 0.020 and about 0.040 in.

Figure 56:
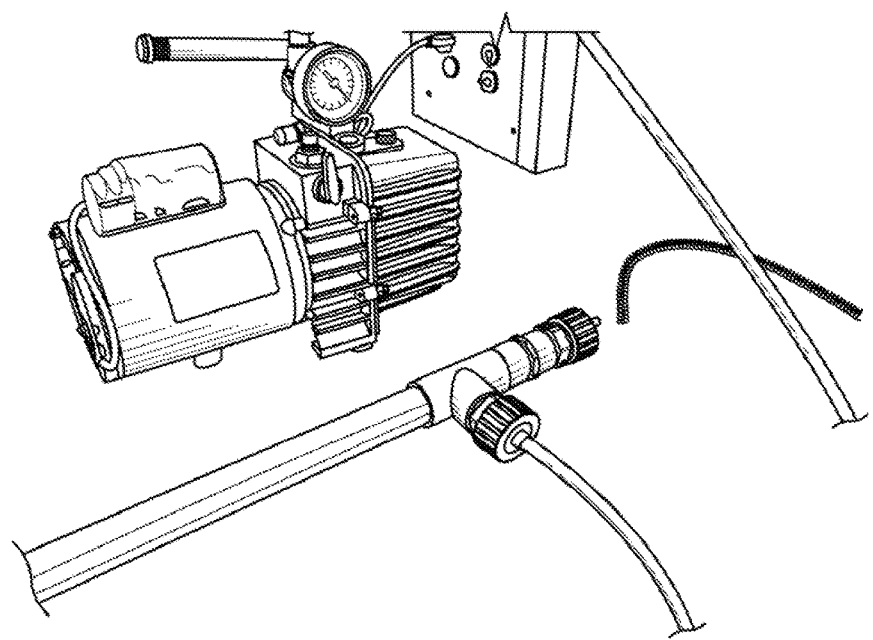
FIGS. 56-57 illustrates a method for manufacturing air supply tubing.
Figure 57:
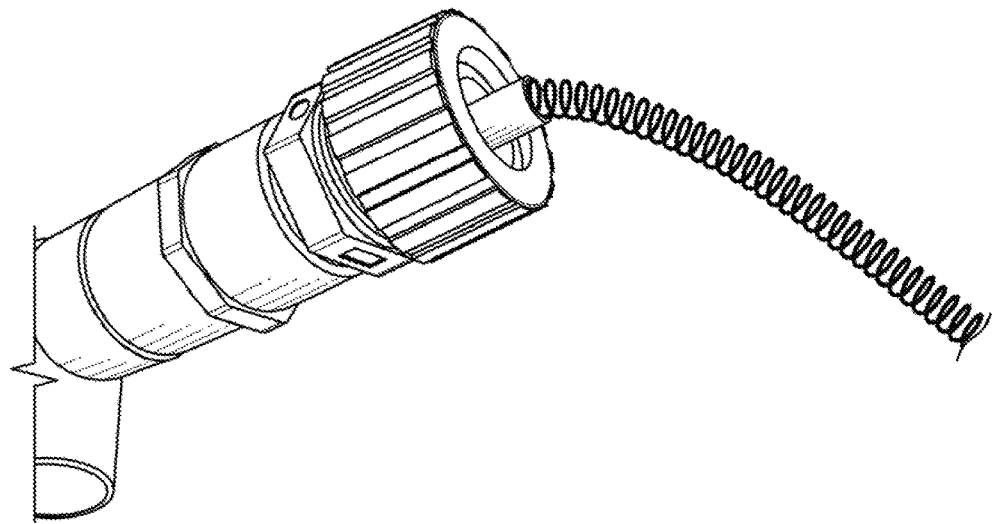

To create the composite tube, the extrusion can be placed through an elongate piece of piping (see FIG. 56). Thin walled stainless steel bushings can be slid into each end of the extrusion. The elongated piping can have "iris" type annular clamps on each end. The extrusion can be secured in place with the iris clamps, which also creates an airtight seal. The elongated pipe can be connected through a small port to vacuum. When the vacuum is applied, the extrusion expands and the coil can be inserted into the extrusion (see FIG. 57). Releasing the vacuum causes the extrusion to shrink back down over the coil in an interference manner. This produces a composite tube with desirable properties of kink, crush, and flop.

Further, the tubing can be coated with an inherent tack reducing substance (e.g., parylene). Surface treatments can also give the silicone a frosted texture or microscopic roughness and reduce tackiness. Reduction of tackiness is important for comfort since the air supply tube may contact the face, arm, torsos of a person wearing and attempting to sleep.

An alternate manner to create the tubing is to utilize the coil with particular shrink tubing. The shrink tubing is slid over the coil and then heated to shrink it in place. The shrink tube can be formed from a suitable polymer, such as PEBAX. PEBAX is a less common shrink tube material, but it is softer than traditional shrink tube materials. The tubing can have a recovered wall thickness of about 0.001 in. to maintain flexibility. It can be useful to place the coil over a mandrel before applying the heat shrink. Further, it can be desirable to use a mandrel that is close fitting to the ID of the coil to minimize the depth of convulsion.

Air Flow Generator

As described earlier, the device 400 can be in communication with an air flow generator, such as the exemplary generator 700 illustrated in FIGS. 38A to 38G. The air flow generator 700 can supply air to the user in addition to the ambient air flowing in through the inspiratory valve 410, which can help maintain pressure. For example, if the user stops breathing during exhalation, the pressure generated from the air flow generator 700 can help increase pressure until the expiratory valve opens. If the user stops breathing during inhalation, the inspiratory valve closes and the pressure from the air flow generator 700 can help raise the pressure again until the user inhales normally.

Traditional CPAP devices modulate pressure by supplying air flow at flow rates greater than or equal to about 150 L/min. These high flow rates can cause patient discomfort during exhalation due to increased resistance, nasal dryness, dry mouth, ear pain, rhinitis, abdominal bloating, and/or headaches. In addition, the high flow rates can create unintentional leak paths that can cause patient discomfort or physiological complications, such as aerophasia or GERD. These drawbacks ultimately lead to poor patient compliance. Over half of all patients who try CPAP stop using the device.

Traditional CPAP devices can deliver air flow at a slope ratio of about 5/2 (L/min/cm H20). This ratio is based on the air flow rate at the user interface. The slope ratio between flow and pressure can be much higher at the CPAP air flow generator to compensate for a long air hose and intentional and unintentional leak paths. Intentional leak paths are often necessary in traditional CPAP devices to vent exhaled carbon dioxide. These inefficiencies generate loud noise and consume large amounts of energy.

In addition, traditional CPAP air flow generators weigh approximately five pounds and measure approximately 10" by 8" by 6". Due to the size of the CPAP air flow generator, traditional generators must be positioned on a bedside table or on the floor near the bed. The positioning of the CPAP air flow generator necessitates a longer air hose, which is less user friendly. The weight of traditional CPAP air flow generators also makes it difficult to travel with CPAP devices.

In contrast to traditional CPAP devices, the air flow generator 700, in combination with the air supply tubings described above (e.g., tubing 702, tubing 702a, or tubing 702a), can create air flow at a rate of less than or equal to about 60 L/min, less than or equal to about 40 L/min, less than or equal to about 30 L/min, less than or equal to about 20 L/min, or otherwise. In certain aspects, the air flow generator 700 alone, or in combination with the air supply tubing, can create air flow rates of at least about 10 L/min and/or less than or equal to about 40 L/min, such as between about 10 L/min and about 20 L/min or between about 20 L/min and about 30 L/min. In certain aspects, the air flow rates can be at least about 20 L/min and/or less than or equal to about 30 L/min. These flow rates can be programmed into the air flow generator 700 or mechanically adjusted at an exit port.

Lower flow rates can minimize patient discomfort and unintentional leak paths. The air flow generator 700 and air supply tubing 702 do not create unintentional leak paths because of the decreased air flow rate and non-constant pressure, which can increase patient comfort and compliance. In addition, these lower flow rates produce less noise and require less energy.

The air flow generator 800 can supply a pressure between about 4 cm H2O and about 20 cm H2O. The pressure can be adjusted in 0.5 cm H2O increments. In certain aspects, the air flow generator 700 can create a pressure of at least about 5 cm H2O and/or less than or equal to about 20 cm H2O. In certain aspects, the air flow generator 700 can create a pressure of less than or equal to about 10 cm H2O.

In certain aspects, the diameter of the tubing 702 can be less than or equal to about 20 mm, less than or equal to about 15 mm, less than or equal to about 5 mm, or otherwise. In certain aspects, the diameter of the tubing 702 can be at least about 4 mm and/or less than or equal to about 6 mm. In certain aspects, the airflow generator 700 can create a pressure of up to 20 cm H2O at a flow rate of less than 40 L/min delivered through a tube 702 with an internal diameter of less than 4 mm and a length of more than 30 cm.

Figure 39:
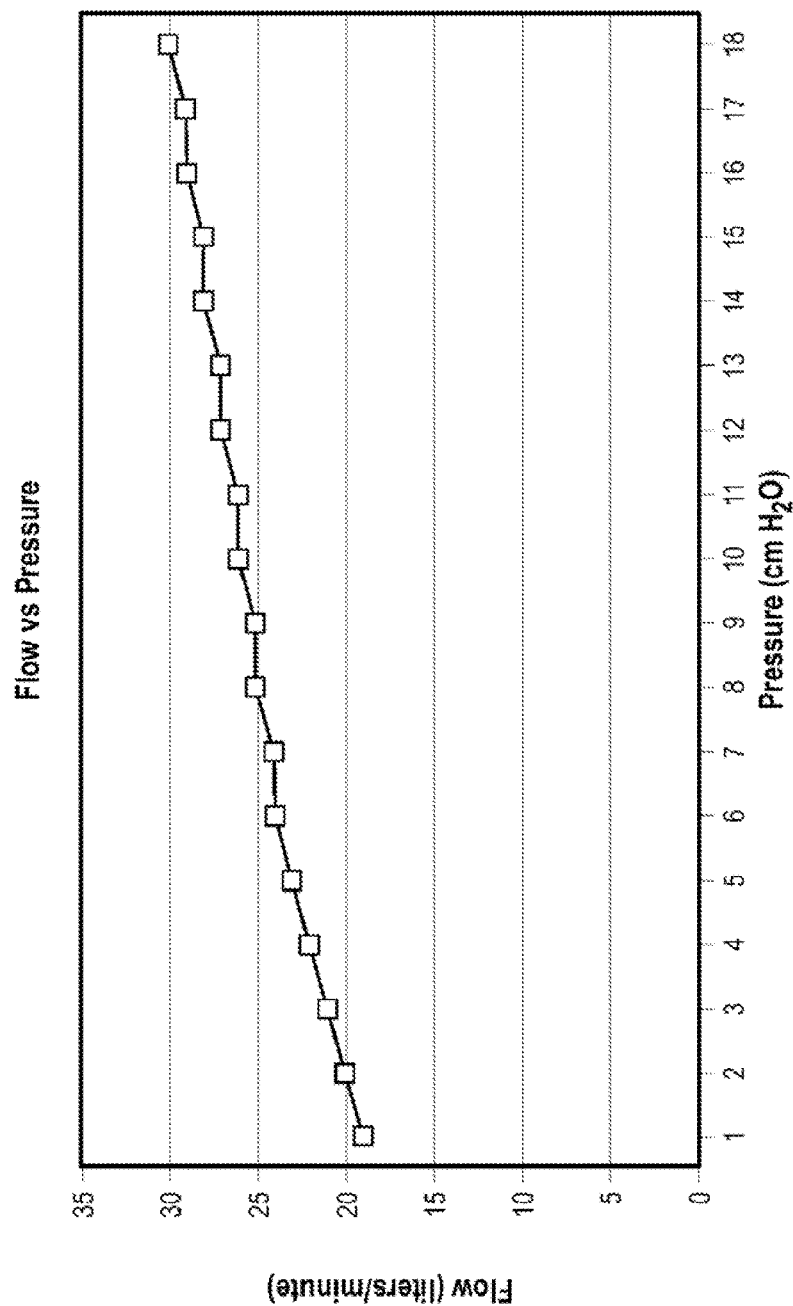
FIG. 39 is a graph demonstrating the relationship between flow and pressure for the air flow generator.

As shown in FIG. 39, the air flow generator 700 can deliver air flow at a slope ratio of less than or equal to about 7/5 (L/min/cm H20). For example, the air flow generator 700 can deliver air at a rate between about 20 L/min and about 30 L/min, or between about 10 L/min and about 20 L/min, at a pressure between about 4 cm H2O and about 20 cm H2O. The slope ratio for the air flow generator 700 is approximately the same at both the user interface and the air flow generator 700 because of a shorter air hose and no intentional or unintentional leak paths. In contrast to traditional CPAP, the air flow generator 700 can supply a pressure between about 4 cm H2O and about 20 cm H2O but at lower flow rates.

In certain aspects, the air flow generator 700, in combination with the inspiratory 410 and/or expiratory valve 414 can be configured to rapidly re-pressurize the system in less than or equal to about one second. In certain aspects, the air flow generator 700, in combination with the inspiratory 410 and/or expiratory valve 414, can be configured to rapidly re-pressurize the system up to P critical or the threshold pressure of the expiratory valve 414 to quickly eliminate any apneas. If an apnea occurs, the rescue pressure from the air flow generator 700 can immediately pressurize the system above the P critical pressure such that the pharynx opens.

In certain aspects, the system can re-pressurize the system to a threshold pressure in less than or equal to one second. In certain aspects, the threshold pressure can be at least about 5 cm H2O and/or less than or equal to about 20 cm H2O. In certain aspects, the threshold pressure can be about 8 cm H2O, about 10 cm H2O, about 15 cm H2O, or otherwise. In certain aspects, the system can re-pressurize the system at a rate of at least 20 cm H2O/second.

Returning to FIGS. 38A to 38G, the air flow generator 700 can be sized and shaped for portable use and/or to be positioned less than two feet from the user without obstructing the user. For example, the air flow generator 700 can be positioned on a bedside table, in the bed, or worn by the user (e.g., around the user's arm, coupled to a belt, secured to a chest strap, etc.). When the air flow generator 700 is positioned in the bed, the air flow generator 700 can be positioned on the mattress, within a pillow, or secured to a mattress handle. The air flow generator 700 can include a strap or clip to maintain the unit in a stable position.

In certain aspects, the air flow generator 700 can weigh less than or equal to about 500 grams, or less than or equal to about 400 grams. In certain aspects, the volume of the air flow generator 700 can be less than or equal to about 25 cubic inches, less than or equal to about 22.5 cubic inches, or less than or equal to about 20 cubic inches. For example, the dimensions of the air flow generator 700 can be about 5"×3"×1.5". These parameters are significantly smaller than the traditional CPAP air flow generators, which makes the device easier to carry during travel and position in various sleeping positions.

The air flow generator 700 can include a generally rectangular or generally rounded housing 706. The housing 706 can include generally flat or rounded upper and lower surfaces and/or generally rounded corners. In certain aspects, the housing 706 can include a light weight metal (e.g., titanium, palladium, aluminum, nitinol, or otherwise) and/or a polymer (e.g., nylon, Pebax®, ABS, PVC, PEEK, urethanes, or otherwise).

The housing 706 can include one or more vents 708 to provide ambient air. The ambient air entering the air flow generator 700 can converge into the air supply tubing 702. The vents 708 can be profiled and/or static diffused to impede dust and particulate from entering the system. In certain aspects, a HEPA filter can be used to impede particulate from entering the system without hampering flow performance. In certain aspects, the system can be configured to operate in reverse to back blow particulate or contaminants out of the vents to remove blockages and provide a clean air path.

For travel purposes, the air flow generator 700 can include a reservoir attachment to help balance pressure at elevations greater than 5000 feet above sea level. The reservoir can be a bag or air cartridge, carrying compressed air and/or oxygen enhanced air.

In certain aspects, the air flow generator 700 can include a display screen (not shown). The screen can display one or more parameters, including, but not limited to, pressure, flow rate, flow temperature, elevation, and humidity. In certain aspects, the display screen can display one or more parameters related to the user's environment, such as time or temperature. In certain aspects, The display screen may display battery levels and indicate whether the battery is charging. For example, the display screen can indicate "charging," "charging complete," or "low battery." Alternatively, the air flow generator 700 can include one or more indicator lights to indicate battery levels and/or whether the battery is charging.

The air flow generator 700 can include one or more features to permit the user to control the unit. For example, the air flow generator 700 can include a number of actuation members (e.g., buttons or switches), a touch screen, and/or be configured for voice recognition. These features can permit the user to control power and/or flow rate (e.g., "off," "low," "medium," and "high."). For example, as shown in FIG. 38A, the air flow generator 700 can include an on/off button 710 and/or a switch 712 to control the air flow rate. For example, the switch 712 can toggle between different flow rates. The buttons and switches 710, 712 can be actuatable by less than 300 gram-force.

The air flow generator 700 can include a system to monitor the user and/or the user's environment. For example, the generator 700 can include an electromechanical system to sense vibrations to assess the user's sleeping patterns (e.g., user movement, sleep cycles, sleep times, arousal times, etc.). The short distance between the user and the air flow generator 700 can make it easier to monitor the user's movements. In certain aspects, the air flow generator 700 can monitor noise and/or motion and vibration external to the user.

Figure 40:
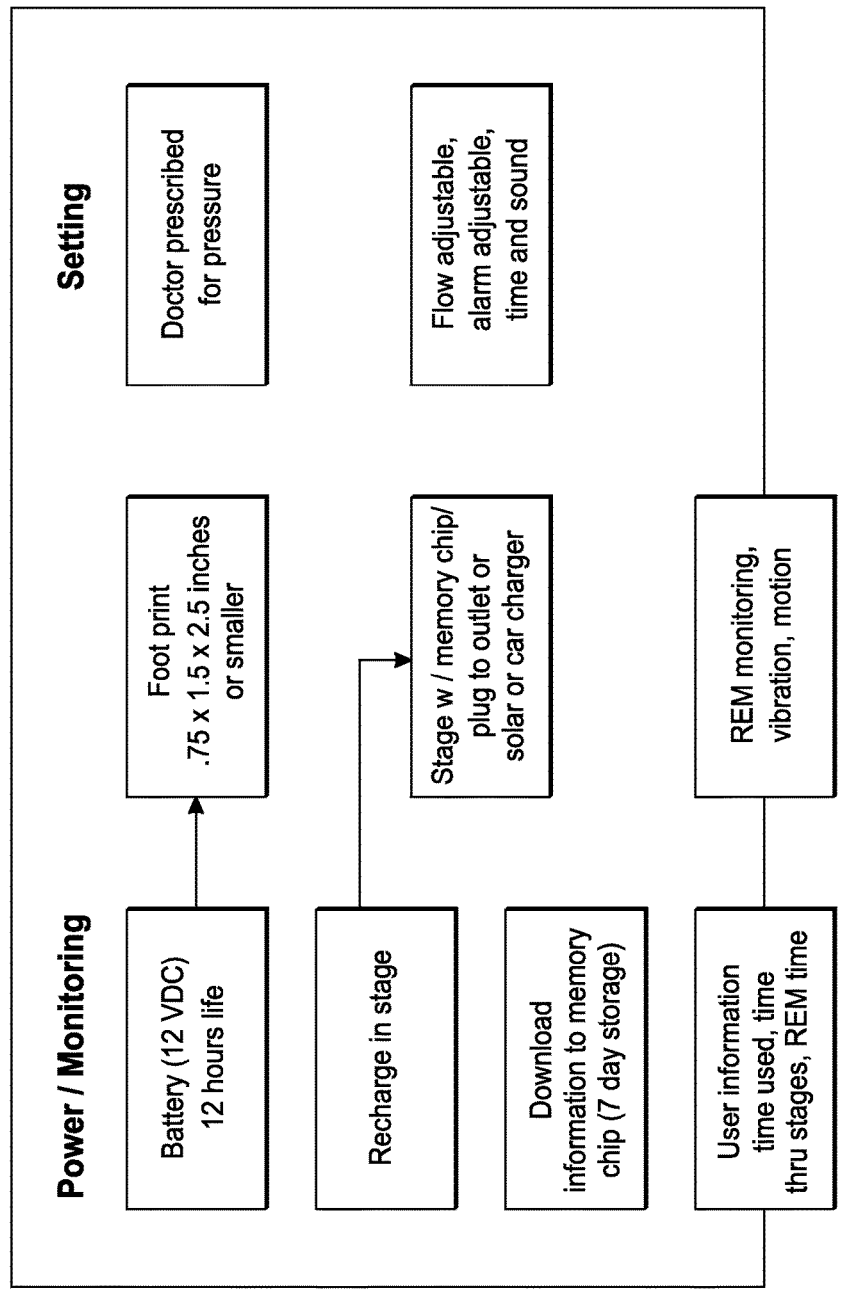
FIG. 40 is a flow diagram illustrating possible components of the air flow generator.

FIG. 40 illustrates a diagram of a number of possible features for the air flow generator 700. For example, the device 400 and/or air flow generator 700 can include memory to store the user's breathing profile for at least seven days. The user's breathing profile can include, but is not limited to, changes in pressure, flow rates, and time elapsed per breathing cycle. The air flow generator 700 can also record usage statistics (e.g., user interacting, settings, duration of use, or otherwise). In certain aspects, the data can be stored on a removable memory card.

In certain aspects, the device 400 and/or air flow generator 700 can include a wireless transmitter to communicate the data stored on the memory to a health care provider or to the cloud. If valve adjustments are necessary, the health care provider can adjust one or more of the valves or send a new valve to the patient.

The air flow generator 700 can be powered using a battery and/or include an AC adaptor port to connect the generator 700 to a wall outlet. The battery can power the air flow generator for at least 12 hours without a direct power connection. The air flow generator 700 can be powered by 24 VDC or 12 VDC and functional at 0.24 amp/hr. If the air flow generator 700 is powered by AC power, the generator 700 can be powered by 110-220 VAC nominal and functional at 3 amps.

The battery can be charged by plugging in the battery using an AC adaptor or connecting the battery to a charging station. The charging station can include a wireless transceiver configured to receive information and/or transmit information stored on the air flow generator 700 to a memory stick, to the cloud, or to a care giver over Wi-Fi.

In certain aspects, the air flow generator 700 can be powered using a mechanical system. For example, the air flow generator 700 can include a wind-up spring or other spring based mechanism to generate a small amount of power to power the air flow generator for a short duration. This mechanical system can be useful for short trips, when the user sleeps upright, or when the battery is running low.

In certain aspects, the air flow generator 700 can generate less than 30 dBA at least in part because of low flow rates. In certain aspects, the housing 706 can include a mechanical shell to sound proof the air flow generator. For example, the shell can include materials such as rubber foams or melamine sponges. In certain aspects, the air flow generator 700 can include an internal noise cancellation system electrically integrated with the air flow generator 700.

In certain aspects, the air flow generator 700 can include a water proof seal system to protect against any water damage to the electronic or measurement boards. For example, the circuit boards and internal cavities of the air flow generator 700 can be coated with a soft durometer material (e.g., less than or equal to about 95 A durometer). The soft durometer material can include, but is not limited to, urethane, parylene, polyethylene, silicone, or a gel.

The air flow generator 700 can include a power management system configured to monitor the patient's sleep patterns, adjust power delivered to a motor, and/or reserve battery power based on those sleep patterns. For example, the power management system can deliver power based on the patient's breathing rate. The power management system can increase the incline of slope ratio between flow and pressure if the user is having difficulties breathing. When the patient stabilizes or at certain REM stages, the power management system can decrease the slope ratio to optimize comfort and minimize disruptions. As another example, the power management system can deliver more power to the motor after the generator detects a significant apneic event.

In certain aspects, the air flow generator 700 can include a pressure sensor and/or a flow sensor for sensing back pressure or pressure spikes. The air flow generator can include an electrical feedback system to alarm the patient and/or shut off the air flow generator to prevent the generator from over-heating.

In certain aspects, the air flow generator can include a mechanical or software lockout feature to prevent the user from altering the prescription settings. The air flow generator can be configured such that the prescription settings can only be adjusted by a single user interface.

In certain aspects, the sleep apnea devices described herein can be used in connection with a mobile device, such as an iPhone®. For example, the mobile device can be used as the air flow generator display screen and/or to control the air flow generator 700. The mobile device can also be used for data storage, communicating data, social networking, and/or telemedicine. In certain aspects, the air flow generator 700 can be secured to the mobile device such that the air flow generator 700 can communicate with the mobile device over a hard wired connection. In certain aspects, the air flow generator can communicate wirelessly with the mobile device.

In certain aspects, the air flow generator 700 can be used in connection with one or more applications programmed on the mobile device. For example, the applications can be programmed to monitor the user (e.g., user movement, sleep cycles, sleep times, arousal times, etc.).

Figure 41:
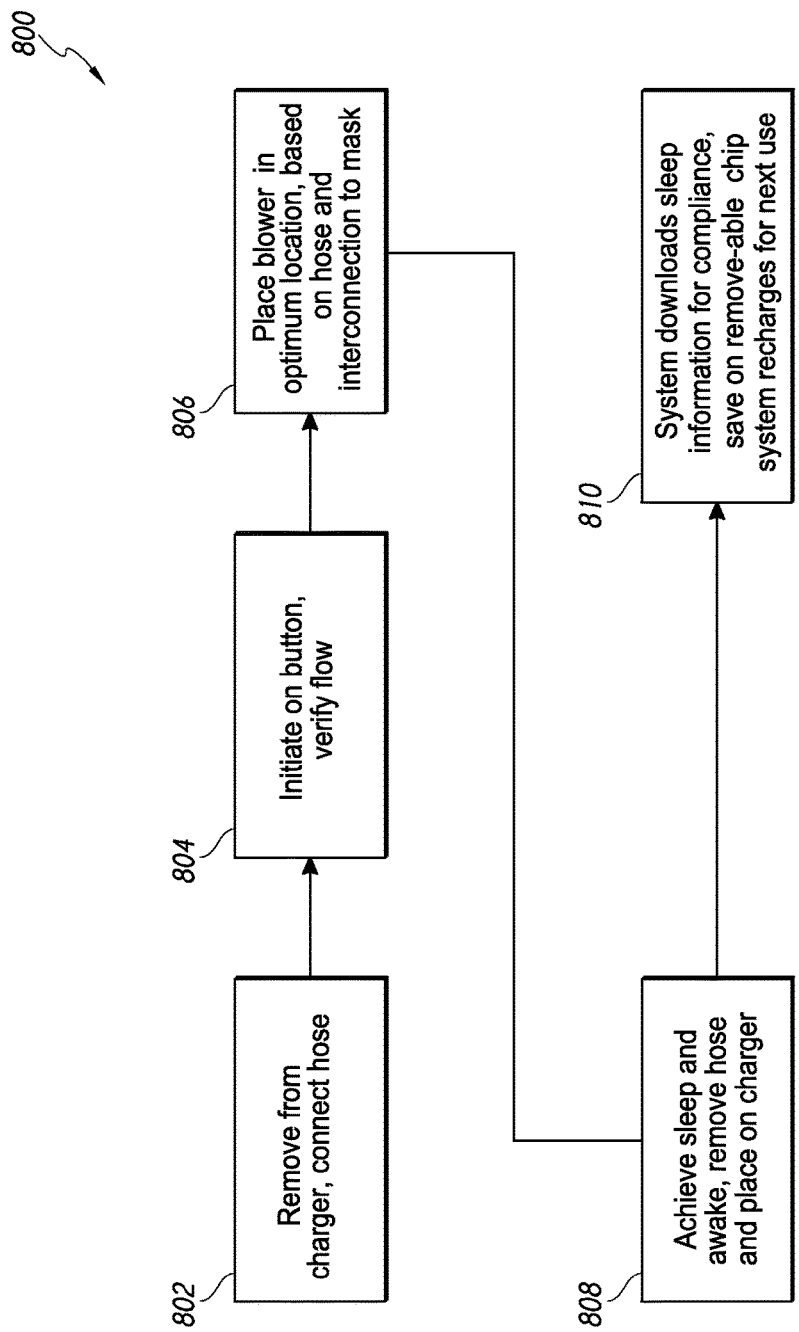
FIG. 41 is a flow diagram illustrating a method of using the air flow generator.

FIG. 41 is a flow diagram 800 illustrating one method of using the air flow generator 700. The method can include removing the air flow generator 700 from the charging station and connecting the air flow generator 700 to the air supply tubing 700 using any of the connection mechanisms described above (block 802). After connecting the air supply tubing 700, the power button 710 can be activated (block 804). After the user verifies air flow, the air flow generator 700 can be positioned in an optimal location and the user can go to sleep (block 806). When the sleep period is complete, the user can remove the hose and connect the air flow generator 700 to the charging station (block 808). The charging station can recharge the generator 700 and download sleep information, transmit the data to the cloud, or transmit the data over Wi-Fi to the care giver (block 810).

In general, the air flow generator 700 can operate at temperatures between 40° and 95° F. The air flow generator 700 can be transported at temperatures between −5° and 140° F. The air flow generator 700 can also operate at an atmospheric pressure between 81 to 102 kPascals.

FIGS. 38H and 38I illustrate another embodiment of an air flow generator 1400. The air flow generator 1400 can include a lid portion 1402 pivotably connected to a base portion 1406. The lid portion 1402 can include a display screen 1410 that can display any of the features described in connection with the air flow generator 700. The lid portion 1402 can move between a closed configuration and an open configuration to position the screen 1410 according to the user's preferences. In certain aspects, the air flow generator 1400 can include a control feature 1404 (e.g., a button or a switch) to control power, air flow rate, or other functionality.

The air flow generator 1400 can include a removable battery 1408. For example, as shown in FIG. 38H, the battery 1408 can be positioned below the base portion 1406. Although the air flow generator 1400 includes the battery 1408, the air flow generator 1400 can be powered by a wall power source.

The air flow generator 1400 can be connected to any of the air supply tubings described herein with any of the connections described herein. In certain aspects, the air supply tubing can be magnetically connected to the air flow generator 1400 (e.g., using toroidal magnetic features).

The air flow generator 1400 can include a removable or replaceable air filter (not shown) positioned in the base portion 1406, so that the filter is not visible when the lid portion 1402 is in the closed configuration.

In certain aspects, the volume of the air flow generator 700 can be less than or equal to about 100 cubic inches, less than or equal to about 90 cubic inches, or less than or equal to about 80 cubic inches. For example, the dimensions of the air flow generator 700 can be about 5"×4"×4.25".

In some embodiments, the air flow generator 1400 may be a computing device that includes one or more processors and a memory, which may contain software applications executed by the processor(s). The display screen 1410 can be a touch screen to provide a user-interface for the user to control the computing device using physical touch. The display screen 1410 can permit the user to turn the machine on or off. Further, the display screen 1410 can permit the user to: adjust air delivery settings such as time delayed or ramped pressure settings, adjust the system between a CPAP or APAP model, monitor use information; receive use or fault messaging; adjust therapeutic pressure settings; provide a clock or alarm clock; detect sleep states (e.g., to avoid activation during the discrete phases of sleep that may result in groggy arousal); access music or movies; select sleep inducing sounds (e.g., flowing water, ocean waves, or breeze); and/or access photos.

In some embodiments, the air flow generator 1400 may include motion sensors (e.g., using cameras, infrared sensors, capacitive sensors, and/or accelerometers) to monitor patient activity, such as by sensing movement or breathing by monitoring chest or thorax motion. These features may allow the user to control system function using hand motions or gestures. In certain embodiments, these features can be used to assess sleep quality (e.g., by detecting length of sleep or how deep a patient is sleeping), for example, to adjust air delivery based on the patient's sleep state. In some scenarios, significant patient motion may be indicative of an awake or lightly sleeping patient. When the patient is not in deep sleep, the air flow generator 1400 can be programmed to decrease or cease. In some scenarios, certain motions may be indicative of an apnea. When an apnea occurs, the air flow generator 1400 can respond by turning on or increasing the therapeutic pressure.

In some embodiments, the mask or head gear may include fiducial markers to facilitate motion detection. In some embodiments, the user may sleep with a specialized blanket having fiducial markers to facilitate motion detection.

Similar to the air flow generator 700, the air flow generator 1400 can have wireless communication capabilities to permit the air flow generator 1400 to store information remotely (e.g., sleep data) or provide tele-medicine capabilities. For example, the air flow generator 1400 may have access to the Internet via a wired or Wi-Fi connection, or via another wireless connection, for example, Bluetooth, a cellular telephone network (e.g., a Long Term Evolution or LTE network), or some combination thereof.

The air flow generator 1400 may be able to communicate with other electronic systems, such as portable cellular smart phone. For example, the smart phone can become a "remote control" or data storage/transmittal system that can physically dock to the box in place of the touch screen.

In some embodiments, the air flow generator 1400 can communicate with other health management devices (e.g., caloric monitors, weight scales, pedometers, heart rate sensors, heart activity sensors (EKG), etc.). Data collected by the air flow generator 1400 (e.g., sleep data) can be used in connection with other health related data to assess or predict patient wellness. For example, the combined data may show that sleep quality equates to higher metabolism (during wakeful periods), which results in a downward or stable trend in body weight. As another example, the combined data may demonstrate that poor sleep quality puts a patient at risk of more erratic or inefficient heart activity In some embodiments, the air flow generator 1400 can provide data to social media networks (e.g., sleep apnea support groups). Users could monitor, motivate, encourage other peers to maintain a high quality level of usage/compliance.

Although the embodiments of the air flow generator 700 described herein have been discussed in connection with a sleep apnea device, the air flow generator can also be used for non-CPAP purposes, such as personal air purification devices for travel or emergency situations. In certain aspects, the air flow generator can be used as an alarm clock.

For example, based on the user's movements, the air flow generator can be configured to determine sleep cycles and wake the patient (e.g. by alarm) when the patient nears the end of a sleep cycle. As another example, the air flow generator can be configured wake the user by emitting a noise, vibration, static discharge, or altering air flow temperature or rate.

Although certain embodiments have been described herein with respect to the device 400 or 400a, the features described in connection with these devices can be interchangeable.

Additionally, the devices described herein can include features that are designed for comfort, which will help promote compliance. For example, returning to the device 400a. The mask 402a can include pliable portions that extend at least partially into the user's nose. In certain embodiments, the mask 402a can be configured to surround the user's entire nose. In certain embodiments, the device 400a can include a plate or additional mask portion to cover the users mouth to prevent air from escaping through the user's mouth. In certain embodiments, the mask 402a or manifold 404 can extend downward to cover the user's mouth. In some instances, the user can be provided with a kit having components that allow the user to alternate between these different mask 402a embodiments.

Further, the kit can include one or more straps. For example, the kit can include an adjustable, bifurcated strap, as shown in FIG. 19B. The kit can also include other strap configurations, such different single strap configurations or different strap materials, that may be more suitable for certain conditions, such as traveling.

As described above, the device can include one or more openings to connect to an air supply tube. For example, the device can include two openings to permit the user to select air supply tube placement for greater comfort. The device and air flow generator can include connectors to facilitate the removal of the air supply tube. For example, the device can include a magnetic connector, a screw fit, a friction fit, or otherwise.

Additionally, each of the components can be constructed from an easily washable material, such as plastic. Once the air flow generator has been disconnected from the device, the device can be washed.

Generally, the devices described herein are configured to reduce the total number of apneic events a user experiences during sleep. During six hours of sleep, the user can experience less than or equal to three apneic events per hour, less than or equal to about two apneic events per hour, or less than or equal to one apneic events per hour. In addition, the devices described herein can reduce the number of times a user wakes up during the night. The user can wake up less than or equal to about 15 times per night, less than or equal to about 12 times per night, less than or equal to about 10 times per night, less than or equal to about 8 times per night, or less than or equal to about 5 times per night. Using the devices described herein, the user's oxygen saturation can be at least about 87, at least about 90, or at least about 93.

Modified Sleep Apnea Device

FIG. 52 illustrates another embodiment of a sleep apnea device 1100. The device 1100 can include any of the features (e.g., valves, connectors, tubing etc.) described in connection with the device 400 shown in FIG. 19 or 400a shown in FIG. 19A. Further, any of the features described in connection with the device 1100 can be incorporated into the device 400 or the device 400a.

Figure 53A:
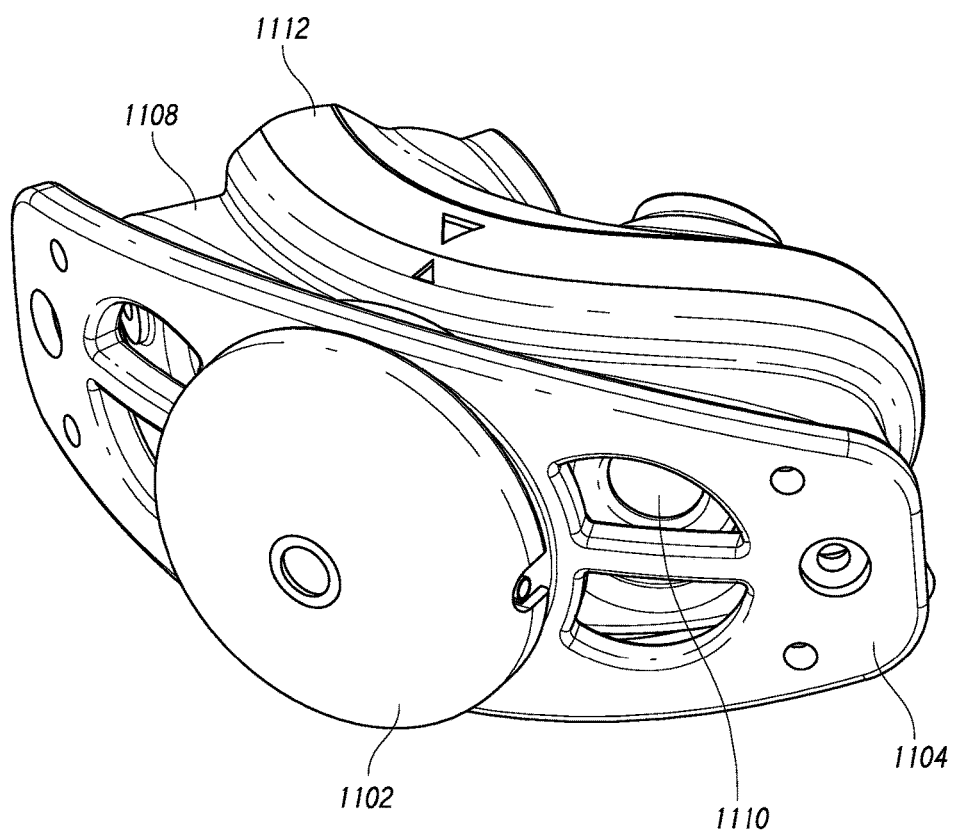
FIG. 53A illustrates a perspective view of a mask portion of the sleep apnea device shown in FIG. 52.

As shown in FIG. 52, the device 1100 can include a mask portion 1101 (see also FIG. 53A). The mask portion 1101 can be removably or permanently secured to a headgear portion 1103 for securing the mask portion 1101 to a user's head. Further, an air supply tubing 1114 can be removably or permanently connected to the mask portion 1101 to provide airflow from a blower having any of the features of the air flow generator 700 described above.

Figure 53B:
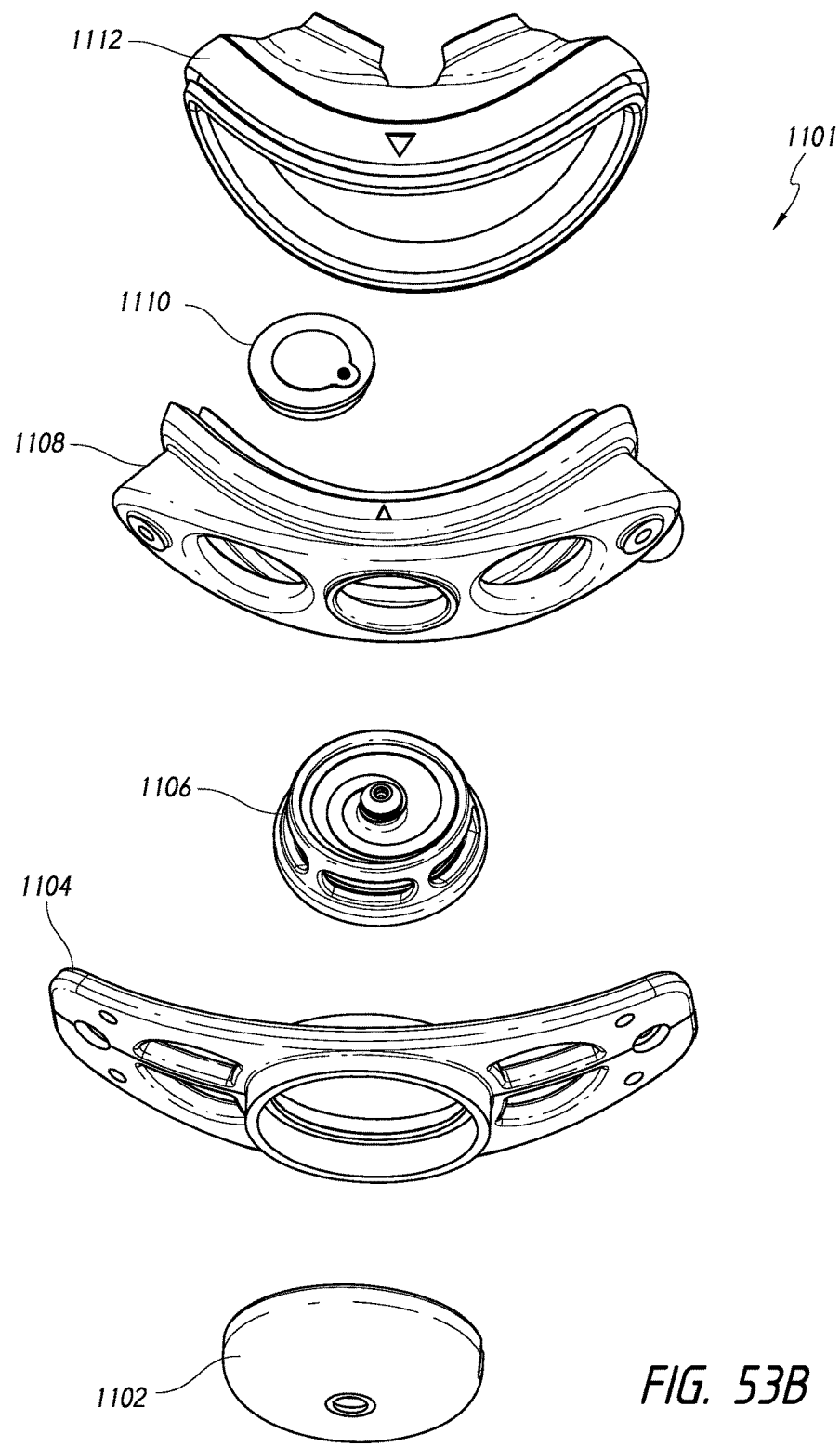
FIG. 53B illustrates an exploded view of the mask portion shown in FIG. 53A.

In general, the mask portion 1101 can be designed to be modular such that components can be easily added, exchanged, or removed. As shown in FIG. 53B, the mask portion 1101 can include one or more of a nasal pillow 1112, at least one inspiratory valve 1110, one or more body portions 1108, 1104, at least one expiratory valve 1106, and a noise mitigating member 1102. FIGS. 53C-53H illustrate each of these components.

Figure 53C:
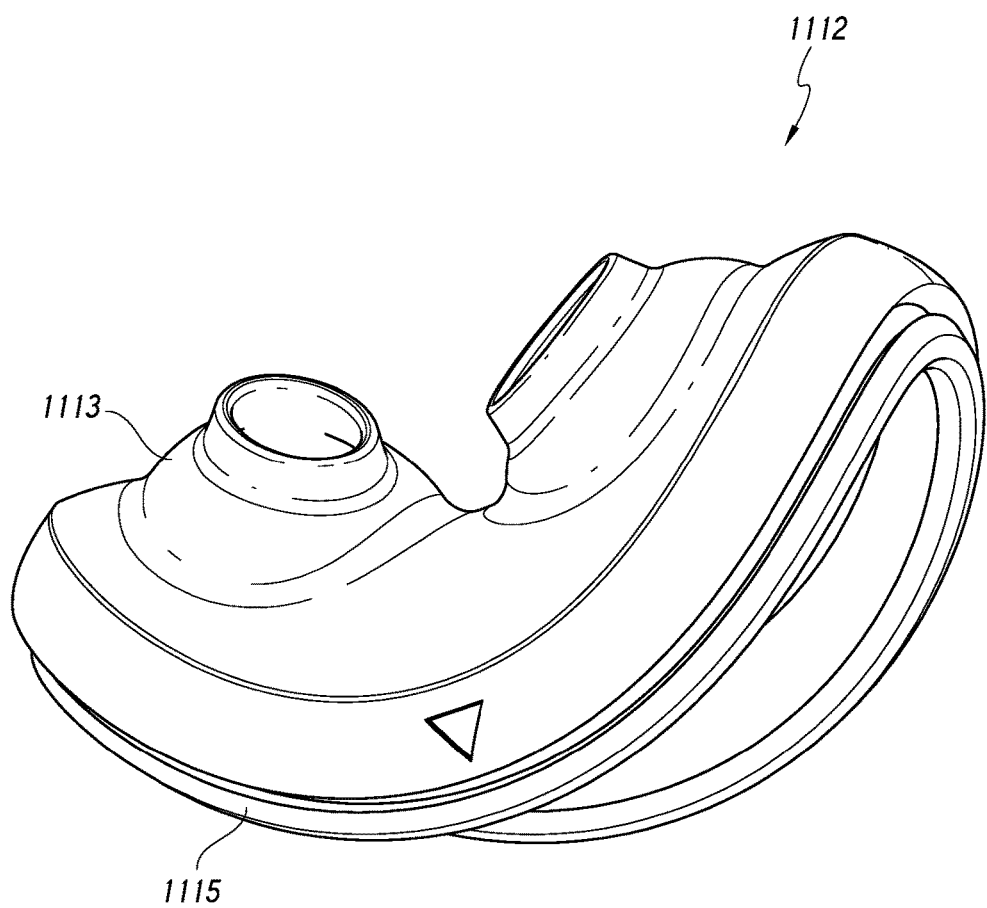
FIG. 53C illustrates a nasal pillow of the mask portion shown in FIG. 53A.

As shown in FIG. 53C, the nasal pillow 1112 or alternatively a nasal mask can be removably secured to a first body portion 1108. The nasal pillow 1112 can include nostril stalks 1113 shaped for insertion into the user's nose. Further, the nasal pillow 1112 can include a flexible lip portion 1115 along a front side of the nasal pillow 1112. The flexible lip portion 1115 can be secured over a corresponding lip portion 1117 on a rear side of the first body portion 1108. The flexible lip portion 1115 can provide an airtight seal while still making it easy to remove the nasal pillow 1112 from the first body portion 1108. The ability to remove the nasal pillow 1112 from the first body portion 1108 easily can make it easier to clean the device 1100. In other embodiments, the nasal pillow 1112 can be integrally formed with the first body portion 1108.

Figure 53D:
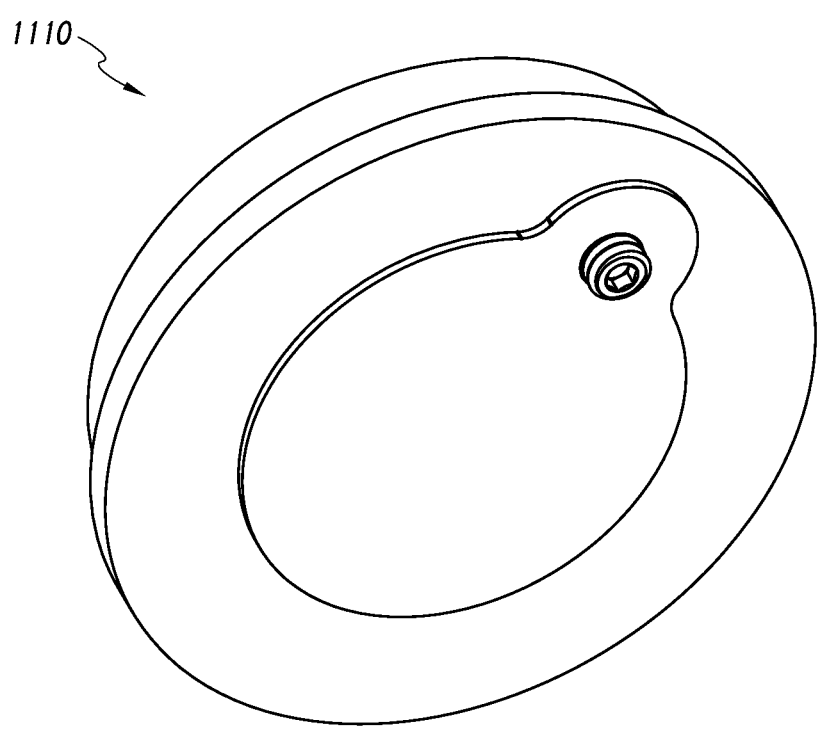
FIG. 53D illustrates an inspiratory valve of the mask portion shown in FIG. 53A.
Figure 53E:
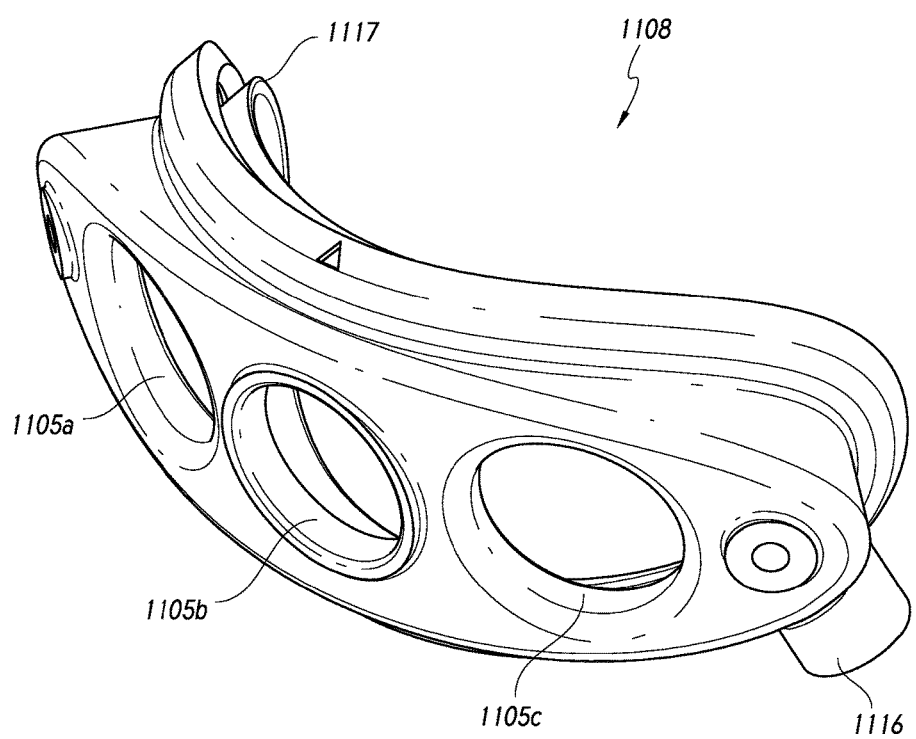
FIG. 53E illustrates a first body portion of the mask portion shown in FIG. 53A.

The first body portion 1108 can include one or more openings 1105a, 1105b, 1105c to receive one or more valves (see FIG. 53E). For example, the first body portion 1108 can receive one or more expiratory valves 1106 and/or one or more inspiratory valves 1110. The illustrated embodiment of the first body portion 1108 can support an expiratory valve 1106 and two inspiratory valves 1110. The valves 1106, 1110 can be positioned in a horizontal array such that an inspiratory valve 1110 is disposed on either side of the expiratory valve 1106. For example, the opening 1105b can support the expiratory valve 1106, and the openings 1105c and 1105a can each support an inspiratory valve 1110.

As shown in FIG. 53D, the inspiratory valve 1110 can be a flap valve. The inspiratory valve 1110 can move from a closed position to an open position. In the open position, the flap can be at an angle greater than 0 degrees and less than about 90 degrees relative to the horizontal axis, such as between about 15 degrees and about 30 degrees, between about 30 degrees and about 45 degrees, between about 45 degrees and about 60 degrees, or between about 60 degrees and about 75 degrees. In other embodiments, the inspiratory valve 1110 can be any inspiratory valve described herein, such as the inspiratory valve 410.

When the device 1100 is fully assembled, each inspiratory valve 1110 can be substantially aligned with a nostril stalk 1113 of the nasal pillow 1112, such that when the inspiratory valve 1110 opens, ambient air can flow directly and symmetrically into both nostrils to mimic natural breathing.

The mask portion 1101 can include one or more air supply ports 1116, such as one port or two ports. As shown in FIG. 53E, the first body portion 1108 can include two air supply ports 1116. The air supply ports 1116 can be positioned on either side of the first body portion 1108, such that the user can choose which side to connect the air supply tubing 1114. The user can connect the tubing 1114 to the port 1116 that is most comfortable based on the user's sleeping position. The unused air supply port 1116 can be plugged or capped when not in use. Although the ports 1116 are illustrated on the first body portion 1108, the ports 1116 can alternatively be positioned on the nasal pillow 1112 or any other body portion of the mask portion 1101.

Figure 53F:
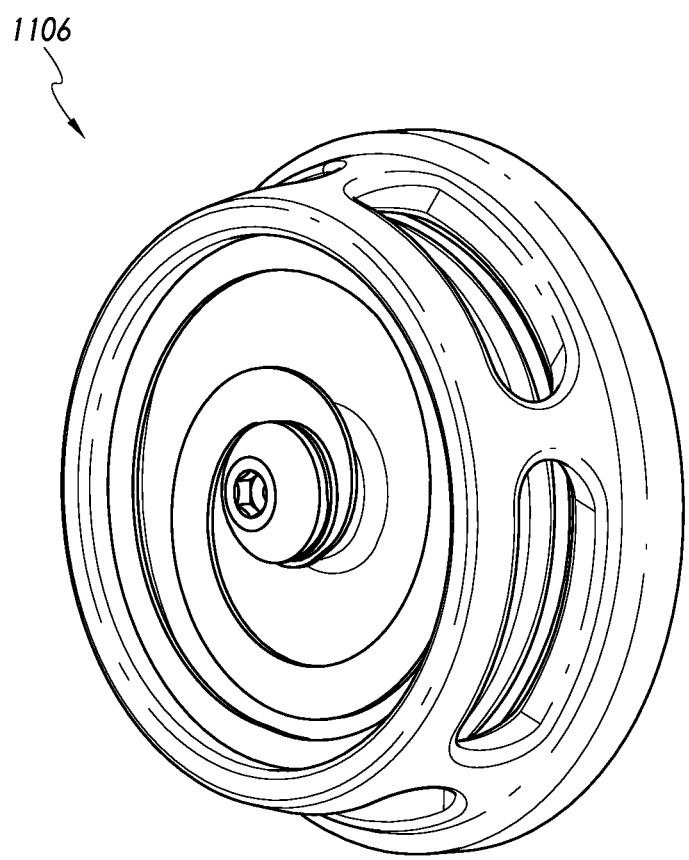
FIG. 53F illustrates an expiratory valve of the mask portion shown in FIG. 53A.

As described above, the mask portion 1101 can include an expiratory valve 1106. The expiratory valve 1106 can be centrally disposed along the first body portion 1108. As shown in FIG. 53F, the expiratory valve 1106 can be a spring valve. The expiratory valve 1106 can include any of the features of the expiratory valve 414.

Figure 58:
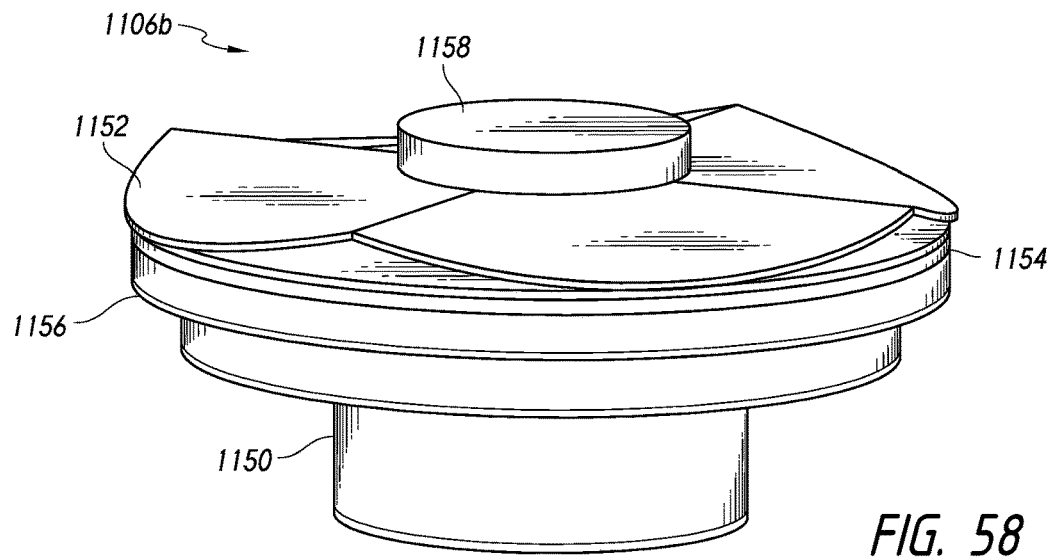
FIG. 58 illustrates a perspective view of yet another embodiment of an expiratory valve.
Figure 59:
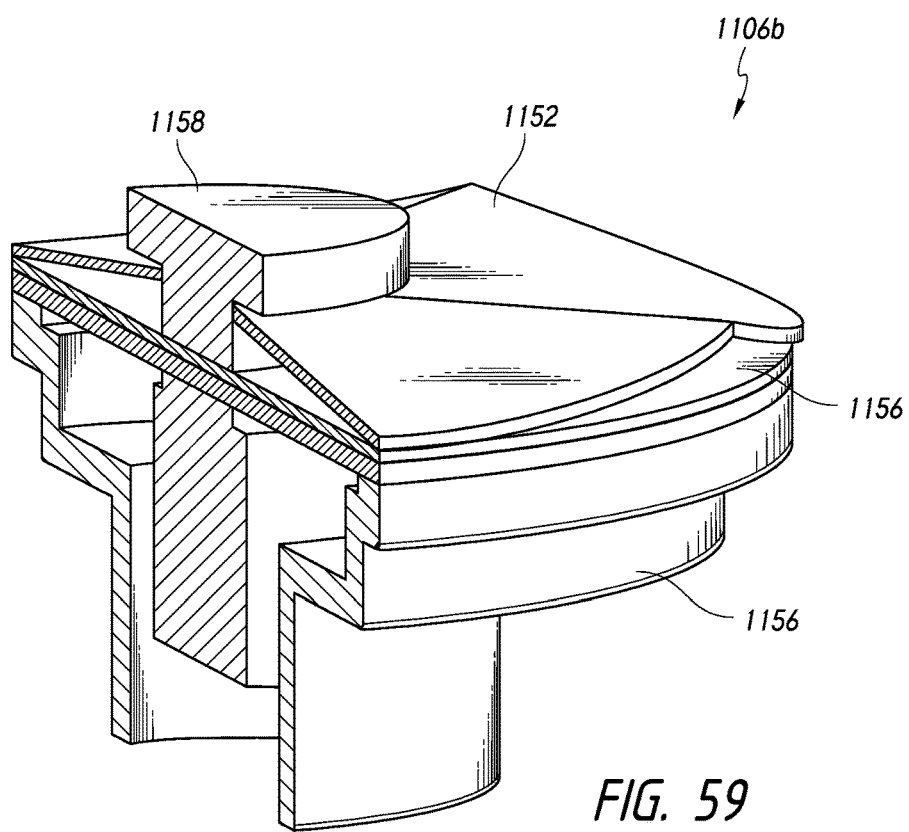
FIG. 59 illustrates a cross-section of the expiratory valve shown in FIG. 58.

FIGS. 58 and 59 illustrate another exemplary expiratory valve 1106b. The expiratory valve 1106b can provide a substantially consistent back pressure across a range of flows, such that the therapeutic pressure is independent of how intensely the user breathes. To accomplish this, the expiratory valve 1106b can have a low spring constant so that the valve 1106b provides substantially constant back pressure independent of flow rate. The valve 1106b can also apply back pressure resistance to an intended level and then open in an over-center non-linear manner where the opening force diminishes greatly after the intended level has been reached.

As shown in FIGS. 58 and 59, the valve 1106b can include a body portion 1150 supporting one or more layers. For example, the valve 1106b can include an inner layer 1156, an intermediate layer 1154, and an outer layer 1152. Each of the layers can define a centrally located opening through which a stem 1158 can secure the layers to the valve body portion 1150. In some embodiments, the valve 1106b only includes one or two of those layers.

The outer layer 1152 can be folded to provide a spring layer that supplies a resistance up to a threshold pressure, but then opens over center when the pressure exceeds the threshold pressure. As shown in FIG. 58, the outer layer 1152 can include four folds 1160. However, more or less folds 1160 can also be imagined, such as two folds, six folds, eight folds, or more. In some embodiments, the outer layer 1152 can be constructed from a thin metal or plastic, such as Mylar.

The inner layer 1156 can provide a seal across the body portion 1150. In some embodiments, the inner layer 1156 can be constructed from a soft plastic or elastomer, such as rubber, to provide a flexible layer that can flex with the outer layer 1152.

The intermediate layer 1154 can provide a firm plate to help distribute the spring forces from the outer layer 1152 such that the entire perimeter of the layers moves away from the body portion 1150 when the valve 1106b moves to an open position. In some embodiments, the intermediate layer 1154 can be constructed from a plastic.

The valve 1106b can move between an open position and a closed position. In the open position, the folded outer layer 1152 uses its elastic material properties and its preloaded convex shape to create the sealing force against the valve body portion 1150. When the valve 1106b opens at the predetermined pressure, the perimeter of each of the layers moves away from the valve body portion 1150, while the central portion remains secured to the valve body portion 1150. This configuration provides a large escape opening to allow expiratory air to escape at high flow rates and provide a relatively constant pressure independent of flow rate. Further, the expiratory valve 1106b provides sufficient escape room for carbon dioxide to prevent carbon dioxide from running down the air supply tubing 1114 and consequently causing the user to inhale the carbon dioxide.

The folded configuration of the outer layer 1152 provides a non-linear, flow independent resistance force. It takes a greater amount of force to bend the outer layer to open the valve 1106*b* than it does to keep the valve 1106*b* open. This allows the valve 1106*b* to stay in the open position until the pressure falls below the threshold pressure. At that time, the valve 1106*b* immediately moves to the closed position.

Figure 53G:
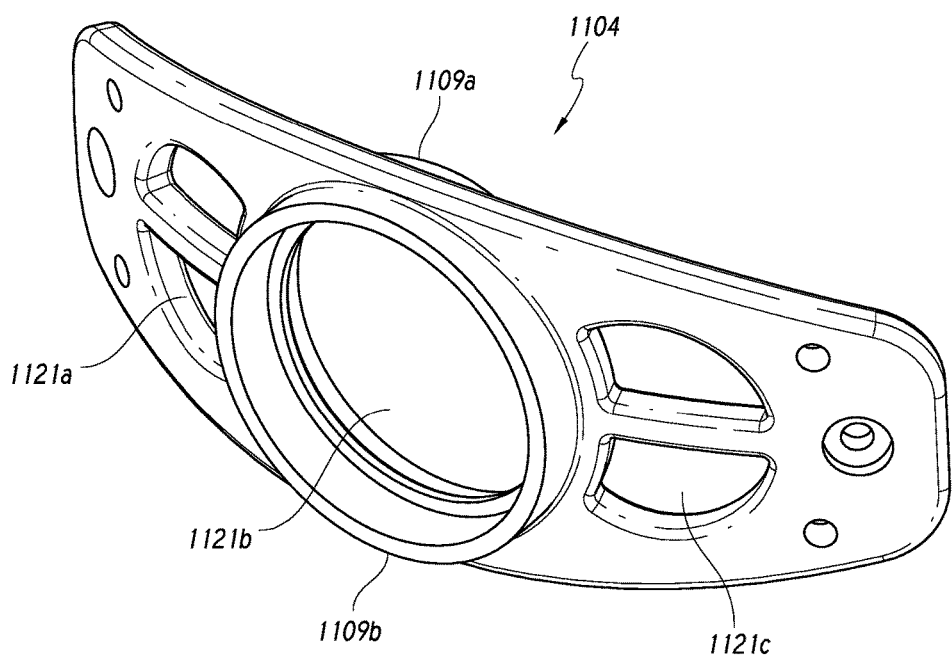
FIG. 53G illustrates second body portion of the mask portion shown in FIG. 53A.

Referring to FIG. 53G, in some embodiments, the mask portion 1101 can include a second body portion 1104 that can be secured to the first body portion 1108. Depending on the configuration of the valves, the second body portion 1104 can help maintain the position of one or more of the valves. Further, the second body portion 1104 can include one or more openings 1121*a*, 1121*b*, 1121*c* corresponding to each of the valves 1106, 1110. The second body portion 1104 can also include a first flange 1109*a* extending from a rear surface of the second body portion 1104. The first flange 1109*a* can surround at least a portion of, substantially the entire, or the entirety of the expiratory valve 1106. In some embodiments, the second body portion 1104 can include a second flange 1109*b* extending from a front surface of the second body portion 1104. The second flange 1109*b* can engage a noise-mitigating member 1102 (if present).

In some embodiments, it can be desirable to limit the noise produced from the mask portion 1101. As shown in FIG. 53A, the mask portion 1101 can include a noise-mitigating member 1102 that can be integrally or separately formed from the second body portion 1104. The noise-mitigating member 1102 can be secured to the second body portion 1104 such that the noise mitigating member 1102 surrounds the expiratory valve 1106. In this configuration, exhaled air can flow from the expiratory valve 1106 and exit through a second end 1102*b* of the noise mitigating member 1102. The second end 1102*b* can define a centrally disposed outlet on the noise-mitigating member 1102.

Figure 53H:
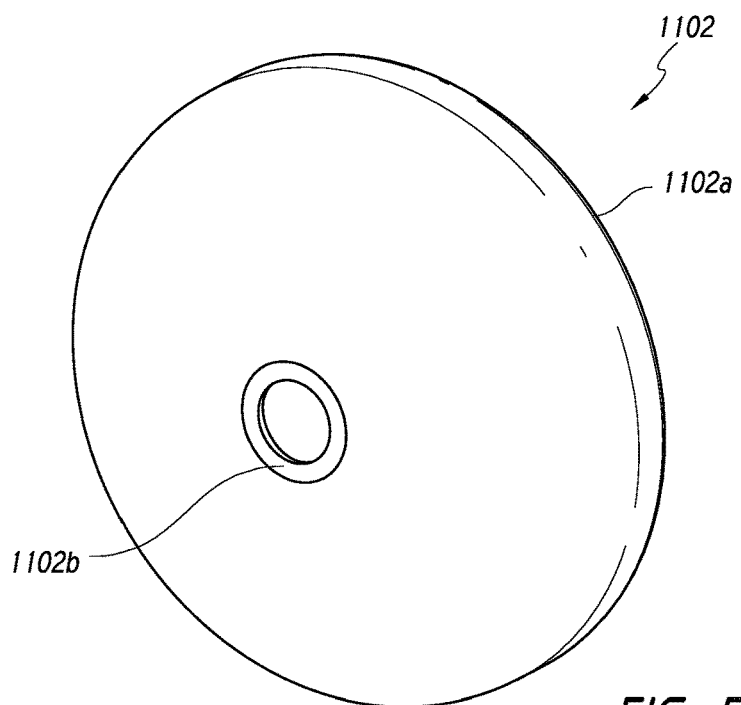
FIG. 53H illustrates a noise mitigating member of the mask portion shown in FIG. 53A.

The noise-mitigating member 1102 can be shaped to produce laminar or near laminar airflow. For example, as shown in FIG. 53H, the noise-mitigating member 1102 can include a first end 1102*a* and a second end 1102*b*. The first end 1102*a* of the noise-mitigating member 1102 can be positioned closer to the expiratory valve 1106 than the second end 1102*b* of the noise-mitigating member 1102. Further, a diameter of the first end 1102*a* can be greater than a diameter of the second end 1102*b*. The first end diameter can be at least about two times, at least about three times, or at least about four times greater than the second end diameter. Directing the airflow from a larger opening to a smaller opening can help reduce noise. Further, the laminar or near laminar airflow can produce less back pressure such that intranasal pressure can be more easily controlled.

Figure 54:
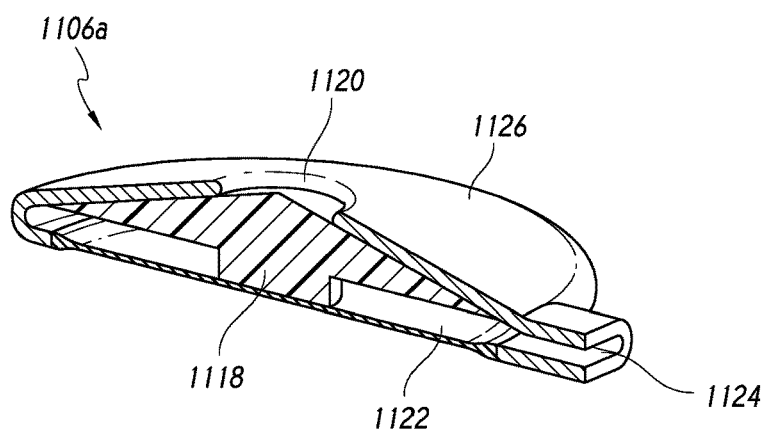
FIG. 54 illustrates another embodiment of an expiratory valve.

In an alternative configuration, the mask portion 1101 can include an expiratory valve 1106*a* designed to reduce noise without a separate noise mitigating component. As shown in FIG. 54, the expiratory valve 1106*a* can include a membrane 1122 and a body portion 1126 that define an interior space. The expiratory valve 1106*a* can also include an internal structure 1118 disposed within the interior space and connected to the membrane 1122. When exhaled air flows through an inlet 1124, the membrane 1122 can bow to move the internal structure 1118 away from an outlet 1120 of the body portion 1126. The exhaled air can flow around the internal structure 1118 and exit through the outlet 1120.

The internal structure 1118 can be shaped to direct airflow to produce laminar or near laminar airflow. For example, the internal structure 1118 can include a conical portion to direct airflow from the interior space to the outlet 1120. A diameter of the expiratory valve 1106 can be at least about two times, at least about three times, or at least about four times greater than a diameter of the outlet 1120.

Figure 55:
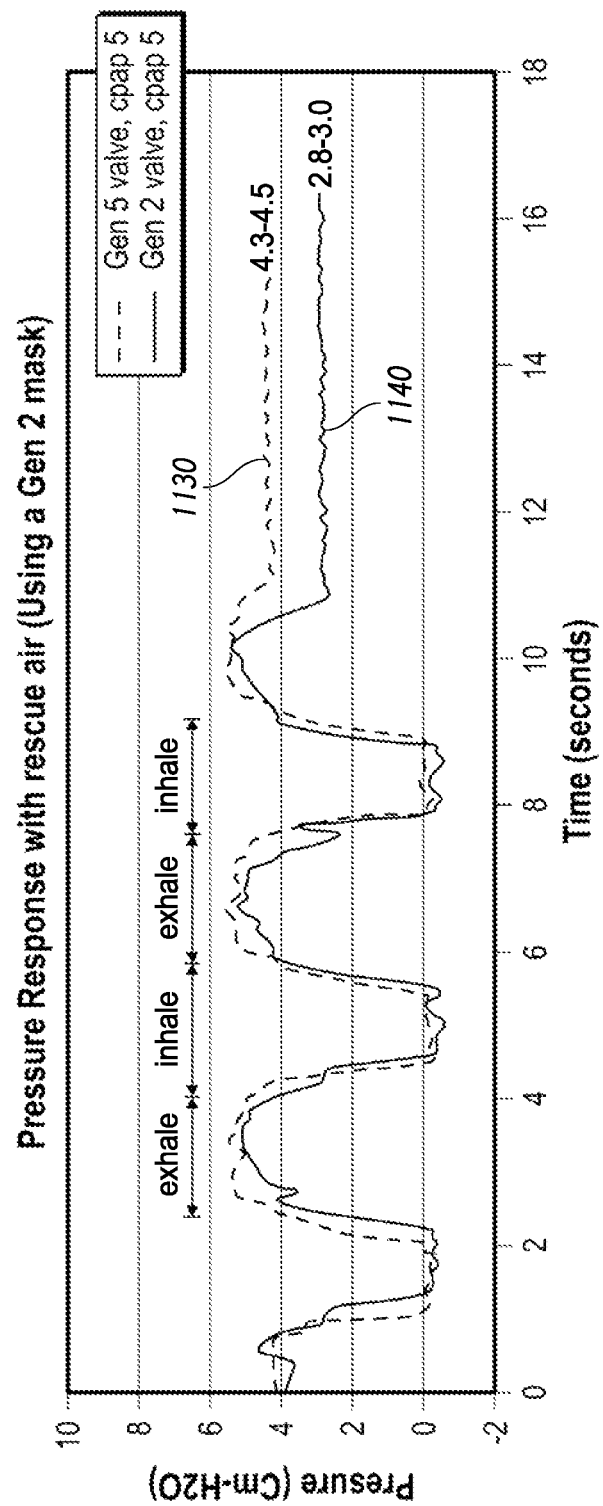
FIG. 55 is a graph illustrating breathing curves for the sleep apnea device shown in FIG. 19 comparing two different expiratory valves.

FIG. 55 illustrates a flat valve breathing curve 1130 for a sleep apnea device 400 with the expiratory valve 1106*b* that provides substantially the same amount of therapeutic pressure independent of airflow. The flat valve breathing curve 1130 can be compared to the standard valve breathing curve 1140, which demonstrates a similar sleep apnea device 400 having an expiratory valve that provides a less constant amount of therapeutic pressure within varying flow rates. As shown in FIG. 55, the flat valve breathing curve 1130 demonstrates pressure that is more constant during exhalation than the standard valve breathing curve 1140. Further, the flat valve breathing curve 1130 demonstrates that the therapeutic pressure following an apneic event (i.e., around 10.5 seconds) is closer to the desired therapeutic pressure than the standard valve breathing curve 1140. During the apneic event, all of the inspiratory and expiratory valves close to create a closed system in which rescue air from the airflow generator flows to the user. The rescue air can re-pressurize the intranasal pressure in less than or equal to about 1 second, often less than or equal to about 0.5 seconds. For example, the airflow generator can re-pressurize the intranasal pressure at a rate of at least about 10 cm H2O/s and/or less than or equal to about 30 cm H2O/s, such as between about 15 cm H2O/s and about 25 cm H2O/s. The airflow generator can re-pressurize the intranasal pressure quickly, while still maintaining a low flow rate of less than or equal to about 20 L/min.

Spring-based Expiratory Valve

Figure 60A:
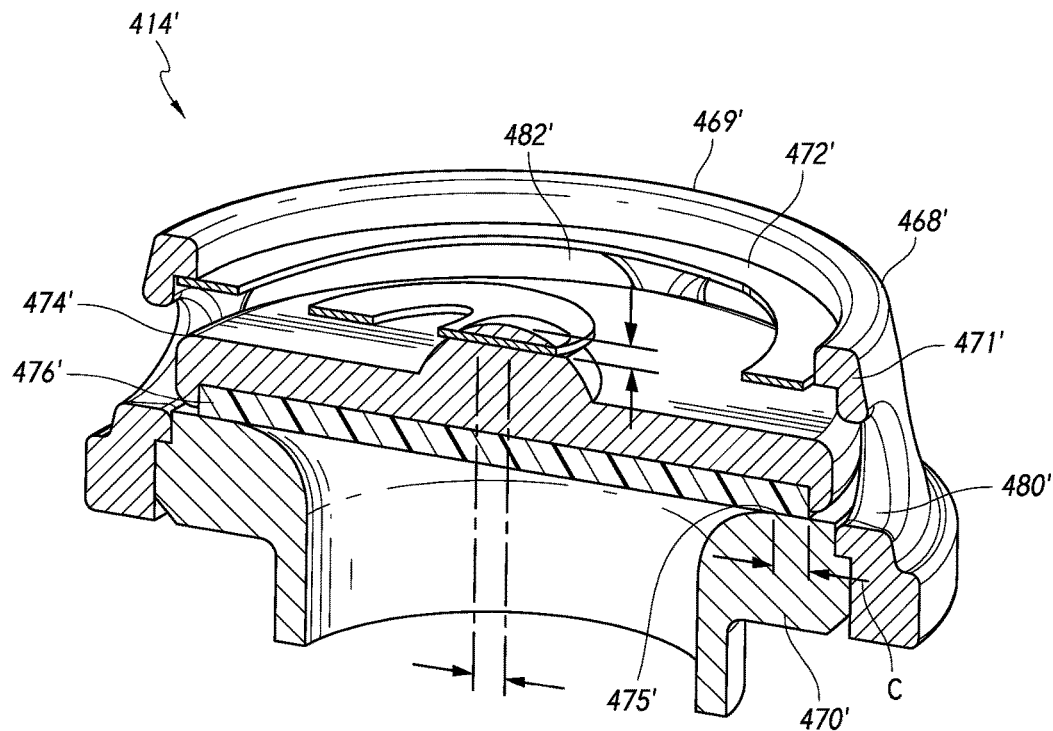
FIG. 60A illustrates another embodiment of the spring-based expiratory valve shown in FIGS. 28A-28C.

As discussed above, the expiratory valve 414 can be used in connection with the sleep apnea device 1100. FIG. 60A illustrates a modified expiratory valve 414'. Many aspects of the expiratory valve 414' can resemble or be identical to the expiratory valve 414. Accordingly, numerals used to identify features of the expiratory valve 414 include an apostrophe (') to identify like features of the expiratory valve 414'.

For example, as shown in FIG. 60A, the expiratory valve 414' can include a cap 468', a body 470', a spring 472', a follower 474', and/or a seal 476'. The cap 468' can have an open outer face 469', such that a noise mitigating member (e.g., noise mitigating member 1102) can be secured to the open outer face 469'. Further, the outer wall 471' of the cap 468' can protrude radially inward to provide a guide for the follower 474'.

The central axis of the protruding portion 482' can be offset from a central axis of the spring 472'. The offset permits only a portion of the follower 474' and/or the seal 476' to lift off from the body 470', while maintaining contact between another portion of the follower 474' or the seal 476' and the body 470'. This tilting motion minimizes the tendency of the follower 474' to flutter and cause noise.

As shown in FIG. 60A, the valve body seat 475' can be generally planar. However, in other implementations, the valve body seat 475' can be toroidal or otherwise shaped to minimize noise. It can be desirable to minimize the contact region C between the valve body seat 475' and the seal 476' to minimize back pressure. For example, the ratio between a width of the contact region C and a diameter of the seal 476' can be about 1:10, 1:15, 1:20, 1:25 or other ratios between the aforementioned ratios.

Figure 60B:
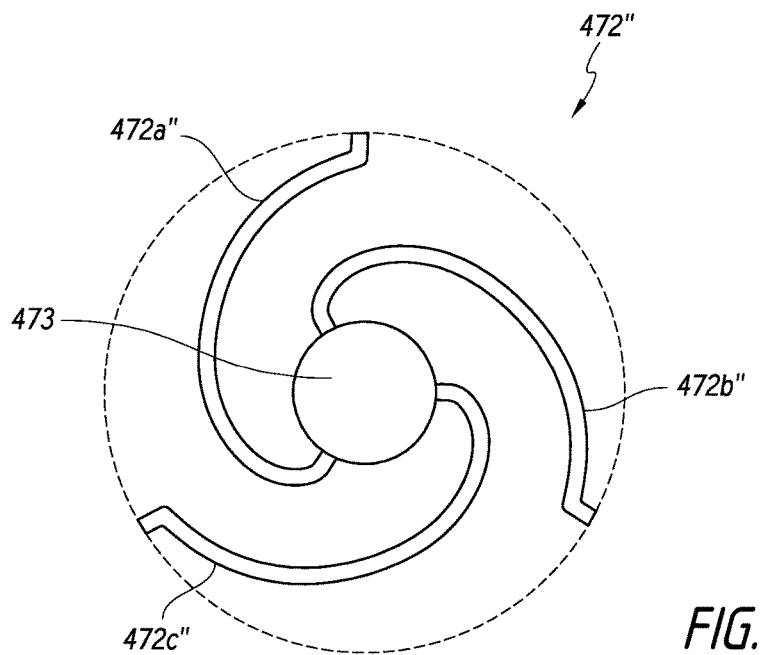
FIG. 60B illustrates another embodiment of a spring that can be used with the expiratory valve shown in FIG. 60A.

FIG. 60B illustrates an alternative embodiment of a spring 472" having a plurality of spring spirals 472*a*", 472*b*", 472*c*" extending from a central point 473". The spirals 472*a*", 472*b*", 472*c*" can be shaped to such that the valve moves quickly and evenly between the open and closed configurations at the threshold pressure. A plurality of shorter spiral 472*a*", 472*b*", 472*c*" can be more responsive to slight changes in pressure than a single longer spiral.

Membrane-based Expiratory Valve

Figure 61A:
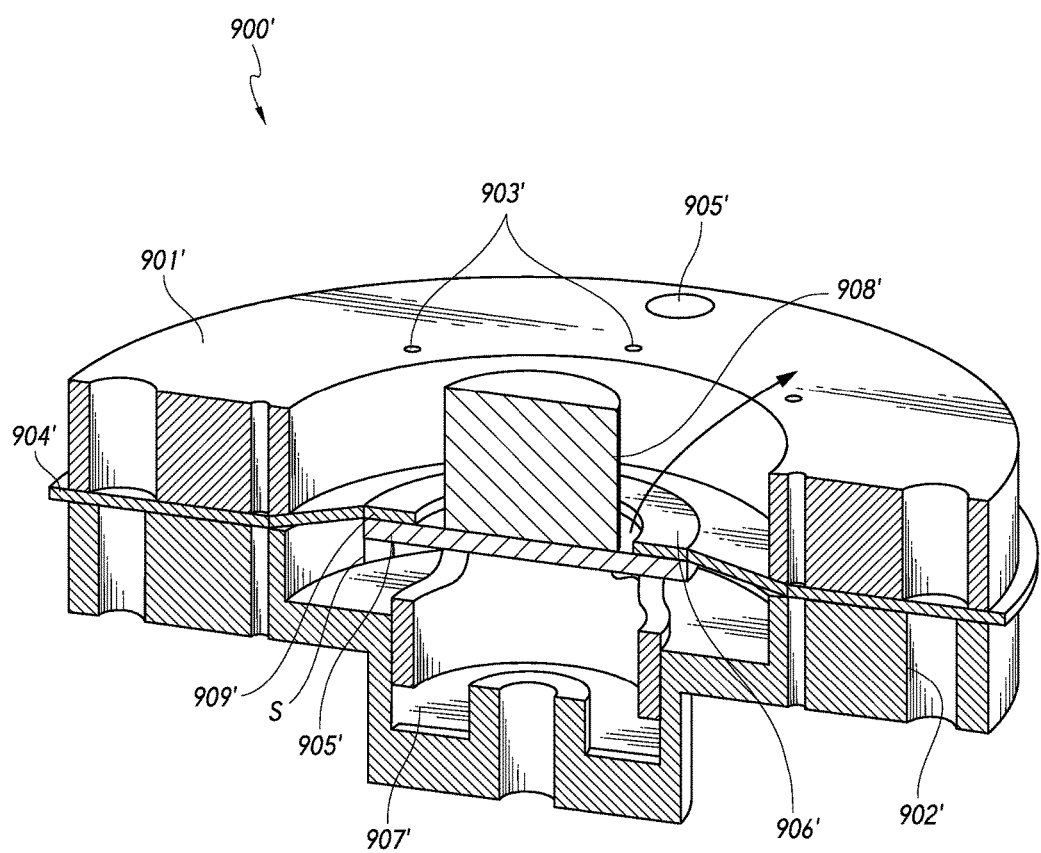
FIG. 61A illustrates another embodiment of the membrane-based expiratory valve shown in FIG. 42.

The membrane valve 900 can also be used in connection with the sleep apnea device 1100. FIG. 61A illustrates a modified membrane valve 900'. Many aspects of the membrane valve 900' can resemble or be identical to the membrane valve 900. Accordingly, numerals used to identify features of the membrane valve 900 include an apostrophe (') to identify like features of the membrane valve 900'.

Similar to the membrane valve 900, the membrane valve 900' can generally include a valve frame 902', a membrane 904', and an occluder 908'. In a closed configuration (as shown in FIG. 61A), the membrane 904' rests against the occluder seat 909' to form a sealing region S. Although not shown, the occluder seat 909' can include a number of openings to maximize the open area through which air can flow when the membrane 904' moves away from the occluder seat 909'. Further, the valve frame 902' can include an occluder pocket 907' in which the occluder 908' can be height adjusted to adjust the tension on the membrane 904'.

As the intranasal pressure increases, the membrane 904' can elastically deform and move away from the occluder 908', thereby permitting air to flow around the occluder 908' and out of the opening 906'. The membrane valve 900' can also include cover plate 901' that can reduce movement of the membrane 904' to mitigate noise. For example, the cover plate 901' can be have an annular body that generally aligns with the valve frame 902'. The cover plate 901' can include a number of openings 903' for receiving tensioning pins and a number of larger openings 905' for receiving bolts or other structures to secure the cover plate 901' to the valve frame 902'.

Figure 61B:
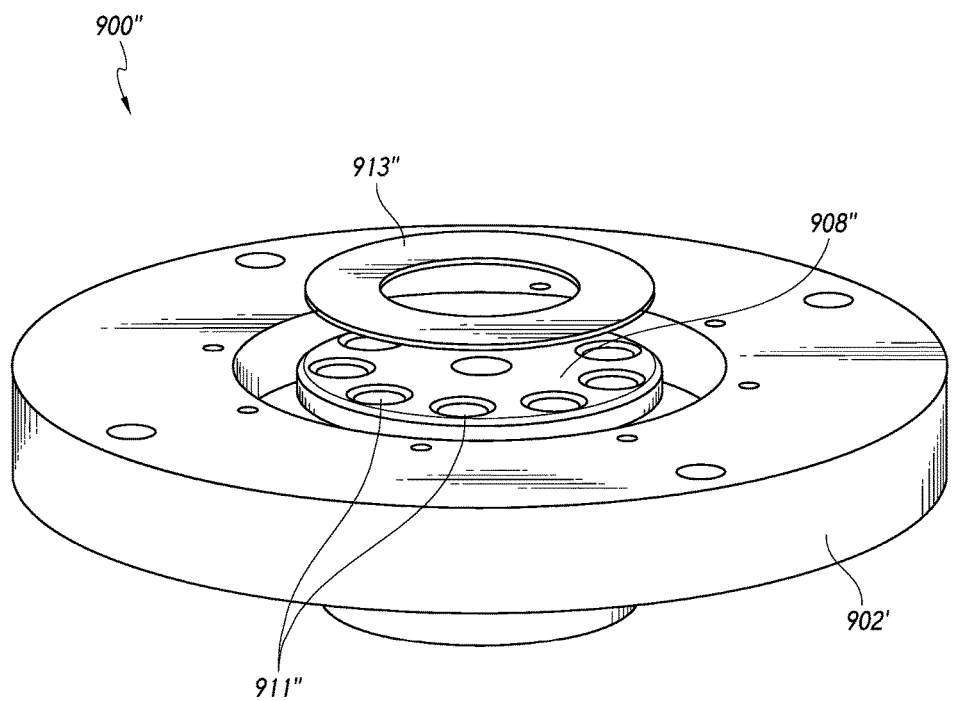
FIG. 61B illustrates another embodiment of the membrane-based expiratory valve shown in FIG. 61A having a plurality of magnets.

FIG. 61B illustrates an alternate embodiment of the valve frame 902" and the occluder 908" that can be used in connection with the valve 900'. A ferrous member 913" (e.g., washer) can be secured to the membrane 906'. The ferrous member 913" can reduce the vibrations of the membrane 906', thus reducing noise from membrane vibrations.

The occluder 908" can also include a number of openings 913" in a circular configuration for receiving a number of magnets. The magnets can promote the sealing engagement between the membrane (not shown) (and ferrous member 913") and the occluder 908". As the pressure behind the membrane exceeds the strength of the magnets, the membrane immediately moves away from the occluder 908". The magnets can be arranged symmetrically to promote even separation when membrane moves away from the occluder 908", which can reduce noise. Further, the number and position of the magnets can be varied to adjust the strength of the seal. Advantageously, the magnets can withstand a high amount of pressure and maintain the sealing engagement between the membrane and the occluder 908" when the intranasal pressure is below the threshold pressure, but once the intranasal pressure exceeds the threshold pressure, separation between the membrane 906' and the occluder 908" can be easily maintained. As the intranasal pressure falls below the threshold pressure, the membrane 906' can immediately move back to sealing engagement with the occluder 908". The functionality of the valve 900" can provide substantially constant therapeutic pressure independent of air flow rate.

Figure 61C:
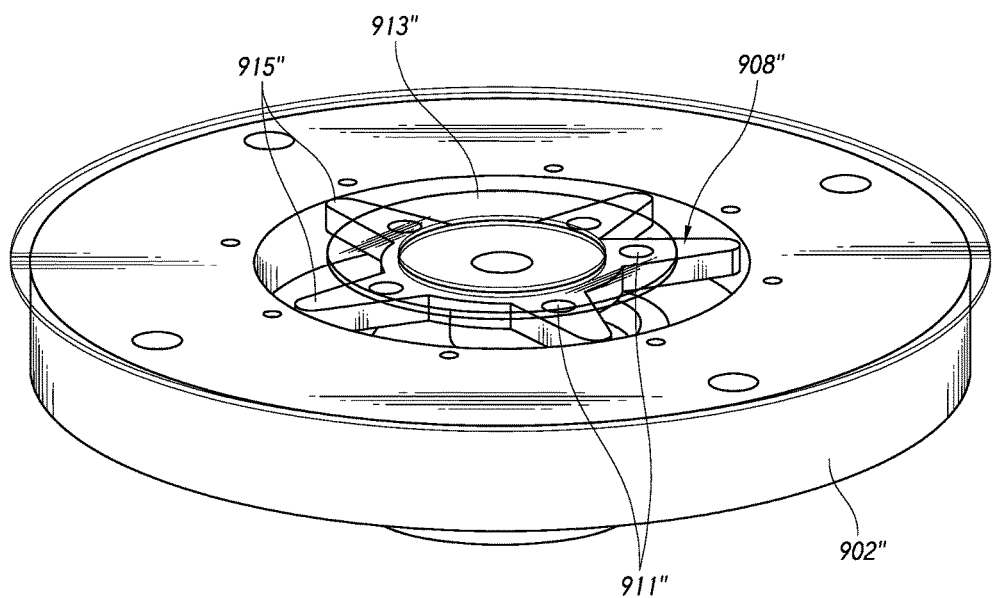
FIG. 61C illustrates another embodiment of the membrane-based expiratory valve shown in FIG. 61B having a differently shaped occluder.

FIG. 61C illustrates an occluder 908' having an alternate shape that can be used with any of the membrane valves 900, 900' described herein. An upper portion of the occluder 908''' can include a number of projections 915''' (e.g., five projections to form a star shape) to increase the flow area between the valve body 902''' and the occluder 908'''.

Magnet-based Expiratory Valve

Figure 62:
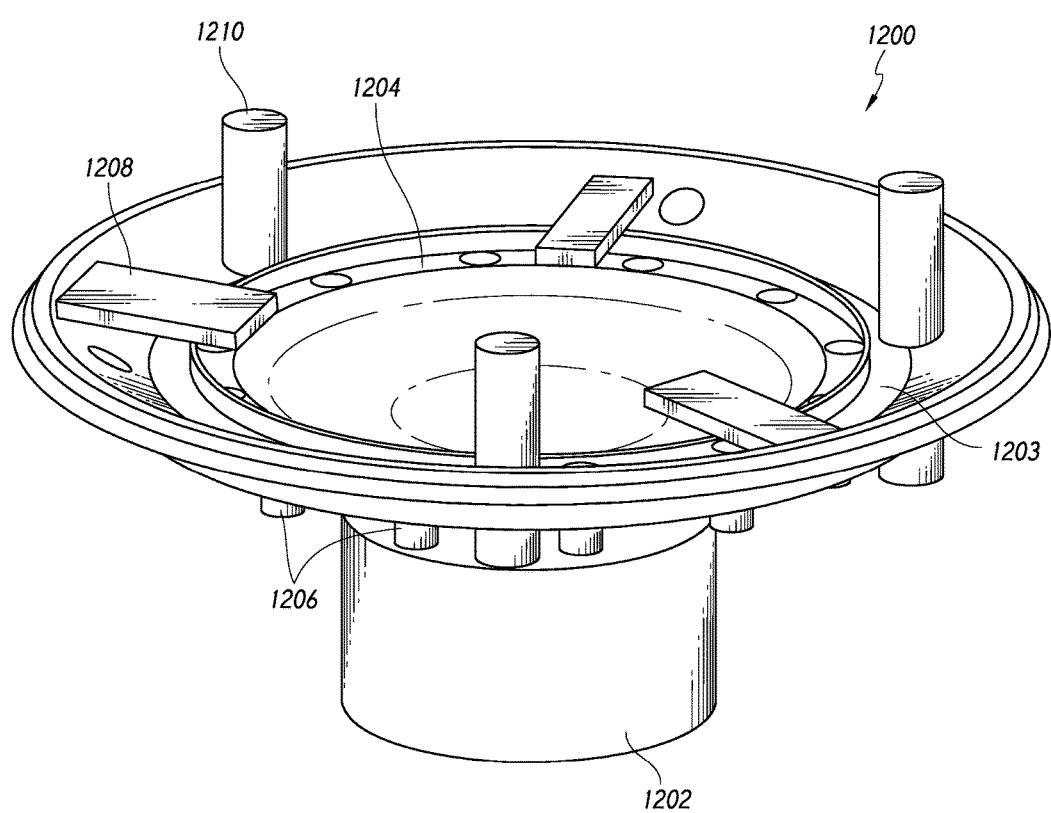
FIG. 62 illustrates an embodiment of a magnet-based expiratory valve.

FIG. 62 illustrates a magnet valve 1200 that can be used with the sleep apnea device 1100. The magnet valve 1200 can include a valve body 1202 defining a passageway through which air can flow. The valve body 1202 can include an annular valve seat 1203 against which a plate 1204 can form a seal. A plurality of magnets 1206 can be positioned around the valve seat 1203. The number and position of the magnets 1206 can be varied to adjust the strength of the seal.

The plate 1204 can include a ferrous material that can be releasably secured to the plurality of magnets 1206. The plate 1204 can also include a seal (e.g., rubber, silicone, Delrin, or other suitable material) on a bottom surface of the plate 1204. When the pressure behind the plate 1204 exceeds the strength of the magnets, the plate 1204 can move away from the valve seat 1203. Advantageously, the plate 1204 can immediately move away from the valve seat 1203 when the intranasal pressure exceeds the strength of the magnets. As flow increases, the magnet valve 1202 provides linear back pressure.

A number of guide posts 1210 positioned around the valve body can limit the lateral movement of the plate 1204. Further, a number of stoppers 1208 can limit the longitudinal movement of the plate 1204. In some embodiments, the stoppers 1208 can be constructed from a flexible or spring-like material.

Auto-Feedback Expiratory Valve

Figure 71:
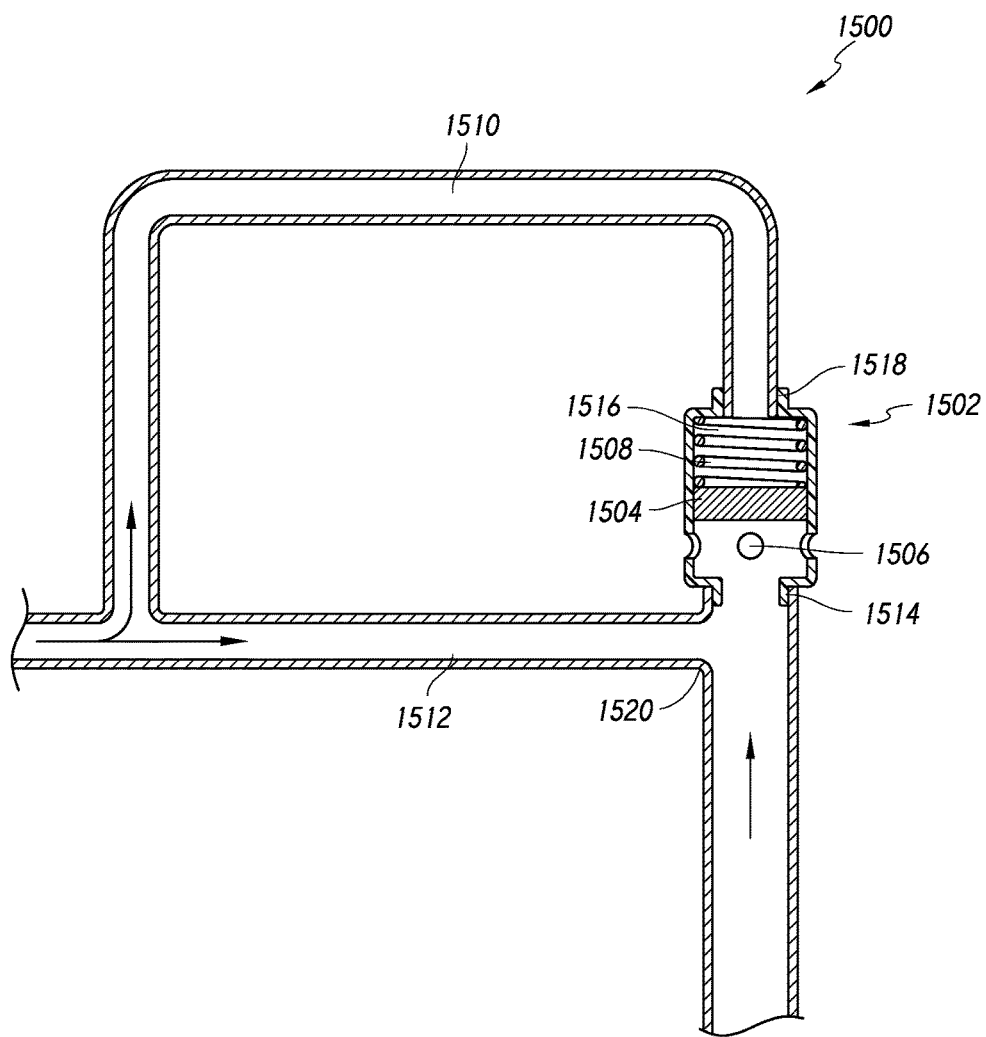
FIG. 71 is a partial schematic diagram of a sleep apnea system having an auto-feedback valve.

FIG. 71 is a partial schematic diagram of a sleep apnea device 1500 having an expiratory valve 1502 that can adjust an opening pressure based on the therapeutic air pressure. As shown in FIG. 71, the expiratory valve 1502 can include a plunger 1504 that can move between an open configuration and a closed configuration to control air flow through an outflow path 1506 (e.g., one or more vent holes). In certain aspects, the expiratory valve 1502 can optionally include a biasing feature 1508 (e.g., a spring, piston, diaphragm, etc.) to maintain the valve 1500 in a closed configuration. Optionally, there can be a sealing ring 1526 positioned between the plunger 1504 and the valve inlet 1514.

Figure 74A:
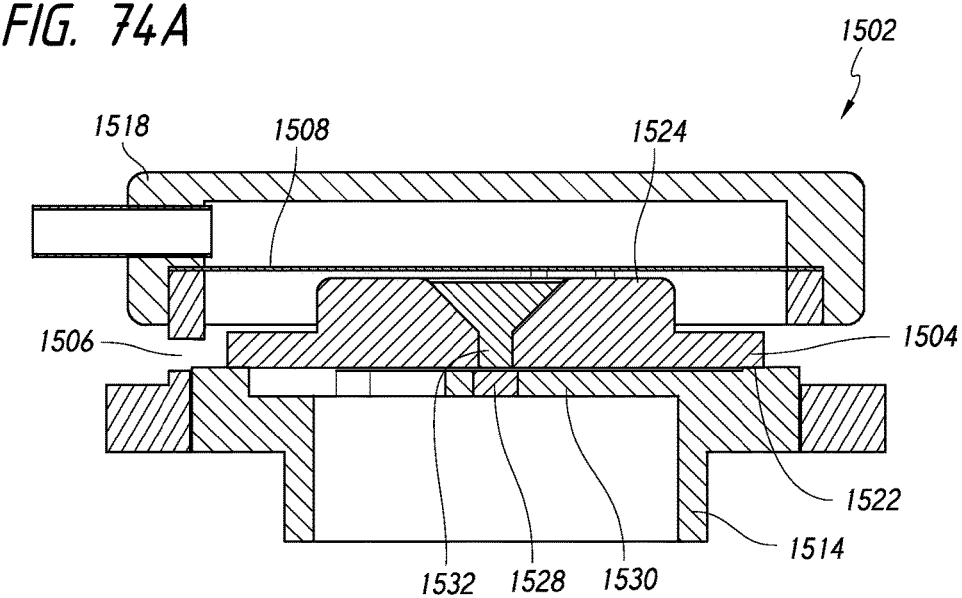
FIG. 74A illustrates yet another embodiment of an auto-feedback valve in a closed configuration.
Figure 74B:
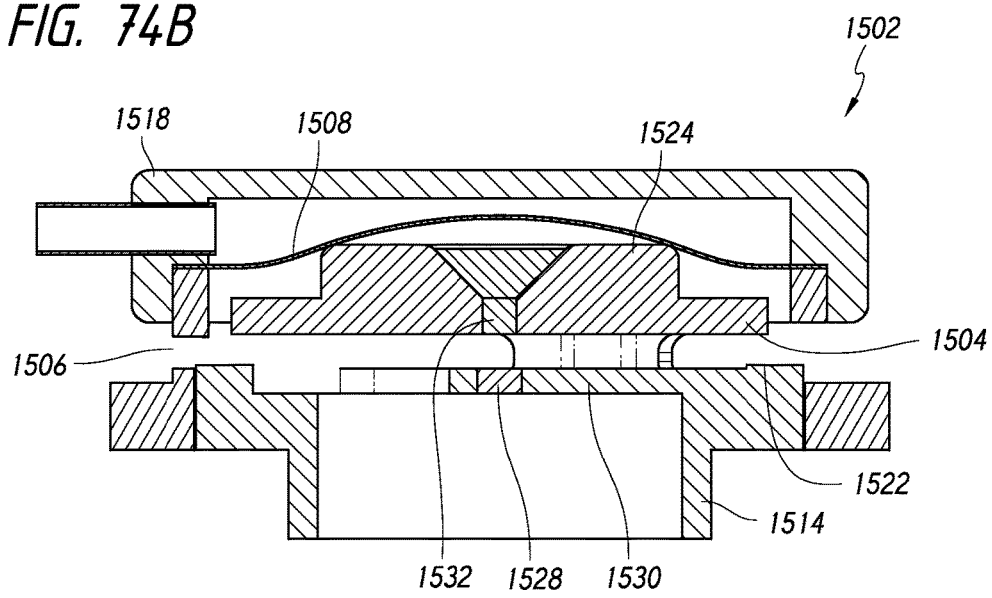
FIG. 74B illustrates the auto-feedback valve shown in FIG. 74A in an open configuration.

FIGS. 72A to 74B illustrate various auto-feedback valves 1502 that can be used in connection with the sleep apnea system 1500. In some embodiments, as shown in FIGS. 72A and 72B, the biasing feature 1508 can be a spring. The spring can include an outer diameter of less than or equal to about 0.5 inches. In certain aspects, the spring constant can be between about 0.1 lbf/in and 0.15 lbf/in, such as about 0.125 lbf/in. In some embodiments, as shown in FIGS. 74A and 74B, the biasing feature 1508 can be a diaphragm. Alternatively, as shown in FIGS. 73A and 73B the expiratory valve 1500 may not include a biasing member. It may be desirable to use the feedback air pressure as main the closure/restorative force because the air pressure will supply a constant closure force on the plunger, whereas springs supply a restorative force that is proportional to the displacement.

It may be desirable to have an expiratory valve 1502 that operates the same or very similarly regardless of the orientation of the valve 1502 relative to gravity, so that the user can sleep on their back, side, or front. To achieve this, a weight of the plunger 1504 can be minimized such that the valve closure force is substantially the same in all cases. The plunger 1504 can weigh less than or equal to about 1.7 gram, e.g., between about 1.0 gram and about 1.5 gram. In certain aspects, the plunger can have a wall thickness of less than or equal to about 0.005 in., such as between about 0.004 in. and about 0.005 in.

The plunger 1504 can have a first end 1522 and a second end 1524. The first end 1522 can be closer to the user than the second end 1524 when the user is using the device 1500. In certain aspects, as shown in FIGS. 72A and 72B, the first end 1522 can be a closed end and the second end 1524 can be an open end. Alternatively, as shown in FIGS. 73A and 73B, the first end 1522 can be an open end and the second end 1524 can be a closed end. The first end 1522 can form a portion of chamber A, while the second end can form a portion of chamber B (see FIGS. 73A and 73B). A surface area of the chamber B can be less than a surface area of the chamber B to provide greater control on the resistance provided. The cup-shaped plunger 1504 minimizes weight, while providing a height to align the plunger in the valve body. In some embodiments, as shown in FIGS. 74A and 74B, the plunger 1504 can be disc-shaped.

The expiratory valve 1502 can provide the desired functionality, while being sized to maintain a low profile sleep apnea device 1500. For example, the height of the expiratory valve can be less than or equal to about 1.5 inches, preferably less than or equal to about 0.5 inches.

In use, an increase in air pressure at the expiratory valve inlet 1514 will push the plunger 1504 into the open configuration (see, e.g., FIG. 72B). When the pressure at the inlet 1514 falls below the threshold pressure, the plunger 1504 will move to the closed configuration (see, e.g., FIG. 72A).

The air flow generator (not shown) can deliver therapeutic pressure to the device through a therapeutic tubing 1512. The therapeutic tubing 1512 can connect to a manifold port 1520. Separately, the air flow generator can deliver air to a pressurized chamber 1516 of the expiratory valve 1502 through a feedback tubing 1510. The feedback tubing 1510 can connected to a feedback port 1518. As the therapeutic pressure increases, the pressure in the pressurized chamber 1516 increases, thus causing the valve 1502 to stay closed to higher pressures. Similarly, as therapeutic pressure decreases, the pressure in the pressurized chamber 1516 decreases causing the valve 1502 to open more easily.

Various features of the expiratory valve 1502 can be modified to control the relationship between the therapeutic air pressure and the amount of resistance provided by the plunger 1504. For example, the surface area of the first end 1522 and/or the second end 1524 of the plunger 1504 can be modified to control the relationship between the therapeutic air pressure and the resistance provided by the expiratory valve 1502. The surface area of the second end 1524 of the plunger 1504 can be larger than the surface area of the first end 1512 to magnify the restorative force on the plunger 1504 created by the feedback air. In certain aspects, a diameter of the first end and/or the second end of the plunger 1504 can be between about 0.125 inches and about 2.0 inches, preferably less than or equal to about 1.0 inch. For example, a diameter of the first end can be about 0.75 inches, while a diameter of the second end can be about 1.0 inch. A ratio of the first end diameter to the second end diameter can be between about 1:2 and about 4:5, such as about 3:4.

As another example, the size of the feedback tube 1510 can be controlled to dampen a response in the pressurized chamber 1516. For example if the tube 1510 was sized particularly small or long, there could be a pressure drop or a delayed pressure response to the pressurized chamber 1516. This could be useful in eliminating sharp changes in the pressure response, if for example, better therapy or comfort was achieved by a slower response. Similarly, this damping could normalize chaotic small changes in pressure to reduce "noise" in the response. To create the dampening response, an inner diameter of the feedback tube 1510 can be less than or equal to about 0.125 inches, such between about 0.05 and 0.01 inches.

In some embodiments, the sleep apnea device 1500 can include one or more one-way valves (not shown) to shield the feedback tube 1510 or therapeutic tubing 1512 from the back pressure of actual patient breathing. This feature can reduce the potential effect of exhalation breath on the feedback air and reduce $CO_2$ entrapment or circulation in the system.

The plunger 1504 and/or outflow path 1506 can be shaped (e.g., graduated, tapered, staggered, or staged) to reduce or magnify the effect of exhaust flow on the plunger 1502. For example, the outflow path 1506 can have a smaller width when the plunger first moves into an open configuration. The width of the outflow path 1506 can increase as the plunger 1502 moves further toward the open configuration so that flow spikes are expelled faster as the plunger 1502 moves to the open configuration.

In some embodiments, the plunger 1504 can be augmented with other restorative features such as elastic membranes (see e.g., FIGS. 74A and 74B), bands, or magnets to create preferential pop-off or closing responses. For example, as shown in FIGS. 74A and 74B, the expiratory valve can include a magnet 1528 supported by one or more struts 1530 (e.g., centrally supported by two, three, four, or more struts 1530). A ferro-magnetic pin 1532 can be positioned in the plunger 1504. When the plunger 1504 is in the closed configuration, the plunger 1504 can be magnetically connected to the magnet 1528. When the plunger 1504 is in the open configuration, the plunger 1504 can be spaced apart from the magnet 1528. The size of the magnet 1528 can be used to control an immediate pop-off response when the user's intranasal pressure reaches a threshold pressure and an immediate closing response when the user's intranasal pressure falls below the threshold pressure.

Sleep apnea devices having the auto-valve 1500 allow the user to breathe normally when the air flow generator is in an off-condition. In the off-condition, the base mask pressure will be at a minimum and hence inspiratory valves will open readily and most easily. Since the air flow generator is not delivering air to the auto-valve 1500, the auto-valve will provide minimal to no resistance pressure.

The user can breathe normally when the air flow generator is in an off-condition at least in part because of the effective orifice size of the inspiratory and expiratory valves. For example, the effective orifice size of the expiratory valve can be between about 0.05 sq. in. and about 0.1 sq. in., such as between about 0.05 sq. in. and about 0.075 sq. in. The effective orifice size of the inspiratory valves (e.g., one or two) can be between about 0.1 sq. in. and about 0.15 sq. in., such as between about 0.1 sq. in. and about 0.125 sq. in. At a normal breathing rate of about 15 breaths/min (e.g., about 500 mL tidal volume), the sleep apnea device produces a "passive" back pressure between about 1 to 2 cm H20. In contrast, traditional CPAP devices have an effective orifice size of less than or equal to about 0.025 sq. in.

When breathing through the sleep apnea device alone (without the air supply tubing or air flow generator), during exhalation, the peak pressure is less than or equal to about 2.0 cm H20, preferably less than or equal to about 1.5 cm H20, such as between about 1.0 cm H20 and about 1.25 cm H20. During inhalation, the pressure can drop to less than −6.0 cm H20, such as between about −0.7 cm H20 and about −1.0 cm H20. In contrast, when breathing through a traditional CPAP mask alone, the peak pressure during exhalation is at least about 8 cm H20 and drops to about −5.5 cm H20 during inhalation. These values can be obtained by connecting the mask to a respirator set at 500 mL tidal volume and about 15 breaths per minute.

Advantageously, this design reduces the risk of asphyxiation since both inspiratory and expiratory valves are passive when the air flow generator is in the off-condition. In contrast, conventional CPAP devices require separate anti-asphyxia valves to prevent patient suffocation in the event the air flow generator malfunctions or the power fails.

The ability to operate in an off-condition also provides a level of comfort when the user is going to sleep. For example, the air flow generator can be intentionally adjusted to an off-condition when the user is going to sleep. This provides the user with a more natural sleeping environment. The air flow generator can be configured to turn on after a certain period of time (e.g., when the user is expected to be in a deep sleep). When the air flow generator is activated, the air flow generator can immediately deliver the therapeutic air pressure or gradually increase the therapeutic air pressure. In certain aspects, the air flow generator includes an automatic timer for activation. In certain aspects, the user and/or physician can set a timer for activation. In certain aspects, the air flow generator can have breathing/sensing algorithms to initiate blower air when a "sleeping condition" is sensed in the breathing pattern (e.g., by detecting motion using an accelerometer, motion detectors, cameras, etc., by detecting breathing rates, or otherwise).

Other Expiratory Valves

Any of the expiratory valves designs described above can be used in connection with the device 400, 400a, or 1100. Other valves can also be imagined, such as a tesla valve that provides one-way flow through a pathway without any moving parts, which can mitigate noise during exhalation. The valve can be shaped like a hose and connected to the sleep apnea device.

The structure of the tesla valve pathway provides the desired resistance during exhalation. In certain embodiments, the structure can be a series of connected funnel-shaped pathways. In certain embodiments, the tesla valve can be constructed from an open celled foam with a lattice pattern that allows preferential flow.

Head Gear Assembly

Various head gear assembly embodiments are described below to illustrate various examples that may be used in connection with any of the sleep apnea devices described herein. The sleep apnea device 1300 referenced in the Figures can be any of the sleep apnea devices 400, 400a, 1100 described above. Further, the present examples are not intended to be limited to the particular embodiments shown. Rather, components can be added, removed, or interchanged between different embodiments.

As shown in FIGS. 19A and 19B, the sleep apnea device can include straps 405a. The straps 405a can be constructed from a flexible material such as neoprene rubber, foam, cloth, elastic, or Velcro, although stiffer materials, such as plastic or silicone, can also be used for the straps 405a. Two lateral straps can extend from the manifold 404a to a buckle that extends above a crown of a user's head. A rear strap can extend between the two lateral straps and can extend below the crown of the user's head. In some embodiments, the straps 405a can removably snap onto the manifold 404a using an attachment tab at the ends of the straps 405a. The tabs can be constructed from a stiffer material than the straps 405a.

Figure 63:
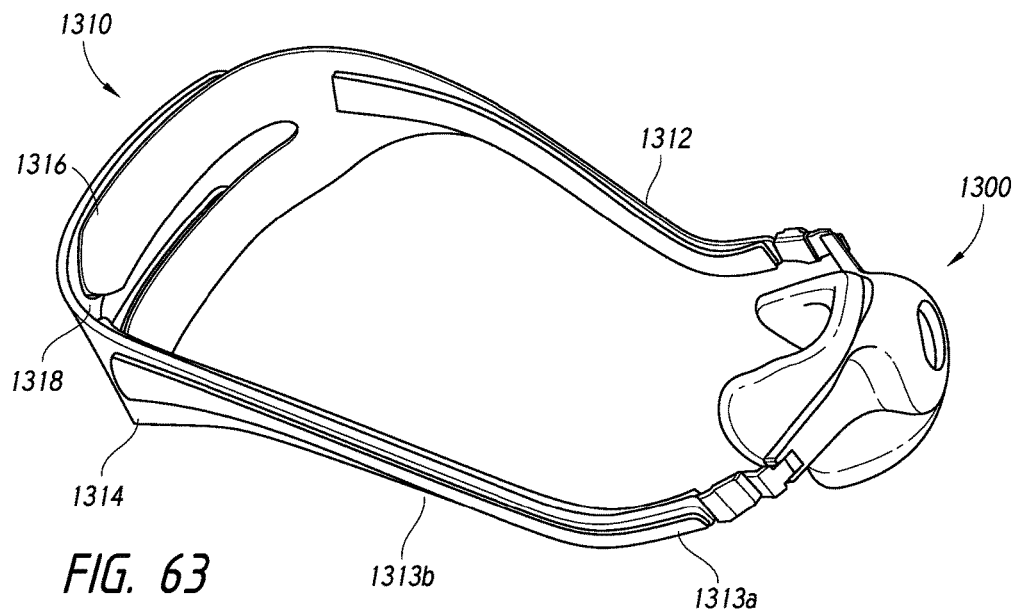
FIG. 63 illustrates an embodiment of a head gear assembly having hockey stick shaped lateral straps.
Figure 64:
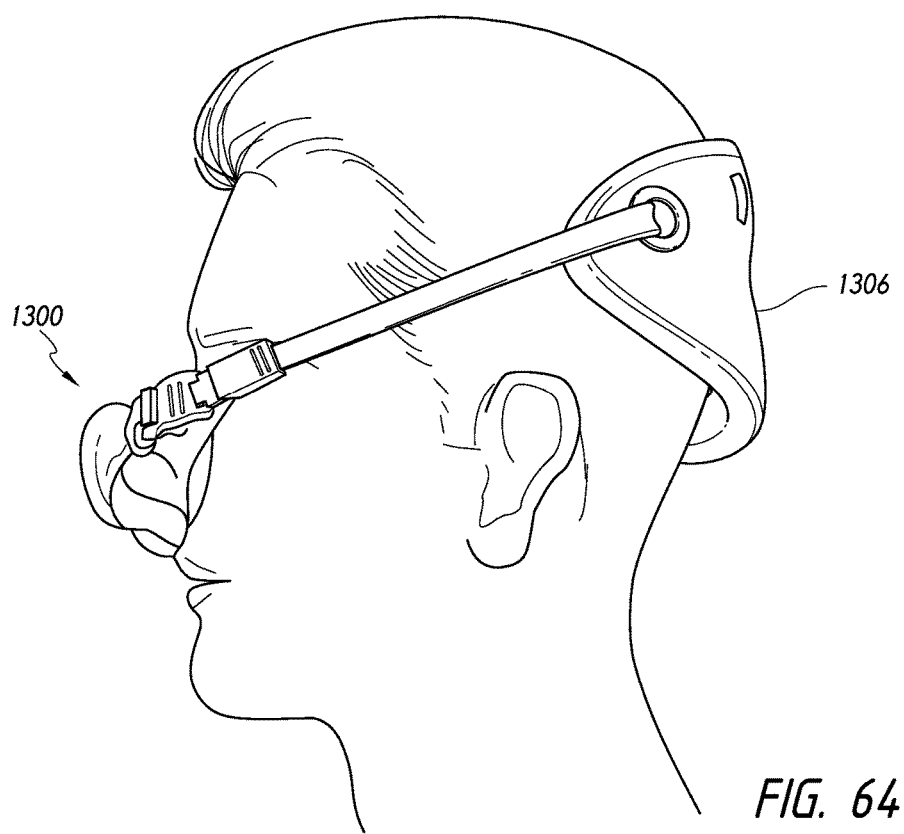
FIG. 64 illustrates another embodiment of a head gear assembly having a skull cap.

In some embodiments, as shown in FIG. 63, the head gear assembly 1310 can include lateral straps 1312 and/or lateral reinforcements 1314 that are stiffer than the lateral straps 1312. For example, the lateral straps 1312 can be constructed from foam, cloth, elastic, or Velcro, while the lateral reinforcements 1314 can be constructed from plastic or silicone. As shown in FIG. 63, a rear portion of the head gear assembly 1300 can include one or more straps 1316, 1318 shaped to cradle a top portion of the user's head and secured together using Velcro. In some embodiments, the lateral straps 1312 can extend to a rear portion of the user's head and connect to a turn buckle to make the length of the lateral straps 1312 adjustable (e.g., as shown in FIGS. 19A and 19B). In other examples, the straps can extend through a tube with an opening disposed along the tube through which a portion of the strap can be pulled to shorten the length of the strap. As another example, as shown in FIG. 64, the rear portion of the head gear assembly can include a cap 1306 shaped to cradle a top portion of the user's head. In yet another example, the cap 1306 can be shaped to be positioned at the base of the skull for securement.

Referring back to FIG. 63, the lateral straps 1312 and/or lateral reinforcements 1314 of the head gear 1310 can be generally hockey-stick shaped with a lower region 1313a that is shorter than an upper region 1313b. The ratio between the length of the lower region 1313a and the upper region 1313b can be 1:4, 1:5, 1:6, 1:7, 1:8, 1:9, 1:10, or ratios in between the aforementioned ratios. The hockey-stick configuration is shaped such that the lateral regions are out of the line of sight, raised off the cheek bones, and directed over the ears to a cap or rear strap. In some embodiments, the lateral straps 1312 and/or lateral reinforcements 1314 can be inverted such that the upper region has the shorter length.

Figure 65:
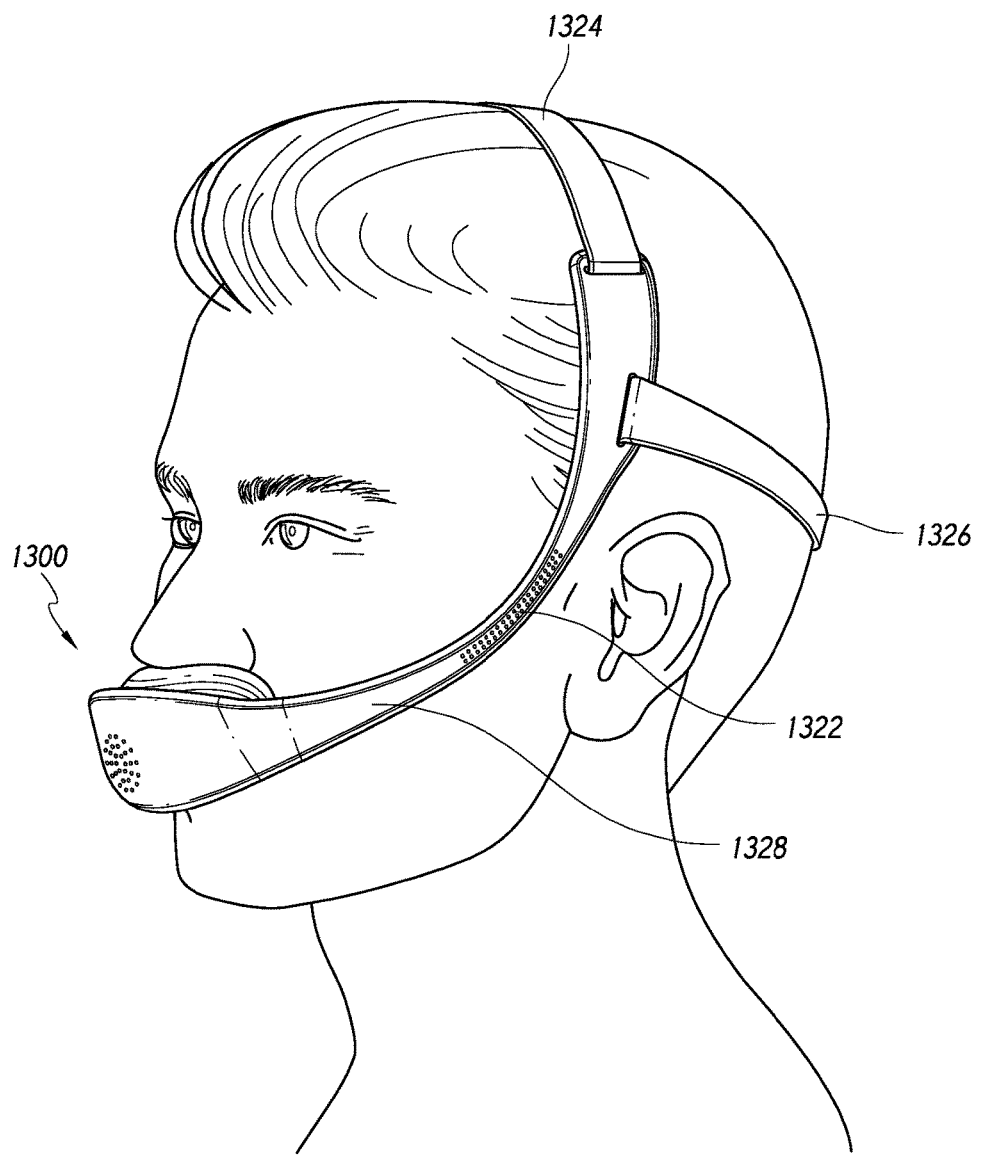
FIG. 65 illustrates yet another embodiment of a head gear assembly having a plurality of holes for breathability.

In some embodiments, as shown in FIG. 65, the hockey-stick shaped lateral regions 1328 can include a plurality of small holes 1322 to encourage breathability. A first strap 1324 can connect the two arms 1328 and extend over the user's head, and a second strap 1326 can connect the two arms 1328 and extend around a rear portion of the user's head.

Figure 66:
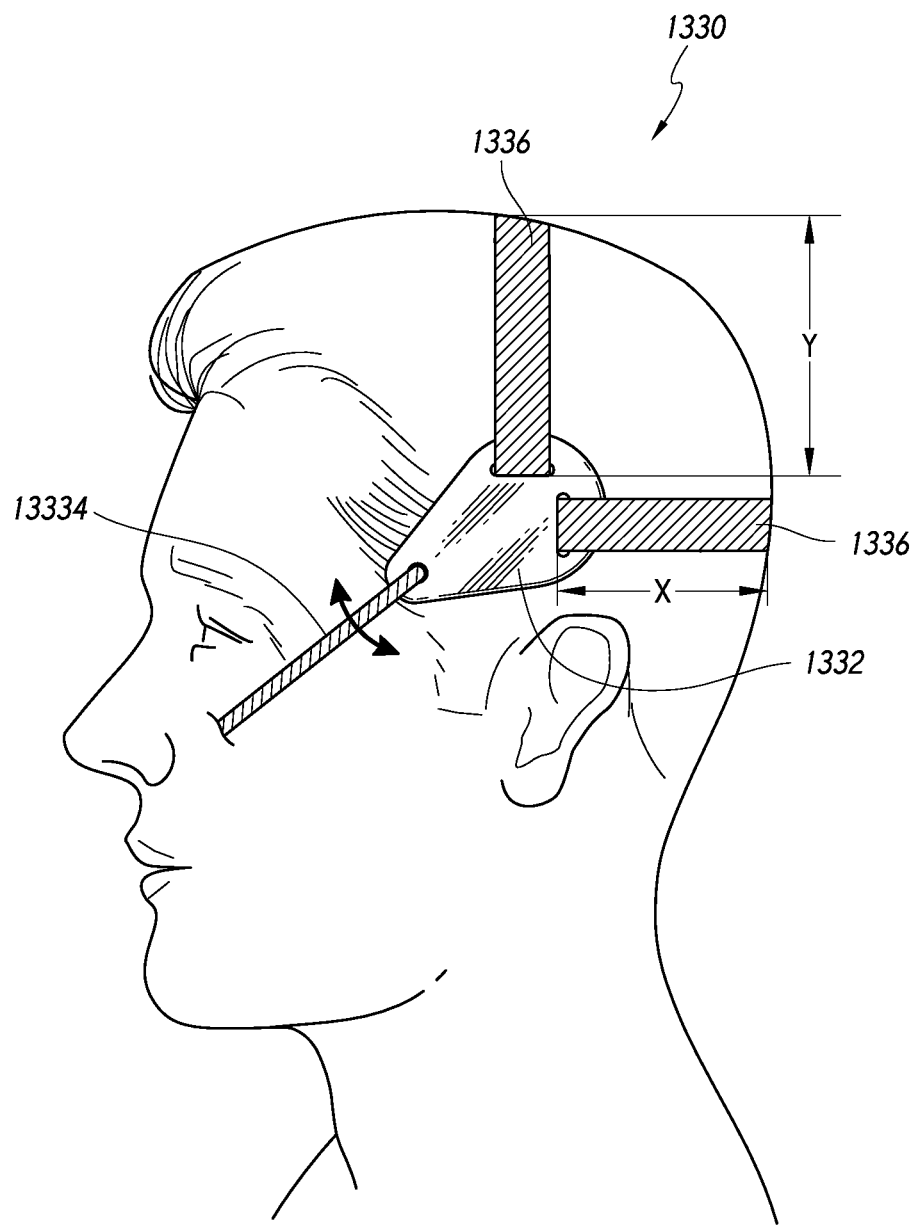
FIG. 66 illustrates a strap manifold for a head gear assembly.

FIG. 66 illustrates a strap manifold 1332 that can be used to connect one or more straps 1334, 1336. One or more rear straps 1336 can cradle an upper portion of the user's head, while a cord strap 1334 can extend from the strap manifold 1332 to the mask. The rear straps 1336 can be wider and less elastic than the cord strap 1334. The wider rear straps 1336 can consistently orient and position the head gear assembly 1330 across the same region of the user's head and can evenly distributed the load across a larger region of the user's head. The cord strap 1334 generally does not touch the user's face and can pivot relative to the manifold to achieve the most comfortable angle for the user.

Figure 67:
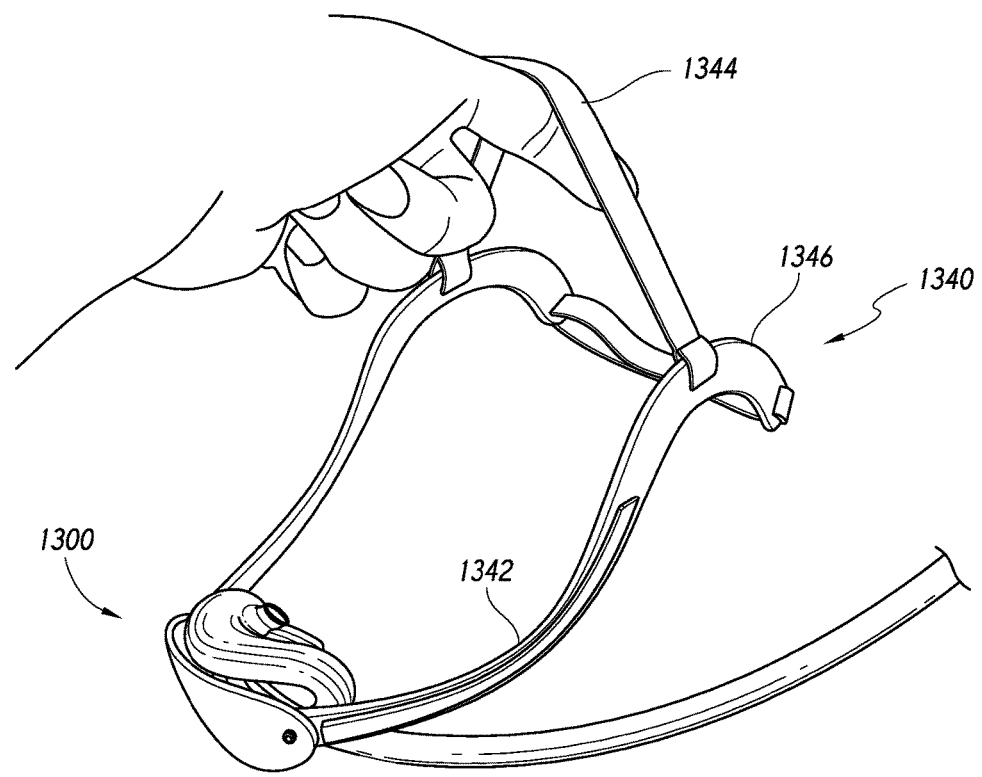
FIG. 67 illustrates another embodiment of a head gear assembly having lateral straps with a curved upper region.

FIG. 67 illustrates another embodiment of a head gear assembly 1340 having lateral arms 1342 having a curved upper region 1346 to extend over the user's ears. One or more rear straps 1344 can connect the two lateral arms 1342 and extend along an upper or a rear portion of the user's head.

Figure 68:
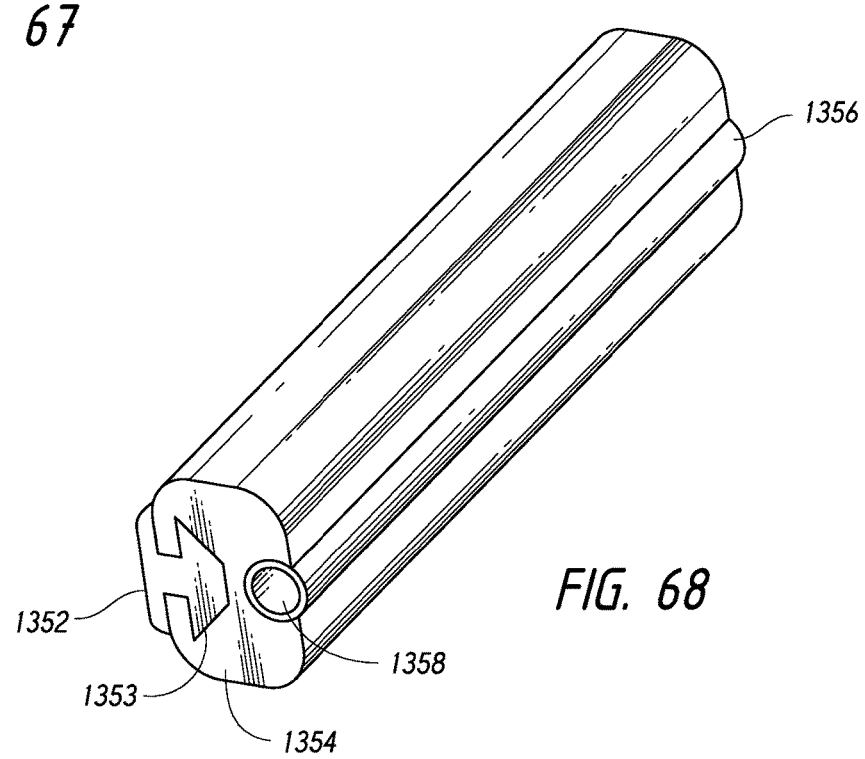
FIG. 68 illustrates a connector for connecting an air supply tube to a head gear assembly.

Any of the head gear assemblies described above can include a connector 1354 that can secure a portion of the air supply tube 1356 to a strap (see FIG. 68). The connector 1354 can be positioned anywhere along the strap and can include a channel 1358 on a first side for receiving the air supply tube 1356 and a padded insert 1352 on a second side for abutting the user's face. For example, an air supply tube 1356 can extend from a bottom portion or a side portion of the mask and extend along the straps of any of the head gear assemblies described herein.

Figure 69:
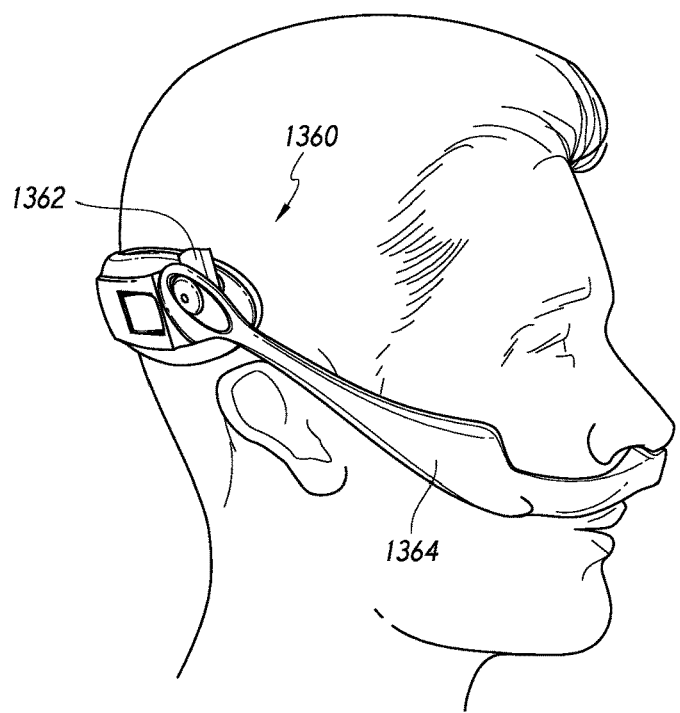
FIG. 69 illustrates an embodiment of a strapless head gear assembly having stability pads.

FIG. 69 illustrates a strapless embodiment of a head gear assembly 1360. The strapless assembly 1360 does not extend around a rear portion or over a top portion of the user's head. Rather, the head gear assembly 1360 includes two concave stability pads 1362 positioned on either side of the user's head to maintain the position of the mask. The arms 1364 extend from the stability pads 1362 to the user's nose. In other embodiments, a single strap can connect the two stability pads 1362 to each other.

Figure 70:
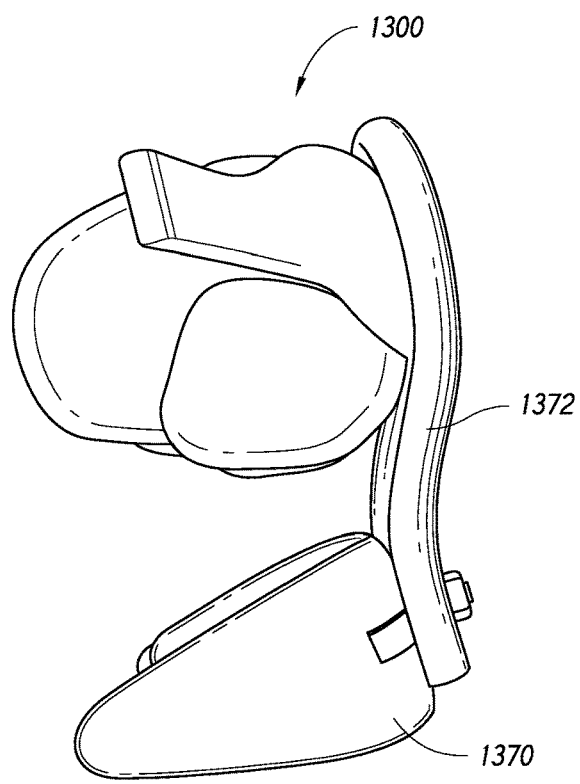
FIG. 70 illustrates yet another embodiment of a strapless head gear assembly having a mouth guard.

FIG. 70 illustrates another strapless embodiment of a head gear assembly in which the mask 1300 is secured to a mouth guard 1370 with a connector 1372. The mouth guard 1370 can be fit to the user's teeth to create a stable mount.

Terminology

Although the devices described herein are primarily described for users who have sleep apnea or snore, the device can also be used for non-therapeutic purposes. For example, the device can include a filter configured to filter particulate in the air. In some instances, the device is used without the airflow generator.

Although the systems described herein may be described or illustrated with certain components (e.g., air flow generator or expiratory valve), any of the components described herein can be used with other components of the system described herein.

As described above, the systems described herein can generate the desired breathing profiles with therapeutic air flow rates of less than or equal to about 30 L/min (e.g., between about 20 L/min and about 30 L/min or between about 10 L/min and about 20 L/min). In some embodiments, the air flow generator produces an air flow rate of less than or equal to about 20 L/min. In some embodiments, the air flow generator produces the industry standard flow rate of at least about 150 L/min, but the air supply tube assembly reduces the air flow rate to less than or equal to about 20 L/min.

As used herein, the relative terms "front" and "rear" shall be defined from the users face relative to the device. Thus, rear refers to the side of the device or component that is closer to the face of the user and front refers to the opposite side of the device or component.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of the stated amount.

Various embodiments have been disclosed above. These various embodiments may be used alone or in combination, and various changes to individual features of the embodiments may be altered, without departing from the scope of the invention. For example, the order of various method steps may in some instances be changed, and/or one or more optional features may be added to or eliminated from a described device. Therefore, the description of the embodiments provided above should not be interpreted as unduly limiting the scope of the invention as it is set forth in the claims.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "flowing air into a manifold" include "instructing the flowing of air into a manifold."

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 3 mm" includes "3 mm."

Example Embodiments

The following example embodiments identify some possible permutations of combinations of features disclosed herein, although other permutations of combinations of features are also possible.

1. A device for treating a patient suffering from obstructive sleep apnea or snoring, the device comprising:
   a manifold;
   an expiratory valve connected to the manifold, the expiratory valve comprising a first end and a second end, the first end being closer to the patient when the patient is using the device, the expiratory valve further comprising:
  a body portion comprising a feedback port configured to be connected to an air flow generator;
  a plunger at least partially disposed in the body portion, the plunger comprising a first end and a second end, the first end being closer to the patient when the patient is using the device; and
  a pressurizing chamber positioned between the second end of the plunger and the second end of the expiratory valve, the pressurizing chamber configured to receive air from the air flow generator through the feedback port,
  wherein the plunger is configured to move between a first position and a second position.

2. The device of claim 1, wherein the body portion further comprises at least one vent hole, the at least one vent hole positioned between the pressurizing chamber and the first end of the expiratory valve.

3. The device of Embodiment 2, wherein when the plunger is in the first position, the plunger prevents air from escaping through the at least one vent hole, and wherein when the plunger is in the second position, the plunger permits air to escape through the at least one vent hole.

4. The device of any one of the preceding embodiments, wherein the plunger is configured to move along a longitudinal axis of the expiratory valve.

5. The device of any one of the preceding embodiments, wherein expiratory valve further comprises a diaphragm positioned between the plunger and the second end of the expiratory valve.

6. The device of any one of the preceding embodiments, wherein the expiratory valve further comprises a magnet positioned between the first end of the plunger and the first end of the expiratory valve.

7. The device of Embodiment 6, wherein the plunger is spaced apart from the magnet when the plunger is in the first position, and wherein the plunger is not magnetically connected to the magnet when the plunger is in the second position.

8. The device of any one of the preceding embodiments, wherein the manifold comprises a manifold port configured to connect to the air flow generator.

9. The device of any one of the preceding embodiments, wherein the expiratory valve has a height of less than or equal to about 1.5 inches.

10. The device of Embodiment 9, wherein the expiratory valve has a height of less than or equal to about 0.5 inches.

11. The device of any one of the preceding embodiments, further comprising at least one inspiratory valve connected to the manifold.

12. The device of Embodiment 11, wherein the at least one inspiratory valve comprises a first inspiratory valve and a second inspiratory valve.

13. The device of Embodiment 11, wherein the at least one inspiratory valve comprises a flap valve.

14. The device of any one of the preceding embodiments, wherein the second end of the plunger is a closed end and the first end of the plunger is an open end.

15. The device of any one of Embodiments 1-13, wherein the second end of the plunger is an open end and the first end of the plunger is a closed end.

16. The device of any one of Embodiments 1-13, wherein the plunger is disc-shaped.

17. A system for treating a patient suffering from obstructive sleep apnea or snoring, the system comprising:
  the device of any one of the preceding embodiments;
  an air flow generator connected to the device.

18. The system of Embodiment 17, further comprising a feedback hose connecting the air flow generator to the feedback port, the hose having a diameter of less than or equal to about 1.75 mm.

19. The system of Embodiment 17 or 18, further comprising a manifold hose connecting the air flow generator to a manifold port.

20. A method of manufacturing the device of any one of Embodiments 1 to 16, the method comprising:
  forming the expiratory valve, wherein forming the expiratory valve comprises:
    positioning a plunger at least partially in the body portion to form the pressurizing chamber between the second end of the plunger and the second end of the plunger; and
  connecting the expiratory valve to the manifold.

21. A device for treating a patient suffering from obstructive sleep apnea or snoring, the device comprising:
  a manifold comprising a manifold port configured to be connected to an air flow generator;
  an expiratory valve connected to the manifold, the expiratory valve comprising a first end and a second end, the first end being closer to the patient when the patient is using the device, the expiratory valve further comprising:
    a body portion comprising a feedback port configured to be connected to an air flow generator;
    a plunger at least partially disposed in the body portion;
    a first chamber configured to receive air delivered through the feedback port; and
    a second chamber configured to receive air delivered through the manifold port.

22. The device of Embodiment 21, further comprising at least one vent configured to permit air to escape from the second chamber.

23. The device of Embodiment 21 or 22, wherein the plunger is configured to move along a longitudinal axis of the expiratory valve.

24. The device of any one of Embodiments 21 to 23, wherein the first chamber is positioned between the plunger and the second end of the expiratory valve.

25. The device of any one of Embodiments 21 to 24, wherein the expiratory valve further comprises a diaphragm.

26. The device of any one of Embodiments 21 to 25, wherein the expiratory valve further comprises a magnet positioned between the first end of the plunger and the first end of the expiratory valve.

27. The device of Embodiment 26, wherein the plunger is magnetically connected to the magnet when the plunger is in a first position, and wherein the plunger is not magnetically connected to the magnet when the plunger is in a second position.

28. The device of any one of Embodiments 21 to 27, wherein the expiratory valve has a height of less than or equal to about 1.75 inches.

29. The device of Embodiment 28, wherein the expiratory valve has a height of less than or equal to about 0.5 inches.

30. The device of any one of Embodiments 21 to 29, further comprising at least one inspiratory valve connected to the manifold.

31. The device of Embodiment 30, wherein the at least one inspiratory valve comprises a first inspiratory valve and a second inspiratory valve.

32. The device of Embodiment 30, wherein the at least one inspiratory valve comprises a flap valve.

33. The device of any one of Embodiments 21-32, wherein an inner surface area of the first chamber is less than an inner surface area of the second chamber.

34. A system for treating a patient suffering from obstructive sleep apnea or snoring, the system comprising:
the device of any one of Embodiments 21 to 33;
an air flow generator connected to the device.

35. The system of Embodiment 34, further comprising a feedback hose connecting the air flow generator to the feedback port, the hose having a diameter of less than or equal to about 1.5 mm.

36. The system of Embodiment 34 or 35, further comprising a manifold hose connecting the air flow generator to a manifold port.

37. A method of manufacturing the device of any one of Embodiments 21 to 33, the method comprising:
forming the expiratory valve, wherein forming the expiratory valve comprises:
positioning a plunger at least partially in the body portion to form the first chamber and the second chamber; and
connecting the expiratory valve to the manifold.

38. A device for treating a patient suffering from obstructive sleep apnea or snoring, the device comprising:
a manifold;
an expiratory valve connected to the manifold, the expiratory valve comprising a first end and a second end, the first end being closer to the patient when the patient is using the device, the expiratory valve further comprising:
a body portion;
a diaphragm connected to the body portion;
a plunger at least partially disposed in the body portion, the plunger comprising a ferro-magnetic member; and
a magnet positioned between the plunger and the first end of the expiratory valve.

39. The device of Embodiment 38, wherein the body portion further comprises at least one vent hole, positioned between the magnet and the diaphragm.

40. The device of Embodiment 39, wherein when the plunger is in a first position, the plunger prevents air from escaping through the at least one vent hole, and wherein when the plunger is in the second position, the plunger permits air to escape through the at least one vent hole.

41. The device of any one of Embodiments 38 to 40, wherein the plunger is configured to move along a longitudinal axis of the expiratory valve.

42. The device of any one of Embodiments 38 to 41, wherein the manifold comprises a manifold port configured to connect to the air flow generator.

43. The device of any one of Embodiments 38 to 42, wherein the expiratory valve has a height of less than or equal to about 1.5 inches 44. The device of Embodiment 43, wherein the expiratory valve has a height of less than or equal to about 0.5 inches.

45. The device of any one of Embodiments 38 to 44, further comprising at least one inspiratory valve connected to the manifold.

46. The device of Embodiment 45, wherein the at least one inspiratory valve comprises a first inspiratory valve and a second inspiratory valve.

47. The device of Embodiment 45, wherein the at least one inspiratory valve comprises a flap valve.

48. A system for treating a patient suffering from obstructive sleep apnea or snoring, the system comprising:
the device of any one of Embodiments 38 to 47;
an air flow generator connected to the device.

49. The system of Embodiment 48, further comprising a hose connecting the air flow generator to the device, the hose having a diameter of less than or equal to about 15 mm.

50. A method of using a system for treating a patient suffering from obstructive sleep apnea or snoring, the method comprising:
flowing air into an expiratory valve through a feedback port, the expiratory valve connected to a manifold, the expiratory valve comprising a first end and a second end, the first end being closer to the patient when the patient is using the device, the expiratory valve further comprising:
a body portion;
a plunger at least partially disposed in the body portion, the plunger comprising a first end and a second end, the first end being closer to the patient when the patient is using the device;
a pressurizing chamber positioned between the second end of the plunger and the second end of the expiratory valve, the pressurizing chamber configured to receive air through the feedback port; and
at least one vent hole, the at least one vent hole positioned between the pressurizing chamber and the first end of the expiratory valve;
moving the plunger between a first position in which the plunger prevents air from escaping through the at least one vent hole and a second position in which the plunger permits air to escape through the at least one vent hole.

51. The method of Embodiment 50, wherein flowing air to the expiratory valve comprises delivering air from an air flow generator.

52. The method of Embodiment 50 or 51, further comprising delivering air from an air flow generator to the manifold through a manifold port.

53. The method of any one of Embodiments 50 or 52, further comprising adjusting a pressure of the air being delivered to the pressurizing chamber, wherein adjusting the pressure of the air adjusts a resistance to the plunger moving between the first position and the second position.

54. The method of any one of Embodiments 50 to 53, wherein moving the plunger comprises moving the plunger along a longitudinal axis of the expiratory valve.

55. The method of Embodiment 51, further comprising flowing ambient air into the manifold for a first amount for a first amount of time, wherein during the first amount of time, the air flow generator is in an on condition.

56. A method of using a system for treating a patient suffering from obstructive sleep apnea or snoring, the method comprising:
delivering air from an air flow generator to a manifold through a manifold port;
delivering air from the air flow generator to an expiratory valve through a feedback port, the expiratory valve connected to the manifold, the expiratory valve comprising a first end and a second end, the first end being closer to the patient when the patient is using the device, the expiratory valve further comprising:
a body portion;
a plunger at least partially disposed in the body portion;
a first chamber configured to receive air delivered through the feedback port; and
a second chamber configured to receive air delivered through the manifold port.
at least one vent hole configured to permit air to escape from the second chamber;

moving the plunger between a first position in which the plunger prevents air from escaping through the at least one vent hole and a second position in which the plunger permits air to escape through the at least one vent hole.

57. The method of Embodiment 56, further comprising adjusting a pressure of the air being delivered to the first chamber, wherein adjusting the pressure of the air adjusts a resistance to the plunger moving between the first position and the second position.

58. The method of Embodiment 56 or 57, wherein moving the plunger comprises moving the plunger along a longitudinal axis of the expiratory valve.

59. The method of any one of Embodiment 56 to 58, further comprising flowing ambient air into the manifold through at least one inspiratory valve.

60. The method of Embodiment 59, wherein when flowing ambient air into the manifold, the air flow generator is in an on condition.

61. A system for treating a patient suffering from obstructive sleep apnea or snoring, the device comprising:
   a manifold;
   an expiratory valve connected to the manifold;
   at least one inspiratory valve connected to the manifold
   a braided hose comprising a plurality of strands, the braided hose connecting an air flow generator to the manifold, the braided hose having a diameter of less than or equal to about 15 mm, the braided hose configured to deliver air to the manifold at a rate between about 5 L/min and about 25 L/min.

62. The system of Embodiment 61, wherein the hose is configured to deliver air having a pressure between about 4 cm H20 and about 20 cm H20.

63. The system of Embodiment 61 or 62, wherein the braided hose comprises a plurality of strands, each strand having a diameter of less than or equal to about 0.006 inches.

64. The system of any one of Embodiments 61 to 63, wherein the plurality of strands comprise PET.

65. The system of any one of Embodiments 61 to 64, wherein the braided hose can expand from a first diameter to a second diameter, the second diameter being between about 2.0 times and about 2.5 times the first diameter.

66. The system of any one of Embodiments 61 to 65, wherein each of the plurality of strands crosses over at least one strand and under at least one strand.

67. The system of Embodiment 66, wherein each of the plurality of strands crosses over at least two consecutive strands and under at least two consecutive strands.

68. The system of any one of Embodiments 61 to 67, wherein the hose weighs less than or equal to about 20 grams.

69. The system of any one of Embodiments 61 to 68, wherein the braided hose is configured to bend around a rod between about 0.5 inches and about 0.75 inches without kinking.

70. A system for treating a patient suffering from obstructive sleep apnea or snoring, the device comprising:
   a manifold;
   an air flow generator connected to the manifold, the air flow generator configured to transition between an off condition and an on condition;
   an expiratory valve connected to the manifold, the expiratory valve comprising an effective orifice size of less than or equal to about 1.5 square inches; and
   at least one inspiratory valve connected to the manifold.

71. A method of using the system of Embodiment 70, comprising:
   going to sleep when the air flow generator is in the off condition;
   transitioning the air flow generator from the off condition to the on condition after a period of time.

72. The method of Embodiment 71, wherein the user sets the period of time.

73. The method of Embodiment 71, further comprising sensing when the patient is asleep.

74. The method of Embodiment 73, wherein the airflow generator transitions to the on condition after the system detects that the patient is asleep.

75. The method of Embodiment 73 or 74, wherein sensing when the patient is asleep comprises detecting movement using an accelerometer.

The following is claimed:

1. A device for treating a patient suffering from obstructive sleep apnea or snoring, the device comprising:
   an air flow generator generating an air flow at only a positive therapeutic pressure during the treatment;
   a manifold connected to an air flow generator;
   an expiratory valve connected to the manifold, the expiratory valve comprising a first end and a second end, the first end being closer to the patient when the patient is using the device, the expiratory valve further comprising:
      a body portion comprising a feedback port connected to the manifold;
      a plunger at least partially disposed in the body portion, the plunger comprising a first end and a second end, the first end of the plunger being closer to the patient when the patient is using the device; and
      a pressurizing chamber positioned between the second end of the plunger and the second end of the expiratory valve, the pressurizing chamber receives air from the air flow generator through the feedback port,
      wherein the plunger moves between a first position and a second position and wherein the movement from the first to second position is biased based on the therapeutic pressure from the air flow generator;
      wherein the plunger bias exerts a back pressure upon each exhalation from the patient sufficient to create a pneumatic splint in the patient's respiratory tract;
      wherein the exhalation from the patient has a first half followed by a second half and the back pressure is varied such that during the start of the first half the back pressure is between 0 and 5 cm H2O and increases to a peak back pressure of greater than 5 cm of H2O in the second half;
   an air conduit with a first end connected to the manifold and a second end configured to provide air flow at a therapeutic pressure from the air flow generator to the patient, the air conduit further comprising an one-way valve that allows air from the first end of the air conduit to the second end of the air conduit; and
   wherein the first position comprises the plunger forming a seal that inhibits air flow across the expiratory valve and the second position comprises a disengagement of the seal thereby allowing air flow across the expiratory valve, wherein the expiratory valve further comprises a magnet positioned between the first end of the plunger and the first end of the expiratory valve, wherein the magnet maintains the plunger in the first position during the entire inspiration phase of the patient and allows movement to the second position when the patient exhales.

2. The device of claim 1, wherein the body portion further comprises at least one vent hole, the at least one vent hole positioned between the pressurizing chamber and the first end of the expiratory valve.

3. The device of claim 2, wherein when the plunger is in the first position, the plunger prevents air from escaping through the at least one vent hole, and wherein when the plunger is in the second position, the plunger permits air to escape through the at least one vent hole.

4. The device of claim 1, wherein the plunger moves along a longitudinal axis of the expiratory valve.

5. The device of claim 1, wherein the expiratory valve further comprises a diaphragm positioned between the plunger and the second end of the expiratory valve.

6. The device of claim 1, wherein the expiratory valve has a height of less than or equal to about 1.5 inches.

7. The device of claim 6, wherein the expiratory valve has a height of less than or equal to about 0.5 inches.

8. The device of claim 1, wherein the one-way valve comprises a first valve and a second valve.

9. The device of claim 1, wherein the one-way valve comprises a flap valve.

10. The device claim 1, wherein the second end of the plunger is a closed end and the first end of the plunger is an open end.

11. The device claim 1, wherein the second end of the plunger is an open end and the first end of the plunger is a closed end.

12. The device claim 1, wherein the plunger is disc-shaped.

13. The device of claim 1, wherein the one-way valve reduces $CO_2$ entrapment in the device.

14. The device of claim 1, wherein the one-way valve is positioned to shield the feedback port from the back pressure of patient breathing.

* * * * *